(12) United States Patent
Galiana Bujanda et al.

(10) Patent No.: US 12,226,336 B2
(45) Date of Patent: Feb. 18, 2025

(54) WEARABLE DEVICES FOR PROTECTING AGAINST MUSCULOSKELETAL INJURIES AND ENHANCING PERFORMANCE

(71) Applicant: President and Fellows of Harvard College, Cambridge, MA (US)

(72) Inventors: Ignacio Galiana Bujanda, Cambridge, MA (US); Conor J. Walsh, Cambridge, MA (US); Michael T. Rouleau, Cambridge, MA (US); Jinwon Chung, Cambridge, MA (US); Tim-Fabian Moser, Cambridge, MA (US); Ye Ding, Cambridge, MA (US); Danielle L. Nathanson, Cambridge, MA (US); Nicolas Menard, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 9 days.

(21) Appl. No.: 16/969,937

(22) PCT Filed: Feb. 15, 2019

(86) PCT No.: PCT/US2019/018258
§ 371 (c)(1),
(2) Date: Aug. 13, 2020

(87) PCT Pub. No.: WO2019/161232
PCT Pub. Date: Aug. 22, 2019

(65) Prior Publication Data
US 2021/0007874 A1    Jan. 14, 2021

Related U.S. Application Data

(60) Provisional application No. 62/757,138, filed on Nov. 7, 2018, provisional application No. 62/631,666, filed on Feb. 17, 2018.

(51) Int. Cl.
*A61F 5/02* (2006.01)
*A61F 5/01* (2006.01)
*B25J 9/00* (2006.01)

(52) U.S. Cl.
CPC ............ *A61F 5/028* (2013.01); *A61F 5/0102* (2013.01); *B25J 9/0006* (2013.01); *A61F 2005/0162* (2013.01); *A61F 2005/0167* (2013.01)

(58) Field of Classification Search
CPC .. A61F 5/01; A61F 5/0102; A61F 5/02; A61F 5/024; A61F 5/026; A61F 5/028;
(Continued)

(56) References Cited

U.S. PATENT DOCUMENTS 4,964,628 A  * 10/1990 Poplawski ............ A61F 5/0102
                                                                   482/51
6,190,342 B1   2/2001 Taylor
(Continued)

FOREIGN PATENT DOCUMENTS

CN       1838933 A    9/2006
CN     104411274 A    3/2015
(Continued)

OTHER PUBLICATIONS

Machine translation of Gao CN107486842A, created Feb. 15, 2022 from patents.google.com (Year: 2017).*
(Continued)

*Primary Examiner* — Ophelia A Hawthorne
*Assistant Examiner* — Gina McCarthy
(74) *Attorney, Agent, or Firm* — Wolf, Greenfield & Sacks, P.C.

(57) ABSTRACT

Wearable devices protect against musculoskeletal injuries and enhance performance. Systems and methods provide wearable devices to assist with human motion during physi-
(Continued)

cal activities, such as performing movements (e.g., lifting) and holding static poses (e.g., crouching, or holding a tool while working overhead). Materials, constructions, and system architectures allow the wearable devices to be worn over, under, or integrated into clothing for extended periods of time to improve performance or reduce risk of injury. Sensors may be included in the wearable devices to detect various activities, motions, and postures of the wearer, and various active and semi-active controls approaches may leverage sensor information to provide tailored assistance to individual users. Various controls optimization techniques ensure the wearable devices operate at peak efficiency.

28 Claims, 75 Drawing Sheets

(58) Field of Classification Search
CPC ...... A61F 2005/0132; A61F 2005/0134; A61F 2005/0137; A61F 2005/0139; A61F 2005/0155; A61F 2005/0162; A61F 2005/0167; A61B 5/1116; B25J 9/0006; B25J 9/0009; B25J 9/104; B25J 9/161; B25J 9/1674; A41D 13/05; F16D 13/58
See application file for complete search history.

(56) References Cited

U.S. PATENT DOCUMENTS

| | | | |
|---|---|---|---|
| 6,436,065 | B1 | 8/2002 | Mitchell |
| 2005/0130815 | A1 | 6/2005 | Abdoli-Eramaki |
| 2008/0228121 | A1* | 9/2008 | Hughes ................... A61F 5/026 602/19 |
| 2012/0165158 | A1 | 6/2012 | Ren et al. |
| 2013/0131560 | A1 | 5/2013 | Ferguson et al. |
| 2013/0261521 | A1* | 10/2013 | Carter .................... A61F 5/028 602/19 |
| 2013/0288863 | A1 | 10/2013 | Yamamoto et al. |
| 2014/0163435 | A1 | 6/2014 | Yamamoto et al. |
| 2015/0088269 | A1 | 3/2015 | Roh |
| 2015/0141889 | A1 | 5/2015 | Ha et al. |
| 2015/0173993 | A1 | 6/2015 | Walsh et al. |
| 2016/0107309 | A1 | 4/2016 | Walsh et al. |
| 2016/0220438 | A1 | 8/2016 | Walsh et al. |
| 2016/0235615 | A1 | 8/2016 | Yamamoto et al. |
| 2017/0202724 | A1 | 7/2017 | De Rossi et al. |
| 2017/0239821 | A1 | 8/2017 | Lessing et al. |
| 2017/0360645 | A1 | 12/2017 | Sodeyame et al. |
| 2018/0008502 | A1 | 1/2018 | Asbeck et al. |
| 2018/0153722 | A1* | 6/2018 | Cromie ............... A61B 5/7267 |
| 2018/0297214 | A1 | 10/2018 | Lessing et al. |
| 2019/0358074 | A1* | 11/2019 | Zelik ..................... F16D 13/58 |
| 2020/0331150 | A1 | 10/2020 | Vitiello et al. |
| 2021/0077335 | A1 | 3/2021 | Yoshimi et al. |
| 2021/0290422 | A1* | 9/2021 | Park ...................... A41D 13/05 |

FOREIGN PATENT DOCUMENTS

| | | | |
|---|---|---|---|
| CN | 106562869 | A | 4/2017 |
| CN | 107486842 | A * | 12/2017 |
| JP | 2008-067762 | A | 3/2008 |
| JP | 2010-029480 | A | 2/2010 |
| JP | 2011-251001 | A | 12/2011 |
| JP | 2012-024557 | A | 2/2012 |
| JP | 2014-150861 | A | 8/2014 |
| JP | 2015-529574 | A | 10/2015 |
| JP | 2017148488 | A * | 8/2017 |
| WO | WO 200/5018525 | A1 | 3/2005 |
| WO | WO 2012/124328 | A1 | 9/2012 |
| WO | WO 2014/013662 | A1 | 1/2014 |
| WO | WO 2014/194257 | A1 | 12/2014 |
| WO | WO 2016/031376 | A1 | 3/2016 |
| WO | WO 2016/089466 | A2 | 6/2016 |
| WO | WO 2016/157217 | A2 | 10/2016 |
| WO | WO 2018/023109 | A1 | 2/2018 |
| WO | WO 2019/172209 | A1 | 9/2019 |

OTHER PUBLICATIONS

Machine Translation of Publication No. JP 2017148488A created Jul. 28, 2023 from Espacenet.com (Year: 2017).*
International Search Report and Written Opinion for International Application No. PCT/US2019/018258, mailed Jun. 19, 2019.
PCT/US2019/018258, Jun. 19, 2019, International Search Report and Written Opinion.
Ali et al., Systematic Review of Back-Support Exoskeletons and Soft Robotic Suits. Frontiers in Bioengineering and Biotechnology, Nov. 2, 2021;9:755257(1-15).
Chen et al., A Real-Time Lift Detection Strategy for a Hip Exoskeleton. Frontiers in Neurorobotics, Apr. 12, 2018;12:17(1-11).
Chen et al., Classification of Lifting Techniques for Application of A Robotic Hip Exoskeleton. Sensors, Feb. 25, 2019;19(4):963(1-13).
Chen et al., Lift Movement Detection with a QDA Classifier for an Active Hip Exoskeleton. Wearable Robotics: Challenges and Trends. WeRob 2018. Biosystems & Biorobotics, Oct. 14, 2018;22:1-2.
Lanotte et al., A Low-Back Exoskeleton can Reduce the Erector Spinae Muscles Activity During Freestyle Symmetrical Load Lifting Tasks. 2018 7th IEEE International Conference on Biomedical Robotics and Biomechatronics (Biorob). Aug. 26-29, 2018; p. 701-6.
Perera et al., Exoskeletons for Manual Handling: A Scoping Review. IEEE Access, Oct. 11, 2023;11:1115568-98.
Poliero et al., Active and Passive Back-Support Exoskeletons: A Comparison in Static and Dynamic Tasks. IEEE Robotics and Automation Letters, Jul. 4, 2022;7(3):8463-70.
Toxiri et al., Back-Support Exoskeletons for Occupational Use: An Overview of Technological Advances and Trends. IISE Transactions on Occupational Ergonomics and Human Factors, Aug. 7, 2019;7(3-4):237-49.

* cited by examiner

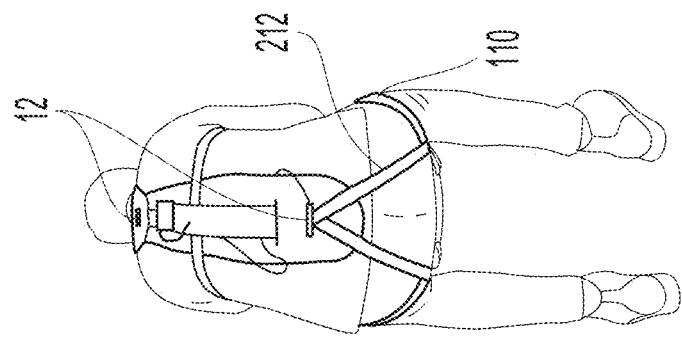
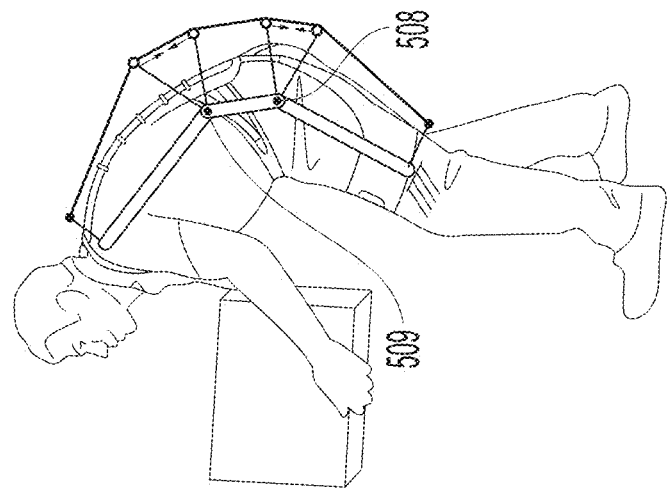
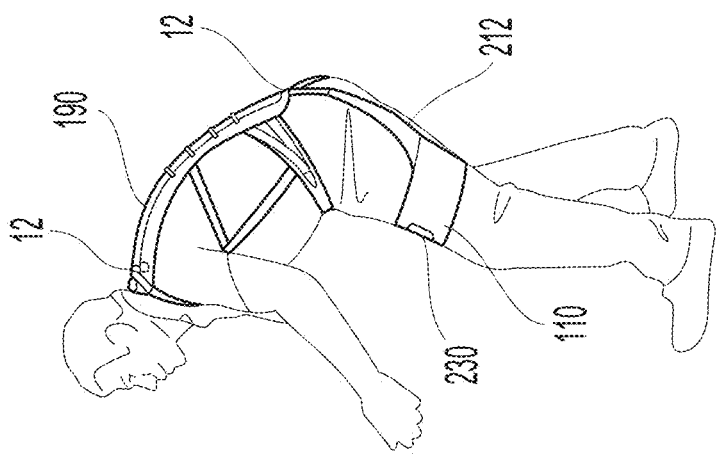
FIG. 10

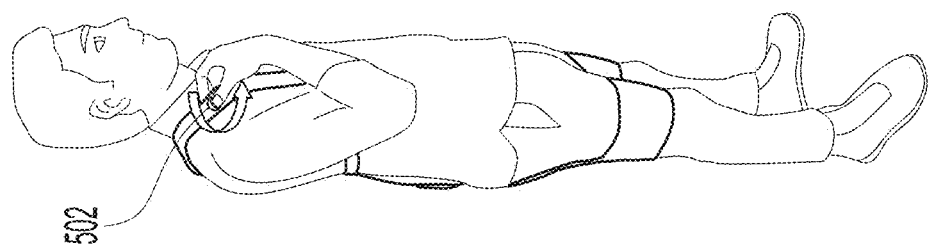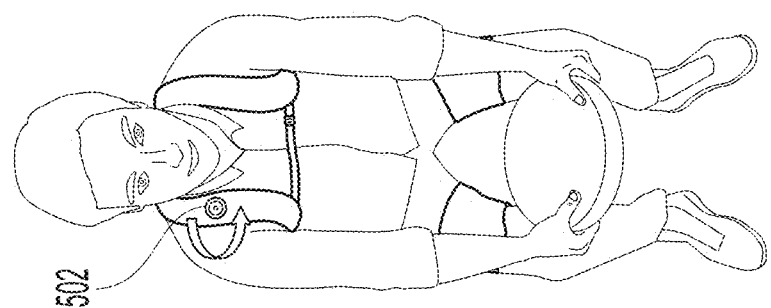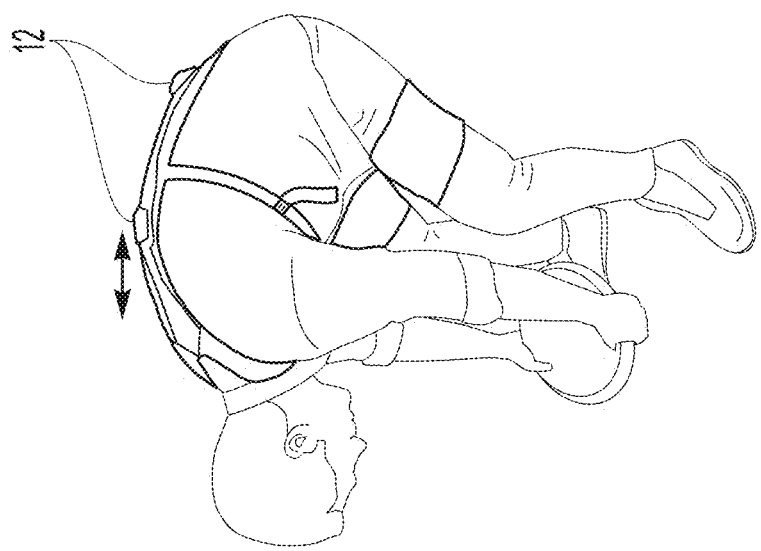
FIG. 15

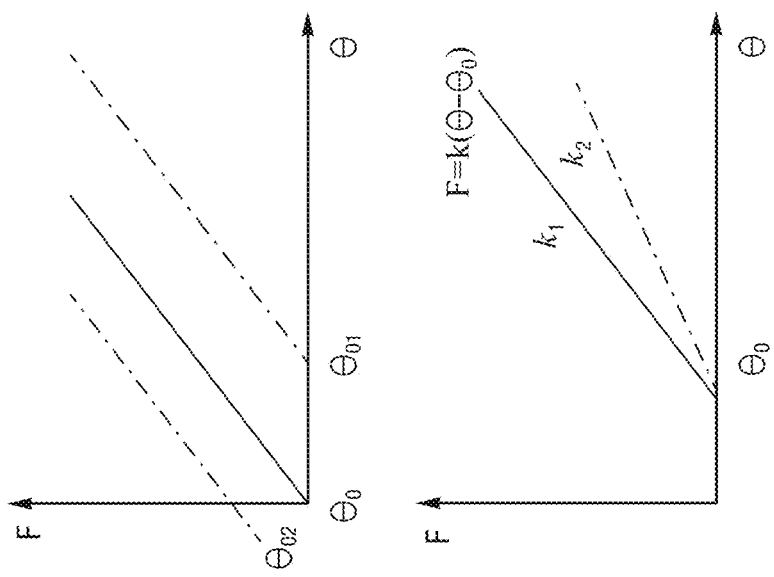
FIG. 19
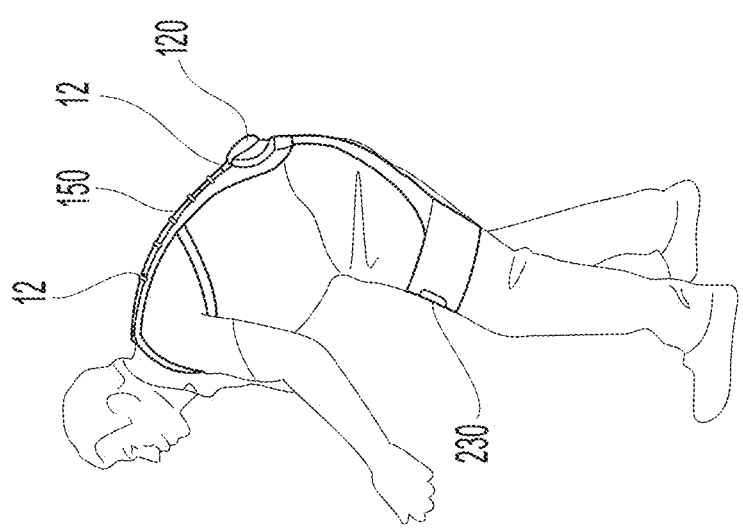
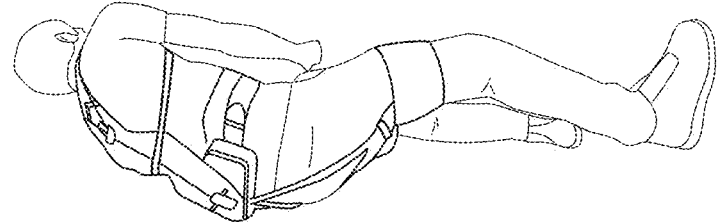
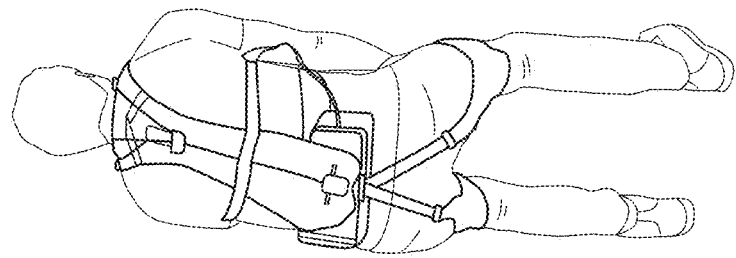
FIG. 18

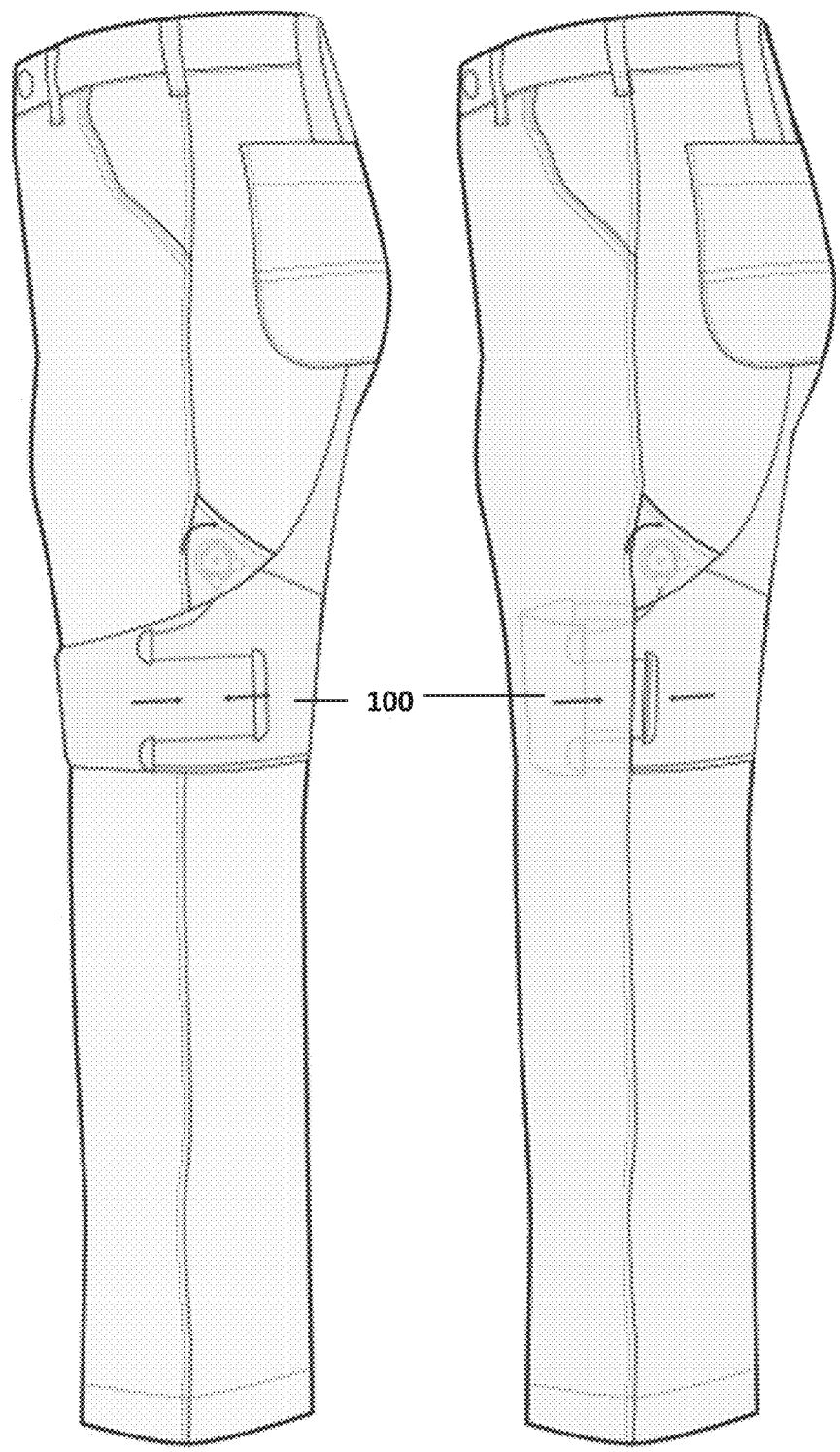
*FIG. 26A*     *FIG. 26B*

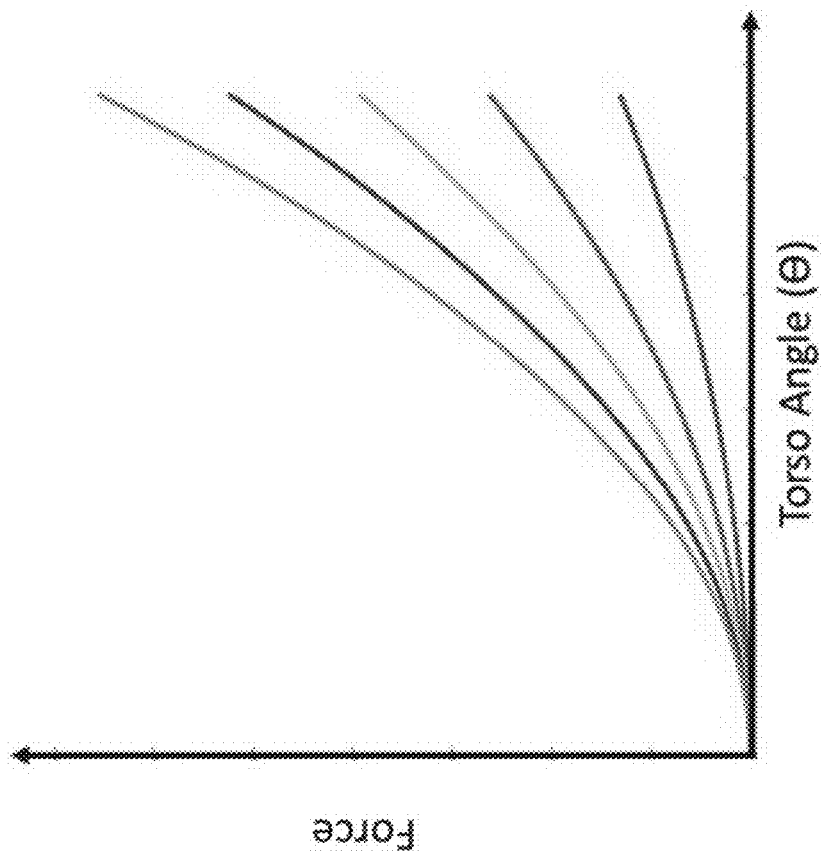
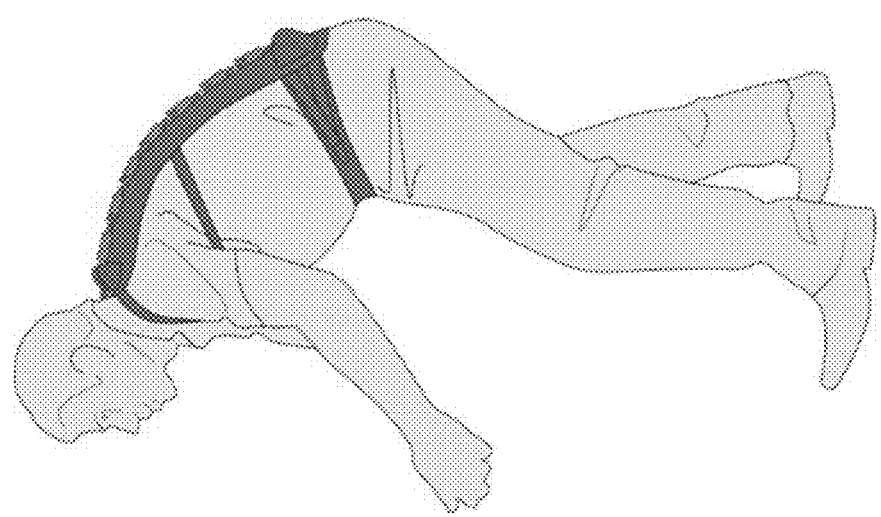
FIG. 31

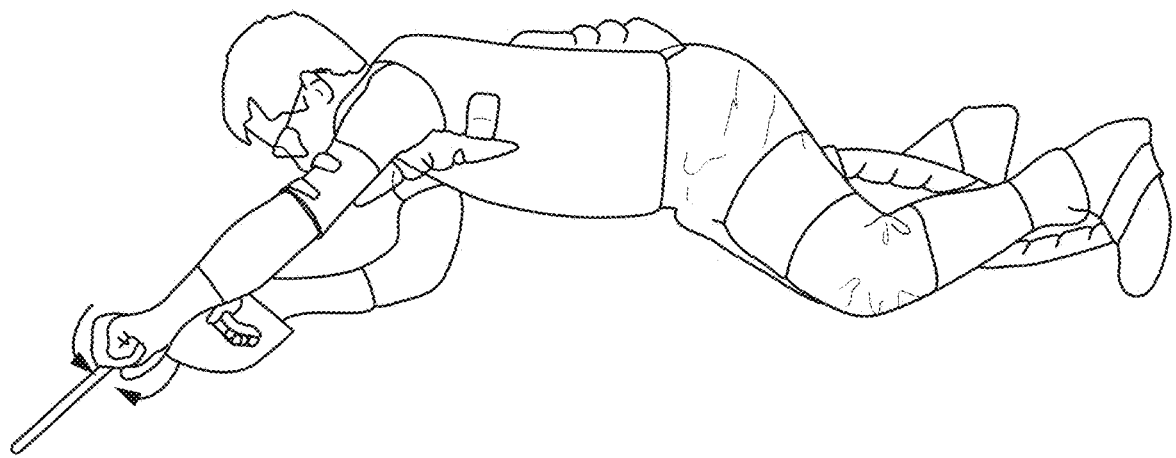
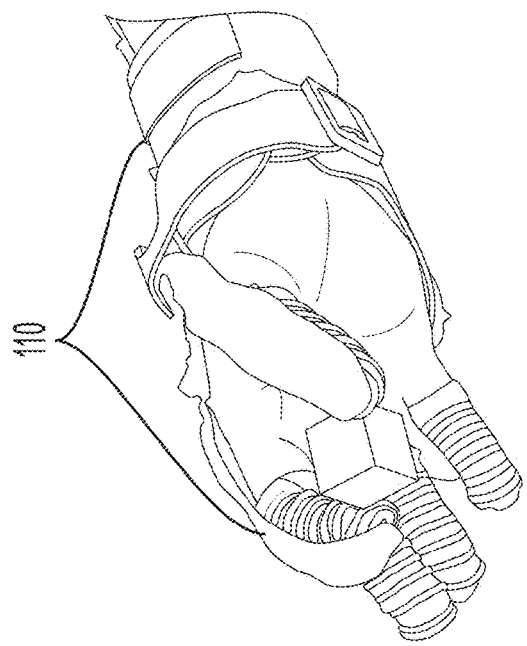
FIG. 32

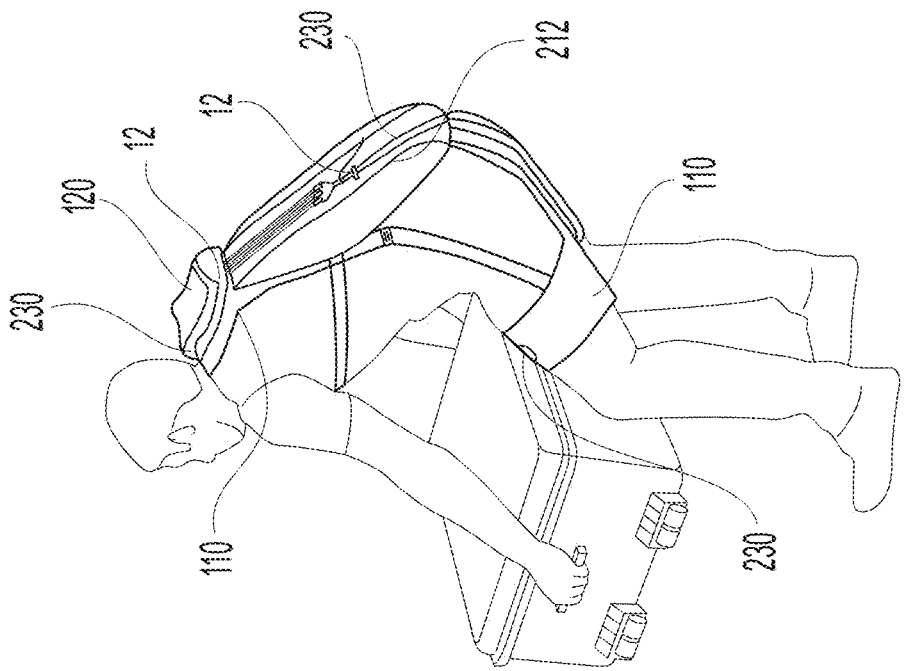
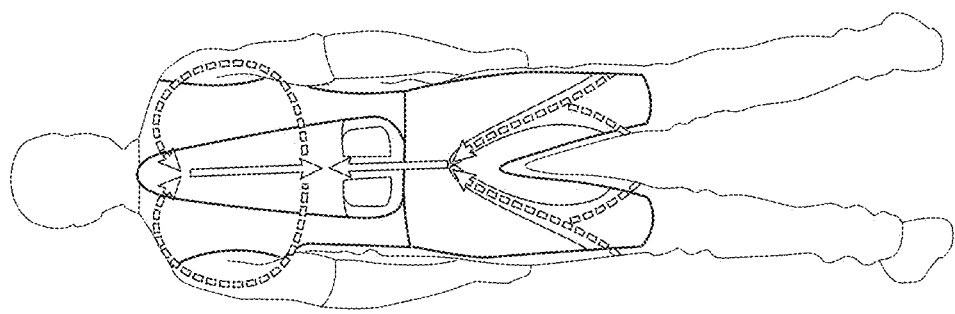
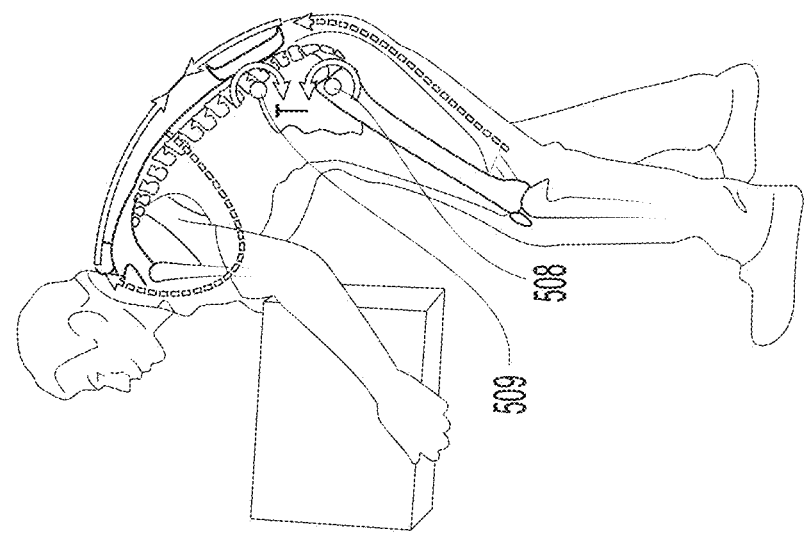
FIG. 37A
FIG. 37B

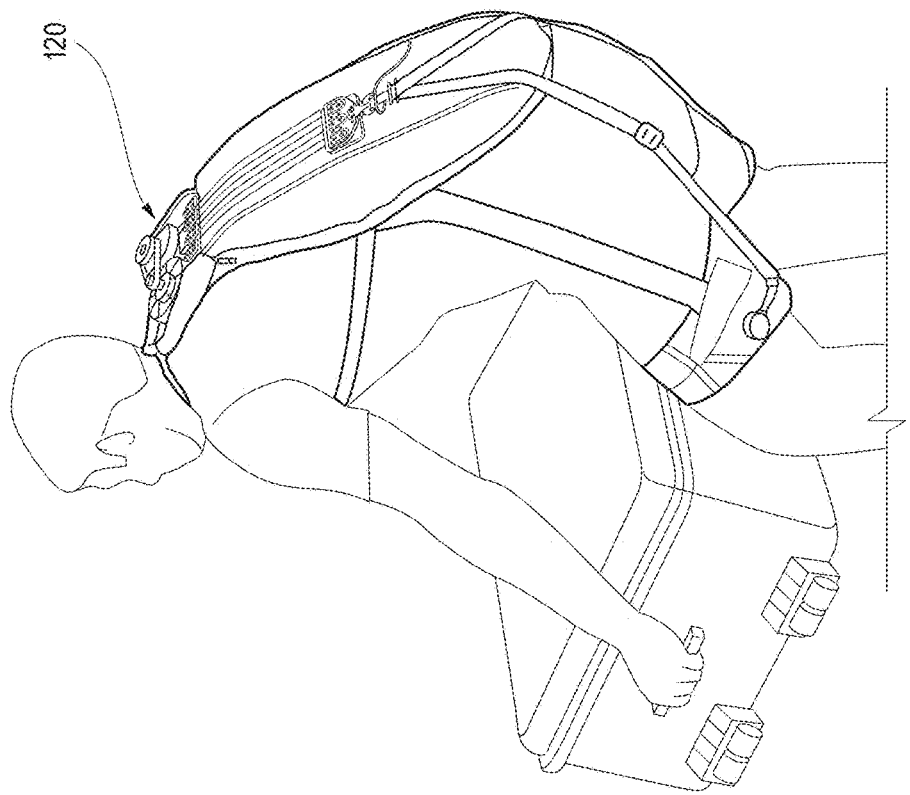
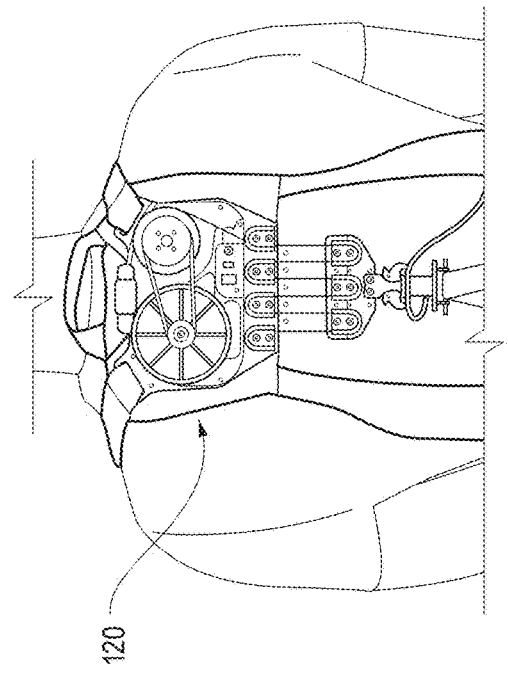
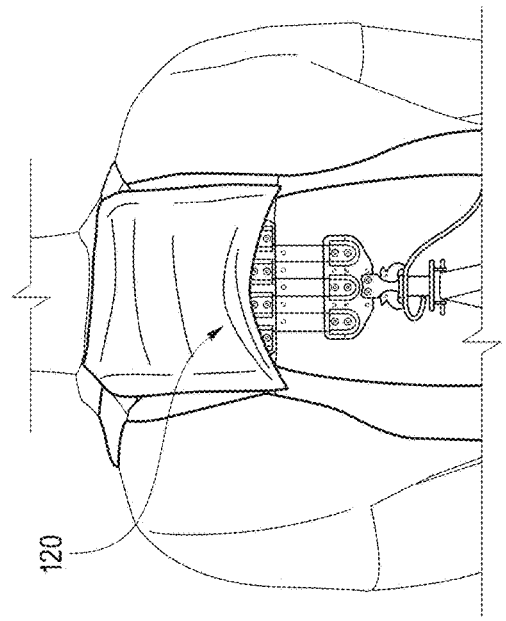
FIG. 43A
FIG. 43B
FIG. 43C

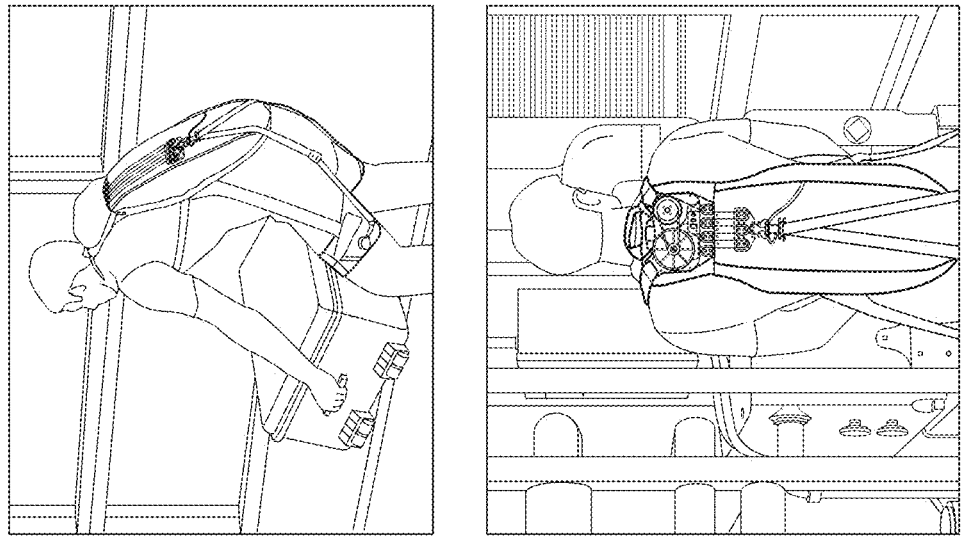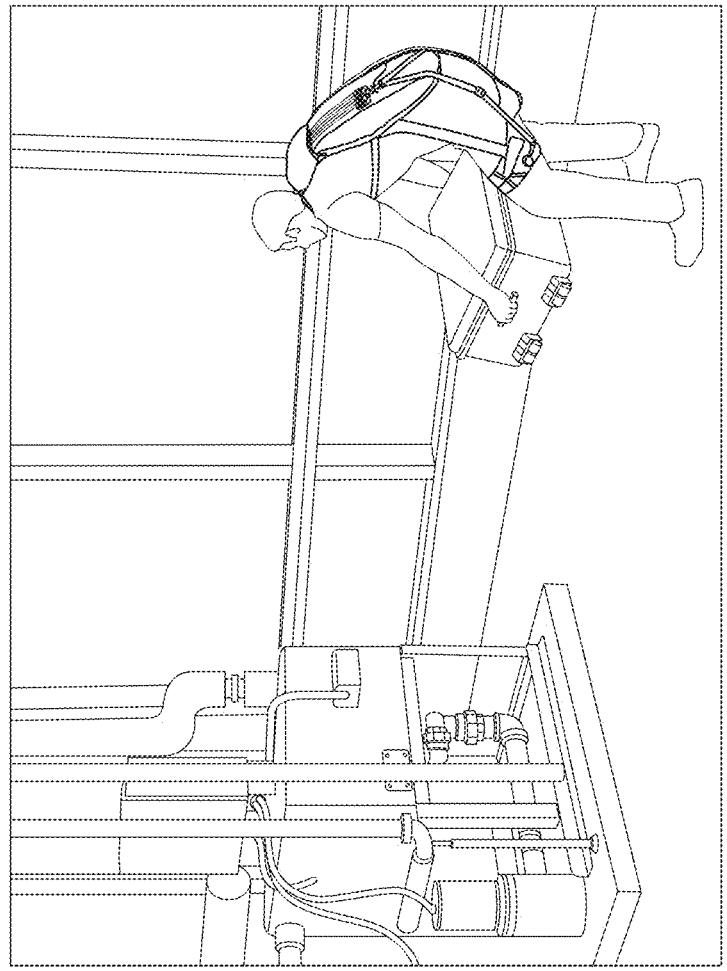
FIG. 44

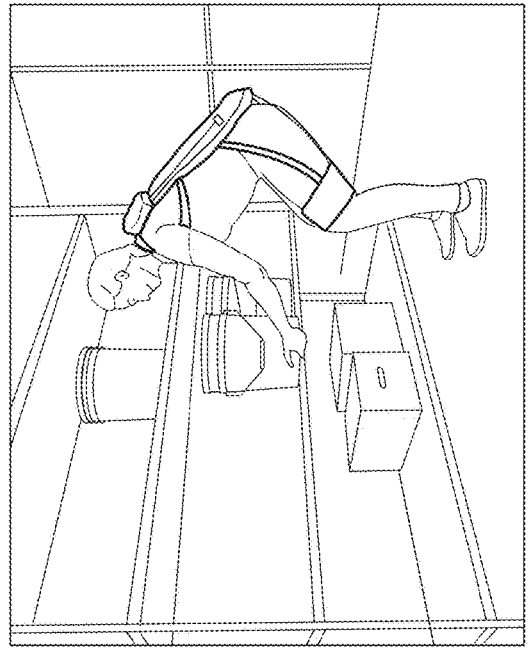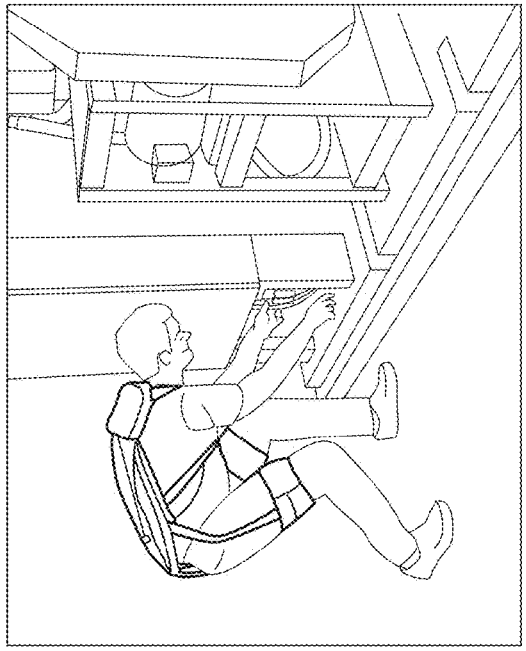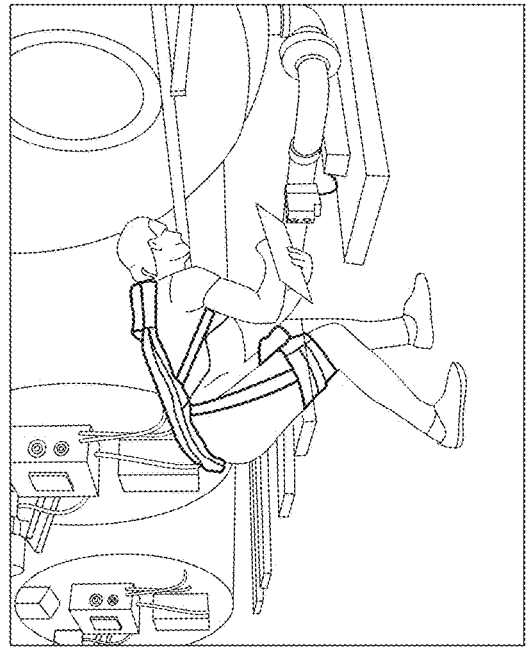
FIG. 45

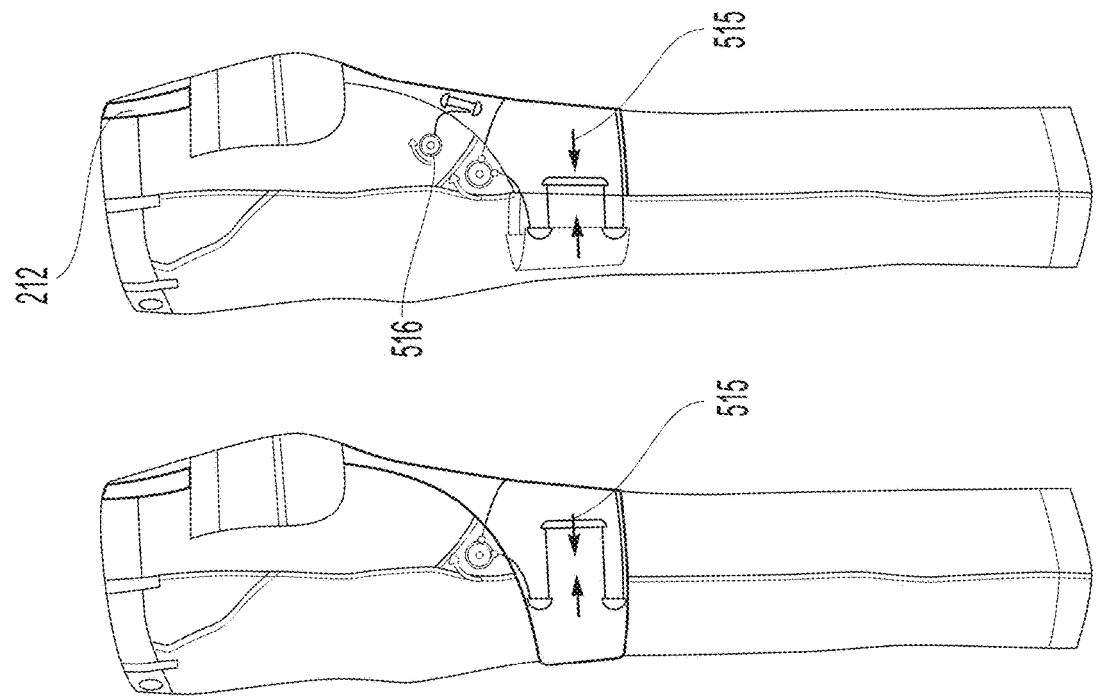
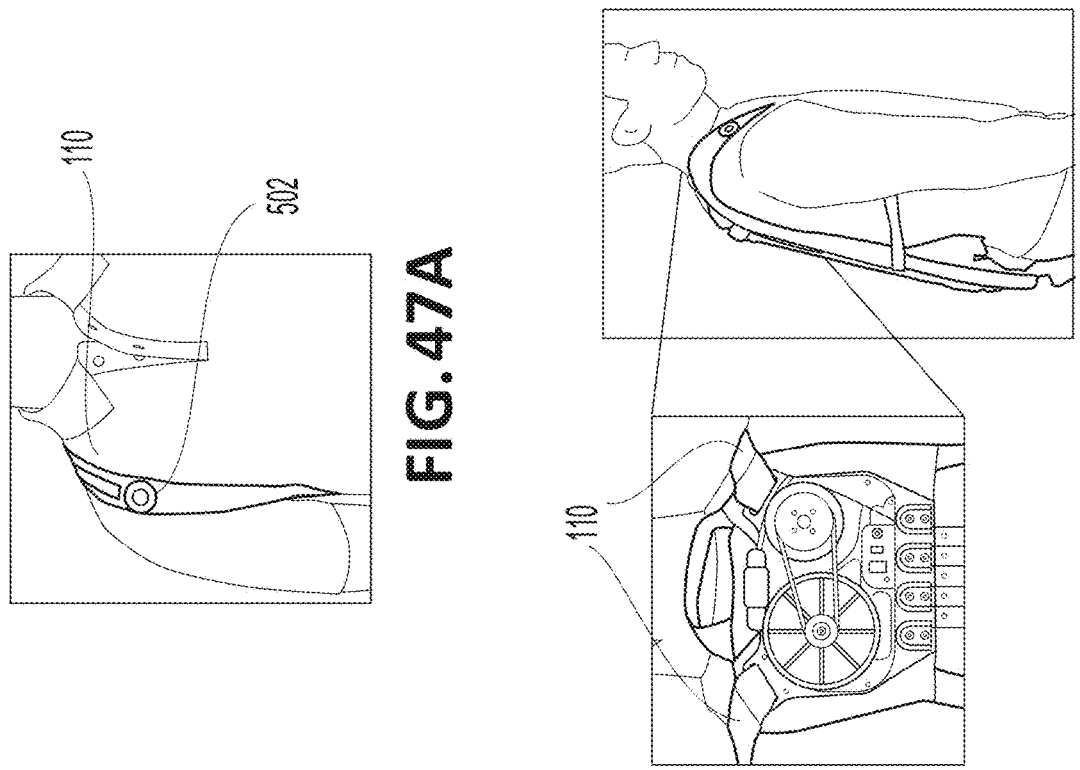
FIG. 47A  FIG. 47B  FIG. 47C  FIG. 47D

Assistance Strategy – programming of impedance curves

Assistance Strategy – States of lifting

Assistance Strategy – 3-D impedance state

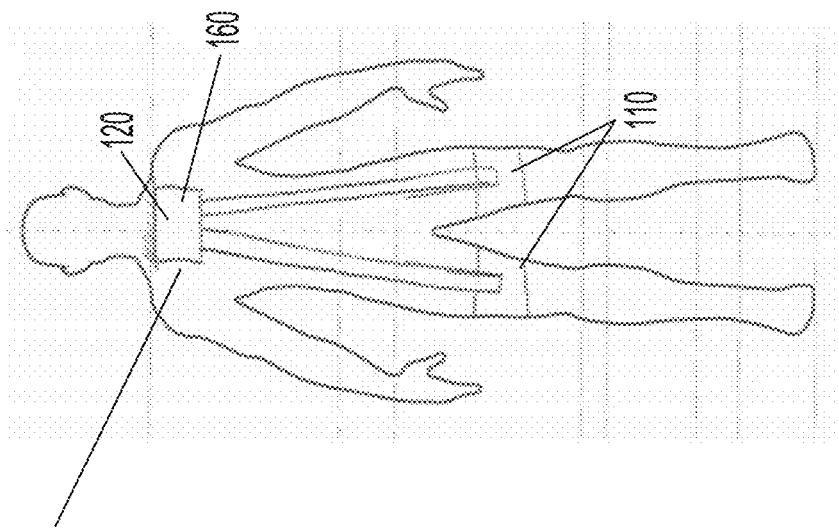
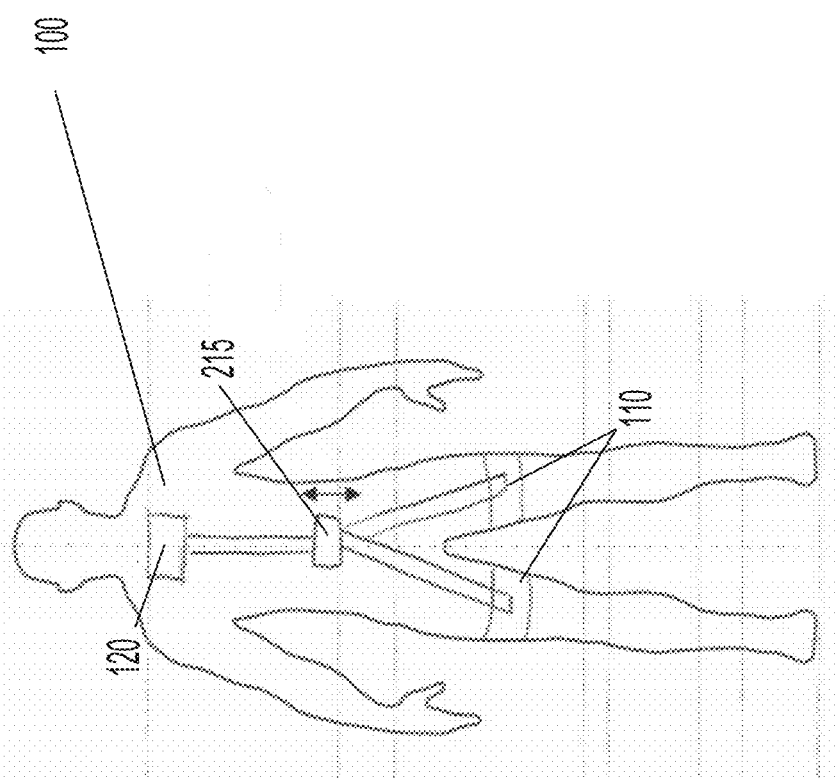
FIG. 68A
FIG. 68B

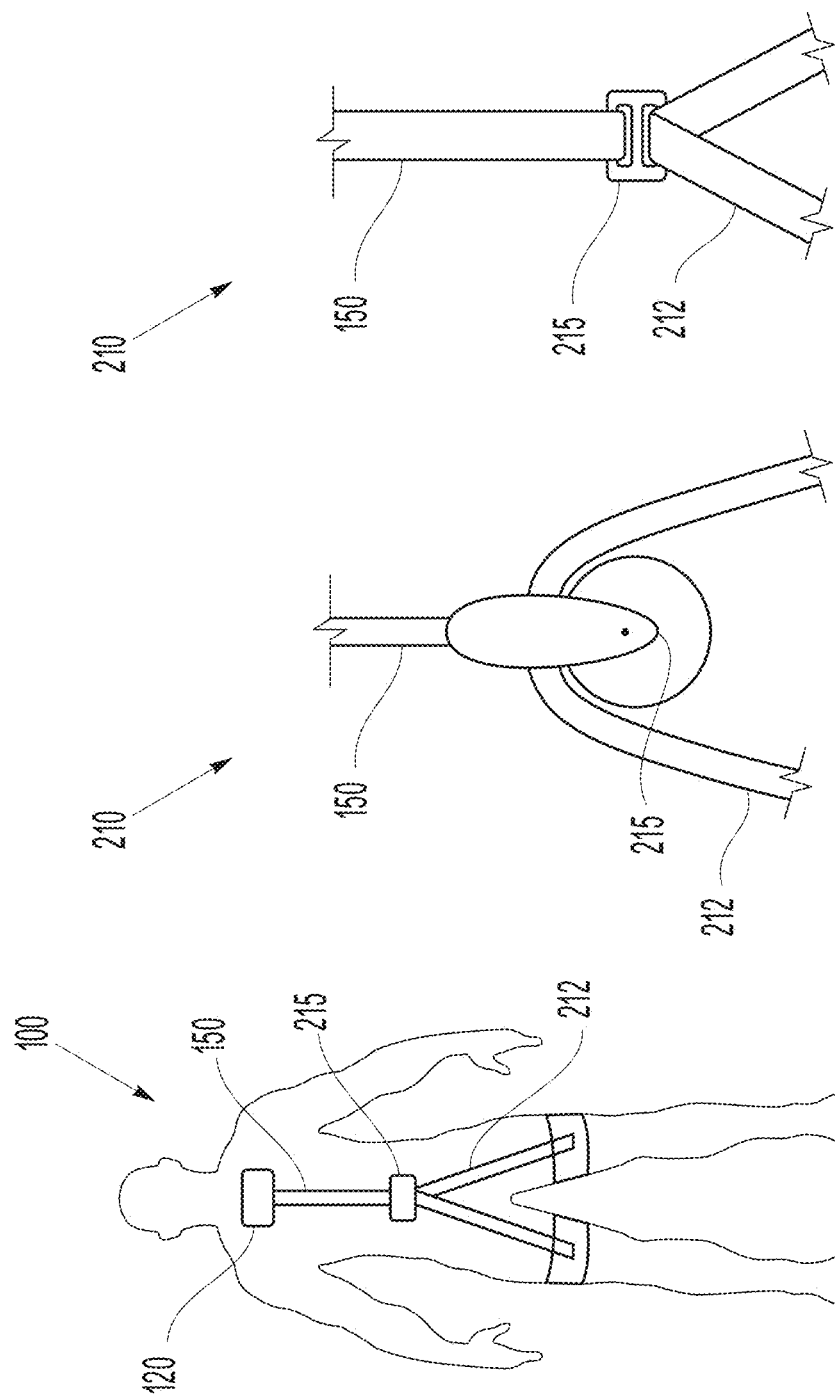

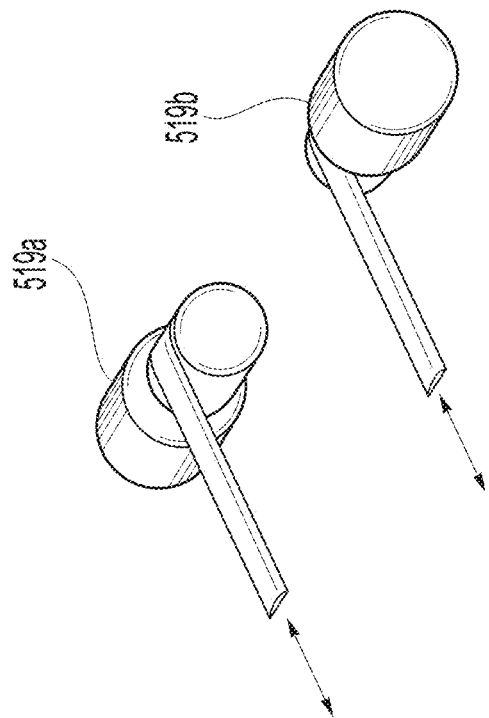
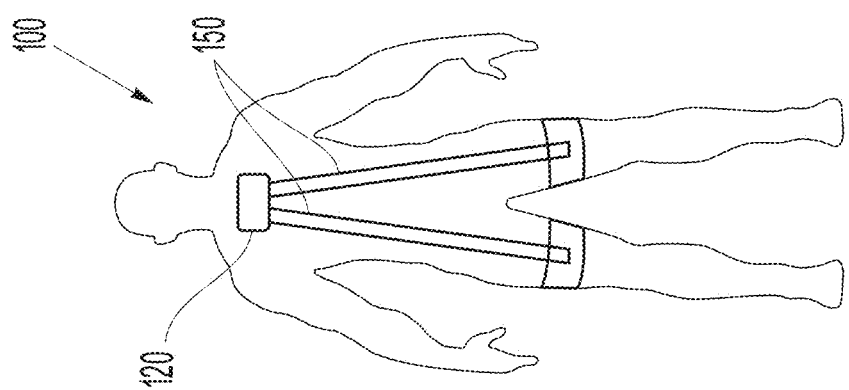
FIG. 70

WEARABLE DEVICES FOR PROTECTING AGAINST MUSCULOSKELETAL INJURIES AND ENHANCING PERFORMANCE

CROSS-REFERENCE TO RELATED APPLICATIONS

This application is a national stage filing under 35 U.S.C. § 371 of international application PCT/US2019/018258, filed Feb. 15, 2019, which claims the benefit of and priority to U.S. Provisional Patent Application No. 62/631,666, filed Feb. 17, 2018, and to U.S. Provisional Patent Application No. 62/757,138, filed Nov. 7, 2018, the entirety of all these applications are hereby incorporated by reference.

BACKGROUND

As part of their daily activities, individuals perform physically strenuous tasks can be fatiguing and increase the risk for musculoskeletal injuries. For example, workers in the manufacturing, construction, warehouse, and logistics industries routinely perform physically demanding activities such as repetitive lifting, lifting heavy loads, transporting equipment and materials over long distances, and holding various postures for long periods. These activities can lead to recurrent and disabling episodes that reduce work function and quality of life. In the US, overexertion accounts for the majority of all nonfatal industrial injuries, resulting in more than $13B spent annually on direct costs by US companies. Thus, there is a pressing economic and public health need for solutions that can keep our workforce safe and productive.

As another example, reduced strength in the older adult population may limit and reduce their ability to perform activities of the daily living. Activities such as sit-to-stand motions, shopping, gardening, etc. may be challenging to perform and often lead to fatigue and musculoskeletal injuries.

Individuals may need to perform tasks that are of higher intensity or effort compared to what they are used or trained for which could lead to injuries, pain or discomfort (e.g. installing furniture or appliances at home, moving to a new place, shopping and transporting heavy equipment).

Accordingly, wearable robot systems that reduce the physical burden, mitigate the risk of injury and/or improve performance of the wearer will have a broad impact including industrial, consumer, elderly and medical applications. Soft wearable robots may be used as part of personal protective equipment or integrated into everyday clothing to not only mitigate injury risk during physically demanding activities, but also become fully transparent during other activities to not restrict or limit performance in other ways.

SUMMARY

Wearable devices for protecting against musculoskeletal injuries and enhancing performance are disclosed. Systems and methods provide wearable devices to assist with human motion during physical activities, such as performing movements (e.g., lifting) and holding static poses (e.g., crouching, or holding a tool while working overhead).

The present disclosure is directed to a wearable device comprising of a first anchor member configured for positioning on a first body part of a person wearing the wearable device; a second anchor member configured for positioning on a second body part of a person wearing the wearable device; and at least one actuator directly or indirectly coupling the first anchor member to second anchor member, wherein actuation of the at least one actuator generates a tensile force in the wearable device for generating a moment about one or more joints of the wearer. In an embodiment the first body part comprises an upper body of the wearer and the second body part comprises a lower body of the wearer; and wherein the one or more joints of the wearer comprise at least one of: (i) one or more hip joints, and (ii) one or more back joints. And wherein the first body part comprises at least one shoulder of the wearer, the second body part comprises at least one thigh of the wearer, and wherein the one or more joints of the wearer comprise at least one of: (i) one or more hip joints, and (ii) one or more back joints. In an embodiment the first body part comprises a torso of the wearer, the second body part comprises an upper arm of the wearer, and wherein the one or more joints of the wearer comprise at least a shoulder joint. In various embodiments the first body part comprises an upper leg of the wearer, the second body part comprises a lower leg of the wearer, and wherein the one or more joints of the wearer comprise at least a knee joint. In an embodiment the first body part comprises a waist of the wearer, the second body part comprises an upper body of the wearer, the one or more joints of the wearer comprise at least one or more back joints, and further comprising a semi-rigid component extending between the first anchor member and the second anchor member, wherein the semi-rigid component is flexible to bending but resistant to deformation under compression forces.

In various embodiments the first body part comprises an upper body of the wearer, and the second body part comprises a first leg of the wearer, further comprising a third anchor member configured for positioning on a second leg of the wearer, wherein actuation of the at least one actuator generates a tensile force in the wearable device for generating a moment about at least one of: (i) a hip joint of the first leg and a hip joint of the second leg of the wearer, and (ii) one or more back joints of the wearer; and further comprising a load balancing connector coupling the actuator to the second anchor member and the third anchor member, the load balancing connector comprising a flexible elongate member having a first end coupled to the second anchor member and a second end connected to the third anchor member, and a mechanism coupling the actuator to an intermediate portion of the flexible elongate member between the first end and the second end, and configured to allow the flexible elongate member to translate within the mechanism and thereby balance the tensile force distributed to the first leg and the second leg of the wearer. In an embodiment wherein the first body part comprises an upper body of the wearer; wherein the second body part comprises a first leg of the wearer; further comprising a third anchor member configured for positioning on a second leg of the wearer, wherein actuation of the at least one actuator generates a tensile force in the wearable device for generating a moment about at least one of: (i) a hip joint of the first leg and a hip joint of the second leg of the wearer, and (ii) one or more back joints of the wearer; and further comprising a decoupling mechanism integrated into the actuator, the decoupling mechanism comprising a gear engaging an output of a motor of the actuator and configured to rotate when the motor is activated; a first rotating member situated coaxial with and extending from a first side of the gear; and a second rotating member situated coaxial with and extending from a second side of the gear, wherein the first rotating member and the second rotating member are configured to rotate independently of one another to distribute torque generated by the motor evenly between the second anchor member and the third anchor member and thereby balance the tensile force distributed to the first leg and the second leg of the wearer. In an embodiment wherein the first body part comprises an upper body of the wearer and wherein the second body part comprises a first leg of the wearer; wherein actuation of the at least one actuator directly or indirectly coupling the first anchor member and the second anchor member generates a tensile force in the wearable device for generating a moment about at least one of: (i) a hip joint of the first leg of the wearer, and (ii) a back joint of the wearer; and further comprising a third anchor member configured for positioning on a second leg of the wearer; and at least one actuator directly or indirectly coupling the first anchor member to the third anchor member, wherein actuation of the at least one actuator directly or indirectly coupling the first anchor member and the third anchor member generates a tensile force in the wearable device for generating a moment about at least one of: (i) a hip joint of the second leg of the wearer, and (ii) a back joint of the wearer. In an embodiment the first body part comprises a waist of the wearer, the second body part comprises a first leg of the wearer, and further comprising a third anchor member configured for positioning on a second leg of the wearer, wherein the at least one actuator directly or indirectly couples the first anchor member to the third anchor member, and wherein actuation of the at least one actuator generates a tensile force in the wearable device for generating a moment about a hip joint of the first leg of the wearer and about a hip joint of the second leg of the wearer. In an embodiment the first body part comprises a waist of the wearer, the second body part comprises a first leg of the wearer, and further comprising a third anchor member configured for positioning on a second leg of the wearer, wherein the at least one actuator directly or indirectly couples the first anchor member to the third anchor member, and wherein actuation of the at least one actuator generates a tensile force in the wearable device for generating a moment about a hip joint of the first leg of the wearer and about a hip joint of the second leg of the wearer.

In various embodiments wherein the actuator is releasably coupled to the first anchor member and the second anchor member such that the actuator can be selectably attached to and detached from the wearable device. In an embodiment further comprising a mounting plate coupled to at least one of the first anchor member and the second anchor member, to which the actuator releasably couples. And wherein the mounting plate includes one or more electrical connectors for placing one or more electrical components of the actuator in electrical communication with one or more electrical components associated with at least one of the first anchor member and the second anchor member.

In an embodiment wherein the at least one actuator comprises a first planar member coupled to the first anchor member, a second planar member coupled to the second anchor member, a plurality of guides arranged on the first planar member and the second planar member, and a flexible elongate element passing over opposing guides on the first planar member and the second planar member in an alternating fashion to couple the first planar member and the second planar member, wherein a first end of the flexible elongate element is anchored to the first planar member and a second end of the flexible elongate element is coupled to a motor, and wherein actuating the motor pulls the second end of the flexible elongate element, thereby pulling the first anchor member and the second anchor member toward one another.

In an embodiment wherein the at least one actuator comprises a plurality of guides arranged on the first anchor member and the second anchor member, and a flexible elongate element passing over opposing guides on the first anchor member and the second anchor member in an alternating fashion to couple the first anchor member and the second anchor member, wherein a first end of the flexible elongate element is anchored to the first anchor member and a second end of the flexible elongate element is coupled to a motor, and wherein actuating the motor pulls the second end of the flexible elongate element, thereby pulling the first anchor member and the second anchor member toward one another.

In an embodiment wherein the at least one actuator comprises a motor, a first rotating pulley element connected to an output of the motor, a second rotating pulley element situated coplanar with and radially offset from the first rotating pulley element, and coupled to the first rotating pulley element via a timing belt, a third rotating pulley element situated coaxial with and axially offset from the first rotating pulley, and fixedly coupled to the first rotating pulley, and a flexible elongate element wound about the third rotating pulley, wherein an end or an intermediate portion of the flexible elongate element is coupled to the second anchor member, wherein actuating the motor causes the flexible elongate member to shorten, thereby pulling the first anchor member and the second anchor member toward one another.

In another aspect, the present disclosure is directed to a wearable device, comprising of a first anchor member configured for positioning on a first body part of a person wearing the wearable device, a second anchor member configured for positioning on a second body part of a person wearing the wearable device, and at least one connecting element directly or indirectly coupling the first anchor member to the second anchor member; and at least one mechanism configured to selectably lock a length, change a length, or change an impedance of the at least one connecting element to control a level of tension generated in the wearable device by movement or a pose of the wearer, such that the wearable device generates a moment about one or more joints of the wearer. In an embodiment wherein the first body part comprises an upper body of the wearer, wherein the second body part comprises a lower body of the wearer, and wherein the one or more joints of the wearer comprise at least one of: (i) one or more hip joints, and (ii) one or more back joints. In an embodiment the first body part comprises a torso of the wearer, the second body part comprises an upper arm of the wearer, and one or more joints of the wearer comprise at least a shoulder joint. In various embodiments the first body part comprises an upper leg of the wearer, the second body part comprises a lower leg of the wearer, and the one or more joints of the wearer comprise at least a knee joint. In an embodiment wherein the first body part comprises a waist of the wearer, the second body part comprises an upper body of the wearer, the one or more joints of the wearer comprise at least one or more back joints, and further comprising a semi-rigid component extending between the first anchor member and the second anchor member, wherein the semi-rigid component is flexible to bending but resistant to deformation under compression forces.

In another aspect, the present disclosure is directed to a wearable device, comprising of a first anchor member configured for positioning on a first body part of a person wearing the wearable device, a second anchor member configured for positioning on a second body part of a person wearing the wearable device, and at least one connecting element directly or indirectly coupling first anchor member to the second anchor member, and configured to absorb energy generated by movement or a pose of the wearer; and at least one mechanism configured to selectably lock the at least one connecting element to store the absorbed energy, and unlock the at least one connecting element to release the absorbed energy such that the wearable device generates a moment about one or more joints of the wearer. In an embodiment wherein the first body part comprises an upper body of the wearer, the second body part comprises a lower body of the wearer, and wherein the one or more joints of the wearer comprise at least one of: (i) one or more hip joints, and (ii) one or more back joint. In an embodiment wherein the first body part comprises a torso of the wearer, the second body part comprises an upper arm of the wearer, and wherein the one or more joints of the wearer comprise at least a shoulder joint. In an embodiment the first body part comprises an upper leg of the wearer, the second body part comprises a lower leg of the wearer, and wherein the one or more joints of the wearer comprise at least a knee joint. In an embodiment wherein the first body part comprises a waist of the wearer, the second body part comprises an upper body of the wearer, the one or more joints of the wearer comprise at least one or more back joints, and further comprising a semi-rigid component extending between the first anchor member and the second anchor member, wherein the semi-rigid component is flexible to bending but resistant to deformation under compression forces.

In another aspect, the present disclosure is directed to a wearable device, comprising of a first anchor member configured for positioning on a first body part of a person wearing the wearable device, a second anchor member configured for positioning on a second body part of a person wearing the wearable device, and at least one passive element directly or indirectly coupling the first anchor member to the second anchor member such that movement or a pose of the wearer generates tension in the wearable device and the wearable device provides a moment about one or more joints of the wearer. In an embodiment the first body part comprises an upper body of the wearer, the second body part comprises a lower body of the wearer, and wherein the one or more joints of the wearer comprise at least one of: (i) one or more hip joints, and (ii) one or more back joints. In various embodiments wherein the first body part comprises a torso of the wearer, wherein the second body part comprises an upper arm of the wearer, and wherein the one or more joints of the wearer comprise at least a shoulder joint. In an embodiment the first body part comprises an upper leg of the wearer, the second body part comprises a lower leg of the wearer, and the one or more joints of the wearer comprise at least a knee joint. In an embodiment wherein the first body part comprises a waist of the wearer, wherein the second body part comprises an upper body of the wearer, wherein the one or more joints of the wearer comprise at least one or more back joints, and further comprising a semi-rigid component extending between the first anchor member and the second anchor member, wherein the semi-rigid component is flexible to bending but resistant to deformation under compression forces.

In another aspect, the present disclosure is directed to a wearable device, comprising of at least one actuator configured to generate a force in the wearable device or to cause a force to be generated in the wearable device, such that the wearable device generates a moment about one or more joints of the wearer to assist the wearer in performing a non-cyclic movement or to hold a pose, at least one sensor configured to measure information for evaluating an objective function associated with at least one of providing physical assistance to the wearer, an interaction between the wearer and the wearable device, and an operation of the wearable device, and at least one controller configured to actuate the at least one actuator according to at least one actuation profile, evaluate the objective function based on the information measured by the at least one sensor to determine a resulting change in the objective function, adjust at least one parameter of the at least one actuation profile based on the resulting change in the objective function, and continue to actuate, evaluate, and adjust to optimize the at least one actuation parameter for maximizing or minimizing the objective function. In an embodiment wherein the at least one controller is configured to identify two or more actuation parameters to be optimized for maximizing or minimizing the objective function, actuate the at least one actuator according to two or more actuation profiles having different sets of baseline values of the two or more actuation parameters to be optimized, evaluate the objective function for each of the two or more actuation profiles based on the information measured by the at least one sensor, define, based on corresponding evaluations of the objective function, a mathematical correlation between the two or more actuation parameters and the corresponding evaluations of the objective function, evaluate the baseline mathematical correlation to determine a candidate set of values of the two or more actuation parameters for maximizing or minimizing the objective function, update the mathematical correlation based on a corresponding evaluation of the objective function for an actuation of the at least one actuator according to an actuation profile associated with the candidate set of values of the two or more actuation parameters, and continue to update the mathematical correlation until an evaluation of the objective function reaches a global maximum or a global minimum value, or when a termination criteria is met.

In another aspect, the present disclosure is directed to A wearable device, comprising of a first anchor member configured for positioning on a first body part of a person wearing the wearable device, a second anchor member configured for positioning on a second body part of a person wearing the wearable device, and at least one connecting element directly or indirectly coupling the first anchor member to the second anchor member; at least one sensor configured to measure information relating to one or more of an angle, a velocity, and an acceleration of one or more joints of the wearer spanned by the wearable device; and at least one controller configured to detect the start and/or type of a movement or a pose of the wearer to be assisted by the wearable device; determine the desired tensile force to be generated in the wearable device as a function of the given angle, velocity, or acceleration of the one or more joints spanned by the wearable device for assisting the wearer in performing the movement or in holding the pose; and adjust an impedance of or a force provided by the wearable device such that the desired tensile force is generated in the wearable device at the given angle, velocity, or acceleration of the one or more joints. In various embodiments wherein the wearable device comprises at least one mechanism configured to selectably lock a length, change a length, or change an impedance of the at least one connecting element, and wherein adjusting the impedance of the wearable device includes locking the length of the at least one connecting element at a length configured to cause the desired tensile force to be generated in the wearable device by movement or a pose of the wearer at the given angle, velocity, or acceleration of the one or more joints. In an embodiment wherein the wearable device comprises at least two connecting elements, wherein the wearable device comprises at least one mechanism configured to selectably engage one or more of the at least two connecting elements; wherein adjusting an impedance of the wearable device includes engaging one or more of the at least two connecting elements having, either alone or in combination, a spring constant or a damping constant configured to cause the desired tensile force to be generated in the wearable device by movement or a pose of the wearer at the given angle, velocity, or acceleration of the one or more joints. In an embodiment wherein the wearable device comprises at least one actuator, and wherein adjusting an impedance of the wearable device includes actively actuating the at least one connecting element to generate the desired tensile force in the wearable device at the given angle, velocity, or acceleration of the one or more joints. In an embodiment wherein the controller is configured to monitor the information relating to one or more of the angle, a velocity, and an acceleration of the one or more joints to detect when one or a combination of the angle, velocity, or acceleration exceeds a threshold indicative of the start of a motion or pose to be assisted. In an embodiment wherein the controller is configured to monitor the information relating to one or more of the angle, a velocity, and an acceleration of the one or more joints to detect when one or a combination of the angle, velocity, or acceleration exceeds a threshold indicative of the end of a motion or pose to be assisted. In an embodiment wherein the motion or pose to be assisted is a lifting motion or a crouching pose, wherein the controller determines a relative angle of one or more of a torso, a thigh joint, and a hip joint of the wearer, and wherein the controller monitors the relative angle to detect when the relative angle exceeds a threshold indicative of the start of the lifting motion or crouching pose to be assisted. In an embodiment wherein the motion or pose to be assisted is a lifting motion or a crouching pose, wherein the controller determines an average angle of the hip joints of the wearer, and wherein the controller monitors the average angle of the hip joints of the wearer to detect when the average angle of the hip joints exceeds a threshold indicative of the start of the lifting motion or crouching pose to be assisted. In an embodiment wherein the controller determines the average angle of the hip joints of the wearer by calculating a relative angle between: (i) a torso of the wearer, and (ii) an average angle of the thighs of the wearer. In an embodiment wherein the controller is configured to identify whether the wearer is engaged in activities other than the lifting motion or the crouching motion to be assisted and, if so, determine that any exceedance of the threshold is not indicative of the start of the lifting motion or the crouching pose to be assisted. In an embodiment wherein the controller identifies whether the wearer is engaged in activities other than the lifting motion or the crouching motion to be assisted by determining a difference between an angle of one of the hip joints and an angle of the other hip joint, applying a penalty term to the difference, subtracting the penalized difference from the average angle of the hip joints, and evaluating whether the resulting determination of the average angle of the hip joints exceeds the threshold. In an embodiment wherein the motion or pose to be assisted is a lifting motion or a crouching pose, wherein the controller determines an average angle of the hip joints of the wearer, and wherein the controller monitors the average angle of the hip joints of the wearer to detect when the average angle of the hip joints exceeds a threshold indicative of the end of the lifting motion or crouching pose to be assisted. In an embodiment wherein the controller is configured to monitor the information relating to one or more of the angle, a velocity, and an acceleration of the one or more joints to detect one or more states of the motion to be assisted. In an embodiment wherein the motion to be assisted is a lifting motion, wherein the controller determines an average angle of the hip joints of the wearer, and wherein the controller monitors the average angle of the hip joints of the wearer to detect when the average angle of the hip joints exceeds a threshold indicative of the start or end of a stage of the lifting motion. In an embodiment wherein the threshold is indicative of an initial moving down state of the lifting motion, and wherein the threshold is an average angle of the hip joints increasing from a neutral angle of the hip joints. In an embodiment wherein the threshold is indicative of a hold state of the lifting motion, and wherein the threshold is an average angular velocity of the hips decreasing to about zero degrees per second. In an embodiment wherein, during the hold state, the controller monitors the average angle of the hip joints to detect a transition to a moving up state or a moving down state, wherein a change in the average angle of the hip joints to a lower angle is indicative of a transition to a moving up state, and wherein a change in the average angle of the hip joints to a higher angle is indicative of a transition to a moving down state. In an embodiment wherein the motion to be assisted is a lifting motion, wherein the controller is configured to classify the lifting motion as a stoop lifting motion, a squat lifting motion, or a bend and twist lifting motion based on the information relating to one or more of the angle, a velocity, and an acceleration of the one or more joints. In various embodiments wherein the controller is configured to adjust the impedance of the wearable device as a function of the state or type of the movement or pose being assisted. And wherein during a hold state, the controller is configured to progressively increase the tensile force to a target value in order to assist the wearer while holding the pose for a prolonged period of time. And wherein the controller is configured to receive input from the wearer for selecting a peak tensile force for assist different movements, and wherein the controller is configured to scale the impedance of or the force provided by the wearable device to have a maximum peak tensile force corresponding to the selected peak tensile force value. And wherein the controller is configured to receive input from the wearer for disabling the generation of the tensile force by the wearable device.

In another aspect, the present disclosure is directed to a wearable system for monitoring physical activity of a person, comprising at least one sensor configured to measure information relating to one or more of: an angle, a velocity, or an acceleration of one or more joints of the wearer spanned by the wearable system, a force or torque experienced by the wearer, and biometric parameters of the wearer; and at least one processor configured to analyze the information measured by the at least one sensor to evaluate one or more of a risk of injury, performance of a task, biomechanics, and ergonomics metrics associated with the wearer's physical activity while wearing the wearable system. In an embodiment wherein the at least one sensor includes one or a combination of an inertial measurement unit (IMU), a joint angle sensor, a force or pressure sensor, a torque sensor, a metabolic energy measurement device, a muscle activity measurement device (EMG), a ground reaction force sensor, a heart rate sensor, and an insole force or pressure sensor. In an embodiment wherein the processor is further configured to notify the wearer that he or she is performing motions that may lead to an injury. In an embodiment wherein the processor is further configured to determine and notify the wearer of a suitable recovery period for mitigating the possibility of injury before the wearer engages in further activity.

BRIEF DESCRIPTION OF THE DRAWINGS

FIG. 10 shows an embodiment of a robotic apparel in which the anchor members span multiple joints.

FIG. 15 and FIG. 16 show how by defining different initial lengths of the connecting elements, the output tensile forces can be modified and how different stiffness values of the connecting element will provide different outputs.

FIG. 18 presents a device that includes an actuator component that can be used to control a cable that is attached between both anchor members.

FIG. 19 presents how a sample virtual impedance rendered by the actuation may be defined by the stiffness value where F is the resulting force, theta is the relative angle between the thigh and the torso and K is the rendered stiffness.

FIG. 25A, FIG. 25B, FIG. 25C, FIG. 26A, and FIG. 26B show some sample embodiments of how the proposed device may be integrated into typical work clothing for daily use.

FIG. 29A shows the different activities that the device will optimize and assist with.

FIG. 31 shows an example of representative assistance profiles by changing the parameter k. A higher stiffness value can mean that the user is getting higher assistance on the back as a function of his/her torso angle during bending.

FIG. 32 is an example of an assistive device that can include one actuation unit in the back of each finger, that when pressurized can provide assistance to each finger.

FIG. 37A shows a diagram that illustrates how tensile forces can generate assistive torques across the back and hip joints.

FIG. 37B shows an implementation of a fully portable device that is able to assist the back and hip joints by following the architecture depicted in FIG. 37A.

FIG. 43A, FIG. 43B, and FIG. 43C show additional details of the actuator system located on the upper-torso of the user and its integration into apparel.

FIG. 44 and FIG. 45 show different users wearing the proposed system over clothing to perform different tasks that involve reaching or lifting loads.

FIG. 47A, FIG. 47B, FIG. 47C, and FIG. 47D show additional details of an embodiment that integrates robotic components into apparel.

FIG. 68A depicts an embodiment wherein the load balancing assembly may further include a hardware component that may slide up and down the torso to decouple the load-balancing strap movement from the connecting element (e.g., cable component).

FIG. 68B is another embodiment wherein one or more decoupling components may be integrated into the actuation system itself.

FIG. 69A, FIG. 69B, and FIG. 69C shows a concept in which the load balancing strap is decoupled from the cable component by using a component such as a low-friction, roller, bearing, pulley, etc.

FIG. 70 describes a different way of achieving the load balancing mechanism. In this case, two independent motors are used to actuate each strap/cable individually.

DETAILED DESCRIPTION

Wearable devices 100 for protecting against musculoskeletal injuries and enhancing performance are disclosed. Systems and methods provide wearable devices 100 to assist with human motion during physical activities, such as performing movements (e.g., lifting) and holding static poses (e.g., crouching, or holding a tool while working overhead). Materials, constructions, and system architectures allow the wearable devices 100 to be worn over, under, or integrated into clothing for extended periods of time to improve performance or reduce risk of injury. Sensors 230 may be included in the wearable devices 100 to detect various activities, motions, and postures of the wearer, and various active and semi-active controls approaches may leverage sensor information to provide tailored assistance to individual users. Various controls optimization techniques ensure the wearable devices 100 operate at peak efficiency.

Figure 1:
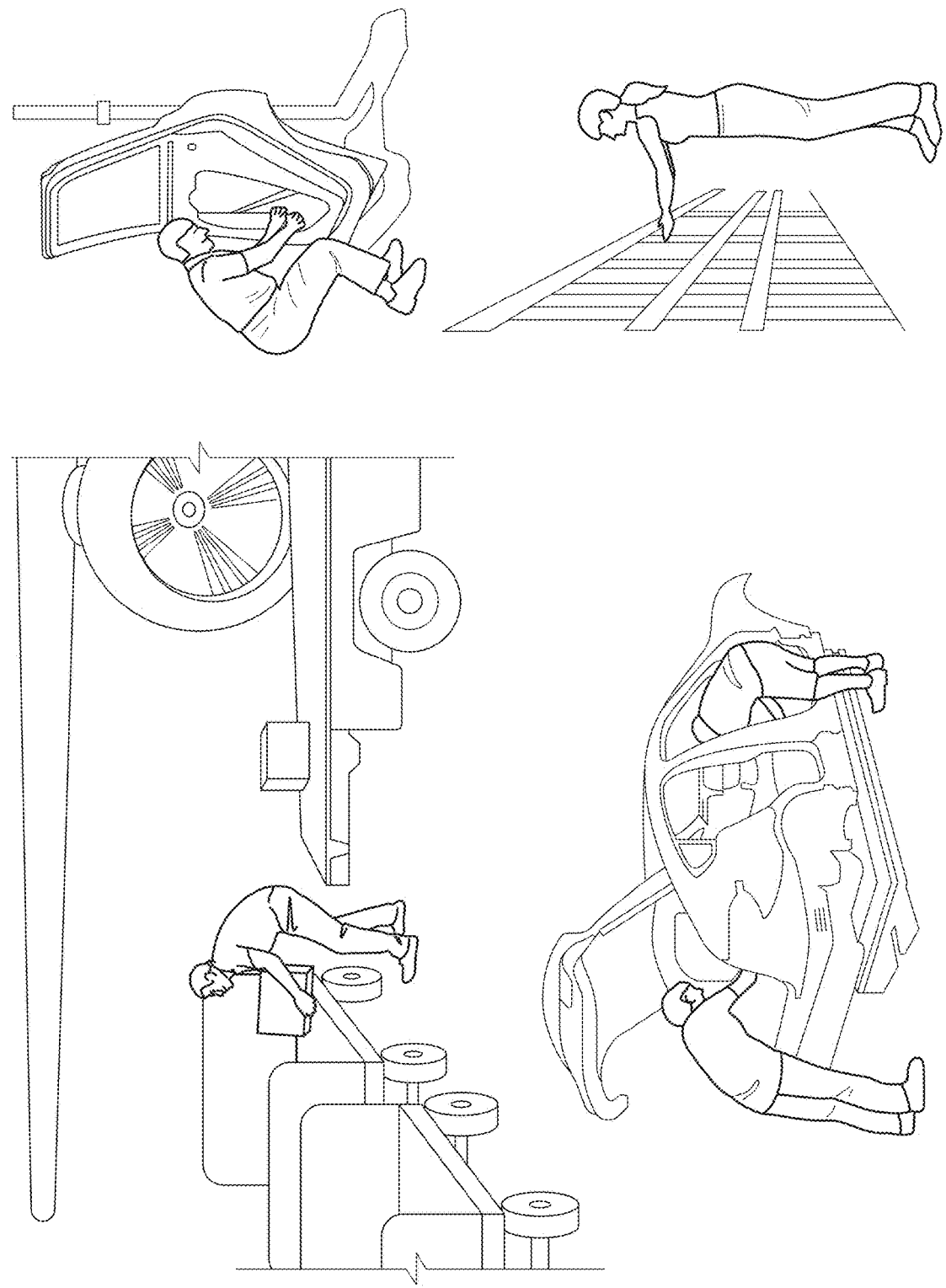
FIG. 1 shows different application areas in which users may benefit from wearing assistive devices to mitigate the risk of musculoskeletal injuries and enhance productivity.

A soft wearable device 100 that enhance and protects workers in different industries (e.g. construction workers, manufacturing, logistics, warehouses, baggage handlers, installers, caregivers, doctors, etc.) or as part of activities of the daily living (e.g. elderly, healthy individuals, medical patients.) will have a broad impact to reduce musculoskeletal injuries, improve productivity and/or performance. As an example, FIG. 1. shows different application areas in which users may benefit from wearing assistive devices to mitigate the risk of musculoskeletal injuries and enhance productivity.

Methods, systems and devices to assist users when performing physical activities or motions that could potentially lead to discomfort, pain, fatigue, injuries, etc. are disclosed. More particularly, the present disclosure is directed to wearable devices 100 (e.g., soft wearable exosuits, exoskeletons, wearable robotic devices, or robotic apparel) that can be worn over extended periods and includes the following elements or combinations of the following elements:

i) Wearable device architecture that is made out of anchor members 110 configured for positioning on various body parts of a person wearing the wearable device 100, and flexible connecting elements 150 (apparel, semi-rigid components, webbing, straps, cables, combinations thereof, etc.) directly or indirectly coupling the anchor members 110. In various embodiments, the connecting elements 150 can be actively actuated to actively generate tensile forces in the wearable device 100, semi-actively actuated to change a level of tension generated in the wearable device 100 by movement or a pose of the wearer, and/or may passively generate tensile forces in the wearable device 100 when the wearer based on movement or a pose of the wearer. As configured, the wearable device 100 delivers forces and/or moments to the body for assisting the wearer in performing various movements or in holding various poses.

ii) Wearable sensors 230 to measure or estimate human biomechanics, interaction between the system and the wearer, and interaction with the environment or objects. As an example, these sensors 230 may be integrated in the apparel components or be compatible with apparel components.

iii) Passive elements 190 may be integrated such that as the user moves a tension or torque is generated in a way that may be beneficial to the human body. Examples of this include elastics, springs, dampers.

iv) Actuation: one or more actuators 120 may be integrated as part of an active system to assist the user or to control the position, force or pretension of a system component. Additionally, in a semi-active system, one or more actuators 120 may be used to set pre-tension levels in the system or to set the initial position of an elastic element to tune when that element will start providing assistive forces passively with respect to the human motion.

The proposed systems can be worn to provide assistance to the wearer by providing tensile forces between anchor members 110 that are located on both sides of a joint (e.g. the hips, back, knee, shoulder, elbow), or that span multiple joints to simultaneously assist multiple joints, body parts or to transfer loads to different areas of the body. The connecting element 150 between those anchor members 110 may provide tensile forces in a way that would be assistive to the user.

Connecting Elements 150

Figure 2C:
FIG. 2A, FIG. 2B, and FIG. 2C show sample embodiments of a passive (FIG. 2A), active devices to assist the body including the back and hip joints (FIG. 2B), and a sensor-only system (FIG. 2C).
Figure 2B:
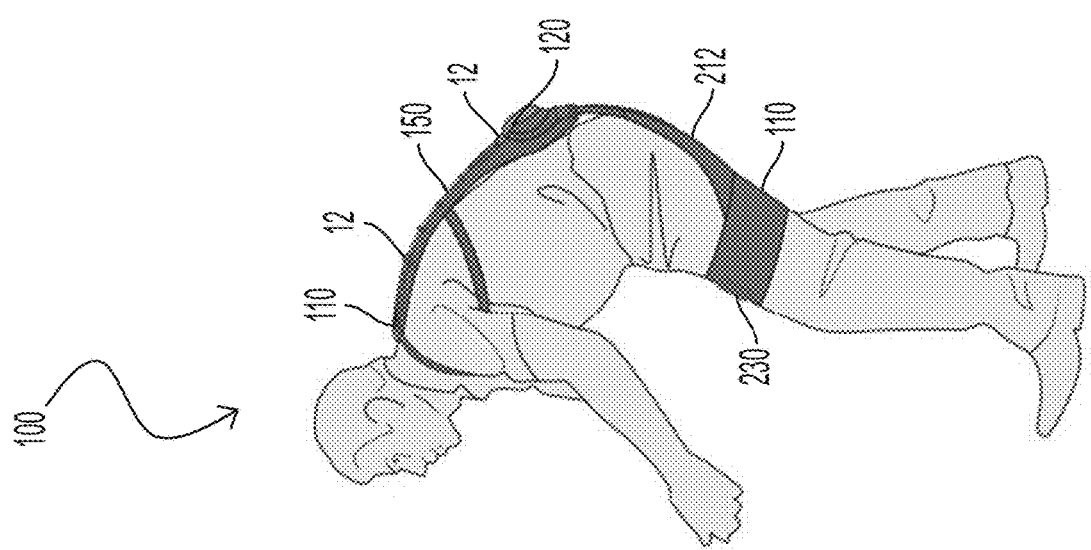
Figure 2A:
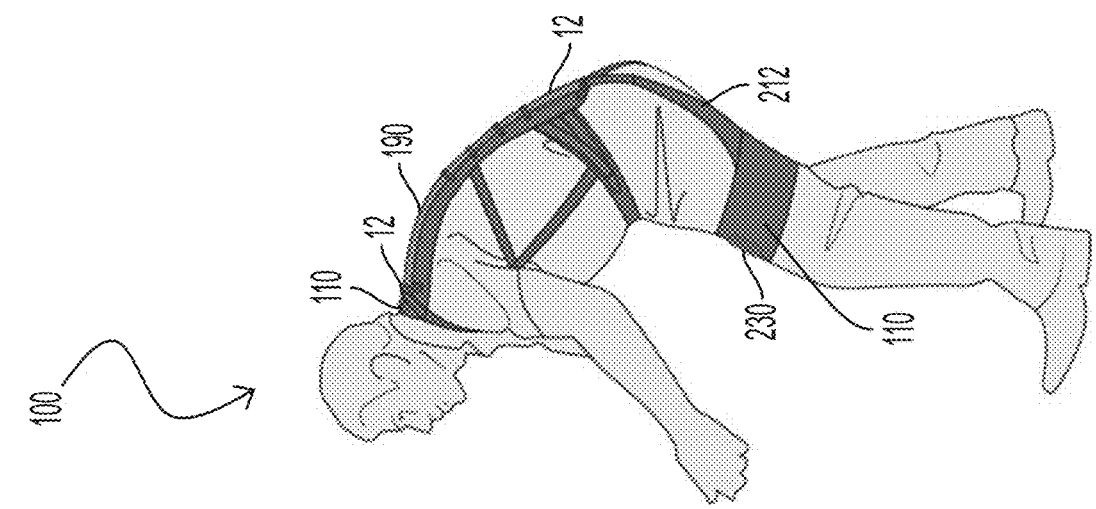

In various embodiments, one or more connecting elements 150 may be controlled by one or more actuators 120 such that the actuator(s) 120 can control the position of this element or the tension force that the connecting element 150 produces to provide customized or different levels of assistance to the wearer (active system). In another embodiment, a passive element 190 may be used as a connecting element 150 (e.g. elastic element, damper, etc.) so that as the user moves, this element 190 produces forces that are assistive to the wearer (passive system). In another embodiment an actuator 120 may be used to set pretension levels of a passive connecting element 190 setting the initial position or tension with respect to the anchor members 110 (semi-active system). This can be useful to allow customizing the assistance (when assistance starts, stops, etc.) with respect to the human motion, to compensate for relative movement of wearable device 100 components over time or to be able to set-up the initial pretension to accommodate different body types. Alternatively, some of these adjustments may be done manually via components such as Velcro® straps, a ratchet system (e.g. Boa®) or buckles. Another embodiment may not include a connecting element 150 at all such that the system doesn't provide any assistance to the user but is still capable of collecting onboard sensor information. FIG. 2A, FIG. 2B, and FIG. 2C show sample embodiments of a passive (FIG. 2A), active devices 100 to assist the body including the back and hip joints (FIG. 2B), and a sensor-only system (FIG. 2C). It should be appreciated that a semi-active system, in various embodiments, may look similar to the active system of FIG. 2B, except that the actuator 120 or clutch 160 may be controlled to set pretension or to engage/disengage an elastic element 150.

Actuated connecting element 150: The connecting element 150 between the anchor points 12 may be actuated. As an example, a cable-driven system in which the user may wear an actuator 120, a Bowden cable that connects the actuator 120 unit to one side of a joint and an inner cable 150 that may connect on one end to the actuator 120 and on the other end to the other side of a joint. In this way, when the inner cable 150 is actuated, a tensile force is generated between both anchor points 12. In another embodiment, the actuator 120 may be worn and directly connected to one side of a joint actuating a cable 150 that connects on one end to said actuator 120 and on the other end to the other side of a joint. On a different embodiment, the actuator 120 may be fluidic (e.g. pneumatic, hydraulic, etc.) where a connecting element 150 may apply tensile forces as an actuator 120 that connects to both attachment points is pressurized or as vacuum is applied. The connecting element 150 may be inextensible such as a cable made out of steel that can be controlled by an actuator 120 when having high actuator 120 bandwidth is critical, in another embodiment, the connecting element 150 may have a series spring element or a connecting element 150 made out of extensible material, in this case bandwidth is traded to have a system that may have benefits such as being able to measure the elastic displacement and correlate it to a force (if the material properties of this elastic element are known) therefore eliminating the need to include additional sensors 230 and also other properties that may be beneficial such as absorb and reduce component or environmental vibrations, by using elastic elements, etc.

Alternative to motor gearing and its integration into wearable device 100 components: On different embodiments, the actuator 120 may need a gear box or transmission such that a series of gear stages decrease the speed and increase the torque of its output to meet requirements. Standard gearboxes have some drawbacks which depending on the implementation include one or more of the following: added size and weight to the design, cost, susceptibility to shock loads, introduce backlash, inefficiencies and noise due to factors such as teeth meshing.

Figure 34C:
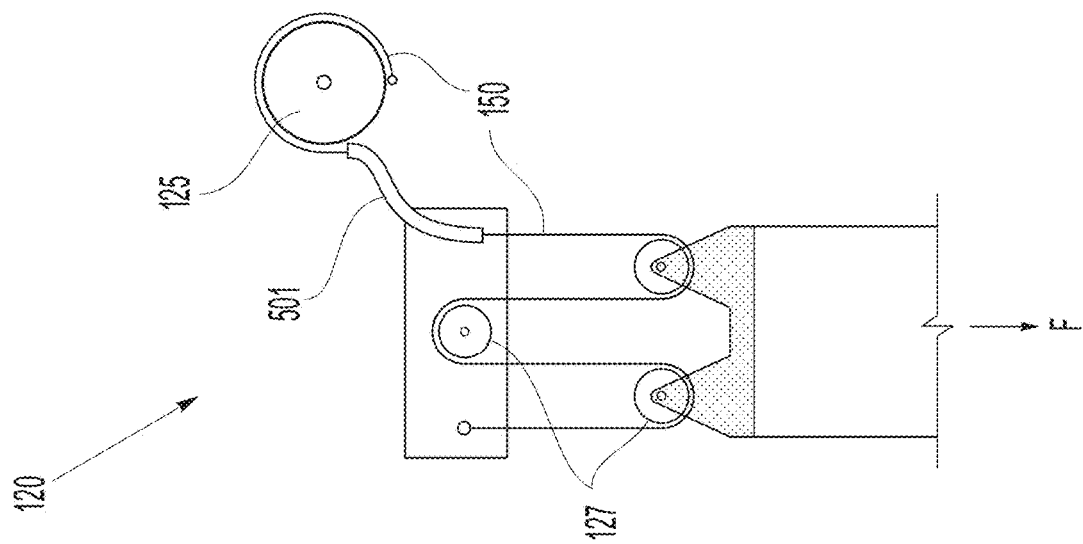
FIG. 34A, FIG. 34B, and FIG. 34C show examples of transmission systems and methodologies.
Figure 34B:
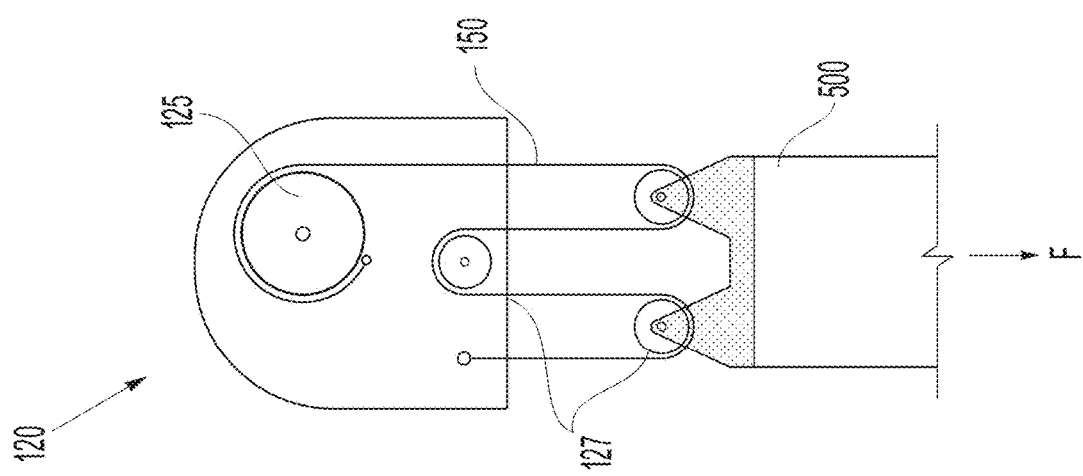
Figure 34A:
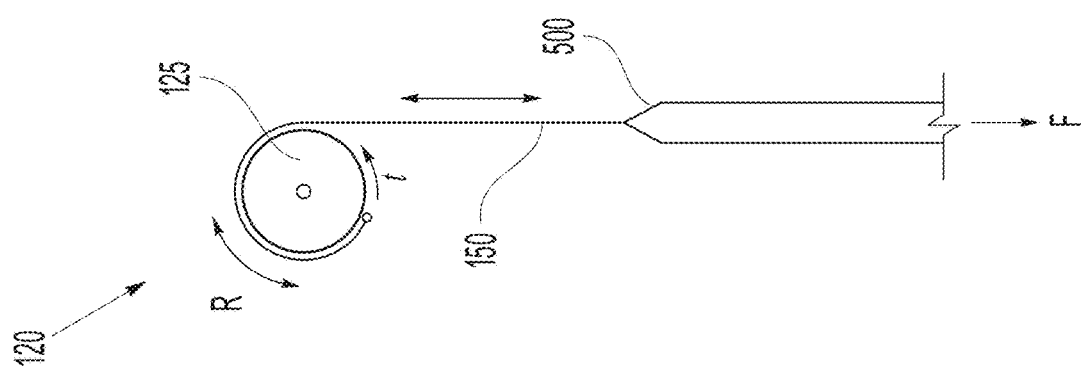

We introduce another solution to overcome the problem of gearing for wearable systems. We propose to use a series of rotary elements (e.g. pulleys, low-friction rollers, etc.) that may be integrated in the construction soft components (e.g. textile straps, textile components) to behave as an alternative to a gearbox which can capture the benefits of a geared reduction without some of its disadvantages. FIG. 34A, FIG. 34B, and FIG. 34C show examples of our proposed transmission method. FIG. 34A shows our standard implementation to attach an actuating element 150 between two anchor points. The example shown in FIG. 34B. or FIG. 34C. shows how by routing the actuating element 150 around guides 127 (e.g., rotating or low-friction elements), we can achieve reductions equivalent to having a (n+1): 1 ratio gearbox where n is the number of guides 127, by removing or adding rotary elements (n) this ratio can be changed. Assuming negligible friction in the guides(s) 127, the entire cable 150 has the same tension, T, throughout its length. The transmission has n+1 parallel cable segments pulling up on the strap 500 which means each segment is pulling the strap up with force, T. As a result the total force pulling the strap 500 is, F=(n+1)T. Due to the conservation of power, if the linear force is increased by a factor of n+1 that too means its speed is decreased by a factor of four. This is the basis of its (n+1):1 reduction. In different implementations, the motor 121 may be attached to a strap component 500 with an exiting cable 150 that routes through the proposed architecture (as shown in FIG. 34B) or include other transmissions such as Bowden cables 501 that attach on one side to one component and on the other side to a different component routed through guides 127 (FIG. 34C). The proposed transmission may be ideal for our use case for several reasons. Its layout is low profile and takes advantage of the large surface area of the users back as opposed to a bulky non-low-profile gearbox. The transmission uses inexpensive pulleys or low-friction materials instead of expensive gears which require high tolerances. Also due to the lack of gears the proposed transmission may have reduced backlash while under tension and reduced efficiency losses or audible noise associated with gear teeth meshing. This concept may be applied to any actuating element that follows a linear movement (electromechanical, fluidic, etc.) by connecting this element through a cable that follows the above-mentioned design. This concept may also be useful in an implementation where there is a single pulley, roller or low-friction element (n=1) resulting in a gear reduction of 2:1, this concept could eliminate the need to add a gearing stage for some applications which would greatly reduce cost and complexity.

Passive connecting element 190: In various embodiments, the connecting element 150 may be passive (e.g., a spring, damper, or flexible element (extensible, semi-extensible, or inextensible) such that as the person moves or bends, a tension between both anchor points is passively generated. This passive element 190 is designed in a way that the passively generated tension may assist one or multiple joints or body parts of the wearer. This element's 190 configuration (e.g. initial length) may be manually adjusted by either using straps such as Velcro® 510, buckles, ratcheting systems 502 (e.g. Boa®) or others. Additionally, in a semi-active system an actuator 120 may be used to modify these parameters e.g. to set pretension level.

Sensor-only system: In various embodiments, the connecting element 150 may not be present so that the system can take advantage of the onboard sensors 230 to, for example, analyze data from one or multiple workers during the workday to be able to evaluate risk of injury, performance of the task, biomechanics and/or ergonomics metrics. This data may be used to optimize different processes within that industry, help notify the user if he/she is performing motions that may lead to an injury or evaluate the areas of risk. Notification methods may include a low-power feedback (e.g. auditory, haptic, visual) to notify the user. These methods may also be useful to mitigate risk of injury for athletes for consumer applications or for the elderly. In an example, athletes may use this information to know when the risk for injury has gone up and use this information to establish recovery periods or to perform exercises. In another example, an athlete or a consumer may use the information from these metrics to improve his/her performance. Example wearable sensors 230 include one or a combination of an inertial measurement unit (IMU), a joint angle sensor 230, a force or pressure sensor 230, a torque sensor 230, a metabolic energy measurement device, a muscle activity measurement device (EMG), a ground reaction force sensor 230, a heart rate sensor 230, and an insole force or pressure sensor 230, amongst others. These sensors 230 may be integrated into apparel components.

Anchor Members 110

The wearable device 100 architecture may be designed to include apparel components such as straps that wrap around body segments to transfer loads to the body and to create anchor points for connecting elements 150. In an embodiment, the system may be designed to actuate different joints or combinations thereof (e.g. the back, shoulder, knee, hips, elbow). The examples depicted below provide detailed descriptions and designs of systems that assist these joints.

Wearable device 100 components that conform to the body to define the wearable device 100 architecture may include:

a. Thigh anchor member(s): this wearable device 100 component is configured for positioning on a thigh of the wearer and provides an anchor point on the thigh to create an attachment point on one side of the hip joint or the knee joint. This component incorporates non-slipping materials and is tight fitting such that it does not move with respect to the leg when forces are applied to it, is composed of textiles that are stiff so that when forces are applied to this component the amount of deformation is minimized. A representative embodiment of a thigh anchor element is a thigh wrap.

b. Waist anchor member(s): a strap that wraps around the waist to define anchor points in the body where an actuator 120 or passive element 190 may be attached. A representative embodiment of a waist anchor element is a waist belt.

c. Shoulder anchor member(s): this wearable device 100 component is configured for positioning on a shoulder of the wearer and provides an anchor point on the shoulder to create an anchor point on the upper side of the back. A representative embodiment of a shoulder anchor element is a shoulder strap.

d. Thigh strap 112: an elongate element (e.g., strap, ribbon, cable) that connects to both thigh anchor members 110 to create an attachment point on the lower side of the back joint. The following picture shows how a strap 112 in which each end 113, 114 attaches to the back of each thigh anchor member 110 and creates a loop that configures an attachment point at the lower-back can be integrated into a system. In some embodiments, thigh strap 112 may act as a load balancing element 212 of a load balancing assembly 210, as later described in more detail.

Figure 3:
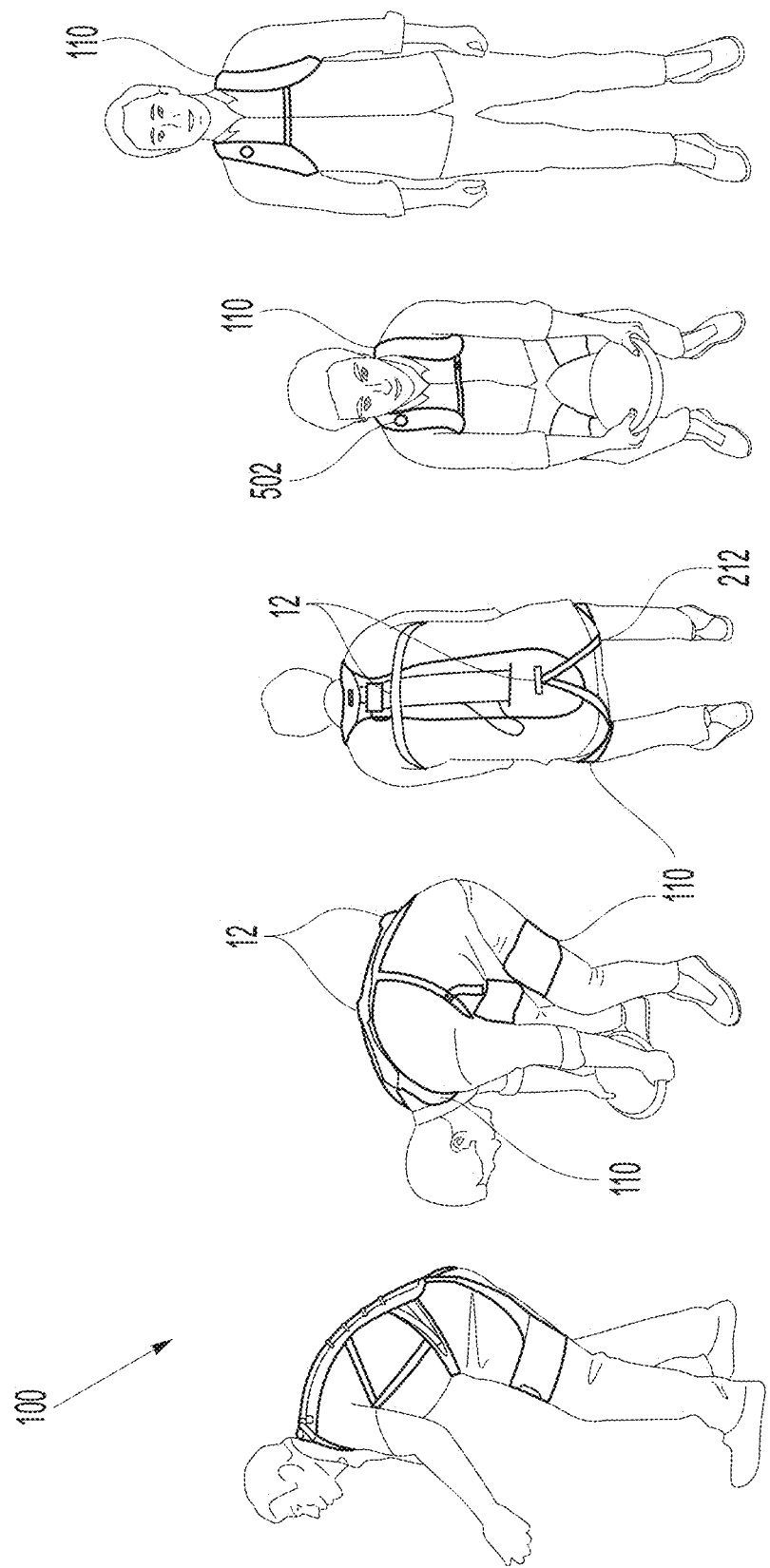
FIG. 3 illustrates multiple views of a representative embodiment of the robotic apparel.

FIG. 3 illustrates multiple views of a representative embodiment of the robotic apparel that includes some of the above-referenced components as labeled.

Sensors 230

A variety of sensors 230 can be used to measure various reactions of the body, interactions with the wearable system 100 or with the environment. In some embodiments, sensors 230 configured to measure human biomechanics can include but are not limited to Inertial Measurement Units (IMUs), accelerometers, gyroscopes, encoders, resolvers, and strain sensors 230 for measuring joint angles, speed and acceleration, a heart rate monitor for measuring heart rate, a pulmonary gas exchange system for measuring metabolic effort, electromyography, and pressure sensing insoles to measure ground reaction forces and instrumented treadmill to measure ground reaction forces. Sensors 230 that can be used to measure wearer-system interaction, including force and pressure, include but are not limited to load cells, force sensors 230, and pressure sensors 230. Motion sensors 230 may be used to estimate joint angles and dynamics (angular speed, acceleration) by positioning a motion sensor on each segment of the body, for instance an IMU on the back may be used to know torso angle when doing activities such as lifting, bending over, holding a static pose, sit-to-stand, etc. the relative angle between the torso and the thighs may be used to define whether a person is walking (cyclic motion of both legs) or squatting to lift an object (both legs bending), the relative angle between an IMU on the shoulder and an IMU on the forearm may be used to detect when a user is doing overhead tasks which may require further assistance by a shoulder assistive device, etc. an IMU on both sides of the knee joint may be used to estimate the knee angle, speed or acceleration to know when a person is in a crouched position that may require assistance by a knee assistive device. As an example, a load cell or force sensor embedded in the connecting element 150 or between the connecting element 150 and the anchor point may be used to know the force that the connecting element is delivering to the user; as another example, a pressure sensor located between the user and a strap may be used to estimate or measure the force or pressure for comfort or pressure distribution purposes, in another example sensors 230 embedded in the robotic apparel and sensors 230 located on the user may be used to know relative movement between the robotic apparel and the user. Sensors 230 that can be used to measure device metrics include but are not limited to current sensors 230, voltage sensors 230, thermistors, and encoders and resolvers to measure motor position, speed and acceleration. As an example, voltage and current sensors 230 may be used to estimate power that an actuator 120 is consuming, in another example, voltage may be used to estimate battery status; thermistors may be used to evaluate the thermal status of the system which may be useful as a prognostic or to take into account thermals to define the magnitude of assistance to stay below a comfortable threshold for any type of environment; sensors 230 such as motor position, speed and acceleration are needed to control the device and can also be effective sensors 230 to evaluate prognostics and status monitoring. In an embodiment, these sensors 230 may be textile based and/or compatible with the textile elements, as an example, the sensor 230 may be composed by fabrics that as they stretch or as pressure is applied to them change the electrical properties (e.g. resistance, capacitance), this change may be measured by an electrical circuit and correlated with a joint movement, interaction forces between the system and the user or with the environment.

Passive Wearable Devices

Wearable devices 100 of the present disclosure, in various embodiments, may be configured for passively generating moments about one or more joints of the wearer to assist the wearer in performing a movement or in holding a pose. Passive wearable devices 100 may generally comprise at least one anchor member 110 configured for positioning on a first body part of a person wearing the wearable device 100, at least one anchor member 110 configured for positioning on a second body part of a person wearing the wearable device 100, at least one connecting element 150 directly or indirectly coupling the at least one first body part anchor member 110 to the at least one second body part anchor member 110 such that movement or a pose of the wearer generates tension in the wearable device 100 and the wearable device 100 provides a moment (e.g., restorative torque) about one or more joints spanned by the wearable device 100.

For example, the representative passive wearable device 100 shown in FIG. 2A includes two upper body anchor members 110 (e.g., shoulder anchor members 110 in the form of shoulder straps), two lower body anchor members 110 (e.g., thigh anchor members 110 in the form of thigh wraps), and a passive connecting element 190 (e.g., a spring, damper, or flexible element (extensible, semi-extensible, or inextensible)) connecting the upper body anchor members 110 to the lower body anchor members 110. As configured, movement or a pose of the wearer may generate tension in the wearable device 100 that causes the wearable device 100 to provide a moment (e.g., restorative torque) about at least one of: (i) one or more hip joints of the wearer, and (ii) one or more back joints of the wearer, as described in more detail throughout the present disclosure.

Reference to back joints in the present disclosure is intended to broadly include any and all portions of the torso that may bend or move relative to other portions of the torso including, without limitation, joints like the lumbar spinal joint, the sacroiliac joint, and other joints, as well as junctures between individual vertebrae.

Semi-Active Wearable Devices

Wearable devices 100 of the present disclosure, in various embodiments, may be configured for semi-actively generating moments about one or more joints of the wearer to assist the wearer in performing a movement or in holding a pose. Generally speaking, semi-active wearable devices 100 do not actively generate a moment about one or more joints of the wearer, but instead adjust an impedance (e.g., stiffness, dampening) of the wearable device 100 such that movement or a pose of the wearer generate a desired level of tension in the wearable device 100 for assisting the wearer in performing the movement or holding the pose. Semi-active wearable devices 100 may generally comprise at least one anchor member 110 configured for positioning on a first body part of a person wearing the wearable device 100, at least one anchor member 110 configured for positioning on a second body part of a person wearing the wearable device 100, at least one connecting element 150 directly or indirectly coupling the at least one first body part anchor member 110 to the at least one second body part anchor member 110, and at least one semi-active actuator 120 configured to control an impedance of the wearable device 100 such that movement or a pose of the wearer generates tension in the wearable device 100. This tension may cause the wearable device 100 to generate a moment about the one or more joints spanned by the wearable device 100 for assisting the wearer in performing the movement or in holding the pose.

By way of example, the representative passive wearable device 100 shown in FIG. 2A could be adapted to be a semi-active wearable device 100 by including a semi-active actuator 120 (e.g., a clutch system, a non-backdrivable actuator, or other suitable mechanism) configured to control how much tension is generated in the wearable device 100 by movement or a pose of the wearer. The semi-active wearable device 100, which extends from the shoulders to the thighs, may be configured to control an impedance of the wearable device 100 such that movement or a pose of the wearer generates a moment about at least one of: (i) one or more hip joints of the wearer, and (ii) one or more back joints of the wearer, as described in more detail throughout the present disclosure.

Figure 4A:
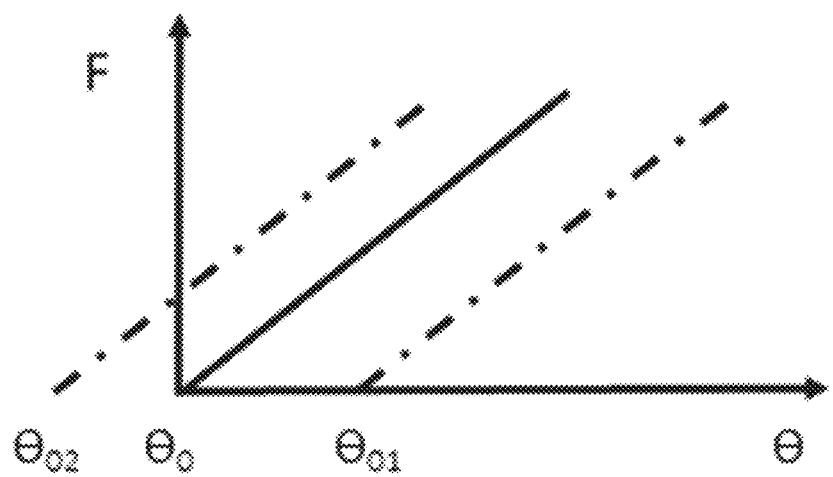
FIG. 4A and FIG. 4B show how by defining different initial lengths of the connecting elements, the output tensile forces can be modified.
Figure 4B:
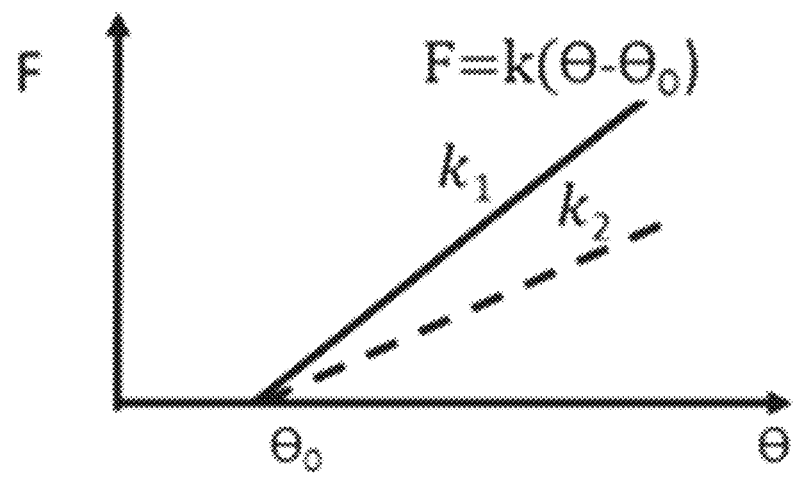

Semi-active actuators 120, in various embodiments, may be configured to control an impedance of the wearable device 100 by controlling parameters such as:

a) Initial length of the connecting element 150: the initial length of the connecting element 150 (x01) defines when the tensile force starts as the user bends with respect to the standing position, the distance between both anchor points when the user is standing is defined as x0. For example, if the initial length of the anchor element (x01) is equal or longer than x0 (x01>=x0), the tensile forces will be generated as the user bends the torso or the legs with respect to the standing position to do an activity. This connecting element 150 may be designed to be shorter than x0 (x01<x0) if the intent is to provide tensile forces while the user is standing. FIG. 4A and FIG. 4B show how by defining different initial lengths of the connecting elements 150, the output tensile forces can be modified. The process for adjusting may include commanding a target position of the actuator 120 and using sensors 230 such as an encoder or potentiometer to define the current position of the actuator 120 and close the loop. Once the initial length is defined, the actuator 120 may be clutched at that position so that it doesn't have to support the resulting forces when assisting the joint or be non-backdrivable which will mean that the motor wouldn't need to use current in order to hold the position in place which will save energy compared to having a backdrivable system hold the position while assistive forces are being produced.

b) slack vs pretension mode: an actuator 120 system or clutch 160 may be used to allow slack in the system when the device is intended to be fully transparent (not apply assistive forces). In this case, the actuator 120 will be commanded to release cable 150 so that there is enough slack (actuation cable 150 is longer than the distance between anchor points), unclutch the connecting element 150 so that it can't produce forces or open a pneumatic system so that the connecting element 150 doesn't apply forces to the body. In an embodiment system may use motion sensors 230 such as IMUS to detect the pose of the user and decide whether this is an activity that the device 100 can support or not. For instance, by classifying activities between walking, standing, lifting, holding static postures, going up/down stairs, etc. an algorithm can define which ones it will support and command the actuator 120 or clutch 160 to be transparent (not produce forces) otherwise by adding slack to the connecting element 150 between anchor points.

c) Impedance of the connecting element: a clutching system 160 or actuator 120 can be used to select between different impedances by clutching different elastic elements, springs, or other passive connecting elements 190 in parallel, or by controlling the initial position of different passive connecting elements 190 in parallel to either add or remove impedance in the system.

d) Compensation of migration of wearable device 100 components: in an embodiment a load cell on the connected element 150 and motion sensors 230 (e.g. IMUs) could be used to monitor the resulting forces relative to the joint angle. If the resulting force for a specific joint angle is less than desired is likely that the wearable device 100 has drifted so that the element 150 connecting the anchor points is not as pretensioned as when the wearable device 100 was initially set-up. A semi-active system will then be able to correct this pretension by following the method describe above taking out slack from the system. In a different embodiment, a displacement sensor 230 such as a potentiometer to measure the distance between anchor points will be used, in this case if for a given posture (defined by for instance when the load cell measures zero force or defined by joint angle measurements such as IMU as a reference) the distance between anchor points has reduced, is likely that the wearable device 100 has migrated overtime and the actuator 120 could be controlled to take out slack from the system.

e) Selective harvesting and delivery of wearer-generated energy. In an embodiment, the connecting element 150 may include an energy storage device 190 (e.g., a spring) that is configured to absorb energy generated by movement or a pose of the wearer, and the semi-active actuator 120 (e.g., clutch 160) may be configured to selectably lock the energy storage device 190 to store the absorbed energy. The semi-active actuator 120 may be configured to subsequently unlock the energy storage device 190 to release the stored energy to assist the wearer in performing a movement or holding a pose. While the released energy may actively generate a moment about one or more of the wearers joints, such an embodiment may still be classified as a semi-active wearable device 100 because the source of the energy for the assistive forces and moments was the wearer's movement or pose, rather than a power source such as a battery.

Active Wearable Devices

Wearable devices 100 of the present disclosure, in various embodiments, may be configured for actively generating moments about one or more joints of the wearer to assist the wearer in performing a movement or in holding a pose. Active wearable devices 100 may generally comprise at least one anchor member 110 configured for positioning on a first body part of a person wearing the wearable device 100, at least one anchor member 110 configured for positioning on a second body part of a person wearing the wearable device 100, at least one connecting element 150 directly or indirectly coupling the at least one first body part anchor member 110 to the at least one second body part anchor member 110, and at least one actuator 120 configured to generate a tensile force in the wearable device 100 for generating a moment about the one or more joints spanned by the wearable device 100.

For example, the representative active wearable device 100 shown in FIG. 2B includes two upper body anchor members 110 (e.g., shoulder anchor members 110 in the form of shoulder straps), two lower body anchor members 110 (e.g., thigh anchor members 110 in the form of thigh wraps), and a connecting element 150 (e.g., actuated cable) connecting the upper body anchor members 110 to the lower body anchor members 110. As configured, the connecting element 150 may be actively actuated by an actuator 120 to a generate a moment about at least one of: (i) one or more hip joints of the wearer, and (ii) one or more back joints of the wearer, as described in more detail throughout the present disclosure.

As explained above, wearable devices 100 can be configured to assist different joints by creating anchor points on both sides of a joint. The assistive profiles can be defined according to the prescribed timing and magnitude of actuation. In some embodiments, an actuation profile can be further reduced into a finite-dimensional set of numerical variables, representing key actuation parameters such as: (i) the timing of the initiation of actuation, of its peak, and of its termination, (ii) the magnitude of the actuation, (iii) coefficients of a polynomial interpolation of the actuation, (iv) a number of points that could then be interpolated using a mathematical function such as a spline or a polynomial, and/or (v) stiffness of an actuator 120.

The developed assistive devices may be configured to assist different joints such as the back, the hips, knees, shoulders, elbows, or a combination of these.

Referring back, FIG. 2B shows a representative architecture to create assistive torques around the hip and back joints. The device can help assist the back and hip joints during tasks such as lifting, holding static postures, transporting heavy equipment or pulling/pushing which are common activities that may result in injuries over time while being fully transparent (like normal clothing) for other motions. A representative device may be impedance controlled such that it can follow prescribed trajectories or to render virtual impedances (stiffness, damping) that are a function of the joint(s) angles. In this case, since the device crosses both the hip and back joints, the impedance may be defined as the relative angle between the torso and the thigh. This angle may be measured by using on-board sensors 230 such as IMUs, or strain sensing elements). A sample virtual impedance rendered by the actuation may be defined by the stiffness value as shown in FIG. 4B where F is the resulting force, theta is the relative angle between the thigh and the torso and K is the rendered stiffness. In this case, the assistive profiles would feel like having a spring between the anchor points of stiffness K. The advantage of an actuation profile like this over a passive device is that there is more flexibility to automatically configure the assistive profile by selecting different impedances optimized for different motions or different users. Moreover, a virtual impedance has the advantage that it may have different properties (rendered stiffness, damping, etc.) for each phase of the movement, for instance, a different impedance depending on the direction of the motion. The action of going down to grab an object may require less energy than the action of going up with the object fighting gravity, a change in rendered impedance as the movement changes direction will allow to provide more energy into the person when going up versus when going down which a passive spring is not be able to do. Moreover, by choosing a different "initial angle", the resulting profile will be able to shift so that the force doesn't start until the user has reached that initial position.

Figure 5A:
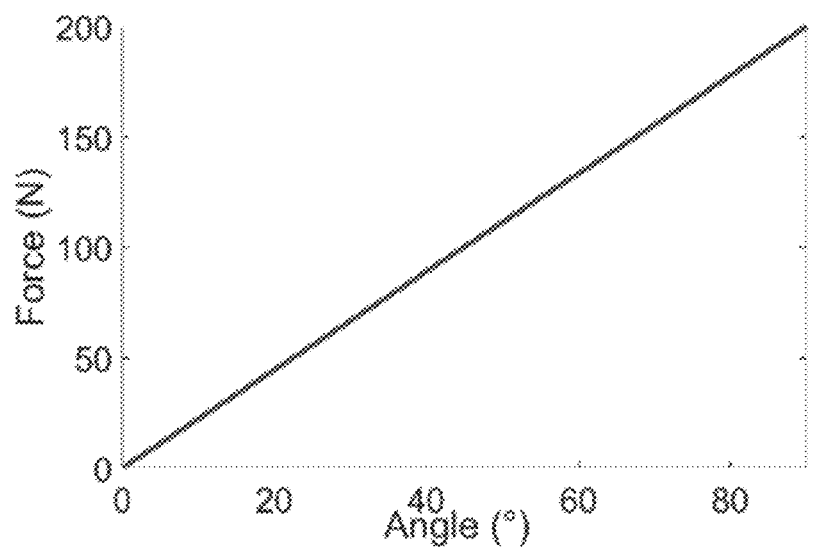
FIG. 5A, FIG. 5B, and FIG. 5C show for a sample user movement in which a joint is moving from an initial position of 0° (standing) to 90° (bending torso to a horizontal position) following a sinusoidal pattern.
Figure 5B:
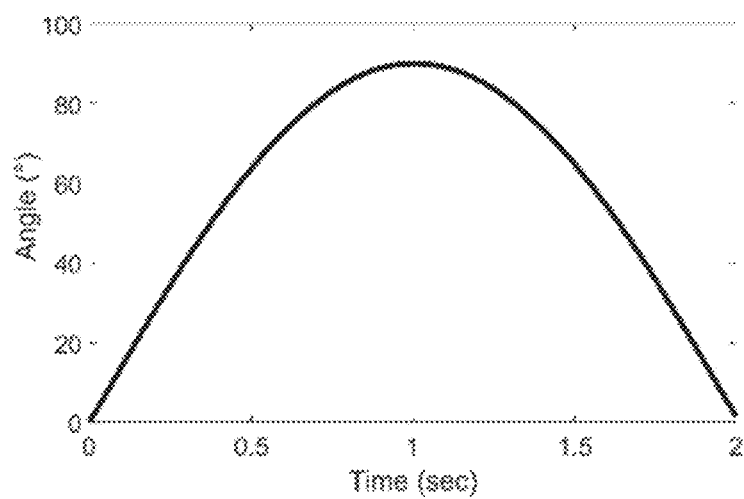
Figure 5C:
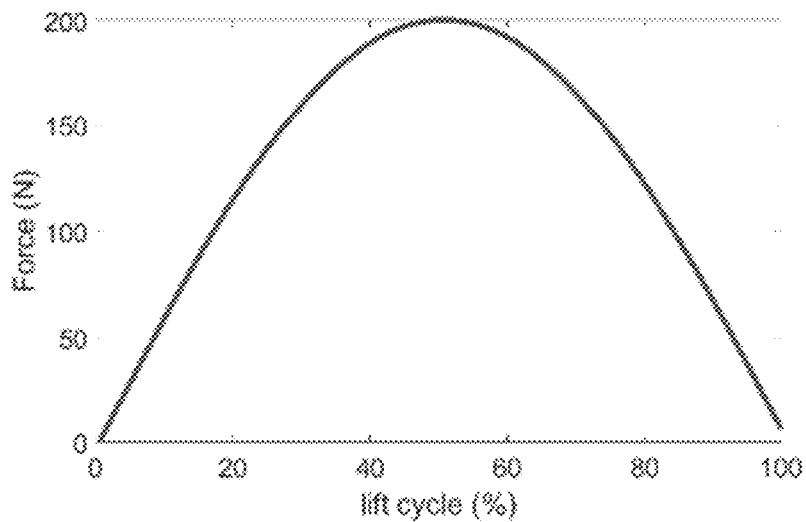

FIG. 5A, FIG. 5B, and FIG. 5C show for a sample user movement in which a joint is moving from an initial position of 0° (standing) to 90° (bending torso to a horizontal position) following a sinusoidal pattern. This movement can be representative for example of bending the torso to grab an object from the ground. The resulting forces are a result of multiplying the prescribed stiffness by the joint angle that the user is performing. Forces are represented as a % of lift cycle in which 0% is defined as when the user is initializing the movement, 50% as when the speed of the joint is zero when the user is changing direction and 100% when the user completes the motion by going back to a straight position.

For impedance controlled devices 100, the system may have different modes depending on the detected motion. Therefore, on-board sensors 230 may be used to detect different activities and select the different pre-defined impedance profiles for each of those. For example there are multiple ways to lift a load, for instance using a squat technique or a stoop technique (legs straight), also the lift may occur with the object in front of the body (back moves on sagittal plane) or with the object on the sides due to space constraints such that the back has to bend and twist during the lift. These different motions may be detected by using onboard motion sensors 230 such as IMUs in which an algorithm could define a initialization threshold (e.g. an initial threshold of the relative angle and angular speed between the torso and the thigh joints that when passed is considered as a initialization of a bending motion. A threshold may also be used to define whether the movement is happening in the sagittal plane or whether the user is bending and twisting the torso for the lift. A different threshold may be used to define whether the user is bending the legs during the lift or not. In another example, the onboard sensors 230 may be used for a classification algorithm (e.g. neural network, linear classifiers, nearest neighbor, decision trees, etc.) to detect which activity the motion falls into. An impedance or assistive profile may be selected for each of these movements.

An impedance or assistive profile may be selected for each of these movements.

In another example, a device may be EMG controlled. In this case, one or more EMGs will be located on the representative muscles that the device aims to assist. The filtered electromyography signal from the targeted muscle may be used to estimate the joint torque that the targeted joint is producing and used to command the delivered force produced by the exoskeleton.

Optimizing Control of Wearable Devices

Since these tasks are characterized either for having multiple repetitions or to be sustained for a long amount of time, an optimization method can be used to measure and/or estimate an objective function over multiple repetitions or over time respectively and update a parametrized assistive profile to optimize a desired objective.

Optimization approaches can be used to maximize or minimize benefits when wearing a wearable device 100, such as an exoskeleton, exosuit or robotic apparel, during various types of activities, including non-walking movements and upper body movement. The wearable devices 100 and optimization approaches can assist different joints, such as the ankles, knees or hips during non-walking movement or elbows, neck, shoulders, and back during upper body movement to either enhance the performance of healthy individuals (e.g. reducing fatigue) or to improve the efficiency of the movements for impaired individuals.

Figure 6:
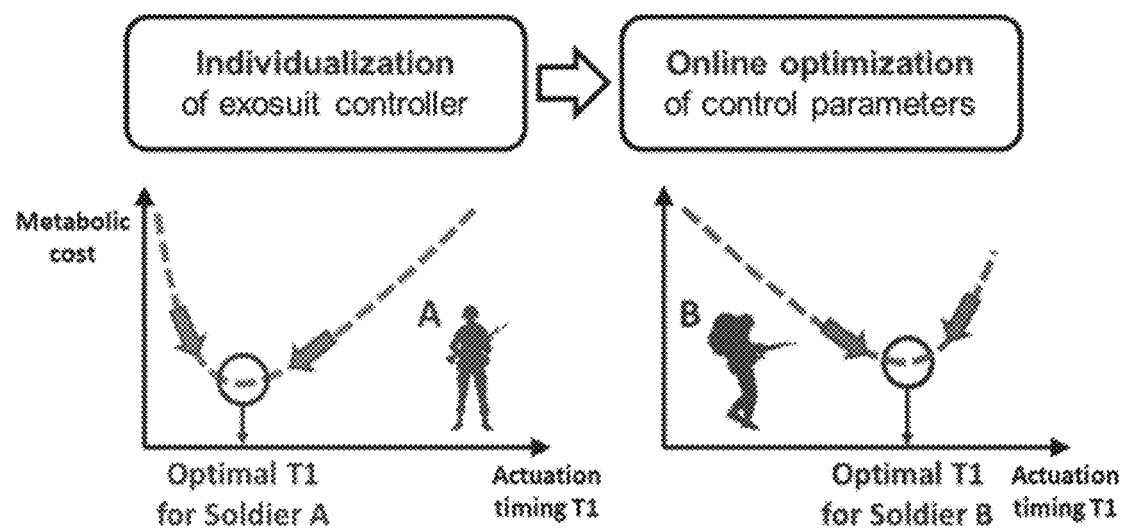
FIG. 6 illustrates how two different healthy individuals may have different outcomes depending on the actuation parameters selected (in this case actuation timing), the maximum performance of the system, is achieved with very different actuation parameters for each subject.

As an example, FIG. 6 illustrates how two different healthy individuals may have different outcomes depending on the actuation parameters selected (in this case actuation timing), the maximum performance of the system, is achieved with very different actuation parameters for each subject. This highlights the need of individualizing the wearable device 100 (e.g., robotic apparel, exosuit or exoskeleton) controller 240 for different individuals. An online optimization algorithm that measures or estimates the objective function by using wearable sensors 230 and adapts different parameters of the assistive profile to maximize or minimize that objective while a given user is performing a task will allow for a higher individualization of the assistance.

In the context of control systems for a wearable device 100, including robotic apparel, exosuit or exoskeleton, an optimization approach may generally entail the choice of an objective function, the choice of a way to evaluate the objective function (e.g., direct measurement; calculations based on measurements of related information, or by proxy), the choice of one or more actuation parameters to optimize for maximizing or minimizing the objective function, and the choice and application of an optimization method.

Systems and methods of the present disclosure can seek to optimize one or more parameters associated with actuating the wearable device 100, such as a robotic apparel, exosuit or exoskeleton, in order to maximize or minimize the selected objective function. Generally speaking, the robotic apparel, exoskeleton or exosuit is actuated according to an actuation profile defining a timing, rate, magnitude, and overall shape of the actuation during a specified period. Oftentimes, an actuation profile is presented in the form of commanded actuator 120 position (e.g., cable position when a Bowden cable(s) connects a motor(s) to portion(s) of the robotic apparel, exosuit or exoskeleton) throughout the specified period. For example, in relating to movement of the upper extremities or non-walking movement, the specified period can be a repetitive motion of the wearer. Of course, any suitable period may be specified according to the biomechanics of the wearer and the portion(s) of the wearer's body being assisted by the wearable device 100, such as the robotic apparel, exosuit or exoskeleton.

An actuation profile can be broken down according to the prescribed timing and magnitude of actuation. In some embodiments, an actuation profile can be further reduced into a finite-dimensional set of numerical variables, representing key actuation parameters such as: (i) the timing of the initiation of actuation, of its peak, and of its termination, (ii) the magnitude of the actuation, (iii) coefficients of a polynomial interpolation of the actuation, (iv) a number of points that could then be interpolated using a mathematical function such as a spline or a polynomial, and/or (v) stiffness of an actuator 120.

Various types of actuators 120 can be used with the wearable devices 100, including but not limited to pneumatic, hydraulic, electromechanical, electromechanical cable-based, electroactive materials, and actuators 120 that can generate force and/or change stiffness.

Various aspects of the biomechanics of the wearer can be affected and optimized using optimization approaches in conjunction with the exosuit or exoskeleton. For example, tasks that are either cyclic in nature, involve multiple repetitions, or that are sustained over time can utilize an optimization algorithm to maximize or minimize an objective function that is evaluated during each repetition or over time respectively. Exemplary cyclical upper body movement can include repetitive work tasks, exercise in rehabilitation, assisting movements such as sit-to-stand, lifting packages which are all common during daily activities.

Activities involving the upper body including, but not limited to, the arms, neck, hands, wrists, shoulders, and/or back, can be enhanced by wearing assistive wearable devices 100, such as robotic apparel, an exosuit or an exoskeleton, which can reduce fatigue, strains and/or injuries. For example, support can be provided to the back, shoulder, elbow, arm and/or hand when either lifting objects or performing over-head work, or a grip assist device can provides additional strength in wrist and/or the hand to either grasp a tool or press a trigger of a tool to avoid strains on muscles or carpal-tunnel symptoms if repeated. In all these cases, wearable devices 100 can be applied to wearers to reduce fatigue, improve ergonomics, prevent injuries, or improve comfort while doing these tasks. Wearable devices 100 can be optimized and used on or across various joints of the wearer including, but not limited to, an ankle, knee, hip, back, neck, shoulder, elbow, hand, or combinations of aforementioned joints. As these tasks are characterized by having multiple repetitions or being sustained over a period of time, various optimization methods can be used to measure and/or estimate an objective function over multiple repetitions or over time respectively and update a parametrized assistive profile to optimize a desired objective.

In the context of exosuit or exoskeleton control systems, an optimization approach may generally entail:

1. The choice of an objective function;
2. The choice of a way to evaluate the objective function (e.g., direct measurement; calculations based on measurements of related information, or by proxy);
3. The choice of one or more actuation parameters to optimize for maximizing or minimizing the objective function; and
4. The choice and application of an optimization method.

As later described in more detail, the present disclosure is directed in relevant part to a wearable device 100 comprising:

at least one actuator 120 configured to generate a force in the wearable device 100 or to cause a force to be generated in the wearable device 100, such that the wearable device 100 generates a moment about one or more joints of the wearer to assist the wearer in performing a movement or to hold a static pose;

at least one sensor configured to measure information for evaluating an objective function associated with at least one of providing physical assistance to the wearer, an interaction between the wearer and the wearable device 100, and an operation of the wearable device 100; and at least one controller 240 configured to actuate the at least one actuator 120 according to at least one actuation profile, evaluate the objective function based on the information measured by the at least one sensor to determine a resulting change in the objective function, adjust at least one parameter of the at least one actuation profile based on the resulting change in the objective function, and continue to actuate, evaluate, and adjust to optimize the at least one actuation parameter for maximizing or minimizing the objective function.

As later described in more detail, the present disclosure is directed in relevant part to a wearable device 100 comprising:

at least one actuator 120 configured to generate a force in the wearable device 100 or to cause a force to be generated in the wearable device 100, such that the wearable device 100 generates a moment about one or more joints of the wearer to assist the wearer in performing a movement or to hold a static pose;

at least one sensor configured to measure information for evaluating an objective function associated with at least one of providing physical assistance to the wearer, an interaction between the wearer and the wearable device 100, and an operation of the wearable device 100; and at least one controller 240 configured to actuate the at least one actuator 120 according to at least one actuation profile, evaluate the objective function based on the information measured by the at least one sensor to determine a resulting change in the objective function, adjust at least one parameter of the at least one actuation profile based on the resulting change in the objective function, and continue to actuate, evaluate, and adjust to optimize the at least one actuation parameter for maximizing or minimizing the objective function.

As further described in more detail, in another embodiment, the at one controller 240 may be configured to:

Identify two or more actuation parameters to be optimized for maximizing or minimizing the objective function, Actuate the at least one actuator 120 according to two or more actuation profiles having different sets of baseline values of the two or more actuation parameters to be optimized, Evaluate the objective function for each of the two or more actuation profiles based on the information measured by the at least one sensor, Define, based on corresponding evaluations of the objective function, a mathematical correlation between the two or more actuation parameters and the corresponding evaluations of the objective function, Evaluate the baseline mathematical correlation to determine a candidate set of values of the two or more actuation parameters for maximizing or minimizing the objective function, Update the mathematical correlation based on a corresponding evaluation of the objective function for an actuation of the at least one actuator 120 according to an actuation profile associated with the candidate set of values of the two or more actuation parameters, and Continue to update the mathematical correlation until an evaluation of the objective function reaches a global maximum or a global minimum value, or when a predetermined termination criteria is met.

Actuation Profiles and Parameters

Systems and methods of the present disclosure seek to optimize one or more parameters associated with actuating the exosuit or exoskeleton in order to maximize or minimize the selected objective function. Generally speaking, the exoskeleton or exosuit is actuated according to an actuation profile defining a timing, rate, magnitude, impedance and/or overall shape of the actuation during a specified period. Oftentimes, an actuation profile is presented in the form of commanded actuator 120 position (e.g., cable position when a Bowden cable(s) connects a motor(s) to portion(s) of the exosuit or exoskeleton).

Figure 7:
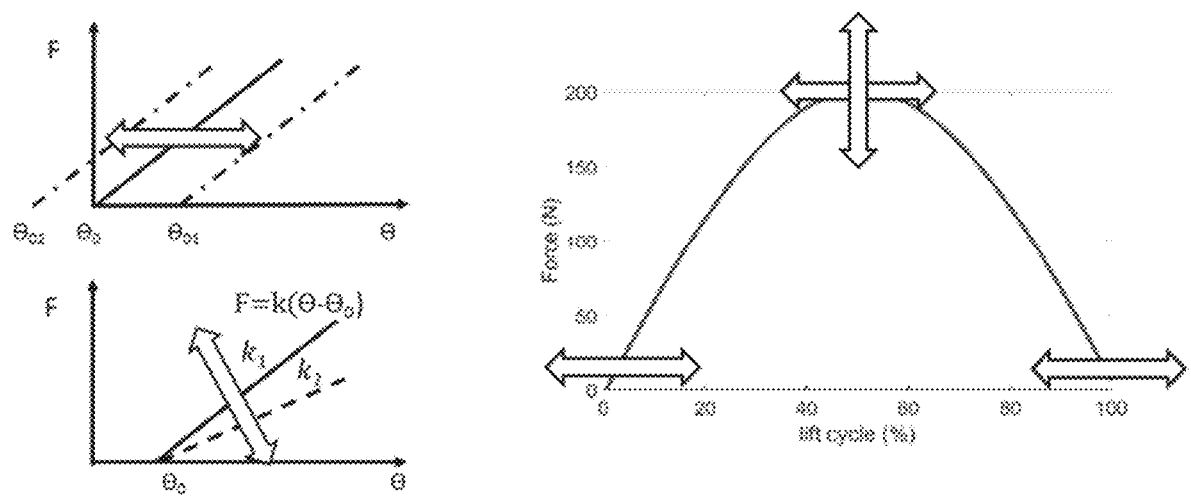
FIG. 7 illustrates how an actuation profile can be broken down according to the prescribed timing, rate, magnitude, and overall shape of actuation.

Referring to FIG. 7, an actuation profile can also be based on force control as shown in the FIG. 7 (right). Here, the specified period is a cycle of the wearer's lift, which can be a useful timeframe when assisting the wearer during activities such as lifting. Of course, any suitable period or function may be specified according to the biomechanics of the wearer and the portion(s) of the wearer's body being assisted by the exosuit or exoskeleton. For instance, a system controlled in impedance mode (e.g. stiffness, damping) in which the resulting forces are a function of the wearer's motion may not require the definition of a period but rather a function that relates the desired forces relative to the body posture or motion as shown in FIG. 7 (left).

In FIG. 7, an actuation profile can be broken down according to the prescribed timing, rate, magnitude, and overall shape of actuation. More specifically, an actuation profile can be further reduced into a finite-dimensional set of numerical variables, representing key actuation parameters such as: (i) the timing of the initiation of actuation, of its peak, and of its termination (FIG. 7, right) (ii) a rate of the actuation, (iii) the magnitude of the actuation, and (iv) coefficients of a function defining a shape of the actuation, such as the coefficients of a polynomial, linear, exponential, sinusoidal, or other function defining a shape of the actuation profile such as impedance (e.g. stiffness, damping) as shown in FIG. 7 (left).

Actuation of the exosuit or exoskeleton in combination with the natural motion of the wearer, causes the exosuit or exoskeleton to deliver forces and moments to the wearer's body. Like an actuation profile, the timing and magnitude of the resulting forces and moments may be characterized by a position assistance profile, as shown in FIG. 7. Here, actuation of the exosuit or exoskeleton according to the actuation profile of FIG. 7 (right) delivers forces and moments to the wearer's back as represented in the assistance profile. In other cases, the assistive profile may be parametrized directly in the impedance space to be controlled by a force controller 240 as shown in FIG. 7 (left). In this example, the actuation is configured to assist the wearer's back joint while lifting an object.

Objective Functions and Proxies, Generally

A common goal of the optimization approaches disclosed herein is to maximize the benefits conferred by the robotic apparel, exosuit or exoskeleton to the wearer. These benefits may vary depending on the given application, but generally speaking, involve providing physical assistance to the wearer. This can include, for example, assisting the wearer's natural motions (e.g., reducing energy expenditure, increasing strength), helping to stabilize the wearer while stationary or moving, or promoting an improvement in a cyclical or repetitive motion of the wearer (e.g., reducing muscle effort or improving posture for lifting tasks), amongst any number of other suitable uses. Depending on the wearer and the purpose of the exosuit or exoskeleton, one may identify a number of metrics that, if maximized or minimized, may make the exosuit or exoskeleton more beneficial to the wearer. Optimization approaches of the present disclosure seek to optimize one or more parameters of how the exosuit or exoskeleton is actuated with the purpose of maximizing or minimizing these metrics, or objective functions.

Systems and methods of the present disclosure, in various embodiments, utilize feedback from one or more sensors 230 of the wearable system to evaluate the impact of actuation adjustments on a given objective function. This feedback helps the wearable system ensure that these actuation adjustments converge in a way that maximizes or minimizes the objective function. As such, in various embodiments, the controller 240 may be configured to evaluate the objective function in response to a given actuation of the exosuit or exoskeleton. As used herein, evaluating the objective function broadly includes any suitable way of quantifying the objective function. For example, in an embodiment, evaluating the objective function may be obtaining a direct measurement of the objective function from the one or more sensors 230 included in the wearable system. In another embodiment, evaluating the objective function may include calculating or approximating the objective function using one or more measurements provided by the one or more sensors 230 of the wearable system. For example, if the objective function is power delivered by the exosuit or exoskeleton to the wearer, the controller 240 may be configured to calculate power by multiplying measurement of force and rotational velocity taken by a load cell and IMU to calculate this metric. In yet another embodiment, evaluating the objective function may include measuring, calculating, or approximating a proxy correlated with the objective function using information measured by the one or more sensors 230 of the wearable system to estimate, via this correlative relationship, the objective function.

The use of a proxy in evaluating the objective function may be particularly well-suited to situations in which it may be impossible or otherwise difficult to directly measure the objective function, or to estimate the objective function via calculations using related measurements from wearable sensors 230. For example, it can be difficult to directly measure metabolic consumption as a metric of exertion, and typically requires expensive equipment or requires the user to wear a mask to measure gas exchange. However, other metrics the ability to sustain a motion for a longer time compared with a baseline, the ability to sustain a cyclic movement (e.g. lifting an object) at a normal frequency or a change in posture may correlate with fatigue and therefore used as objective metrics. As another example, delivering power to a joint during a dynamic movement may reduce the level of effort for certain tasks and therefore an optimization algorithm may use positive power delivered to the biological joint as a proxy for level of unloading of the joint effort. It should be noted, of course, that average positive power, changes in posture along with any other proxy identified in the present disclosure, can itself be used as an objective function within the scope of the present framework. Stated otherwise, an objective function, as the term is used herein, need not always describe the ultimate desired effect (e.g., maximize locomotive efficiency) but rather can be any metric sought to be maximized or minimized (including, within a set of range constraints) through optimization of one or more actuation parameters.

As another example, heart rate has also been found to be correlated with a level of exertion of wearers in some applications, and therefore heart rate, in an embodiment, may be used as a proxy for level of effort. In yet another example, muscle activity of key muscles in the targeted joint may correlate with level of effort and therefore used as an objective measurement.

Generally speaking, objective functions related to robotic apparel, exosuits or exoskeletons may be broken down into three categories: (i) those objective functions associated with providing physical assistance to the wearer, (ii) those objective functions associated with an interaction between the wearer and the exosuit or exoskeleton, and (iii) those objective functions associated with the operation of the exosuit or exoskeleton, as further described in more detail below. It should be understood, of course, that these categories are presented for ease of explanation, and that the optimization approaches described herein may also be used in connection with optimizing actuation for maximizing or minimizing any other suitable objective function that may fall outside of the scope of one of these three general categories.

Objective Functions and Proxies Associated with Providing Physical Assistance to the Wearer As referenced above, many objective functions associated with exosuit or exoskeleton performance relate to the effectiveness of the wearable system in providing physical assistance to the wearer. Below, representative examples of several such objective functions are provided, along with biomechanical context for how each may be maximized or minimized to benefit the wearer.

Similarity of joint kinematics to normative data: An exemplary optimization approach may evaluate how similar a wearer's kinematics are to age-, sex, weight-, and/or speed-matched data from a normative set of healthy users or from an ergonomic recommended posture and optimize an actuation parameter(s) to drive the wearer's kinematics to match (i.e., maximize similarity to or minimize variance from) a desired normative profile. Possible metrics include correlation with user data or percent difference in key points or metrics (e.g. torso angle during lift, distance of the object to the COM).

Similarity of joint kinematics to baseline data: An exemplary optimization approach may evaluate how similar a wearer's kinematics are to the baseline kinematics recorded when the user is either wearing the system in transparent mode (without applying assistance) or when not wearing the system at all and optimize an actuation parameter(s) to drive the wearer's kinematics to match (i.e., maximize similarity to or minimize variance from) baseline kinematics or posture. Possible metrics include correlation with user data or percent difference in key points or metrics (e.g. torso angle during lift, distance of the object to the COM).

Joint kinetics: An exemplary optimization approach may seek to reduce or minimize the biological torque that the targeted joint(s) produce. The biological joint can be measured or estimated by combining kinematic measurements with a ground reaction force measurement or estimation. A sample device may integrate a pressure sensing insole to measure or estimate joint torque or power. Possible kinetic metrics include minimizing peak or RMS joint torque, minimize peak or RMS joint power.

Time integral of muscular activity: This is the integral with respect to time of the muscular activity. An exemplary optimization approach may seek to optimize an actuation parameter(s) to reduce or minimize the overall activity of the muscle(s) during an activity. For instance, one may desire to reduce or minimize the overall effort of back muscles when lifting an object or when holding a static posture or minimize the overall effort of shoulder muscles when doing over-head work.

Peak muscular activity: Similar to time integral of muscular activity, but targeting peak muscle activity. This may be chosen over or in combination with time integral of muscular activity in some applications, for instance for activities in which the peak muscular activity may pose a risk of injury or in which the peak muscle activity is higher than a person is able to perform for a long time (elderly applications, industrial workers, consumer applications).

Similarity of muscle activity profile to baseline or normative data: An exemplary optimization approach may evaluate how similar a wearer's muscle activity are to the baseline measurements recorded when the user is either wearing the system in transparent mode (without applying assistance), when not wearing the system at all or based on normative data for a given activity and optimize an actuation parameter(s) to drive the wearer's kinematics to match (i.e., maximize similarity to or minimize variance from) baseline or normative muscle activity.

Similarity of muscle activity of muscles that are not assisted by device: An exemplary optimization approach may evaluate how similar a wearer's muscle activity (e.g. RMS and/or peak) are to the baseline measurements recorded when the user is either wearing the system in transparent mode (without applying assistance), when not wearing the system at all or based on normative data for a given activity and optimize an actuation parameter(s) to drive the actuation to match (i.e., maximize similarity to or minimize variance from) baseline or normative muscle activity. For instance, during lifting with a device that assists the back muscles, a controller 240 may measure or estimate the muscular activity of the abdominal muscles to avoid undesired interferences with those muscle groups that are not being assisted by the device.

Ergonomics metrics and indexes: the ergonomics field in industry has defined multiple ways of estimating the risk of injury when performing a task. A controller 240 may use these equations or indexes to minimize the risk of injury while providing assistance with robotic apparel, exosuits or exoskeletons. As an example NIOSH defines the lift to evaluate how significant is the risk of performing a lift. This equation is a function of the horizontal and vertical distance of the body with respect to the object, asymmetry angles when lifting the object and frequency and duration of each activity among other factors. The resulting index will be used as part of the objective to minimize the risk of injury, any change in kinematics/dynamics compared to baseline will change the lift index. An algorithm may evaluate this index as the person is performing a task and compare it with baseline or normative data to minimize.

Energy Expenditure: Quantifies the energy consumption or level of effort when performing a task. A system that measures this variable may use this as an objective function to an algorithm to reduce the metabolic effort of a given task (e.g., lifting an object, holding a static posture, pushing, lifting, grasping an object, etc.). This metric may be useful for a wide variety of applications such as healthy people doing strenuous tasks, impaired individuals, the elderly, etc. This objective function may also be referred to herein as metabolic effort.

Stability during lifting: An exemplary optimization approach may seek to optimize an actuation parameter(s) to maximize joint stability or overall body stability during lifting or holding static postures. Stability metrics can be used as part of an optimization strategy to improve stability during lifting or other tasks for healthy individuals performing complex or strenuous tasks.

Joint range of motion: An exemplary optimization approach may seek to optimize an actuation parameter(s) to maximize the range of motion for a particular joint. The range of motion is typically defined as the difference between the maximum and minimum angle of a given joint in a given plane of motion, but the maximum and minimum angles may also be of interest for optimization. For example, the torso or hip range of motion in the sagittal plane or in the dorsal plane during an activity such as lifting.

Time to perform a repetitive task: An exemplary optimization approach may seek to optimize an actuation parameter(s) to minimize the time required to perform a repetitive task such as lifting loads, moving packages from one place to another in a factory environment, etc.

Similarity of center of pressure location of the foot to normative data: An exemplary optimization approach may seek to optimize an actuation parameter(s) to maximize similarities (or minimize variance) between a trajectory of the wearer's center of pressure and that of a desired baseline or normative trajectory during lifting. Center of pressure may be measured using force plates, or estimated by wearable sensors 230, such as an instrumented shoe insole.

Blood oxygenation in muscles: Related to pulse oximetry commonly used in clinical practice, near-infrared spectroscopy (NIRS) is a method of estimating how much blood in a muscle is oxygenated. This measure is directly related to the metabolic demand of that muscle, so this metric could be used as a proxy for evaluating related objective functions (e.g., energy expenditure, locomotive efficiency). An exemplary optimization approach may seek to optimize an actuation parameter(s) to maximize blood oxygenation, for example, in situations where it is desired to minimize energy expenditure or maximize efficiency.

Muscle contraction/strain and tendon strain: Wearable exosuits and exoskeletons can affect how muscles contract and muscle/tendons strain under load. An exemplary optimization approach may seek to optimize an actuation parameter(s) to maximize or minimize these physiological parameters, or to limit them to certain values or ranges. In addition, contraction/strain is often related to the energetic metabolic demand of the corresponding muscle, so this metric may be a suitable proxy for evaluating related objective functions (e.g., energy expenditure, locomotive efficiency). An exemplary optimization approach may seek to optimize an actuation parameter(s) to minimize muscle contraction/strain and tendon strain, for example, in situations where it is desired to minimize energy expenditure or maximize efficiency. Ultrasound or acoustic imaging may, in some embodiments, be used as a way to non-invasively measure of tissue movement.

Exemplary optimization approaches may utilize information associated with providing physical assistance to the wearer in evaluating these objective functions. For example, in some embodiments, the controller 240 may evaluate these objective functions using direct measurements of the objective functions themselves, while in other embodiments, the controller 240 may evaluate these objective functions by calculating or approximating the objective function using various measurements of related metrics from one or more wearable sensors 230 or other measurement equipment. In various embodiments, representative information associated with these objective functions may include any such information described above, as well as one or a combination of an angle, velocity, or acceleration of one or more joints; a force, torque, or power applied by the robotic apparel, exosuit or the exoskeleton; a type of physical activity in which the wearer is engaged; a posture of the wearer; an energy expenditure of the wearer; and an interaction of the wearer's body with a surrounding physical environment.

Representative sensors 230 for measuring said information for evaluating the objective function may include, in various embodiments, inertial measurement units (IMUs), accelerometers, gyroscopes, encoders, resolvers, strain sensors 230, heart rate monitors, pulmonary gas exchange systems, electromyography, pressure sensors 230 (e.g., in a footwear insole for measuring GRFs), amongst other suitable sensors 230.

Objective Functions and Proxies Associated with Interactions Between the Wearable Device and the Wearer As referenced above, many objective functions associated with wearable device 100 performance relate to interactions between the exosuit, exoskeleton, or robotic apparel, and the wearer. As further described below, such interactions may relate to things like wearer comfort and the effectiveness of the wearable system in transmitting loads to the wearer, amongst others. Representative examples of several such objective functions are provided below, along with biomechanical context for how each may be maximized or minimized to benefit the wearer.

Displacement of the wearable device 100: An exemplary optimization approach may seek to optimize an actuation parameter(s) to minimize displacement (or maximize alignment) of the wearable device 100 (including individual components thereof, such as anchor members 110) on the body of the wearer. Displacement of the wearable device 100 components with respect to the body may be measured by using wearable sensors 230 such as IMUs. For instance by using two IMUs, one of them IMU integrated in a wearable device 100 component and another sensor attached to the body and integrating measurements such as the relative speed or acceleration. For cable-driven systems in which the cable anchors on both sides of the joint, relative displacement may be estimated by combining the of exposed cable (e.g. by an encoder) and a measurement of the joint position by using wearable sensors 230 such as IMUs; the amount of exposed cable is a function of the cable required to track the joint movement, the stiffness of the wearable device 100 and the compliance of the interface. If the displacement is measured at points of the gait cycle in which there is no active force applied to the person (only pretension or tracking without applying force), the stiffness of the wearable device 100 will have no effect on the cable travel and therefore the displacement may be calculated by combining the cable movement due to the joint angle (translated to displacement by multiplying by the distance from the joint center of rotation and the cable, which could be a constant or an input to the device) and the total exposed cable measurement. Finally, For cable-driven systems in which the cable anchors on both sides of the joint, relative displacement may be estimated by using the motor encoder and comparing the exposed cable at repeatable points over multiple repetitions such as standing straight giving an estimation of how much the wearable device 100 components has displaced with respect to the body over time.

Comfort: An exemplary optimization approach may seek to optimize an actuation parameter(s) to maximize comfort of the wearer (or to minimize a particular discomfort experienced by the wearer). In various embodiments, potential discomfort can be automatically detected by the controller 240 by, for example, monitoring forces in the wearable device 100 or by monitoring pressures between the wearable device 100 and the wearer, and comparing these forces and/or pressures to levels of each that are known to cause discomfort in the individual wearer, or across a representative sampling of wearers. In cases where the wearable device 100 is, for example, generating forces in excess of comfortable levels (or with improper timing that causes discomfort), a representative optimization approach may seek to optimize an actuation parameter to reduce those forces to within an acceptable range (while still, perhaps, maximizing the level of forces generated within the acceptable range). Similarly, in cases where an interaction between the exosuit or the exoskeleton and the wearer generates an excess level of shear forces (which can cause chafing and other discomfort on the skin), a representative optimization approach may seek to optimize an actuation parameter to reduce those shear forces to within an acceptable range (while still, perhaps, maximizing the level of forces generated within the acceptable range). In practice, this may involve reducing the level of force generated by the wearable device 100, or perhaps increasing a compressive force within the wearable device 100 to better anchor the troubling anchor member 110 to the underlying body part. Similar approaches may be taken to optimizing an actuation parameter to reduce pressure points generated by an interaction of the wearable device 100 and the wearer, as further described below. Additionally or alternatively, comfort may be self-reported through a GUI, hand-held device, voice, pressure measurements, or the like.

Pressure at the interface: An exemplary optimization approach may seek to optimize an actuation parameter(s) to minimize pressures applied to some areas of the wearer's body that may be sensitive to discomfort caused by the textile or rigid interface with the wearable device 100. This may maximize comfort (or minimize discomfort) while, for example, still maximizing assistance within those comfort levels. This pressure may be affected by actuation parameters such as the timing, rate, jerkiness of the profile or magnitude of assistance.

Load transfer along the wearer's body: In some cases, it may be advantageous to utilize the wearable device 100 to help transfer loads away from one area of the wearer's body to another, for example, to help mitigate injuries. An exemplary optimization approach may seek to optimize an actuation parameter(s) to maximize load transfer from the area of the body at issue. This may be particularly useful in situations in which the wearer is lifting a heavy load and is thus susceptible to back injury. In such an embodiment, the controller 240 may seek to optimize an actuation parameter(s) to minimize loads on the spine of the wearer. This may, in an embodiment, be accomplished by optimizing the actuation parameter(s) to maximize force transfer to other areas of the body such as the hips, torso or legs.

Actuator 120 force: An exemplary optimization approach monitor interactions between the wearable device 100, and upon detecting a large generated by the interaction, optimize an actuation parameter(s) to minimize a force generated by the actuator 120, so as not to deliver additional force that may cause discomfort or injury. In an embodiment, the controller 240 may, in optimizing the actuation parameter(s), also seek to keep other biomechanical constraints constant.

Exemplary optimization approaches may utilize information associated with associated with an interaction between the wearable device 100 and the wearer in evaluating these objective functions. For example, in some embodiments, the controller 240 may evaluate these objective functions using direct measurements of the objective functions themselves, while in other embodiments, the controller 240 may evaluate these objective functions by calculating or approximating the objective function using various measurements of related metrics from one or more wearable sensors 230 or other measurement equipment. In various embodiments, representative information associated with these objective functions may include any such information described above, as well as one or a combination of a shearing or compression force generated between the wearer and the exosuit or the exoskeleton, and a position of the exosuit or the exoskeleton on the wearer.

Representative sensors 230 for measuring said information for evaluating the objective function may include, in various embodiments, load cells, force sensors, torque sensors, and pressure sensors, amongst other suitable sensors.

Objective Functions and Proxies Associated with Operation of the Wearable Device As referenced above, many objective functions associated with wearable device 100 performance relate to the operation of the wearable device 100 itself. As further described below, such interactions may relate to things like electrical power consumption, overheating, and consistency in actuator/actuation system functionality, amongst others. Representative examples of several such objective functions are provided below.

Electrical Power Consumption: An exemplary optimization approach may seek to optimize an actuation parameter(s) to minimize electrical power consumption. Electrical power consumption may be measured by combining electrical current draw measurement (via an integrated current sensor) and voltage (via an integrated voltage sensor), by multiplying those measurements electrical power can be calculated, the average power consumption over time will give an estimation of how much electrical power is consumed for a given activity. Another embodiment may use remaining battery voltage to estimate how much battery is left or how much battery has been consumed so far in the system.

Consistency of Assistive Forces: An exemplary optimization approach may seek to optimize an actuation parameter(s) to maximize consistency (or minimize variance) between assistive forces generated in the wearable device 100. If an wearable device 100 aims to provide forces that are consistent in terms of peak force over multiple repetitions, a measurement of consistency may be the variance of the peak force or other features in the force profile that have to remain consistent over multiple repetitions. Forces may be measured by using wearable sensors 230 such as force sensors or load cells. Another embodiment may define consistency of assistive forces as the root mean square deviation of the measured force and the desired force profile, maximizing consistency of this difference over multiple repetitions may be used as an objective for these systems.

Maximum and average actuator position, velocity, acceleration, or jerk: Subject to kinematic or kinetic constraints measured as outlined above, it may be of interest to minimize these metrics related to the level of force that the wearable device 100 is pulling. For example, an exemplary optimization approach could find the optimal parameter or set of parameters that minimize maximum cable acceleration without impacting the lift index.

Temperature: An exemplary optimization approach may seek to optimize an actuation parameter(s) to minimize a temperature of one or more components of the wearable device 100. Like other objective functions described herein, minimizing the temperature may, in an embodiment, mean ensuring the temperature does not exceed an upper threshold of a predetermined range.

Exemplary optimization approaches may utilize information associated with associated with operation of the wearable device 100 in evaluating these objective functions. For example, in some embodiments, the controller 240 may evaluate these objective functions using direct measurements of the objective functions themselves, while in other embodiments, the controller 240 may evaluate these objective functions by calculating or approximating the objective function using various measurements of related metrics from one or more wearable sensors 230 or other measurement equipment. In various embodiments, representative information associated with these objective functions may include any such information described above, as well as one or a combination of a current or a voltage used during actuation of the exosuit or the exoskeleton; a temperature of one or more components of the exosuit or the exoskeleton; a force generated by the at least one actuator 120; a force delivered to the exosuit or the exoskeleton; and a force, torque, or power delivered to the wearer of the exosuit or the exoskeleton.

Representative sensors 230 for measuring said information for evaluating the objective function may include, in various embodiments, current sensors, voltage sensors, thermistors, encoders and resolvers (e.g., for measuring actuator position, speed, and acceleration), amongst other suitable sensors.

Weighted Objective Functions and Proxies

As alluded to in several of the above examples, an objective function (or proxy function) needs not to represent a single variable associated with the motion or biomechanics of a wearer, but can combine multiple optimization targets. Multiple single-variable objective functions can be combined into a single one through different methods, such as weighted averaging, which allows to calibrate the relative importance of each component of the objective function. Eq. 1 below shows an example implementation of weighted sum of multiple objective functions:

$$F = \alpha_1 x_1 + \alpha_2 x_2 + \ldots + \alpha_n x_n \text{ where } \Sigma_{i=1}^{i=n} \alpha_i = 1 \qquad \text{(Eq. 1)}$$

This approach can be followed to combine the optimization of a variable associated with providing physical assistance to the wearer (e.g. peak muscle activity during lifting) with a variable associated with the efficiency of the system (e.g. battery life). Some example weightings of two or more objectives within one objective function include:

Optimizing a variable related to motion (kinematics of lift) and a variable related to the device performance (e.g. battery life of the device).

Optimizing multiple variables such as peak muscular activity, posture during an activity, battery life of the device and comfort through a weighted sum of them.

Optimizing multiple variables related to motion (e.g. difference kinematics compared to baseline) and a variable related to the interaction of the wearable device 100 and the wearer (e.g. user comfort).

Optimizing peak muscular activity of a targeted muscle without affecting the muscular activity of a key muscle that the device is not assisting.

Optimizing multiple variables related to motion (e.g. stability and velocity of performing a task).

Optimizing an index that evaluates the risk of injury when performing a task (e.g. the lift index) and the time to perform an activity.

Optimizing time to complete a task and peak EMG activity of a targeted muscle.

Figure 8:
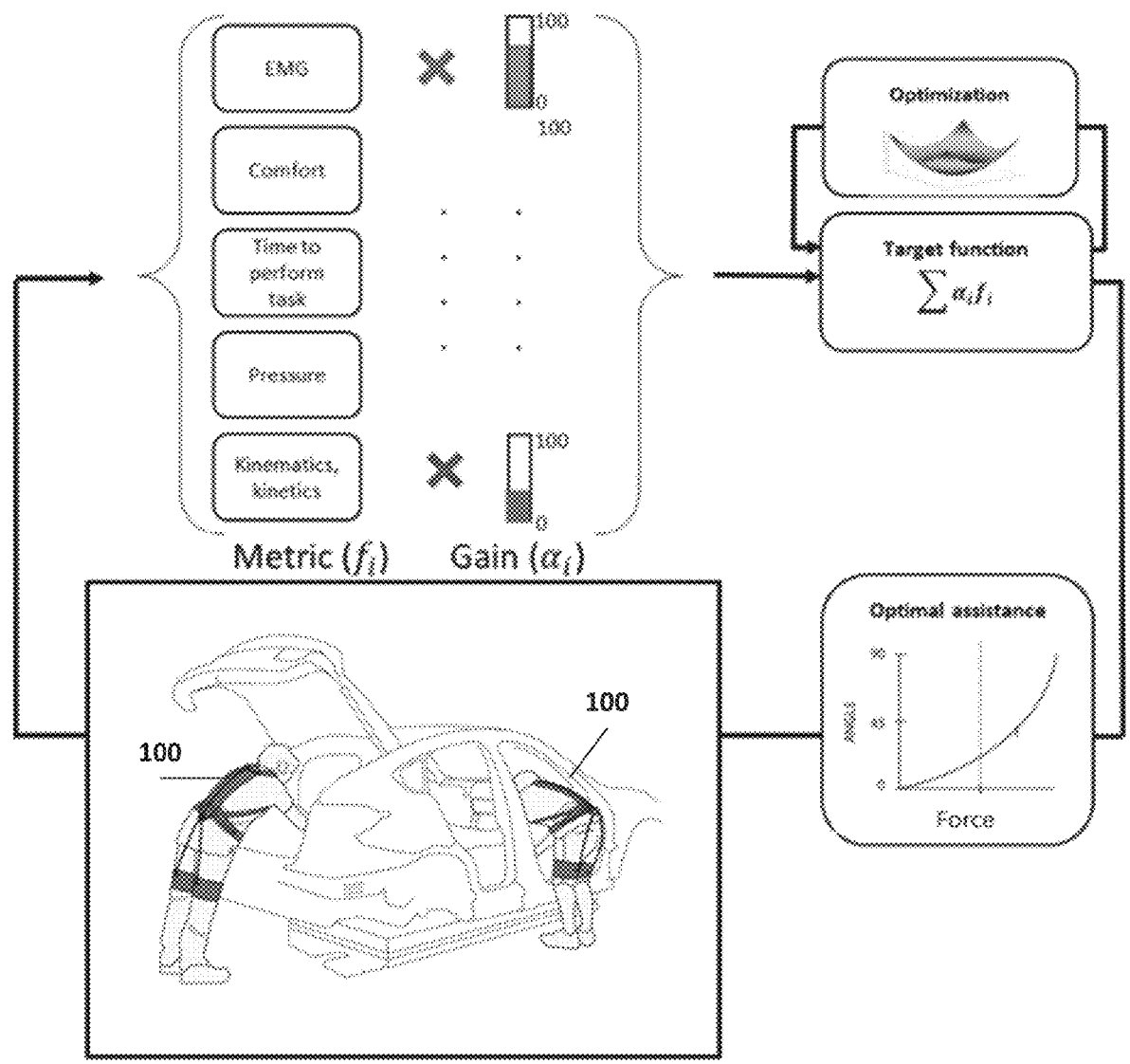
FIG. 8 illustrates representative approaches for optimization control of wearable devices.

The importance of each metric may be different depending on the application. An example of this concept using weighted sum of objectives for impaired individuals is shown in FIG. 8. For healthy population, individual users may be able to change these settings manually.

Optimization Approaches, Generally

Systems and methods of the present disclosure provide for optimizing one or a combination of these actuation parameters to maximize or minimize a selected objective function. Approaches seeking to optimize a single actuation parameter (e.g., finding the optimal actuation onset timing) may be referred to herein as single-parameter optimization, while approaches seeking to optimize a combination of actuation parameters (e.g., finding the optimal combination of actuation onset timing and actuation peak timing) may be referred to herein as multi-parameter optimization. As will be described further below, a number of factors may influence whether a single-parameter or multi-parameter optimization approach is used including, without limitation, the biomechanics of the wearer, the population wearing the wearable device 100, the relative effect of each actuation parameter on the objective function, required optimization time, measurement noise, wearer adaption and available computing power, as further described below.

In various embodiments, known (or modified) methods for optimizing variables (e.g., gradient descent, Bayesian, brute force, and simulated annealing) may be used or otherwise modified to optimize the targeted actuation parameter(s) to maximize or minimize a selected objective function. Of course, the best mathematical method for optimizing the actuation parameter(s) may vary depending on a number of factors including, without limitation, the nature of the objective function landscape relative to the actuation parameter(s) to be optimized, the biomechanics of the wearer, the population wearing the wearable device 100, the relative effect of each actuation parameter on the objective function, required optimization time, measurement noise, wearer adaption and available computing power, as further described below.

In one embodiment, a simplified gradient descent approach may be employed to optimize the actuation parameter(s) to maximize or minimize the objective function. A gradient-descent approach typically leads to convergence, and is often simple and low in computational burden, making it well suited for running on inexpensive processors 250 or when running other computationally-burdensome processes on shared hardware. In one such embodiment, the controller 240 may be configured to determine whether the objective function increased or decreased from one or an average of preceding evaluations of the objective function, and in response, adjust the actuation parameter in a same or different direction depending on whether it is sought to maximize or to minimize the objective function. Likewise, when multiple actuation profiles are tested before adjustments are made, the controller 240 may be configured to compare evaluations of the objective function for each actuation profile to determine which produces the highest or lowest evaluation of the objective function, and in response, generate another set of actuation profiles in which the values of the actuation parameters being optimized have been adjusted according to a derivative of the objective function evaluations associated with the former set of actuation profiles. A gradient-descent approach may optimize the actuation parameter(s) to a local maximum/minimum or a global maximum/minimum depending on the objective function landscape (i.e., relationship between the objective function and the parameter(s) being optimized). For example, in situations when the objective function landscape is substantially convex in shape and the differentiation of the landscape is differentiable and bounded, convergence to the global solution can be achieved. Since the landscape of the objective function is convex, all local minima are also global minima, so in this case gradient descent can converge to the global solution. A gradient-descent approach may optimize the actuation parameter(s) to a global maximum/minimum of the objective function. In other situations, such as those in which the objective function landscape includes multiple peaks or valleys, the gradient-descent approach may optimize the actuation parameter(s) to either a local maximum/minimum or to a global maximum/minimum depending on where the optimization starts, amongst other relevant factors. In such situations in which the landscape is non-convex, gradient descent is more likely to find a local optimum since gradient descent performs a local search comparing points that are relatively close to each other, other approaches that perform a global search of the landscape such as the Bayesian approach described below are more likely to find a global optimum in those cases. However, the low-computation requirements of gradient descent and guaranteed convergence may make this method attractive even with its limitations in some cases. For instance, finding a local optimum that improves upon an initial setting of the device for a specific person or activity may be attractive in some applications. Gradient descent method is particularly applicable in situations in which the noise to signal ratio is very low and the objective is measured in a repeatable way, if the noise of the measurement is high, even with a convex landscape, gradient descent may converge to points in the landscape that are non-optimal due to noise or unrepeatability in the measurements.

In other embodiments, a Bayesian approach may be used to optimize the actuation parameter(s) for maximizing or minimizing the objective function. A Bayesian approach is typically sample-efficient, allowing it to explore the objective function landscape relatively quickly. This feature can make a Bayesian approach well-suited for finding and optimizing the actuation parameter(s) to a global maximum/minimum in more complex objective function landscapes, and tends to make a Bayesian approach relatively more tolerant of noise in evaluations of the objective function than some other approaches. In one such embodiment, a mathematical correlation between the actuation parameter(s) and the objective function can be defined by actuating the wearable device 100 according to several actuation profiles having different baseline values of the actuation parameter(s) being optimized and mapping corresponding evaluations of the objective function for each. From this, the controller 240 may determine a candidate value(s) of the actuation parameter(s) for maximizing or minimizing the objective function. The candidate value(s) may be tested and evaluated, and the mathematical correlation updated, until the controller 240 converges on an optimized value of the actuation parameter(s), or until some other suitable termination criteria is met. In an embodiment, the process of defining the mathematical correlation and identifying candidate values of the actuation parameter may involve generating a posterior distribution (e.g., via a Gaussian process, in an embodiment) and utilizing a probabilistic model (e.g., a Bayesian approach) to identify a candidate value(s) of the actuation parameter based on the posterior distribution. Like a gradient-descent approach, a Bayesian approach may optimize the actuation parameter(s) to a local maximum/minimum or a global maximum/minimum depending on the objective function landscape and where the optimization starts, amongst other relevant factors. However, Bayesian optimization is more likely to find a global optimum since it performs a global search of the landscape based on the posterior distribution as opposed to only looking locally and comparing points that are relative close to each other like the gradient descent does. A Bayesian optimization approach is therefore particularly useful in situations in which the landscape of the objective function is complex, when there are multiple parameters to be optimized and therefore search efficiency is important or when the measurements of the objective function are noisy (e.g. metabolic measurements).

Of course, it should be recognized that these are merely illustrative examples, and that any suitable mathematical approach may be used to optimize any number of actuation parameters for maximizing or minimizing an objective function affected by the selected parameter(s).

In some embodiments, the optimization may run until the objective function is truly maximized or minimized; however, in other embodiments, the optimization process may be further subject to additional or alternative termination criteria. In various embodiments, the optimization algorithm may be configured to terminate when one of the following predefined termination criterion occurs: (i) a difference between evaluations of the objective function for successive adjustments to the at least one parameter of the at least one actuation profile falls below a predetermined threshold, (ii) a difference between successive adjustments to the at least one parameter of the at least one actuation profile falls below a predetermined threshold, (iii) a predefined amount of time since the start of optimization has been exceeded, (iv) the wearer exceeds a predefined number of repetitions since the start of optimization, and (v) a termination command issued by the wearer.

Various exemplary parameters related to biomechanics of the wearer, as explained above, include muscular activity of a targeted muscle (e.g. time integral or peak muscular activity). For example, the parameter can relate to minimizing muscular activity for a given task to reduce fatigue of specific muscles when performing a task. Other exemplary parameters include but are not limited to minimizing time to complete a repetitive task, joint kinematics or kinetics, joint range of motion, metabolic effort, and maximizing stability when performing a task. Objective functions related to interactions between the robotic apparel, wearable device 100 and the wearer include but are not limited to load transfer, pressure at the interface, and comfort.

A variety of sensors 230 can be used to measure various reactions of the body and interactions with the wearable system, as explained above. In some embodiments, sensors 230 that are configured to measure human biomechanics can include but are not limited to Inertial Measurement Units (IMUs), accelerometers, gyroscopes, encoders, resolvers, and strain sensors 230 for measuring joint angles, speed and acceleration, a heart rate monitor for measuring heart rate, a pulmonary gas exchange system for measuring metabolic effort, electromyography, and pressure sensing insoles to measure ground reaction forces and instrumented treadmill to measure ground reaction forces. Sensors 230 that can be used to measure wearer-system interaction, including force and pressure, include but are not limited to load cells, force sensors, and pressure sensors. Sensors 230 that can be used to measure device metrics include but are not limited to current sensors, voltage sensors, thermistors, and encoders and resolvers to measure motor position, speed and acceleration.

FIG. 8 illustrates representative approaches for optimization control of wearable devices 100. Detection of movement initialization: For some applications, the optimization algorithm may need to detect when an activity starts and when it ends in order to know that data collected during that repetition can be used to evaluate an objective function. For instance for a device that supports the back during lifting, the optimization algorithm may need to segment the lift into different phases such as: initialization of movement, move to reach for an object, grab an object and move to the end pose until the lift is finalized. An optimization algorithm may evaluate an objective function for each of these phases. For instance, an optimization algorithm may use on-board motions sensors 230 such as inertial measurement units to detect a change in e.g. joint angle, speed or acceleration to segment the motion and evaluate an objective function. The algorithm will then detect a change in joint angle, speed or acceleration to detect movement initialization to start to evaluate an objective function and measure or estimate the objective metrics until the person has finalized that movement—for instance, by looking at when joint acceleration changes direction or is equal or close (less than a threshold) to 0—. Finally, when the acceleration or speed changes the objective function will be evaluated as the user is going to the final pose until the user stops the movement. This will be registered by the optimization algorithm as one repetition of the movement and evaluate the objective function, decide next set of parameters that will be tested as candidate optimal assistance for the next repetition of the movement.

As an example, a control algorithm may consider different sub-group of activities and find a set of parameters that either maximize or minimize an objective function for each of those activities.

The different key motions that the device supports may be classified into sub-groups: For instance, for a device that assists the back joint, these different sub-groups may be: lifting an object in front while keeping knees straight (stoop lifting), lifting an object in front while bending knees (squat lifting), lifting object to each side following a twisting motion of the trunk with a stoop or squat technique (common motions in multiple industries such as construction, delivery, logistics, military logistics, manufacturing, etc.), holding a static posture at different trunk angles (common posture for surgeons, caregivers, manufacturing industries, etc. that results in strain to the back and ultimately may lead to injuries).

A classification algorithm may use onboard sensors 230 such as motion, force, pressure sensors 230 to classify that activity into a subgroup. For instance, with reference to FIG. 9, IMUs may be used to detect when a movement starts (change of joint acceleration or speed) and the direction of the movement—e.g. torso is bending and/or twisting to define whether the user is executing a motion in the sagittal plane (e.g. lifting an object in front of the user) or whether the torso is bending and twisting (e.g. lifting an object to the sides) and use this to classify the movements outlined previously. Moreover, synchronized movement of different body segments may be used to detect whether the user is doing a stoop lift (torso bending while legs straight) vs. a squat lift (torso and legs bending).

The optimization algorithm will then evaluate an objective as the user performs that motion and optimize a set of parameters.

As the user repeats activities that include motions in the above mentioned sub-groups, the parameters of the device will be automatically modified to maximize or minimize an objective function. As a result of this, a set of parameters for each of the sub-groups will be found.

When the user performs an activity, the control algorithm may detect what type of motion the user is performing and select the right set of parameters based on the sub-group that this activity falls into.

REPRESENTATIVE EXAMPLES

For further context, various non-limiting examples of wearable devices 100 of the present disclosure are presented below.

Representative Example 1A

Passive Device for Back and Hip Support

As described previously, overexertion can often lead to fatigue and musculoskeletal injuries. The back accounts for the majority of all overexertion injuries in industry. Risk factors that can lead to back injuries include lifting heavy weights, repetitive lifting, holding a static posture for a very long time or lifting weights with a body posture that is non-optimal.

Working while bending over is necessary in some environments when performing a task, however, this posture creates strain on the lower back, which can lead to chronic back pain or a more significant back injury over time.

Some examples of activities that could benefit from a device that assists the back include the following:
  a. Lifting an object—Lifting heavy objects or lifting objects in a non-ergonomically optimal posture are activities that could need back support.
  b. Holding an object or transporting it especially if the object is heavy or if the body position is non-optimal may require a lot of effort and potentially cause injuries or discomfort when performing the task so could benefit from back support devices.
  c. Lifting or changing position of a patient—in hospitals, medical personnel may need to manipulate or move those patients that need assistance. These types of activities are common and could benefit from back support.
  d. Static postures—e.g. standing, crouching or holding a position while leaning forward. If this position is sustained over a long time.

A robotic apparel system may be used to reduce the amount of effort that the back muscles must do during tasks such as lifting or holding static postures. FIG. 10 shows an embodiment of a robotic apparel in which the anchor members 110 span multiple joints this system will simultaneously assist the back 509 and hip 508 joints during tasks such as lifting, holding weight or keeping a static posture for an extended period. During these tasks the hip 508 and back 509 joints are both active, therefore, a device that assists both joints would reduce the amount of effort that a user must do.

Figure 9:
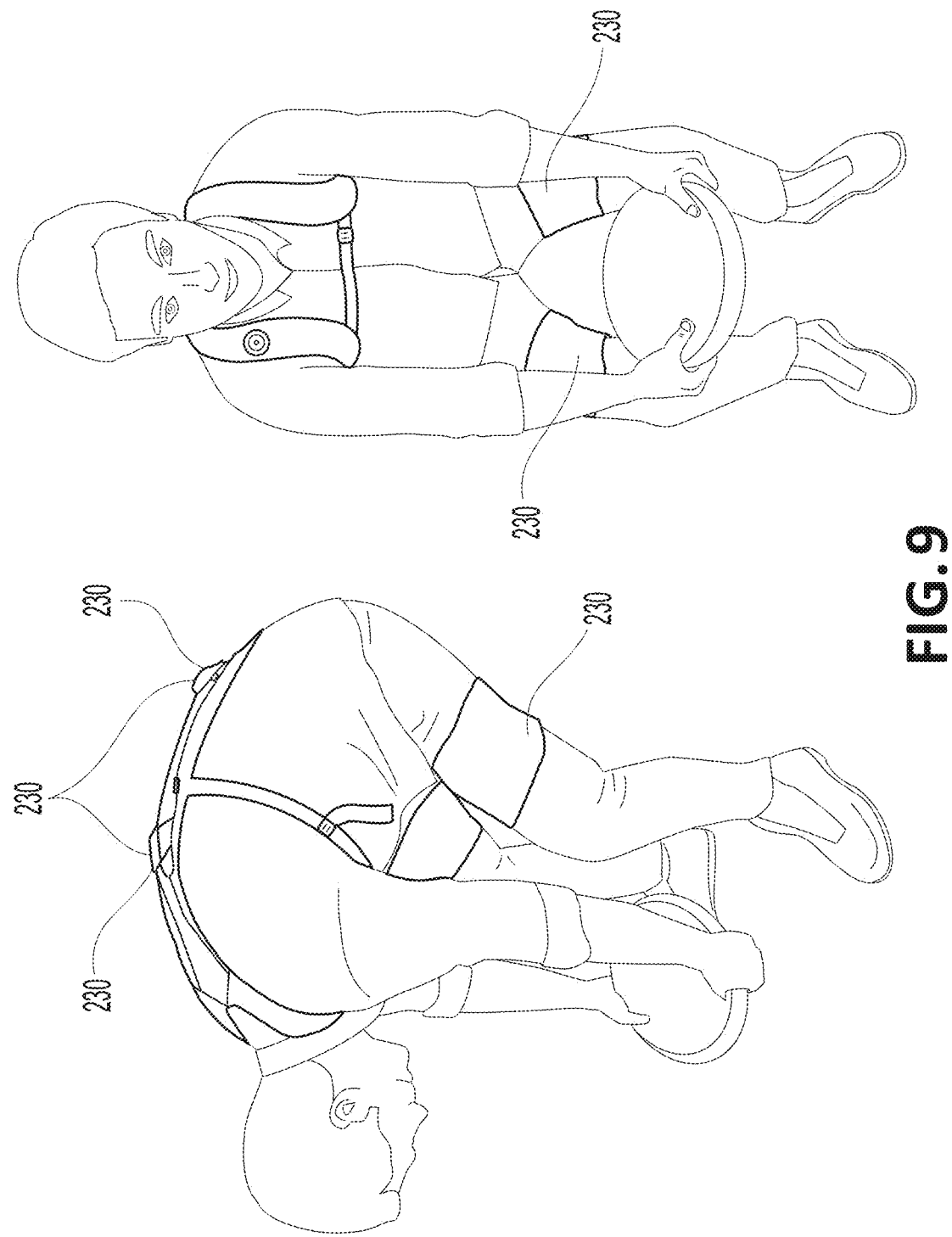
FIG. 9 shows IMUs being used to detect when a movement starts (change of joint acceleration or speed) and the direction of the movement—e.g. torso is bending and/or twisting to define whether the user is executing a motion in the sagittal plane (e.g. lifting an object in front of the user) or whether the torso is bending and twisting (e.g. lifting an object to the sides) and using this to classify the movements.

The device may comprise the following elements:

Sensors 230: the system may include sensors 230 that are able to measure or estimate the speed, acceleration or position of different parts of the body and force sensors 230 to estimate the amount of tensile force that the device is providing to the user. Movement sensors 230 such as inertial measurement units, gyroscopes, accelerometers may be used for this purpose, other examples of sensors 230 include strain sensors 230 that may deform as the user moves and this deformation may be correlated to an acceleration, speed or position of a body part. In this embodiment, the system includes four inertial measurement unit sensors 230 which can be located one on each thigh to measure the thigh movement, one on the lower back and another sensor on the upper back as shown in FIG. 9. These sensors 230 may be used to measure the movement of these body segments but also can be used to calculate joint angles by subtracting the values of the sensors 230 that are located on both sides of the joint. As an alternative to inertial measurement units, strain sensors may be used to correlate to a joint movement. The system may also incorporate force-sensing elements such as load cells, force sensors or strain gauges to measure or estimate the tensile forces that the system is providing to the body. In an embodiment, these sensors 230 may be integrated in apparel components.

Wearable device architecture: the wearable device 100 architecture provides two anchor points on both sides of the back joint. The upper part of the device attaches to the body by anchor members 110 such as shoulder straps, and the point at which both shoulder straps meet at the back of the user creates an anchor point that is located on one side of the back joint. The wearable device 100 may also include lower body anchor members 110, such as thigh anchor members 110, that wraps connect to the thighs to create an anchor point on one side of the hip joint. A load-balancing strap 112 connects to both thigh anchor members 110 creating an anchor point on the other side of the back joint. Finally, a passive element 190, in this case an elastic textile connects both anchor points to provide tensile forces that assist the user. Since these forces are located at a distance from the joint center of rotation, they provide a torque to the user that is equal to the tensile force multiplied by the moment arm. As described previously, the tensile forces cross two joints, the hip joint and the lower back to provide assistance to the user. As shown in the simplified diagram in the FIG. 10 the tensile forces create a torque around the hip joints and low back joints. As an example, when a user lifts a load, the wearable device 100 could unload the amount of effort that the user needs to do with his/her hip and back. This means that the biological muscles will need to do less effort to reduce the fatigue and mitigate risk of injury of the wearer.

Figure 11:
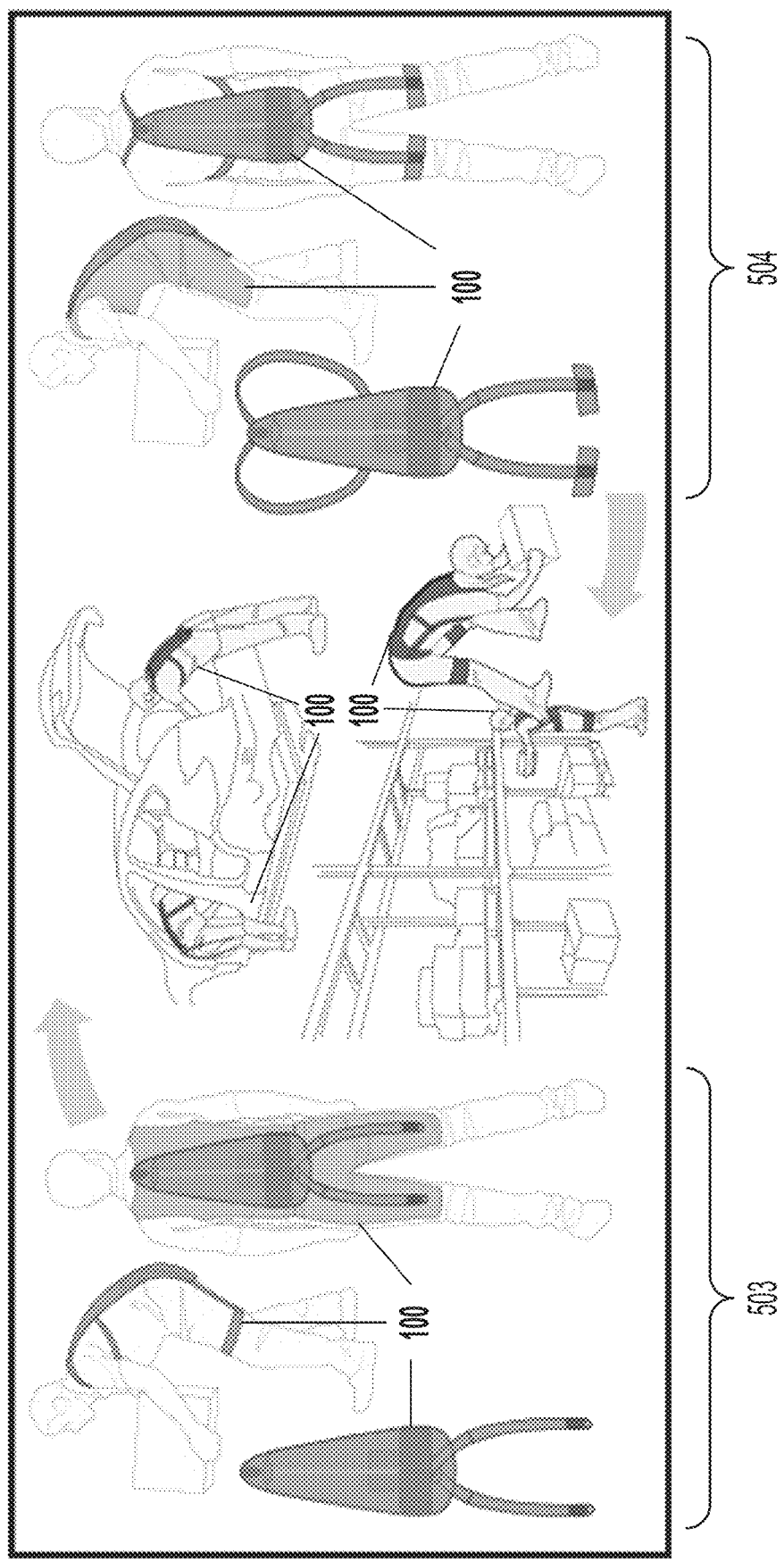
FIG. 11 and FIG. 12 illustrate several industries that the proposed device has multiple application areas.
Figure 12:
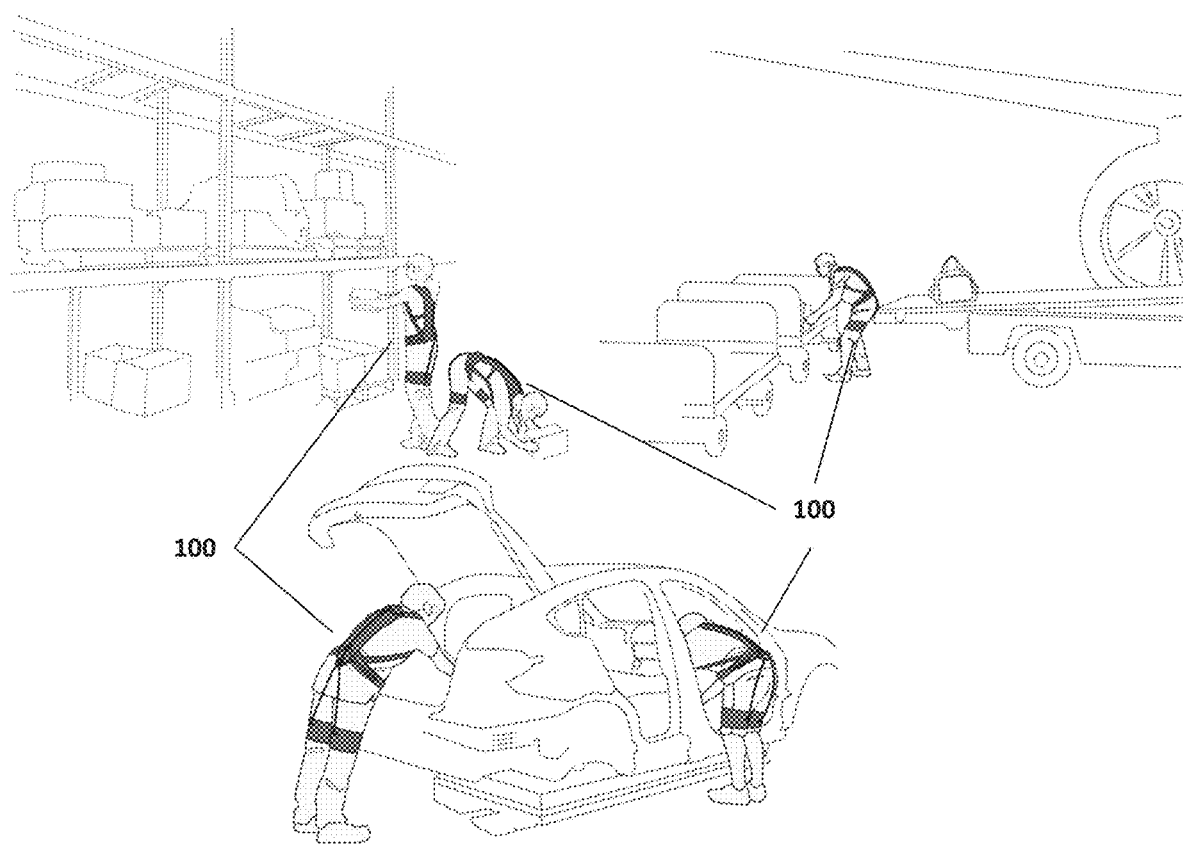

The proposed device has multiple application areas for different industries. FIG. 11 and FIG. 12 illustrate several representative applications. Furthermore, as seen in FIG. 11, the disclosed device 100 may be integrated with existing clothing, 503, or worn over clothing, 504.

One key requirement for a passive device is that it should apply forces/torques that are beneficial to the user when doing tasks such as lifting, holding static postures, etc. However, the system should be fully transparent and not provide forces that would hinder other motions such as walking, going up/down the stairs, etc. The load balancing element 212 serves this purpose.

Figure 13:
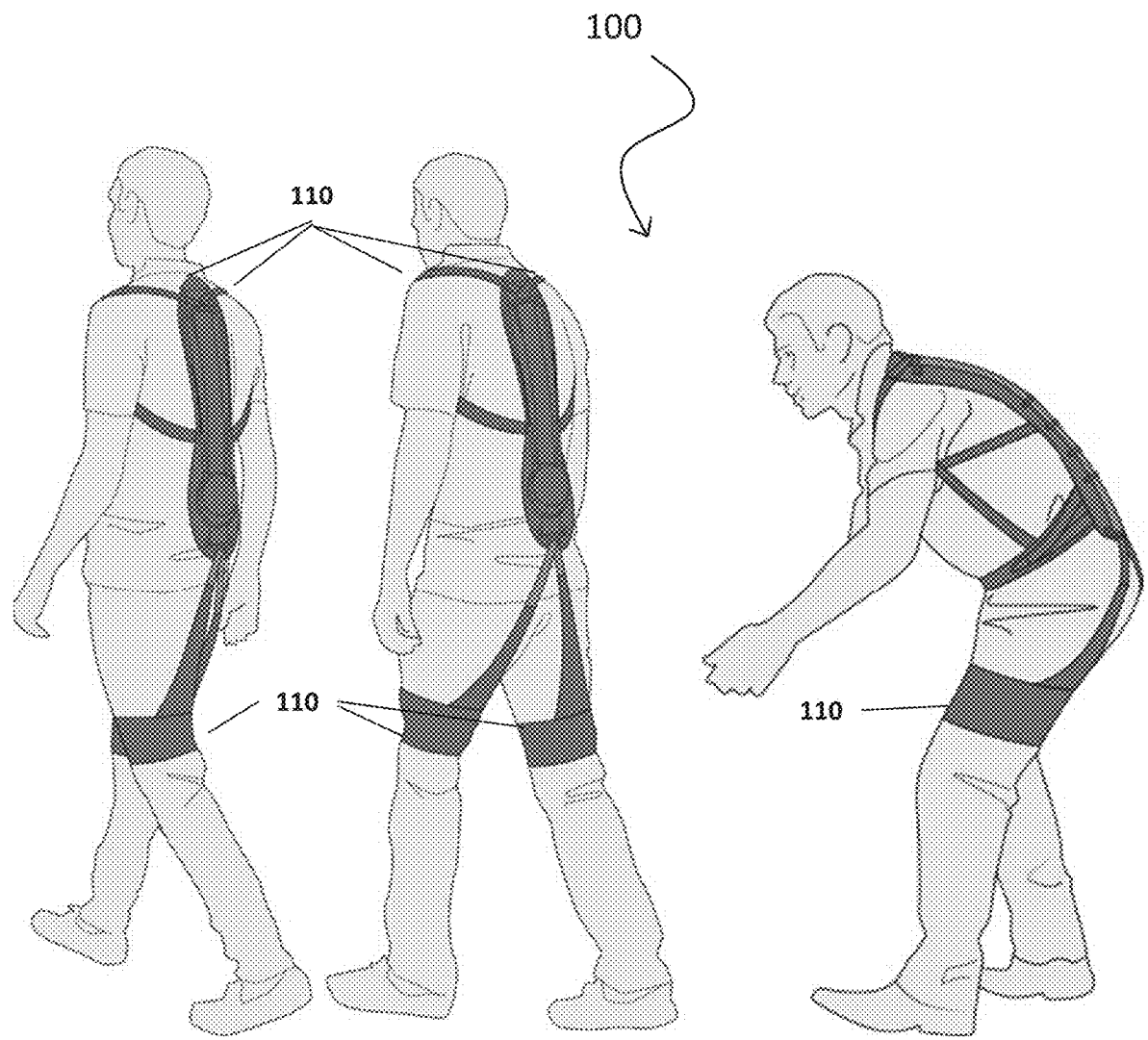
FIG. 13 is one example of the load balancing strap connecting both thigh anchor members to create an anchor point on one side of the back point.

Load balancing strap 212: As explained above, the load balancing strap 212 connects both thigh anchor members 110 to create an anchor point on one side of the back point. The load balancing element 212 (e.g., strap, ribbon, cable) may be rotatably or slidably coupled with a load balancing mechanism 215 that allows the load balancing strap 212 to either rotate or slide with respect to the connecting element 150 during wearer movement such as during walking or lifting. Representative examples of a load balancing mechanism 215 include, without limitation, a low-friction roller, bearing, pulley, low-friction buckle, and the like as shown in FIG. 13. The load balancing element 212 can then rotate or slide with respect to the load balancing mechanism 215 so that it allows the user to move the legs freely during tasks such as walking and creates tension in the wearable device 100 during tasks that involve bending the trunk and/or both legs (lifting, reaching, etc.). Moreover, this load balancing element 212 distributes the tensile forces to both legs by splitting the load to both thigh anchor members 110.

Figure 14:
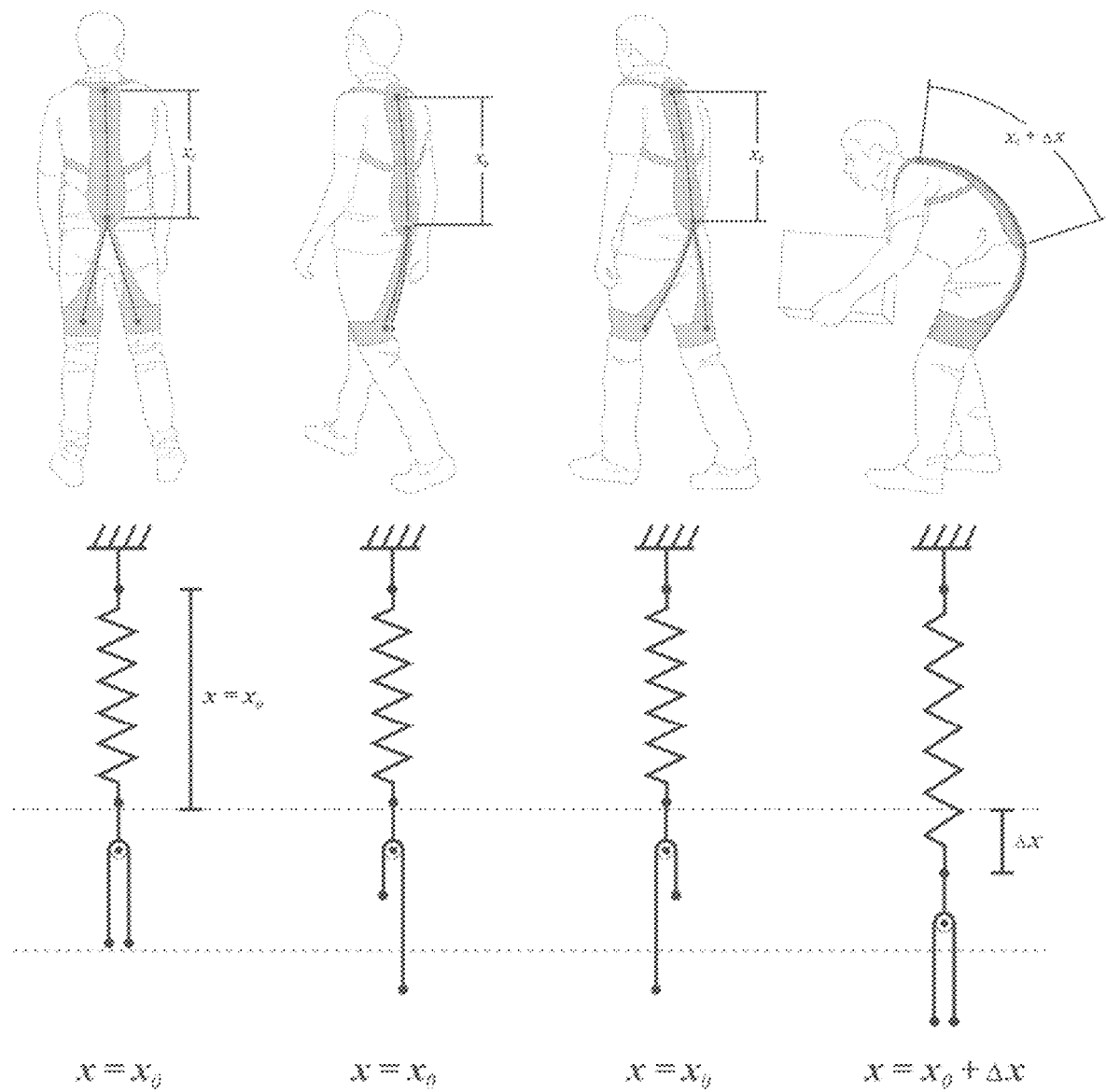
FIG. 14 illustrates the load-balancing strap functionality.

FIG. 14 summarizes the load-balancing strap 112 function. When the user is standing, the initial distance between both anchor points is defined as x0. The elastic anchor element can be dimensioned or adjusted to have a length that is equal to x0 such that it doesn't apply any tensile force to the user during standing but creates a tension as soon as the user bends the torso, the legs or both generating a tensile force.

As illustrated in the diagram, if the user is walking, the self-balancing strap 112 is free to rotate with respect to the anchor point allowing the legs to move freely but without changing the distance between both anchor points (and therefore not generating a tensile force). If this element 112 was not allowed to rotate, moving the leg forward will create a tensile force both to the leg that is trying to move forward and to the back of the user which may not be desired. As shown in FIG. 13 during walking when the wearer takes a step forward with the right leg, the strap 112 is able to rotate with respect to the anchor point therefore translating towards the leg moving forward without creating tension or reducing the amount of tension that is produced on the leg to be able to swing the leg forward freely. During midstance, when both legs are straight, the load balancing element 212 reaches the middle position in which the length between the anchor point and the thigh anchor members 110 is close to equal or slack (neutral position). As the person swings the left leg forward during swing, the balancing strap 112 will rotate with respect to the attachment point allowing the left leg to move forward freely beyond the neutral position.

When the user bends his/her torso or legs such as when reaching or lifting an object, the relative distance between both anchor points increases due to the kinematics of the user. If this distance is longer than the initial dimension of the connecting element 150, it will cause the elastic element to stretch (x=x0+Ax) and therefore provide tensile forces behind the back of the user. These forces are proportional to the elongation by the spring constant k of the elastic (F=k*Ax).

Figure 16:
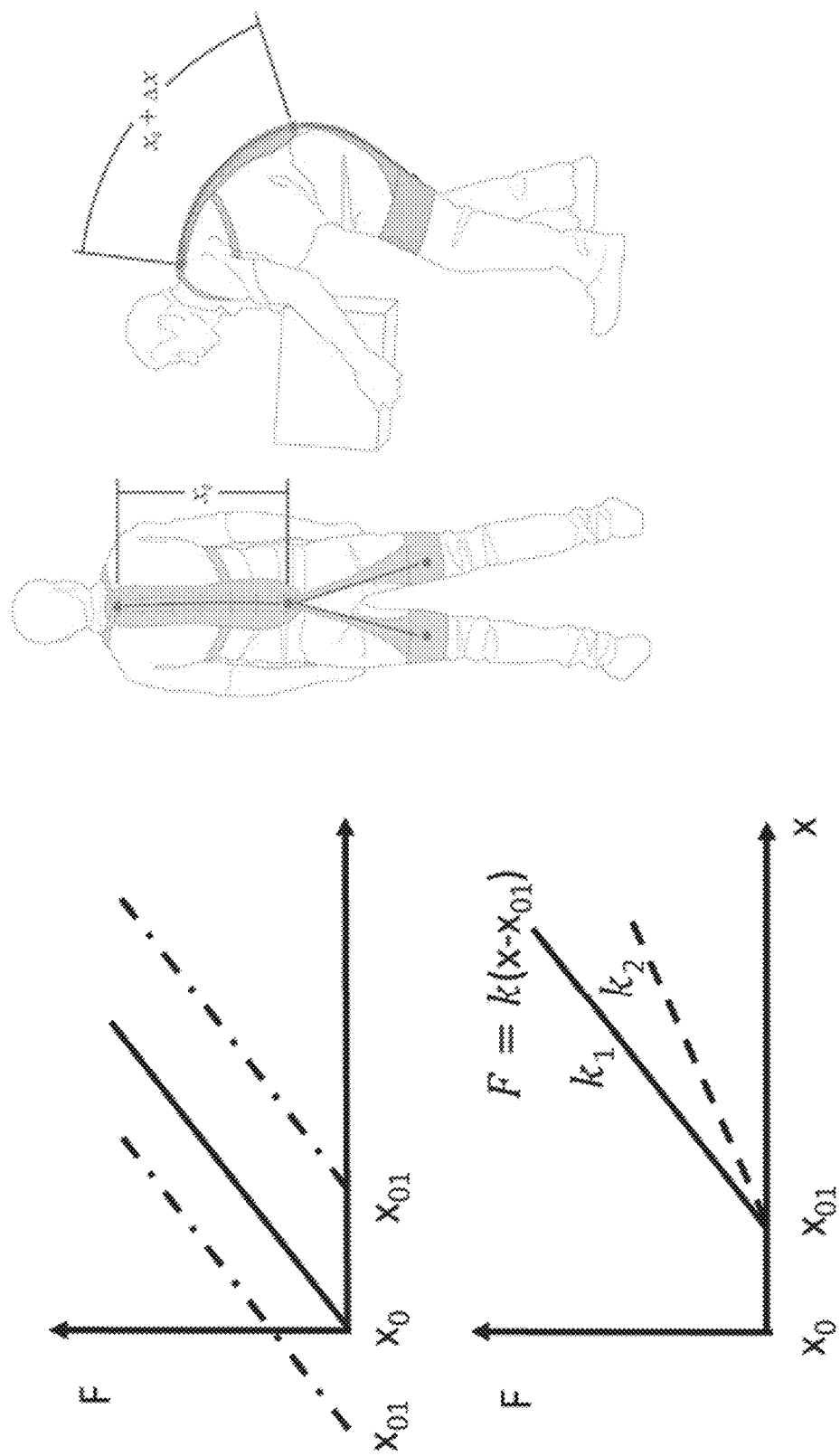

Dimensioning and choosing the passive connecting element 150 based on the desired assistance: different tasks or individuals may require or prefer different types and levels of assistance. The assistance may be tailored by defining one or a combination of parameters such as:
  a) Initial length of the passive connecting element: the initial length of the passive connecting element (x01) defines when the tensile force starts as the user bends with respect to the standing position, the distance between both anchor points when the user is standing is defined as x0. For example, if the initial length of the anchor element (x01) is equal or longer than x0 (x01>=x0), the tensile forces will be generated as the user bends the torso or the legs with respect to the standing position to do an activity. This connecting element 150 may be designed to be shorter than x0 (x01<x0) if the intent is to provide tensile forces while the user is standing. FIG. 15 and FIG. 16 show how by defining different initial lengths of the connecting elements 190, the output tensile forces can be modified. The process for adjusting or deciding the length may include: i) having a suite of connecting elements 190 with different lengths that the user can choose from, ii) having one connecting element 190 with the capability to be adjusted in length e.g. by using a buckle, Velcro® or ratcheting systems such as Boa®. iii) adjusting the initial position of the anchoring points with respect to standing while keeping the connecting element with the same length will have the same effect as changing the length of the connecting element. In the picture below a device that has a BOA ratcheting system routed to the shoulder straps at a position close to the chest that when rotated can control the distance between both anchor points on the back of the wearable device 100. In this example, as the ratchet is rotated, the anchor point located on the upper back can be displaced up and down to control the pretension of the passive element 190. The ratchet can also be clutched to hold a constant once set or unclutched so it can displace freely in order to not produce any force to the person.
  b) Impedance of the connecting element: the connecting element may have a specific impedance based on the deformation (e.g. stiffness, damping), FIG. 15 and FIG. 16 show how different stiffness values of the connecting element will provide different outputs. The process of adjusting the impedance of the connecting element may include a suite of connecting elements with different impedance values that the user or designer can choose from, multiple elements that could be connected in parallel or in series to modify the impedance (e.g. spring constant).

Figure 33:
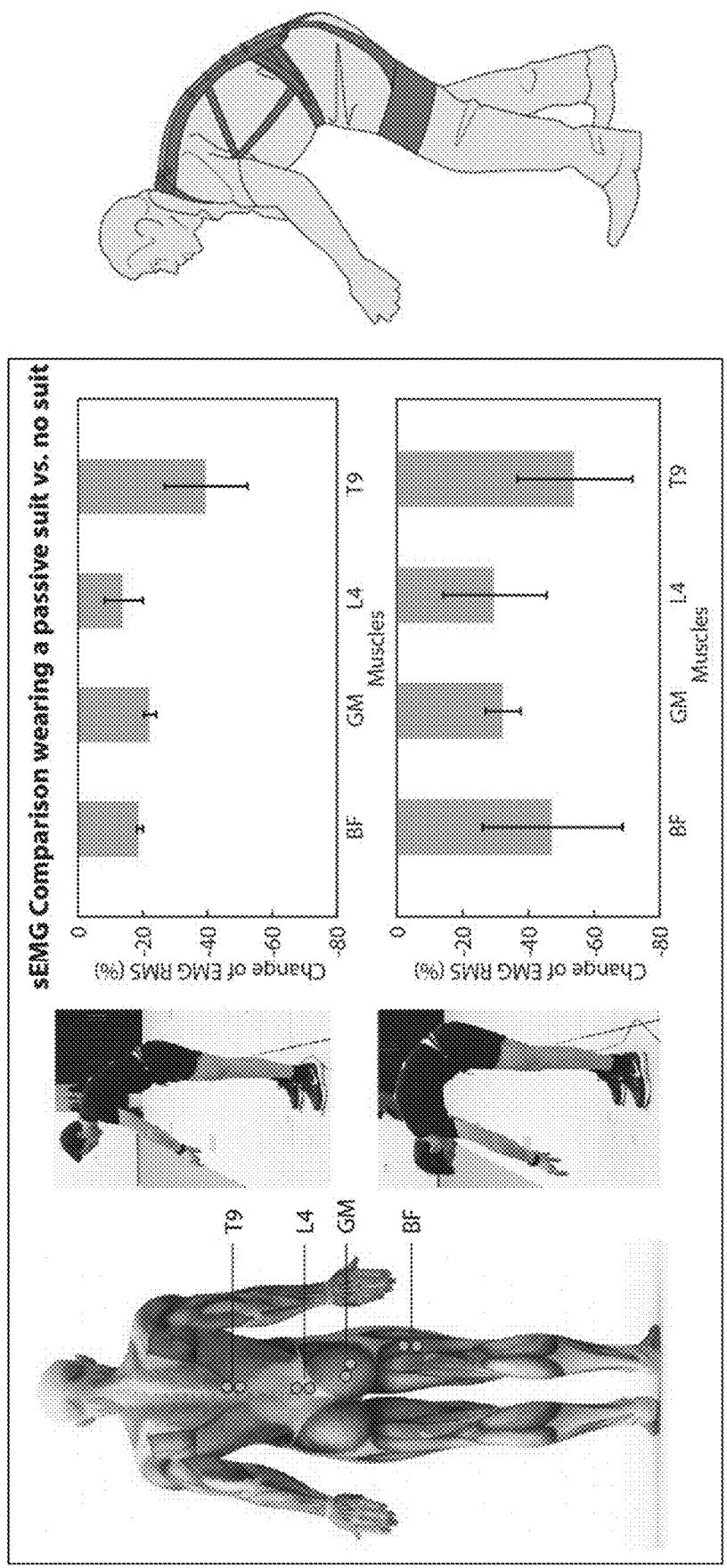
FIG. 33 displays how impedance-controlled robotic apparel; commercially available passive rigid exoskeletons as well as our preliminary results developing a soft passive device to unload the back and hip joints have shown that a passive impedance is effective to unload the targeted back muscles for some motions for some users.

Human subject testing: As a first step towards demonstrating function of this architecture, human subject testing with a passive wearable device 100 that has an elastic connecting element that acts as a spring between both anchor members 110. Through preliminary human subject testing on 3 healthy participants we have shown promising results. As shown in FIG. 33, these studies have shown that the proposed architecture has the potential to reduce muscle activity of key muscles in the back (erector spinae at L4 and T9 levels) and hip joints (biceps femoris, gluteus maximus) of up to 45% in average across 3 subjects when holding static postures at different angles comparing wearing the wearable device 100 versus not wearing any device.

Representative Example #1B

Active Device for Back and Hip Support

The device described in the representative example #1A provides assistive tensile forces to the back joint that are passively generated by the user's body movements, the connecting element 150 may be dimensioned or designed to provide different types of assistance as described in Example 1a. However, to provide customized assistance to different users and tasks or higher levels of assistance compared to a fully passive device, an actuator 120 may be used to control the position or force of the connecting element 150.

Figure 17:
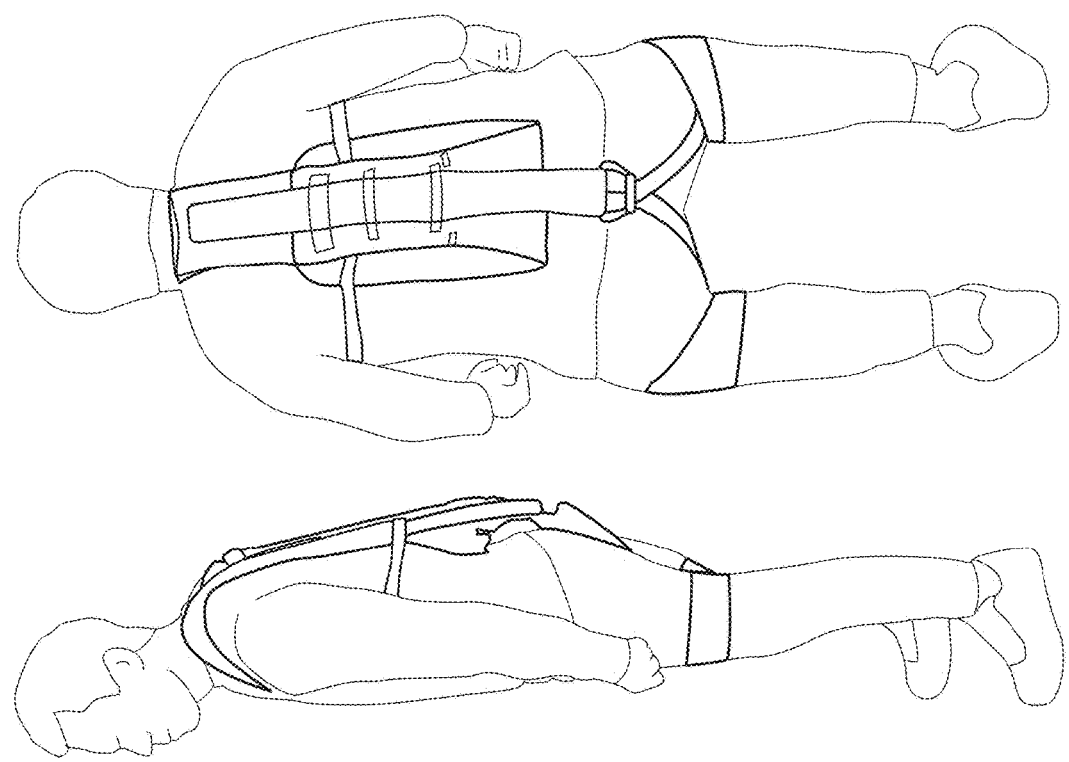
FIG. 17 shows the device described in the representative Example #1B provides assistive tensile forces to the back and hip joints that are passively generated by the user's body movements, the connecting element may be dimensioned or designed to provide different types of assistance as described in Example #1A.

Referring now to FIG. 17, the device described in the representative Example #1B provides assistive tensile forces to the back and hip joints that are passively generated by the user's body movements, the connecting element 150 may be dimensioned or designed to provide different types of assistance as described in Example #1A. However, to provide customized assistance to different users and tasks or higher levels of assistance compared to a fully passive device, an actuator 120 may be used to control the position or force of the connecting element 150. FIG. 18 presents a device that includes an actuator 120 component that can be used to control a cable that is attached between both anchor members 110. The actuator 120 may be used to control the position of the cable to generate tensile forces or to directly control the force that the cable applies to the user.

In this example, the system is identical to that described in example #1A but, in this case, instead of having an elastic element connecting both anchor members 110, a cable-driven actuation system is used. For this system, the user wears an actuator 120 on any part of the body, in this case the waist, a Bowden cable connects that actuator 120 unit to one side of the joint and the inner cable connects on one end to the actuator 120 and on the other end to the other side of the joint. In this way, when the inner cable is actuated, a tensile force will be generated between both anchor members 110. In another embodiment, the actuator 120 may be directly connected to one side of the joint (without requiring a sheath) and drive a cable that connects on one end to the actuator 120 and on the other end to the other side of the joint.

FIG. 18 shows a representative architecture to create assistive torques around the hip and back joints. The device can help assist the back and hip joints during tasks such as lifting, holding static postures, transporting heavy equipment or pulling/pushing which are common activities that may result in injuries over time while being fully transparent (like normal clothing) for other motions. A representative device may be impedance controlled such that it can follow prescribed trajectories or to render virtual impedances (stiffness, damping) that are a function of the joint(s) angles. In this case, since the device crosses both the hip and back joints, the impedance may be defined as the relative angle between the torso and the thigh. This angle may be measured by using on-board sensors 230 such as IMUs, or strain sensing elements). A sample virtual impedance rendered by the actuation may be defined by the stiffness value as shown in FIG. 19 where F is the resulting force, theta is the relative angle between the thigh and the torso and K is the rendered stiffness. In this case, the assistive profiles would feel like having a spring between the anchor members 110 of stiffness K. The advantage of an actuation profile like this over a passive device is that there is more flexibility to automatically configure the assistive profile by selecting different impedances optimized for different motions or different users. Moreover, a virtual impedance has the advantage that it may have different properties (rendered stiffness, damping, etc.) for each phase of the movement, for instance, a different impedance depending on the direction of the motion. The action of going down to grab an object may require less energy than the action of going up with the object fighting gravity, a change in rendered impedance as the movement changes direction will allow to provide more energy into the person when going up versus when going down which a passive spring is not be able to do. Moreover, by choosing a different "initial angle", the resulting profile will be able to shift so that the force doesn't start until the user has reached that initial angle.

Figure 20A:
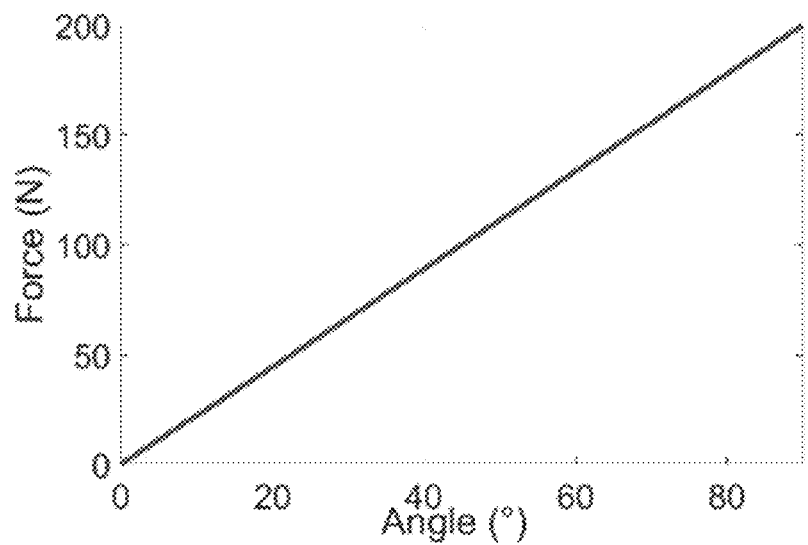
FIG. 20A, FIG. 20B, and FIG. 20C show for a sample user movement in which a joint is moving from an initial position of 0° (standing) to 90° (bending torso to a horizontal position) following a sinusoidal pattern.
Figure 20B:
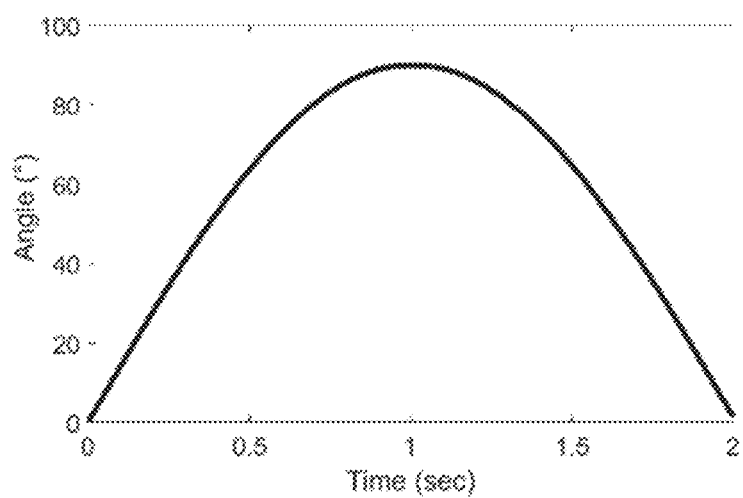
Figure 20C:
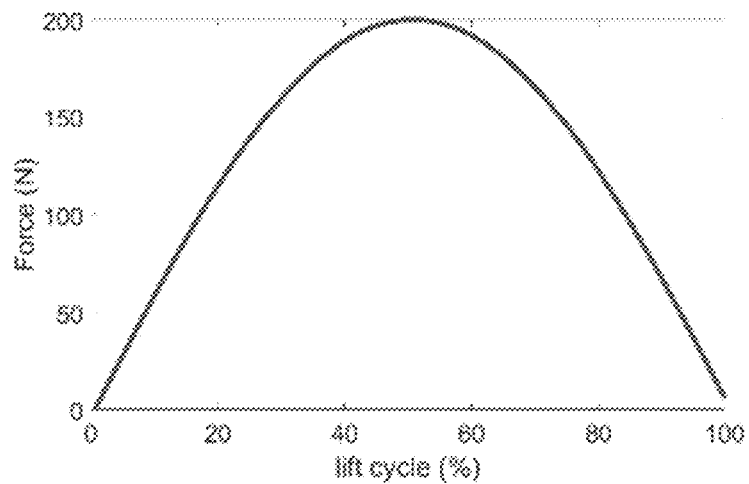

FIG. 20A, FIG. 20B, and FIG. 20C show for a sample user movement in which a joint is moving from an initial position of 0° (standing) to 90° (bending torso to a horizontal position) following a sinusoidal pattern. In particular, FIG. 20A depicts a representative stiffness profile that the device will render as a function of joint angle, FIG. 20B depicts sample joint angle performed by a user following a sinusoidal motion when bending the torso to lift a load from the ground, and FIG. 20C depicts resulting forces from that movement which are the result of multiplying the stiffness by the joint angle segmented as a % of lift cycle.

The sample movement can be representative for example of bending the torso to grab an object from the ground. The resulting forces are a result of multiplying the prescribed stiffness by the joint angle that the user is performing. Forces are represented as a % of lift cycle in which 0% is defined as when the user is initializing the movement, 50% as when the speed of the joint is zero when the user is changing direction and 100% when the user completes the motion by going back to a straight position.

For impedance controlled devices, the system may have different modes depending on the detected motion. Therefore, on-board sensors 230 may be used to detect different activities and select the different pre-defined impedance profiles for each of those. For example there are multiple ways to lift a load, for instance using a squat technique or a stoop technique (legs straight), also the lift may occur with the object in front of the body (back moves on sagittal plane) or with the object on the sides due to space constraints such that the back has to bend and twist during the lift. These different motions may be detected by using onboard motion sensors 230 such as IMUs in which an algorithm could define a initialization threshold (e.g. an initial threshold of the relative angle and angular speed between the torso and the thigh joints that when passed is considered as a initialization of a bending motion. A threshold may also be used to define whether the movement is happening in the sagittal plane or whether the user is bending and twisting the torso for the lift. A different threshold may be used to define whether the user is bending the legs during the lift or not. In another example, the onboard sensors 230 may be used for a classification algorithm (e.g. neural network, linear classifiers, nearest neighbor, decision trees, etc.) to detect which activity the motion falls into. An impedance or assistive profile may be selected for each of these movements.

In another example, a device may be EMG controlled. In this case, one or more EMGs will be located on the representative muscles that the device aims to assist. The filtered electromyography signal from the targeted muscle may be used to estimate the joint torque that the targeted joint is producing and used to command the delivered force produced by the exoskeleton.

Detection of movement initialization: For some applications, the optimization algorithm may need to detect when an activity starts and when it ends in order to know that data collected during that repetition can be used to evaluate an objective function. For instance for a device that supports the back during lifting, the optimization algorithm may need to segment the lift into different phases such as: initialization of movement, move to reach for an object, grab an object and move to the end pose until the lift is finalized. An optimization algorithm may evaluate an objective function for each of these phases. For instance, an optimization algorithm may use on-board motions sensors 230 such as inertial measurement units to detect a change in e.g. joint angle, speed or acceleration to segment the motion and evaluate an objective function. The algorithm will then detect a change in joint angle, speed or acceleration to detect movement initialization to start to evaluate an objective function and measure or estimate the objective metrics until the person has finalized that movement—for instance, by looking at when joint acceleration changes direction or is equal or close (less than a threshold) to 0—. Finally, when the acceleration or speed changes the objective function will be evaluated as the user is going to the final pose until the user stops the movement. This will be registered by the optimization algorithm as one repetition of the movement and evaluate the objective function, decide next set of parameters that will be tested as candidate optimal assistance for the next repetition of the movement.

As an example, a control algorithm may consider different sub-group of activities and find a set of parameters that either maximize or minimize an objective function for each of those activities.

The different key motions that the device supports may be classified into sub-groups: For instance, for a device that assists the back joint, these different sub-groups may be: lifting an object in front while keeping knees straight (stoop lifting), lifting an object in front while bending knees (squat lifting), lifting object to each side following a twisting motion of the trunk with a stoop or squat technique (common motions in multiple industries such as construction, delivery, logistics, military logistics, manufacturing, etc.), holding a static posture at different trunk angles (common posture for surgeons, caregivers, manufacturing industries, etc. that results in strain to the back and ultimately may lead to injuries).

A classification algorithm may use onboard sensors 230 such as motion, force, pressure sensors 230 to classify that activity into a subgroup. For instance IMUs may be used to detect when a movement starts (change of joint acceleration or speed) and the direction of the movement—e.g. torso is bending and/or twisting to define whether the user is executing a motion in the sagittal plane (e.g. lifting an object in front of the user) or whether the torso is bending and twisting (e.g. lifting an object to the sides) and use this to classify the movements outlined previously. Moreover, synchronized movement of different body segments may be used to detect whether the user is doing a stoop lift (torso bending while legs straight) vs. a squat lift (torso and legs bending).

The optimization algorithm will then evaluate an objective as the user performs that motion and optimize a set of parameters.

As the user repeats activities that include motions in the above mentioned sub-groups, the parameters of the device may be fixed or automatically modified to maximize or minimize an objective function.

When the user performs an activity, the control algorithm will detect what type of motion the user is performing and select the right set of parameters based on the sub-group that this activity falls into.

Representative Example #1C

Robotic Apparel to Assist the Hip and Back joints to be Worn Under Clothing

Figure 35:
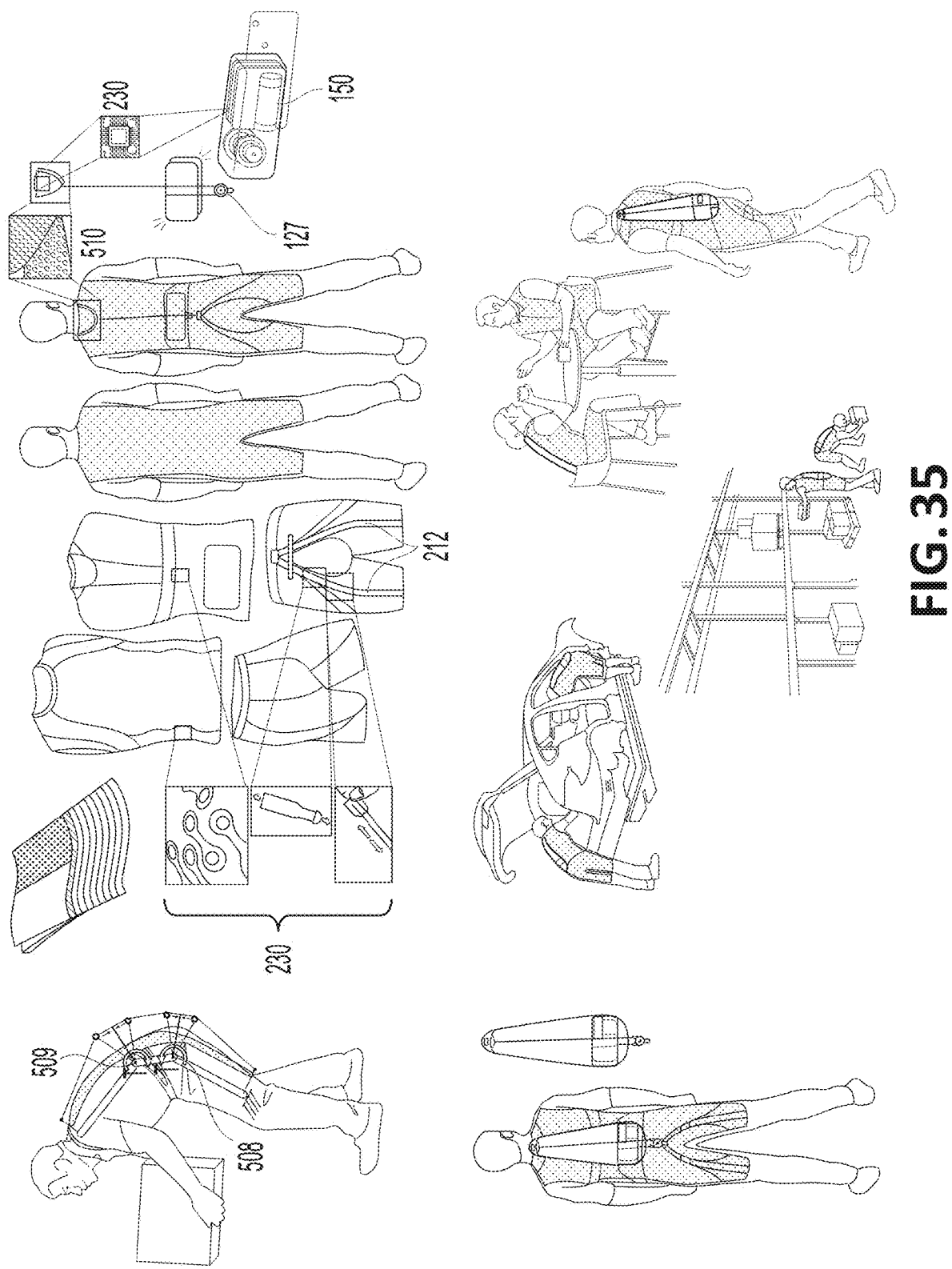
FIG. 35 shows robotic apparel may be designed to be worn under clothing and may be composed of i) a fully soft undergarment that includes soft sensing components and force paths to comfortably transfer assistive forces to the body and ii) a cable-driven actuation module that can meet specific force, power, and bandwidth requirements while being easy to connect to the undergarment to power the distributed sensors and assist the user.

As shown in FIG. 35, robotic apparel may be designed to be worn under clothing and may be composed of i) a fully soft undergarment that includes soft sensing components and force paths to comfortably transfer assistive forces to the body and ii) a cable-driven actuation module that can meet specific force, power, and bandwidth requirements while being easy to connect to the undergarment to power the distributed sensors 230 and assist the user.

Wearable device architecture: for robotic apparel to be effective, a critical aspect is to design adequate force paths that route tensile forces through textile elements (aka wearable device 100 architecture). A force path that crosses multiple joints can produce tensile forces that simultaneously assist those joints by using a single actuation cable. This approach results in optimized systems with reduced weight that simplify requirements. FIG. 35. shows the wearable device 100 architecture that may be used to unload both the back and hip joints. The wearable device 100 architecture is composed of textile components that configure two attachment points: one on the upper side of the back anchored to the body via shoulder anchor members 110 (e.g., shoulder straps) and another on the lower back via a strap that connects to the back of both thighs. A connecting element 150 (e.g., actuating cable) directly or indirectly couples the shoulder and thigh anchor members 110. When actuated, the connecting element 150 actively generates tensile forces that simultaneously cross the back and the hip joints of the user. Since the force paths are offset from the hip and back biological joints (moment arm) these tensile forces will result in assistive torques that unload those joints.

Cable-driven actuators 120: An initial, simplified quasi-static kinematic model of the effect of the wearable device 100 architecture with respect to key anatomic landmarks was developed that included the estimated compliance of the robotic apparel-human interface and actuation and transmission efficiency. One of such modules may be located close to the center of mass of the user (e.g. lower back or waist).

Sensors integrated into apparel: sensors 230 may be integrated in robotic apparel to measure human motion, strap tension, interaction forces/pressure and muscle effort directly into textiles to avoid the need to use IMUs, load cells and EMG sensor into the textile components. Textile-compatible sensors 230 that can measure the above-mentioned parameters may be integrated into textiles and used to be able to control the system to deliver optimally timed assistance to the wearer and to evaluate biomechanics effects of using robotic apparel in industry settings. Sample soft sensors 230 include: stretch sensors to measure motion tracking, tension measuring soft sensors, pressure printed sensors in an insole or textile-integrated EMG sensors for control and evaluation of robotic apparel. Note that alternatively a system may include rigid sensors as well such as IMUs, load cells or EMGs.

Integration of sensors and actuators into robotic apparel: For the development of robotic apparel vision, our team has in-house prototyping processes for soft robotics that combine proven and emerging apparel manufacturing technologies. These processes will allow us to seamlessly combine the previously-mentioned actuators 120 and sensors 230 into textiles to build lightweight modular, soft, and conformal garments. As outlined previously, robotic apparel can be worn under clothing and is composed of a fully soft garment made of textiles with integrated load-transmitting force paths, sensing and a cable-driven actuation module that encloses the only rigid components in the system that can easily be attached to the undergarment.

The soft undergarment will be worn under clothing and may include some or all of the sensing components outlined previously: 1) stretch sensors 230 to measure joint motion, 2) tension sensors 230 to measure human-robot interaction forces, 3) EMG to instrument the key muscles that the device is assisting with, 4) a pressure insole on the foot that can be used to estimate GRF. These sensors 230 may be embedded into the textile components alongside with conductive textile traces that may seamlessly route the different signals to a central connection placement located on the lower back (where the actuation unit will attach).

The Cable-driven actuation unit is located close to the center of mass of the user as this is the most advantageous position to locate weight. This module may integrate the cable-driven actuation, PCB electronic components (high-power and low-power electronics) and battery. The user is able to connect the actuation unit to his/her back by sliding it into a semi-rigid slot panel that is located at the waist, as the actuator 120 is placed, it makes connection with the central panel in order to power the robotic apparel undergarment and receive sensor information. The actuation cable is attached to the undergarment's connecting elements through quick connects. The actuation module may also include two IMUs into the rigid enclosures for additional sensing capabilities, one inside the actuation box and another one at the quick connect where the actuation cable connects to the upper back. Additionally, vibration elements may be integrated within the mounting plate 220 in order to be able to integrate haptic feedback to alert the user, this element may be used to let the user know that he/she is using a non-ergonomic posture during lifting or when holding a static posture.

Representative Example #1D

Optimizing Controls for an Active Back and Hip Support Device

Figure 29B:
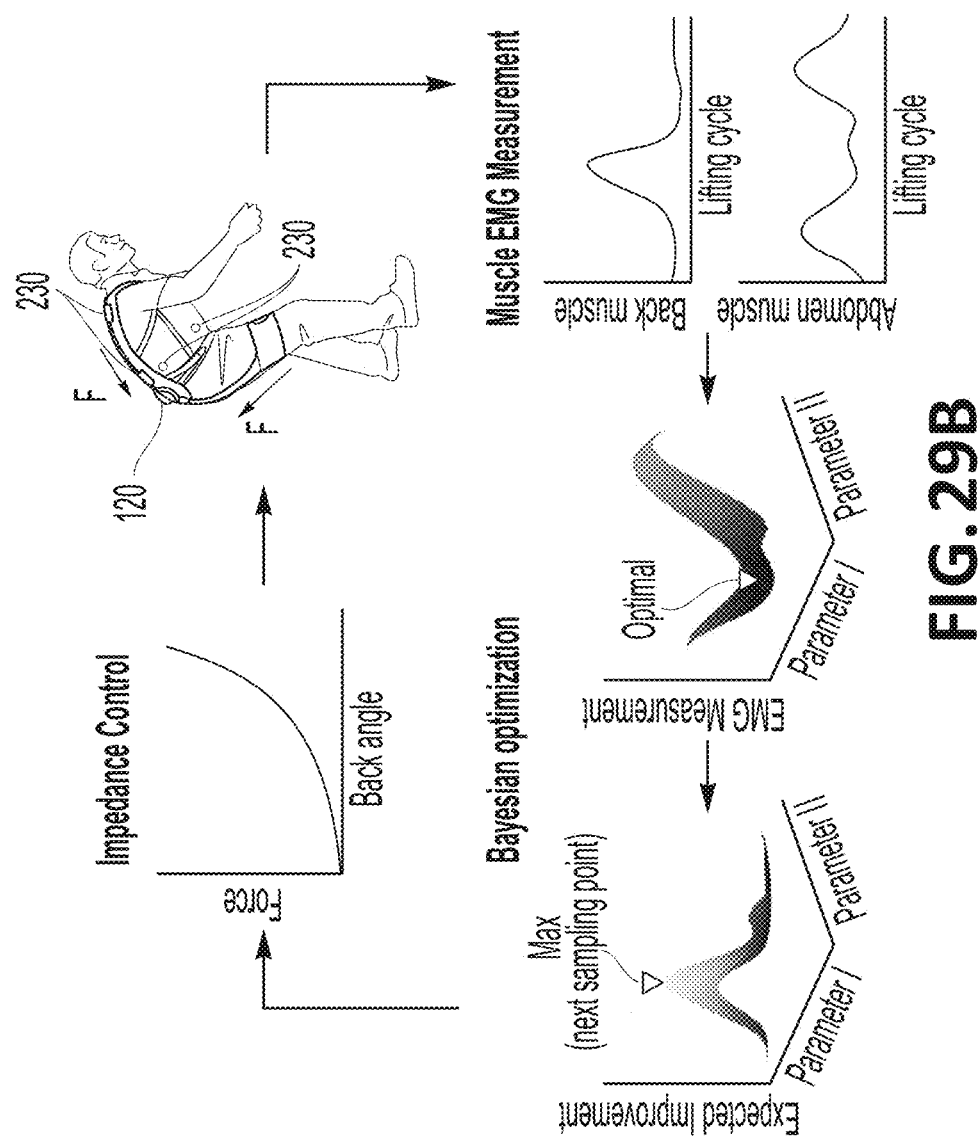
FIG. 29B shows classification algorithms that may classify the different types of activities that the user is performing during the movement initialization phase so as to be able to select different assistance parameters for each of the movements to be able to independently optimize those.
Figure 29A:
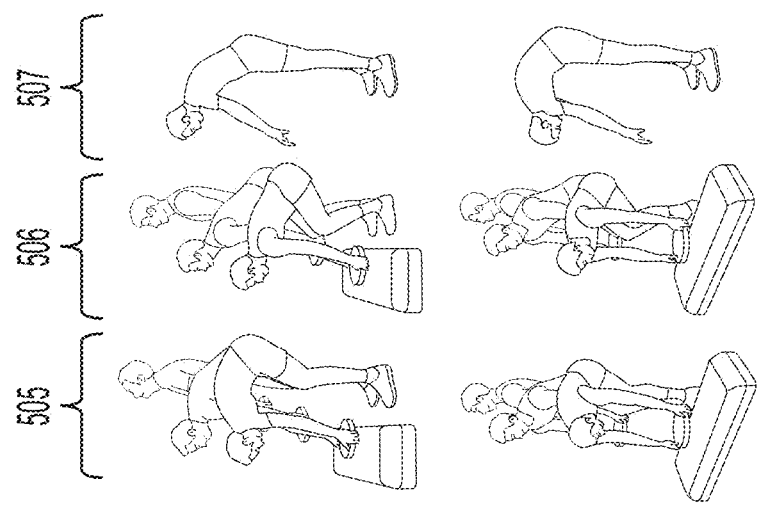

The following motions have been identified as activities that may need optimization: lifting an object in front while keeping knees straight (stoop lifting 505), lifting an object in front while bending knees (squat lifting 506), lifting an object located on one side following a bending and twisting motion of the trunk with both a stoop and squat technique (common motions in multiple industries such as construction, delivery, logistics, military logistics, manufacturing, etc.) and holding a static posture 507 at different trunk angles (common posture for surgeons, caregivers, manufacturing industries, etc). The proposed intuitive and adaptive controller 240 may optimize the assistance for different users with a focus on the motions that have been identified as critical to mitigate risk of injury and enhance productivity for different industries (stoop 505 and squat 506 lifting with object in front and to the sides and holding static postures 507 at different trunk angles). FIG. 29A shows the different activities that the device will optimize and assist with. Optimization controllers 240 may use human biomechanics metrics and optimize assistance parameters to minimize the amount of exertion of the joint and the underlying muscles for those activities as much as possible while not negatively affecting the wearer's natural posture during the targeted motions. The proposed controller 240 will then find the optimal assistance parameters for each of the considered motions for different users. For activities that are not included in the above-mentioned categories (e.g. walking, running, stairs, etc.), the controller 240 may command the system to become fully transparent (no forces applied to the person) so as to not restrict movement.

The controller 240 includes one or a combination thereof: an impedance-controlled robotic apparel, a classification algorithm to differentiate the target motions using onboard motion sensors 230 and efficient optimization algorithms that optimize the device parameters (e.g. impedance, onset) to maximize or minimize the defined objective function for each of the proposed tasks.

Impedance-controlled robotic apparel: commercially available passive rigid exoskeletons as well as our preliminary results developing a soft passive device to unload the back and hip joints (see FIG. 33) have shown that a passive impedance is effective to unload the targeted back muscles for some motions for some users. However, the lack of adaptation of passive systems limit the applicability of these devices to different users and different activities, applying non-optimal assistance to unload the joints may have negative effects on the wearer's performance and even hinder natural movements under some circumstances. Thus, in this example we implement a controller 240 that is able to optimize the resulting impedance of the device and the onset of actuation for different motions and different users. The device will thus, be programmed to render a virtual impedance (e.g. spring, damper) as a function of the movement of the biological joints. We plan to leverage this experience to develop impedance controllers 240 in which the target force is a function of the desired virtual impedance (e.g. onset, stiffness, damping) and the joint's kinematics which will be measured with wearable sensors 230.

Classification algorithms: an algorithm that uses wearable sensor information to classify the initiated motion to understand which activity the subject is performing including lifting strategies (stoop 505, squat 506, front lift, side lift) and static 507 postures as shown in FIG. 29A. Classification algorithms may classify the different types of activities that the user is performing during the movement initialization phase so as to be able to select different assistance parameters for each of the movements to be able to independently optimize those (FIG. 29B).

Optimization controls: as explained above, optimization algorithms can efficiently optimize control policies continuously online using measurements from a variety of body worn sensors 230 to improve key physical quantities such as minimizing the target muscle's effort and minimizing deviations in kinematics, dynamics and muscle activity of the non-targeted muscles with and without the device. Our specific approach improves key metrics such as muscle activity of the targeted joints or joint torque/power as the person performs the task without negatively affecting natural biomechanics of the wearer, =. Compared to the current approach of having a prescribed assistance profile with manual tuning of parameters or a passive system with constant impedance for everyone and for every task, this approach may enable customized assistance profiles to be automatically generated for users after a short period of use of the device.

For personalized wearable devices 100 to be practical, we require that control algorithms be efficient optimizing control parameters online while subjects perform supervised tasks for short durations. For this example we apply Bayesian optimization, a family of global stochastic optimization algorithms. Bayesian optimization algorithms are known to be sample efficient. They also avoid many of the pitfalls associated with traditional gradient descent and parametric response surface methods (i.e. local minima, high bias).

Using real-time data from wearable sensors 230, muscle activity of the targeted muscles, joint angular positions, velocities and interaction forces between the human and the robotic apparel can be estimated to optimize the assistance (in terms of impedance and onset).

During the supervised period using the device, the device may collect sensing information about the baseline natural kinematics and muscle activity of the wearer (when no assistance is applied). After this period, initial control parameters may be used and the device may start to provide assistive forces as the user performs a number of repetitions of the target tasks. The algorithm, will then use onboard sensing to continuously monitor EMG activity and the kinematics of the wearer to optimize the degree of unloading of the underlying muscles while guaranteeing that it doesn't affect the user's natural kinematics and kinetics and muscle activity in an undesired way. The parameters that define the properties of the virtual impedance and the onset of the actuation will be optimized for each of the considered activities and result in an independent set of parameters for each motion and for each user.

Sample objective functions that may be used for this work include:

Maximizing the degree of reduction of main muscle groups of the back (RMS and/or peak) with minimal effects on muscle activity of abdominal muscles. Co-contraction of abdominal muscles and back muscles is critical to guaranteeing stiffness of the structures to stabilize the back. We hypothesize that since the proposed device produces forces that mimic the behavior of the muscles at the back, the muscles in the abdominal region would need to maintain normal muscle activation compared to baseline so as to not affect the risk of injury in a negative way.

Maximizing the reduction in the main muscle groups of the back (RMS and/or peak) without negatively affecting posture: maximizing the degree of unloading of the targeted muscles could be used by itself as an objective or combined with a metric that defines posture quality. Posture quality may be defined in different ways such as avoiding to change kinematics in a way that will imply that the object is further from the body when lifting it comparing to wearing no device. Distance between the object and the body is considered to be one of the primary factors affecting risk of injury when performing lifting techniques. As an alternative, indexes that quantify risk of injury of an activity such as the lift Index may be used as a metrci. The lift index is an equation developed by NIOSH that evaluates how significant is the risk of performing a lift [6], [100], [101]. This equation is a function of the horizontal and vertical distance of the body with respect to the object, asymmetry angles when lifting the object and frequency and duration of each activity. Any change in kinematics/dynamics compared to baseline will change the lift index. Onboard sensing may be used to evaluate the distance of the object to the body and EMG activity of the back muscles. Changing posture in a way that increases the risk of injury may ultimately cause muscles to work harder and therefore using muscle activity of the target muscles may be sufficient as an objective.

Minimize the biological joint torque or power. Peak and cumulative loads at the joint have an increased risk of injury REFs. By minimizing the amount of torque or power that the biological joint has to produce (RMS and/or peak) for each repetition of a task we expect that the biological muscles that are producing those torques will go down. This presents an alternative to using EMG as a means to optimize the assistance that would be worth exploring. A multi-parameter optimization that combines the objective of unloading a joint as much as possible with metrics related to posture such as the lift index or the distance from the body to the object.

In addition, robotic apparel integrates a vibration element into the textile that may be used to alert the user if he/she is using a non-ergonomic posture. This will be useful in different conditions, for example changes in kinematics due to fatigue or distractions.

The proposed method optimizes parameters such as the onset and impedance of the assistive profile, which is a function of how the user moves for each of the defined motions. Thus, there will be some degree of adaptation of the resulting forces based on human motion even if the lift is not identical to the condition that was used for optimization. Compared to the existing approach of having a prescribed assistance profile with manual tuning of parameters or a passive system with constant impedance for everyone and for every task, this approach enables customized assistance profiles to be automatically generated for users after a short period of use of the device. This presents a significant step forward that has the potential to advance the field and the understanding of how to develop optimal controllers 240 that adapt to individual physiological and neurological differences when doing different workplace activities.

Representative Example #1E

Semi-Active Device for Back and Hip Support

In another embodiment, the assistive device may be configured to assist the back and hip joints as outlined in Examples 1A and 1B but include a clutch system or a non-backdrivable actuator 120 to control parameters such as:

a) Initial length of the connecting element: the initial length of the passive connecting element (x01) defines when the tensile force starts as the user bends with respect to the standing position, the distance between both anchor members 110 when the user is standing is defined as x0. For example, if the initial length of the anchor element (x01) is equal or longer than x0 (x01>=x0), the tensile forces will be generated as the user bends the torso or the legs with respect to the standing position to do an activity. This connecting element may be designed to be shorter than x0 (x01<x0) if the intent is to provide tensile forces while the user is standing. FIG. 16 shows how by defining different initial lengths of the connecting elements, the output tensile forces can be modified. The process for adjusting may include commanding a target position of the actuator 120 and using sensors 230 such as an encoder or potentiometer to define the current position of the actuator 120. Once the initial length is defined, the actuator 120 may be controlled to stay at that position, clutched so that it doesn't have to support the resulting forces when assisting the joint or be non-backdrivable which will save energy compared to having a backdrivable system hold the position while assistive forces are being produced.

b) slack vs pretension mode: an actuator 120 system or clutch may be used to allow slack in the system when the device is intended to be fully transparent (not apply assistive forces). In this case, the actuator 120 will be commanded to release cable so that there is enough slack (actuation cable is longer than the distance between anchor members 110), unclutch the connecting element so that it can't produce forces or open a pneumatic system so that the connecting element doesn't apply forces to the body.

b) Impedance of the connecting element: a clutching system or actuator 120 can be used to select between different impedances (e.g. elastic elements, spring, damper) by clutching different elastic elements in parallel or by controlling the initial position of different elastics in parallel to either add or remove impedance in the system.

Representative Example #1F

Back Support Device with Semi-Rigid Elements

In another embodiment, the assistive device may be configured to assist only the back joint as opposed to assisting both the hip and the back as shown in Examples 1A-1E.

In this case, the wearable device 100 architecture will be composed of a waist belt that directly configures an attachment point on the lower-back, shoulder straps that create an attachment point on the other side of the joint. The device may include a semi-rigid component 200 extending between the first anchor member 110 and the second anchor member 110, wherein the semi-rigid component 200 is flexible to bending but resistant to deformation under compression forces. In a different embodiment, the semi-rigid component 200 could be used in combination with anchor members 110 as those presented in previous examples that may attach to the waist belt through a connecting strap for example to provide additional assistance to the hip joint or to reduce relative displacements of the waist belt with respect to the human body during actuation.

Semi-rigid component 200, in various embodiments, may include a plurality of articulating members 202 connected by a plurality of articulating links 204. For example, semi-rigid component 200 may comprise rigid links (articulating members 202) connected by articulated hinges or elastic elements (articulating links 204) inspired by the way that the biological spine is conformed (spine discs and vertebrae). In another embodiment, semi-rigid component 200 may be a semi-rigid structure 206, such as a foam with the above referenced bending and deformation characteristics.

The connecting structure may be fully passive by having an elastic element that connects to each end of the structure. As the user bends this elastic element will generate tensile forces to the structure, the semi-rigid structure 206 will therefore transmit forces at an angle with respect to the user's back as opposed to pure tensile forces which has the benefit of requiring a lower force magnitude to the user to produce the same force.

The connecting element 150 may be actuated such that a motor can control either the relative position or the force between both anchor members 110. A motor may also be used to set the pretension level of the connecting element 150 (semi-active system).

Figure 21:
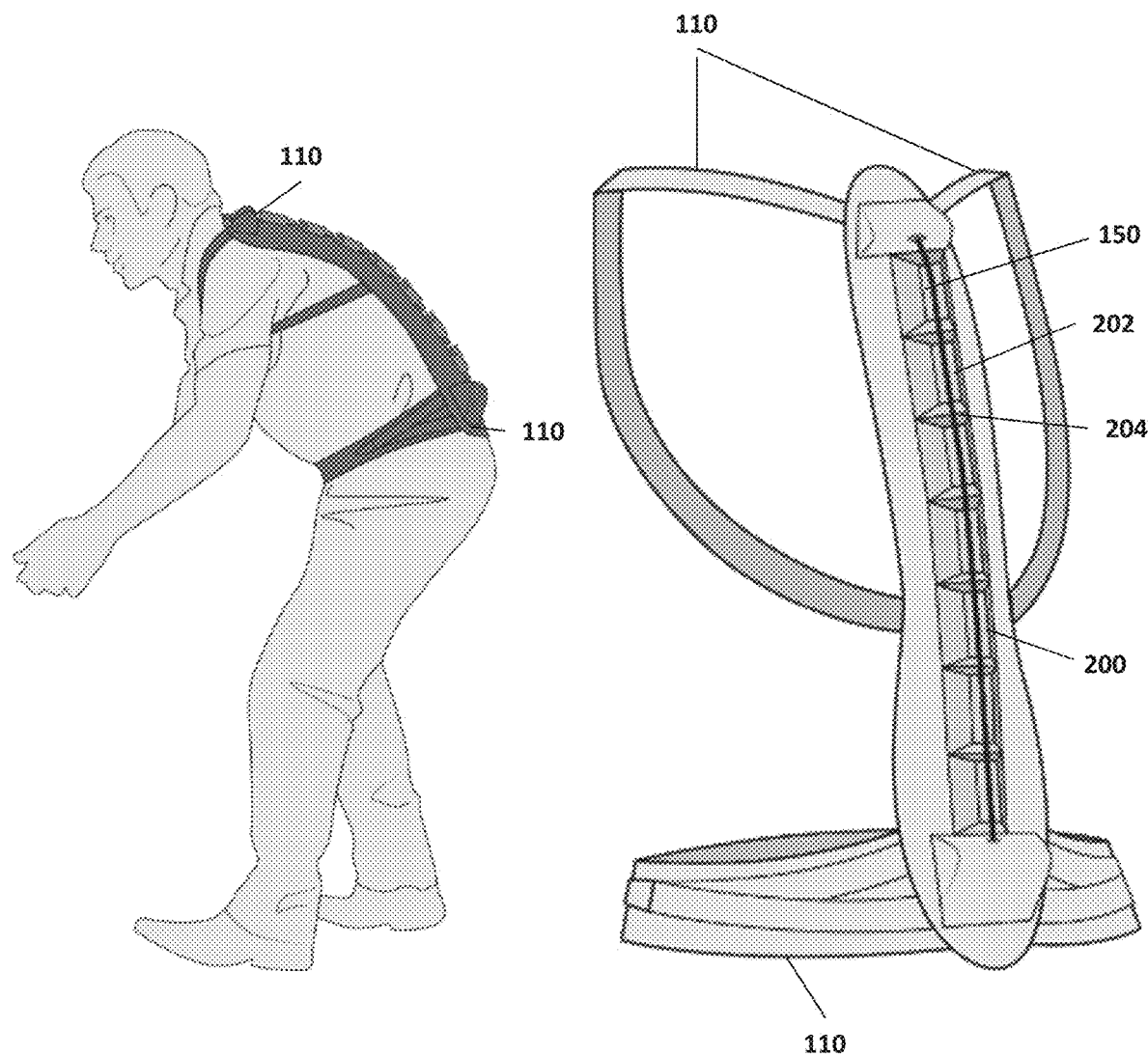
FIG. 21 shows an example of a semi-rigid component that includes two anchor members, one on the top and another one on the bottom part. A connecting element such as an actuation cable or elastic passive element may be connected to provide assistive torque to the user's back.

FIG. 21 shows an example of a semi-rigid component 200 that includes two anchor members 110, one on the top and another one on the bottom part. A connecting element 150 such as an actuation cable or elastic passive element 190 may be connected to provide assistive torque to the user's back.

In order to control active devices and adapt the assistance to wearable device 100 different individuals or different tasks, one approach includes using an optimization method that optimizes control parameters to maximize or minimize an objective function.

Representative Example #2

Knee Support Device

Some activities may require the user to stay static in a crouched position for a long time. As an example, if the worker has to perform task in a tight space he/she may need to stay in a crouched position working on knees. Injuries at the knee may develop from sustaining that non-ergonomic posture for extended periods of time without adequate recovery time. In order to mitigate this issue, an assistive device may provide torque to the knee so that the user knees' have to do less work during that time. This may allow the worker to maintain this posture without affecting his/her musculoskeletal health.

Figure 22:
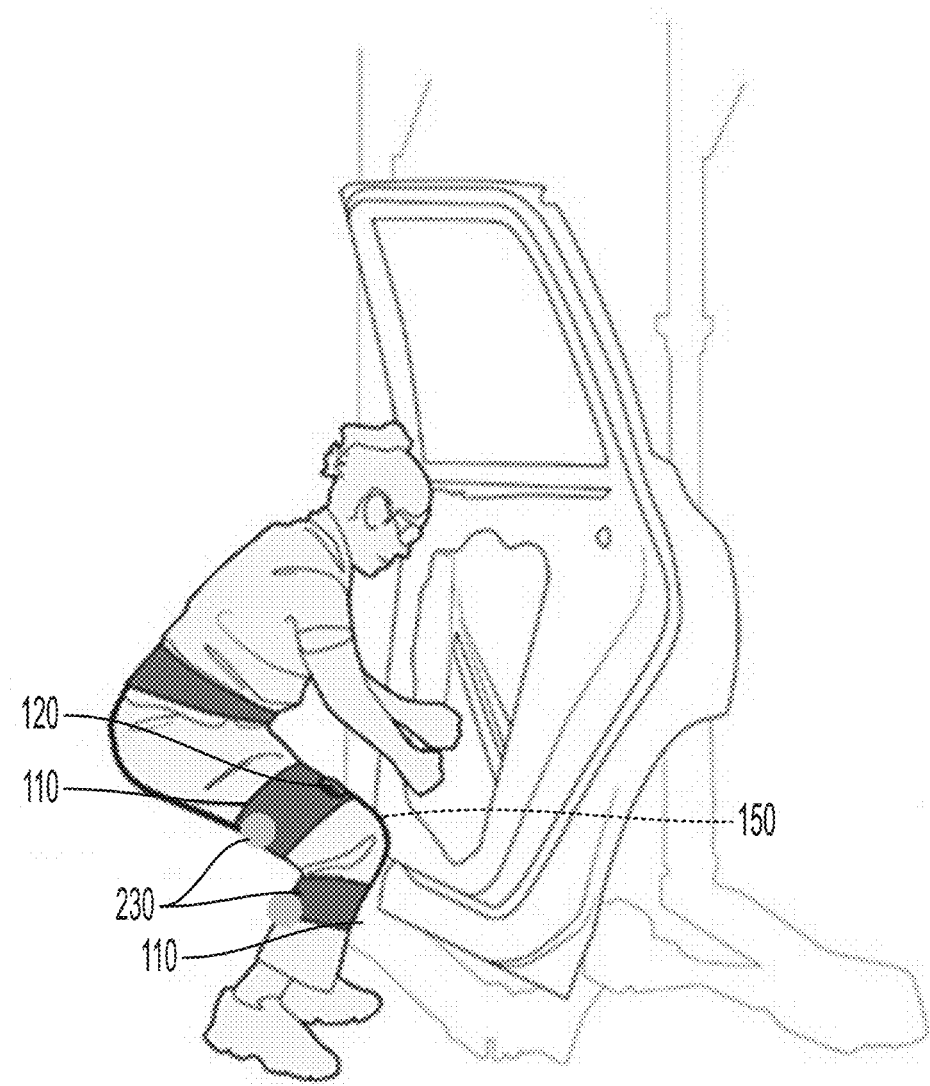
FIG. 22 shows an example of a soft wearable device embodiment that is achieved by placing a cable-driven actuator with anchor members on both sides of the knee (front of the thigh and front of the calf).

FIG. 22 shows an example of a soft wearable device 100 embodiment that is achieved by placing a cable-driven actuator 120 with a similar technology as those described in the previous examples with anchor members 110 on both sides of the knee (front of the thigh and front of the calf). This actuator 120 may be attached to the shank or the calf by wearing calf anchor member 110 (e.g. a calf-wrap device) around the shank and then to the upper-side of the knee by attaching to a thigh anchor member 110 (e.g., thigh wrap). When actuated, the cable will provide forces that will provide knee support during a crouched position. This device could be useful when sustaining a crouching position for a long time to avoid knee injuries. This activity involves a posture that may need to be sustained over time.

Of course, the knee wearable device 100 can additionally or alternatively be configured for semi-active or passive assistance. For example, a semi-active knee wearable device 100 may include a semi-active actuator 120 (e.g., a clutch system, a non-backdrivable actuator 120, or other suitable mechanism) configured to control how much tension is generated in the wearable device 100 by movement or a pose of the wearer. To control the level of tension, the semi-active actuator 120 may be configured to control a length of the connecting element(s) 150 and/or to selectably engage one or more connecting element(s) 150 of suitable stiffness such that the desired tension is produced, as described above. Additionally or alternatively, the connecting element 150 may include an energy storage device 190 (e.g., a spring), and the semi-active actuator 120 (e.g., clutch) may be configured to selectably lock and unlock the energy storage device 190 to store and release energy absorbed by the connecting element 150 from movement or a pose of the wearer to assist the wearer. A passive wearable device 100 for assisting the knee may include a passive connecting element directly or indirectly coupling the at least one torso anchor member 110 to the at least one upper leg anchor member 110 to the at least one lower leg anchor member 110 such that movement or a pose of the wearer generates tension in the wearable device 100 and the wearable device 100 provides a moment (e.g., restorative torque) about at least a knee joint of the wearer.

Representative Example #3

Shoulder Support Device for Over-Head Work

In an example, a healthy subject may need to perform over-head work to assemble different components in a structure that is over the head. This is a very common task, for instance, in the automotive industry where factory workers will be working under a car performing assembly tasks. As an example, in these cases a worker may perform multiple repetitions of grabbing different components from a table (such as screws, nuts, or other parts), extending arms over head to attach those components to the structure by using a power tool, and/or grabbing a new component from a table. Performing work overhead places strain on the muscles of the neck and shoulders. Muscles of the shoulders tend to tire very quickly when performing overhead work which is the reason why this is considered as one of the most prevalent causes of injuries resulting from body position and reaction.

Figure 23:
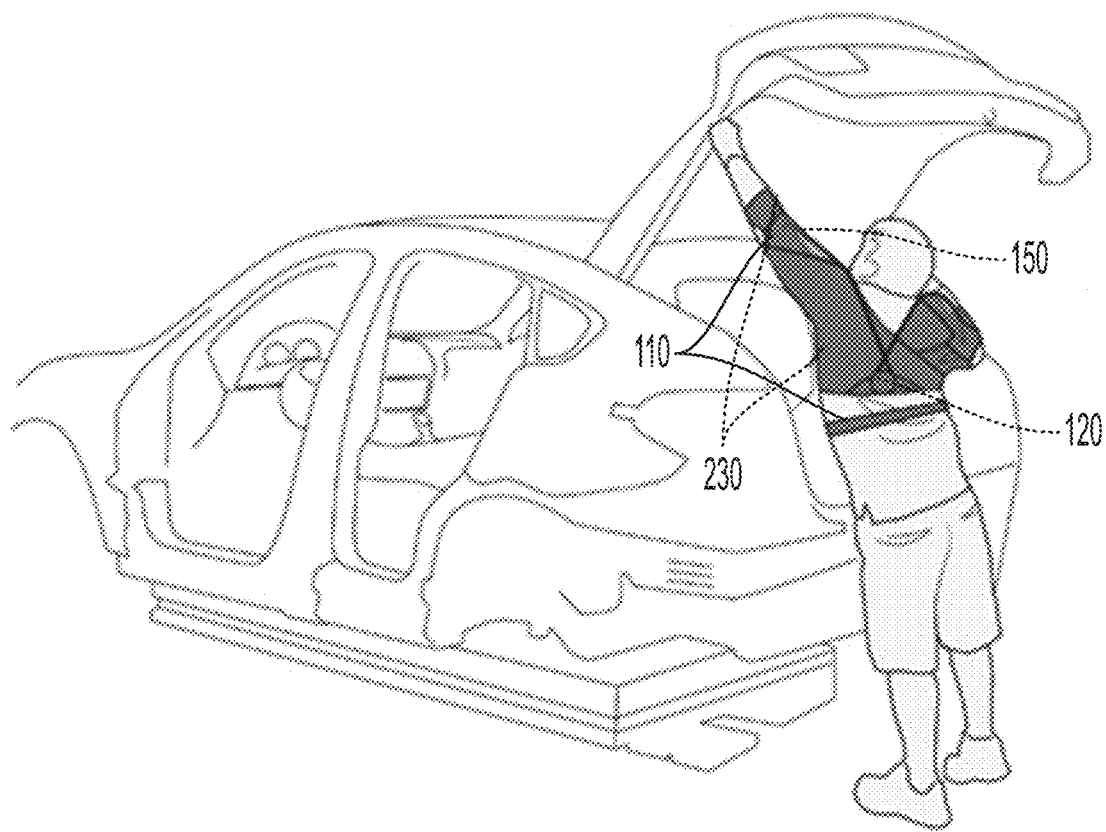
FIG. 23 illustrates a configuration wherein the actuator may have anchors under the arm attached to an apparel component that wraps around the arm and at the side of the chest so that as the cable moves it creates a tensile force which generates a supportive torque on the shoulder joint.

A wearable assistive device may be worn around the shoulder, as shown in FIG. 23, to give support to the shoulder joint when the user extends the arm over head to avoid overexertion of the shoulder joint. The wearable device 100, in various embodiments, may include at least one anchor member 110 configured for positioning on a torso of a person wearing the wearable device 100, at least one anchor member 110 configured for positioning on an upper arm of a person wearing the wearable device 100, and at least one connecting element 150 directly or indirectly coupling the at least one torso anchor member 110 to the at least one upper arm anchor member 110. An active wearable device 100 for assisting these tasks, in an embodiment, may comprise a cable-driven actuation system connected to a shoulder anchor member 110 and an arm anchor member 110 and extending between the shoulder and the arm. The actuator 120 can be composed of an electromechanical motor, a Bowden sheath that connects this motor to one side of the shoulder joint and an inner cable that connects on one end to the motor and on the other end to the arm. For example, as the motor moves, the connecting element 150 (inner cable) will move helping with moving the arm up. The actuator 120 may have anchors under the arm attached to an apparel component that wraps around the arm and at the side of the chest so that as the cable moves it creates a tensile force which generates a supportive torque on the shoulder joint, as shown in FIG. 23.

In some embodiments, the device can include one or more integrated sensors 230, such as an IMU on the arm, an IMU on the chest to measure joint angle/velocity/acceleration, one or multiple EMGs to measure muscle activity of the muscles that this device is assisting, a pressure sensor inside the actuator 120, and/or a pressure sensor in the interface between the user and the actuator 120 to measure the supportive forces to the arm. These sensors 230 may be integrated into the wearable system.

A representative motion can be shoulder movement from a neutral position to an overhead position. A representative actuation profile can show onset once the user reaches a certain shoulder angle, a prescribed stiffness of the actuator 120 unit based on the arm angle (such that the actuator 120 provides assistance in proportion to the arm angle, i.e. the higher the arm angle, the higher the supportive force) and an assistance termination or offset upon a change in direction of rotational velocity as arm starts to lower.

Of course, the shoulder wearable device 100 can additionally or alternatively be configured for semi-active or passive assistance. For example, a semi-active wearable device 100 for assisting the shoulder may include a semi-active actuator 120 (e.g., a clutch system, a non-backdrivable actuator 120, or other suitable mechanism) configured to control how much tension is generated in the wearable device 100 by movement or a pose of the wearer. To control the level of tension, the semi-active actuator 120 may be configured to control a length of the connecting element(s) 150 and/or to selectably engage one or more connecting element(s) 150 of suitable stiffness such that the desired tension is produced, as described above. Additionally or alternatively, the connecting element 150 may include an energy storage device 190 (e.g., a spring), and the semi-active actuator 120 (e.g., clutch) may be configured to selectably lock and unlock the energy storage device 190 to store and release energy absorbed by the energy storage device 190 from movement or a pose of the wearer to assist the wearer. A passive wearable device 100 for assisting the shoulder may include a passive connecting element directly or indirectly coupling the at least one torso anchor member 110 to the at least one upper arm anchor member 110 such that movement or a pose of the wearer generates tension in the wearable device 100 and the wearable device 100 provides a moment (e.g., restorative torque) about at least a shoulder joint of the wearer.

Representative Example #4

Modular Wearable Device

Figure 24C:
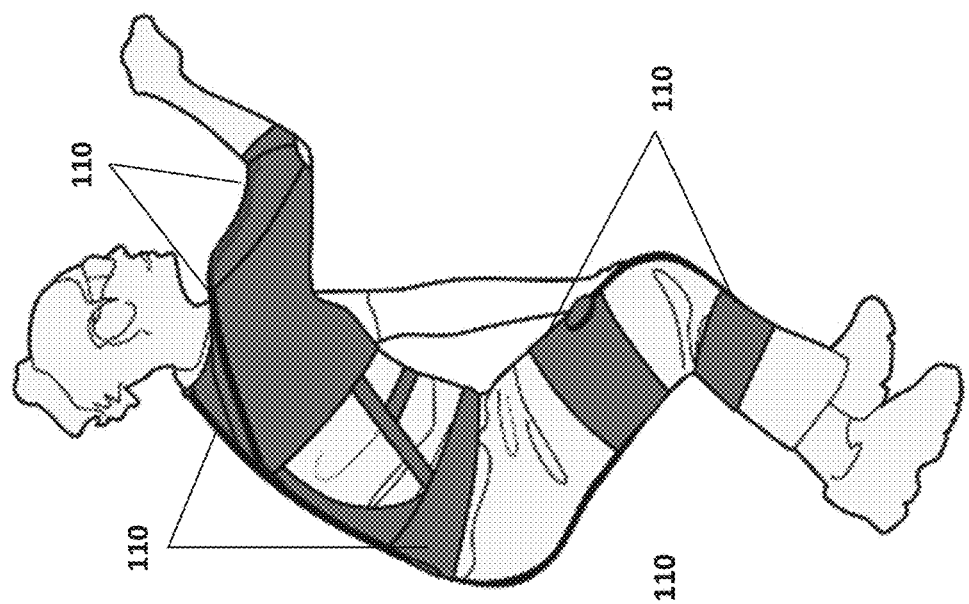
FIG. 24A, FIG. 24B, and FIG. 24C demonstrates how the devices described in the previous examples may be combined to assist multiple joints such as the knee, the back, the shoulder or any combinations thereof.
Figure 24B:
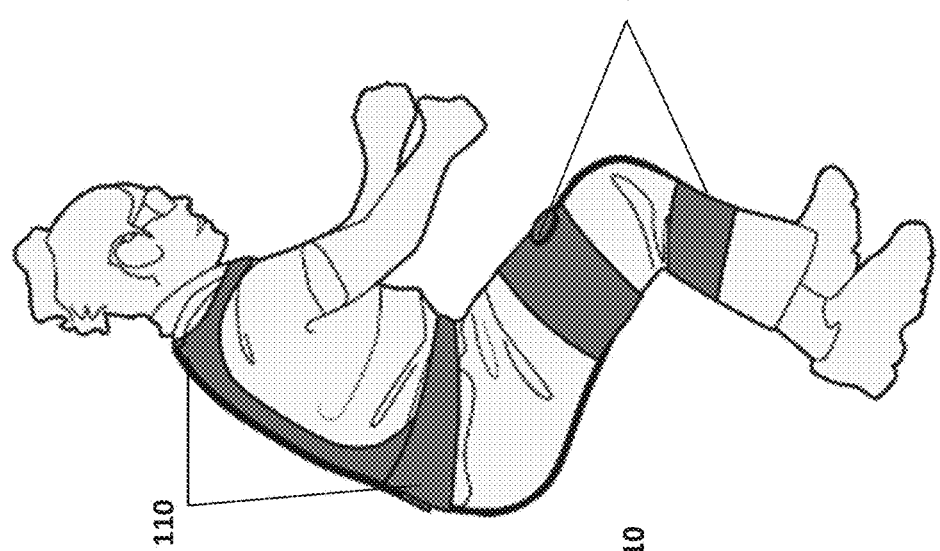
Figure 24A:
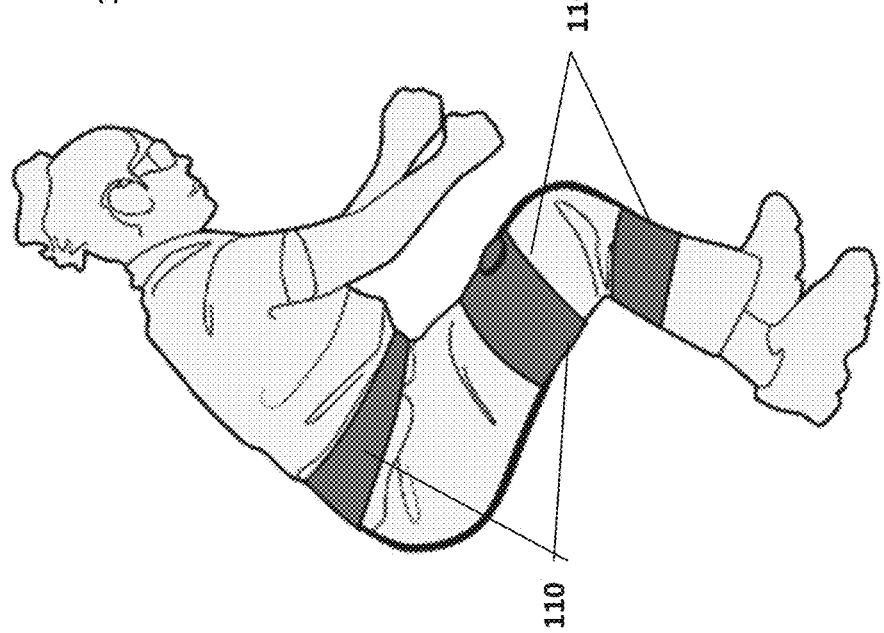

The devices described in the previous examples may be combined to assist multiple joints such as the knee, the back, the shoulder or any combinations thereof. As an example, as shown in FIG. 24C, a device that assists the knee (FIG. 24A) may be combined with apparel to assist the back and/or apparel to assist the shoulder (FIG. 24B) to provide additional support for a given activity. For instance, doing over-head work while crouching may be necessary in some environments due to constraints in the workspace, therefore a device that assists the knee could be combined with a device that assists the shoulder. Given that the devices are purely soft and don't interact with each other, these modules can be combined seamlessly.

Representative Example #5

Integration in Clothing

The proposed assistive device may be integrated into typical work clothing for daily use. FIG. 25A, FIG. 25B, FIG. 25C, FIG. 26A, and FIG. 26B show some sample embodiments of wearable device 100 component integration. The illustrations demonstrate a system that would consist of workwear with attachment points, and a removable, cable-driven sensor and actuator 120 device that could click into the workwear for periods of use.

Garment integration is beneficial because (i) it provides a platform with familiarity of everyday clothing for users, (ii) it reduces user error with alignment since it's difficult to put garments on incorrectly, (iii) it simplifies hygienic considerations since textile pieces that must be machine washed for sweat and debris are easily separated from non-washable sensors 230, electronics, and actuators 120, (iv) it has potential to obscure the fact that the user is wearing an assistive device, a pain point from initial user research, and (v) it reduces don and doff time of the system through fewer components.

Figure 25C:
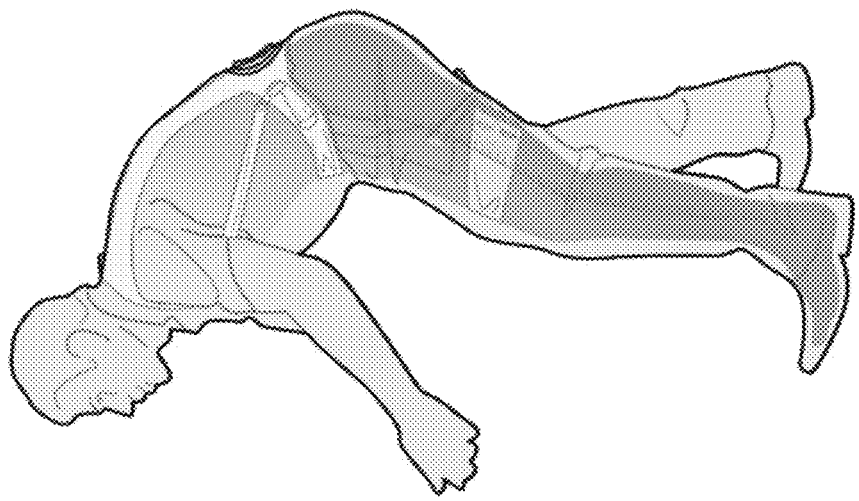
Figure 25B:
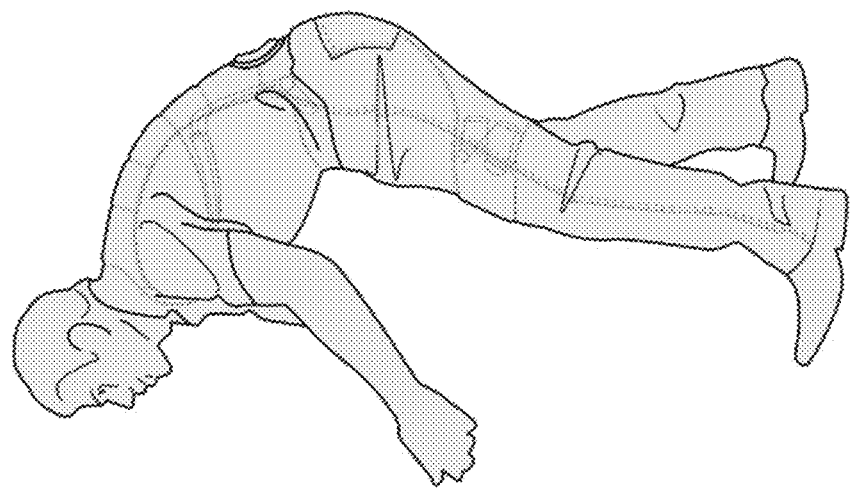
Figure 25A:
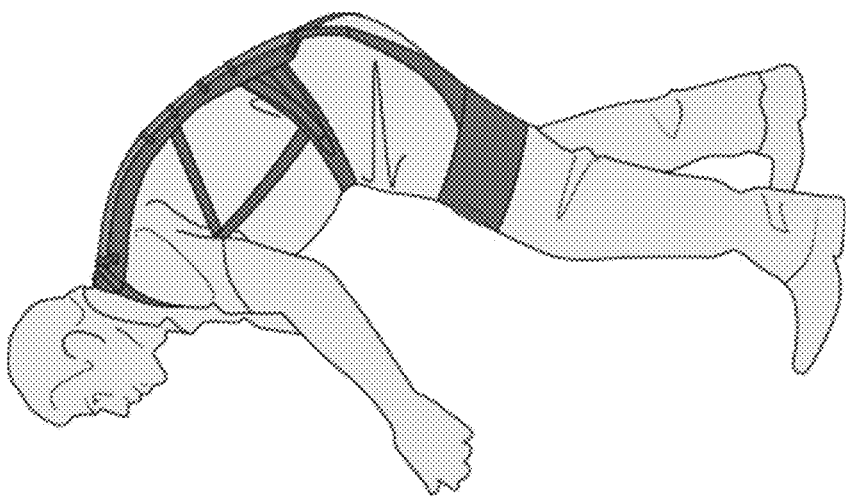

FIG. 25A shows how the system can be worn on top of regular clothing, using wearable device 100 components. FIG. 25B and FIG. 26A show typical work clothing with slightly-padded, sewn insets that function as wearable device 100 components. Small, covered Boa® system dials or Velcro® tabs allow the user to add compression in these slightly-padded insets when they want to activate the system. When the system isn't in use, the user can leave these insets slack. FIG. 25C and FIG. 25B show a concept using hidden yokes, pieces of fabric intended to provide support when tightened by the user with Boa® system dials or Velcro® tabs. This design is beneficial specifically because wearable device 100 components can be concealed beneath the top layer of the garment while in compression, a concern for some users in terms of modesty and perception.

Example 6

Optimizing Controls for Shoulder Assistance to Support Over-Head Work

In an example, a healthy subject may need to perform over-head work to assemble different components in a structure that is over head. This is a very common task, for instance, in the automotive industry where factory workers will be working under a car performing assembly tasks. As an example, in these cases a worker may perform multiple repetitions of grabbing different components from a table (such as screws, nuts, or other parts), extending arms over head to attach those components to the structure by using a power tool, and/or grabbing a new component from a table.

Performing work overhead places strain on the muscles of the neck and shoulders. Muscles of the shoulders tend to tire very quickly when performing overhead work which is the reason why this is considered as one of the most prevalent causes of injuries resulting from body position.

Figure 27:
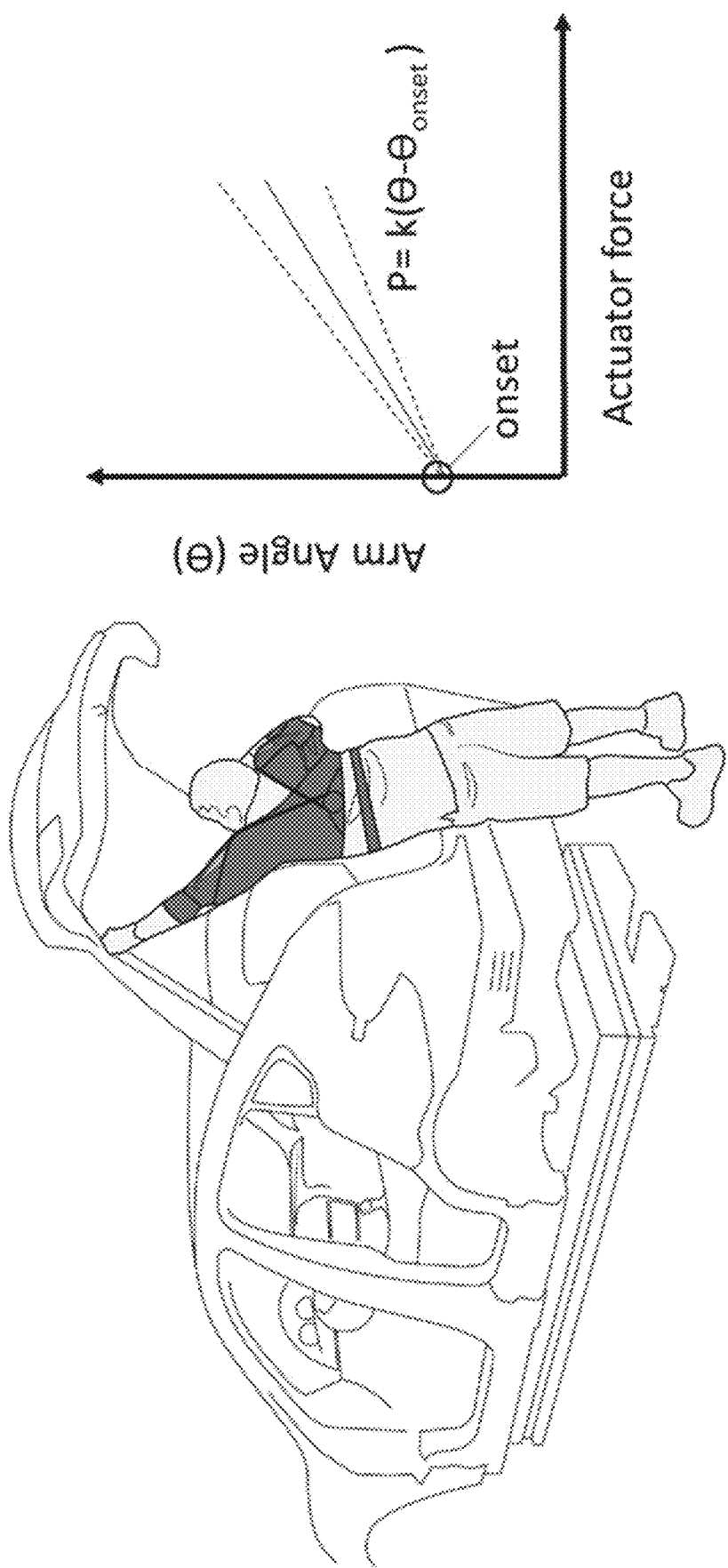
FIG. 27 shows a wearable assistive device worn around the shoulder to give support to the shoulder joint when the user extends the arm over head to avoid overexertion of the shoulder joint.

A wearable assistive device may be worn around the shoulder, as shown in FIG. 27, to give support to the shoulder joint when the user extends the arm over head to avoid overexertion of the shoulder joint. In some embodiments, the device can include one or more integrated sensors 230, such as an IMU on the arm, an IMU on the chest to measure joint angle/velocity/acceleration, one or multiple EMGs to measure muscle activity of the muscles that this device is assisting, a pressure sensor inside the actuator 120, and/or a pressure sensor in the interface between the user and the actuator 120 to measure the supportive forces to the arm.

A representative motion can be shoulder movement from a neutral position to an overhead position. A representative actuation profile may detect an onset once the user reaches a threshold shoulder angle and deliver a prescribed stiffness of the actuator 120 unit based on the arm angle (such that the actuator 120 provides assistance in proportion to the relative angle of the arm with respect to the initial angle that is considered as a start of over-head motion the higher the arm angle, the higher the supportive force) and an assistance termination or offset upon a change in direction of rotational velocity as arm starts to lower.

An optimization algorithm can allow for the selection of the right amount of assistance from the wearable device 100 to avoid overexertion of the muscles that the device is configured to target. For example, an objective function can be peak of the targeted muscle, such as the upper trapezius, where the objective can be to minimize this value to avoid overexertion of that particular muscle while performing the task.

Suitable parameters for optimization include, but are not limited to, an offset of actuation and stiffness of the actuation profile as a function of joint angle. An increased stiffness of the actuator 120 can mean that the wearable assistive device feels more supportive but at the same time too much stiffness may not yield optimal results since a spring that is too strong may mean that the user has to provide resistance against this stiff element so as to not perform a movement that is too fast or uncontrolled. The offset of the actuation as a function of arm angle is also an important parameter since an actuator 120 that supports the arm can need to become transparent or reduce the assistance as the user brings his/her arm down. An example of a simplified assistance profile based on stiffness is shown in FIG. 27. FIG. 27 illustrates an exemplary graph of actuator 120 force versus arm angle. Simplified actuation assistance is shown where the force of actuator 120 or assistance to the shoulder is a rendered stiffness proportional to the arm angle.

Different individuals may perform a task in different ways. Moreover, when wearing an active device, a wearer can react in different ways to the assistance provided by the device and the optimization related to the device. Having an algorithm that automatically optimizes the assistance parameters of the device (for example, stiffness) based on an optimization of an objective (for example, muscular activity) can allow different individuals to get an improved benefit from the system, and the device can be automatically customizable to slightly different activities. Thus, an active wearable device 100 for the shoulder (or for the upper-limb) that uses an on-line optimization process to optimize a parametrized assistance profile to maximize an objective function can be used for a variety of activities and a variety of users. Wearable active devices can automatically adjust assistance parameters by following an optimization approach as described herein.

Figure 28:
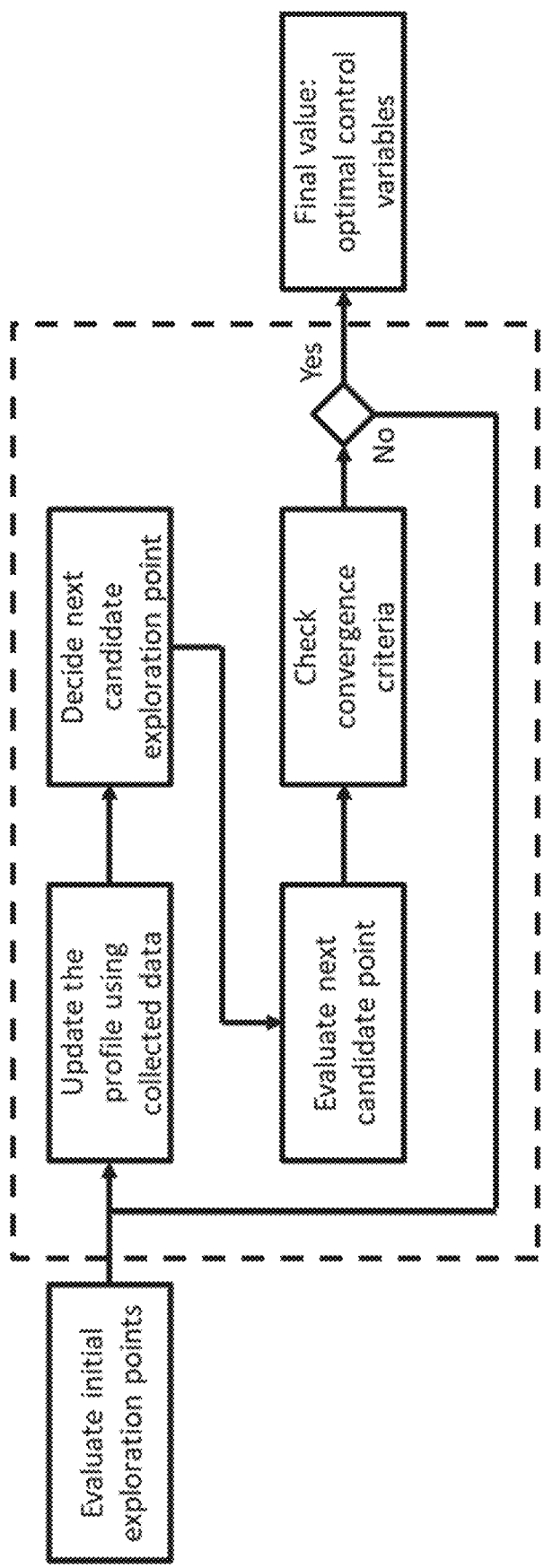
FIG. 28 presents a flowchart as an example of an optimization process that can evaluate the objective based on the initial settings or exploration points, then update the profile using collected data, decide next candidate exploration points, evaluate the objective with these settings, check convergence criteria, etc.

An optimization process can then evaluate the objective based on the initial settings or exploration points, then update the profile using collected data, decide next candidate exploration points, evaluate the objective with these settings, check convergence criteria, etc. An example of a flowchart for this optimization is shown in FIG. 28.

As explained above, a method identical to the example using Bayesian optimization with two parameters could be used to find the optimal assistive parameters for different subjects. For example, in an embodiment, a Bayesian approach may be used to optimize one or more actuation parameters when the relationship between the actuation parameter(s) and the objective function is unknown or complex.

The pseudocode below shows a process for this example using Bayesian optimization.

```
Main:
---------------------------------------------------------------------------------------------
--
Initial_data_points = get_initial_data_points_randomly;
% initialize parameters using prior information
Parameters = initialize(noise, landscape, amplitude)
% evaluate initial data points.
data = evaluate(initial_data_points)
  % initialize candidate data points
new_candidate = initial_data_points
While (1)
    % optimize Gaussian processing hyper parameters
    parameters = optimize_parameters(parameters,data);
    % optimize the next candidate using posterior distribution
    new_candidate = optimize_candidate_points(parameters, data);
```

-continued

```
    If (convergence_criteria_meet)
        Break;
    end
    % if not converged, evaluate the data points
    data = evaluate (new_candidate);
end
function parameters = optimize_parameters(parameters, dat)
    % calculate initial log likelihood
    loglikelihood = calculate_log_likelihood (parameters, data)
    % initialize initial parameters
    optimal_parameter = parameters;
    % optimize hyperparameters of a prior to maximize log likelihood of observed data
    for i=1:random_trials
        % reduce local minima by adding random points in the seed
        [new_parameter,loglikelihood] = gradient_search (parameters + random_points, data)
        If(loglikelihood<loglikelihood_previous)
                Optimal_parameters = new_parameter;
        end
    end
    parameter = optimal_parameter
end
function new_candidate = optimize_candidate_points(parameters, data);
    % find new candidate using gradient search method
    new_candidate = gradient_search( probability_of_improvement);
end
```

Example 7A

Optimizing Controls for Back Assistance to Support Lifting Loads

Figure 30:
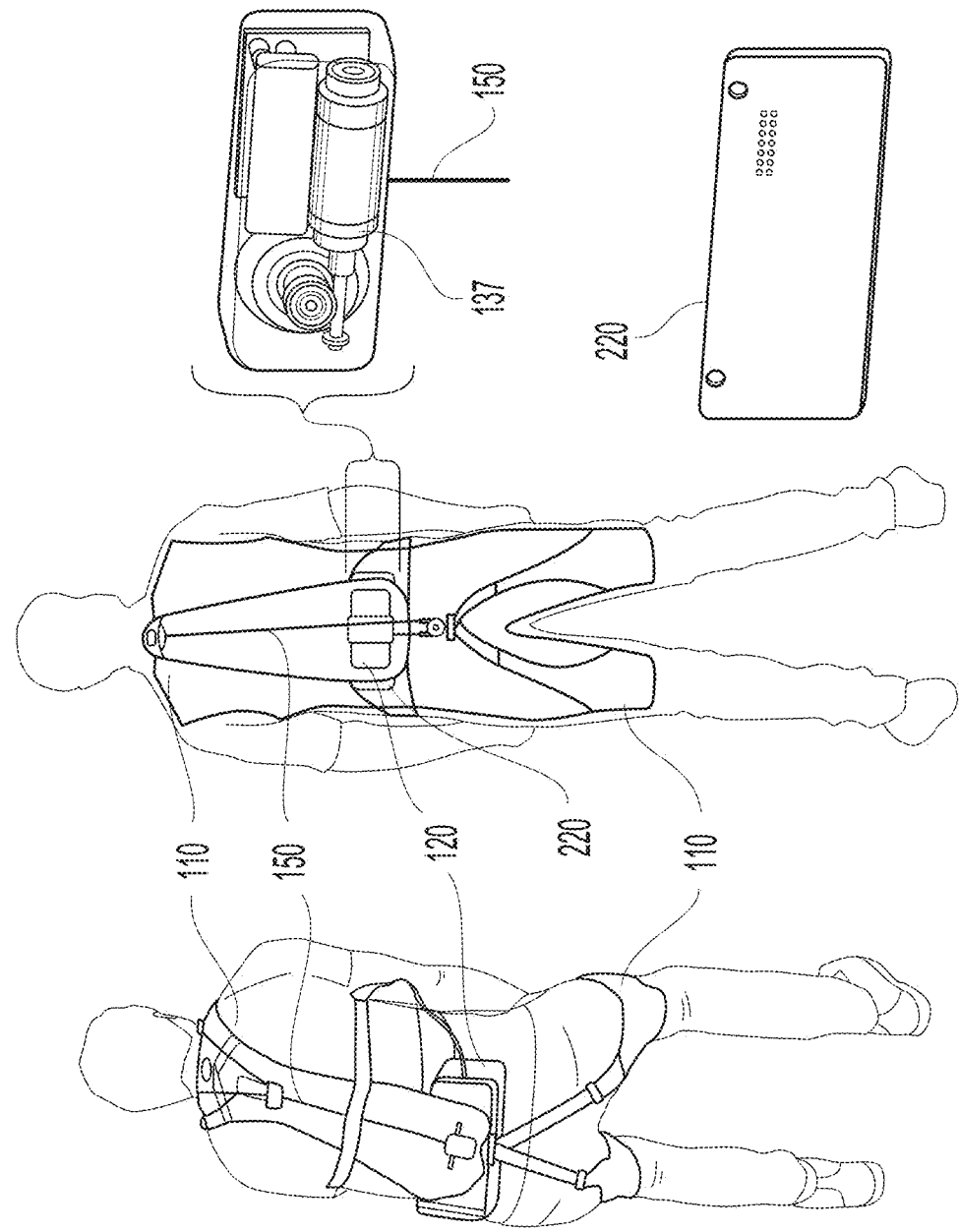
FIG. 30 offers further examples of the combination of small to moderate levels of assistance (20-30% of joint torques typical during comfortable walking), the low inertia and non-restrictive nature of the proposed robotic apparel platform, present new opportunities for the control of wearable robots where assistance is required to be synchronized with the underlying muscle function of the wearer.

Referring now to FIGS. 29A, 29B, and FIG. 30, the combination of small to moderate levels of assistance (20-30% of joint torques typical during comfortable walking), the low inertia and non-restrictive nature of the proposed robotic apparel platform, present new opportunities for the control of wearable robots where assistance is required to be synchronized with the underlying muscle function of the wearer. We hypothesize that by providing an appropriately-timed assistance to the back and hip joints of a magnitude in the range of 20-30% during tasks such as lifting or holding static postures, industry workers will be able to improve performance and reduce the risk of injury.

A control algorithm may optimize the device parameters based on EMG measurements and joint kinematics/kinetics. Using real-time data from the sensors 230, we can estimate muscle activity of the targeted muscles, joint angular positions, velocities and interaction forces between the human and the robotic apparel during the task and use this information to optimize the assistive profile (in terms of impedance and onset of the actuation). During the supervised period using the device, sensing information about the natural kinematics and muscle activity of the wearer (when no assistance is applied) will be collected as a baseline. After this initial period, the user will wear the device with a initial prescribed impedance based on the relative angle between the torso and the thigh. The algorithm, will then continuously monitor EMG activity and the kinematics of the wearer to optimize the degree of unloading of the underlying muscles while guaranteeing that it doesn't affect the user's natural kinematics and kinetics and muscle activity in an undesired way.

The following motions have been identified as critical to optimize—lifting an object in front while keeping knees straight (stoop lifting), lifting an object in front while bending knees (squat lifting), lifting object to each side following a twisting motion of the trunk with both a stoop and squat technique (common motions in multiple industries such as construction, delivery, logistics, military logistics, manufacturing, etc.), holding a static posture at different trunk angles (common posture for surgeons, caregivers, manufacturing industries, etc. that results in strain to the back and ultimately may lead to injuries). The algorithm in this case is composed by:

A classification algorithm to differentiate the above-mentioned motions: onboard sensors 230 (Inertial Measurement Units) to classify the different motions into sub-groups. The classification is developed by using detecting changes in joint angle, speed or acceleration to define when a movement starts, detecting the direction of the movement (torso bending in sagittal plane—lifting in front—vs. torso bending and twisting—lifting to the sides—) and whether is a stoop or a squat lift—legs moving in synchrony with torso vs legs still (segment speed below a threshold).

An optimization algorithm that optimizes the device parameters to maximize or minimize the defined objective function.

Subjects perform a number of repetitions of the described motions when the device is not activated to collect baseline kinematics, kinetics and muscle activity. After this, the subject performs a number of repetitions of each of the motions while the optimization algorithm uses on-board sensing to optimize the device parameters to maximize or minimize the desired objective function. A passive impedance has been proven to be effective when unloading the back joint under some pre-defined motions for some users, however, the lack of adaptation of passive devices limits the applicability of these devices to different user and different movements. In this case, the properties of the device impedance (stiffness, damping, etc.) and the onset of actuation is optimized for different motions and different users. The device is impedance controlled to be able to behave as a virtual impedance (e.g. spring, damper) as the biological joints move. The parameters that define the properties of this virtual impedance and the onset of the actuation will be optimized for each of the considered activities and result in an independent set of parameters for each motion and for each user.

Sample objective functions that can be optimized include:

Maximizing the degree of reduction in the main muscle groups of the back (RMS and/or peak) without affecting the muscle activity of muscles in the abdominal region. Co-contraction of abdominal muscles and back muscles is critical to guarantee stiffness of the structures to stabilize the back, since the proposed device produce forces that mimic the behavior of the muscles at the back, we expect that maintaining abdominal muscles to their normal activity will be critical to not affect the risk of injury in a negative way.

Maximizing the reduction in the main muscle groups of the back (RMS and/or peak) without affecting kinematics in a way that implies that the object is further from the body when lifting it comparing to wearing no device. Onboard sensing will be used to evaluate the distance of the object to the body and EMG activity of the back muscles. Distance between the object and the body is considered one of the primarily variables that affect risk of injury and that imply increased effort for holding or lifting a load.

Maximize the degree of unloading of the muscles in the back (RMS and/or peak) without increasing the Lift Index—the lift index is an equation developed by NIOSH that evaluate how significant is the risk of performing a lift. This equation is a function of the horizontal and vertical distance of the body with respect to the object, asymmetry angles when lifting the object and frequency and duration of each activity. The resulting index can be used as part of the objective to minimize the risk of injury, any change in kinematics will cause this lift index to change.

Our goal is to enable these systems to be used in real industrial environments where the tasks are unstructured. Given that the proposed method optimizes parameters such as the onset and impedance of the force profile which is a function of how the user moves for each of the defined motions that the device intends to assist with, we expect that after the optimization has found the optimal impedance and onset for each of the proposed activities there is some degree of adaptation of the resulting forces based on human motion even if the lift is not identical to the condition that was used for optimization.

Example 7B

Optimizing Controls for Back Assistance to Support Lifting Loads

Working while bending over is necessary in some environments when performing a task. This places strain on the lower back, which can lead to chronic back pain or a more significant back injury over time. A device similar to that described in Example 1 could be attached to the body to provide lower-back support. In this case, an assistive device will consist of an actuator 120 attached via two anchors 110 to the body, one at the waist, and a second one around the chest. A sample system may include an inflatable device behind the back such that when the user is lifting objects, bent forward or reaching an object it may apply a supporting force to the back. Such a device may have the potential of reducing lumbar muscular activity.

In another embodiment, a cable-based actuation approach for the back can be used as the one described in FIG. 21. One or more anchor members 110 on the upper body and on the waist can be used, and cables can be attach to each of these. When the actuator 120 applies a force, it can generate a torque to reduce the work required by the back muscles when performing some of the various tasks described herein, such as lifting and carrying.

As an example, this application focuses on a repetitive motion in which a user may need to lift objects from the ground and place them on a shelf in front of him/her. In this application, the environment is such that the operator has to bend forward to lift these objects.

An example device may include a combination of the following sensors 230 such as an IMU on the chest to measure torso angles, one or more EMG to measure muscle activity of the targeted muscle(s), a pressure sensor to measure the level of assistance of the back-support device and a pressure sensor.

An optimization algorithm may be set-up to optimize an objective function. Example suitable objectives can include peak EMG of the lumbar or thoracic erector spinae muscles, user self-assessed comfort by using a handle or an input device, time to perform each lift, and posture. For example, a device that assists the knee during a crouched position, depending on how much assistance the device gives, the wearer may have an improved posture. Perfect posture, in an embodiment, can be defined as the user having the back as straight as possible while performing the task or as close as possible that the user had when not wearing the device on (reference angle for back).

In this case, the objective function can include one or more of these parameters by using a weighted function. For example, an objective function may include objectives relating to user self-assessment and time for performance above with a 0.5 weight for each of these parameters so that the objective includes both a subjective measurement (user-dependent) and an objective measurement (estimating task performance). For this application, the user self-selected comfort can be assessed as a value from 0 to 1 and the time to perform each lift will be normalized to a number that is considered maximum for a lift so that the value is between 0 and 1 as well. Since both objectives have different units, normalization is applied as described so that both measurements can be added by using a weighted function.

For this application, the user can be instructed to select with a handle the level of comfort when performing the task. Time to perform the task can be defined as the elapsed time between when the user starts bending the torso to reach for an object until the user back goes to the initial position. The IMU on the back can be used to detect when the user is starting the movement by detecting a change in back speed or acceleration, then after completion of the lift, the user will go back and decelerate the torso in a more straight position similar to where it started. This can be estimated using the IMU on the back and looking for changes in speed, acceleration and angle.

The actuator 120 can be controlled to provide different amount of assistance while performing the task. Since for this application the system is providing low-back support during a task that involves bending the torso, the assistance may be delivered as a function of torso angle measured by a sensor such as an IMU. In order to do this, the assistive profile can be parametrized as a second order polynomial $f=k\theta^2$. FIG. 31 shows an example of representative assistance profiles by changing the parameter k. A higher stiffness value can mean that the user is getting higher assistance on the back as a function of his/her torso angle during bending.

In some embodiments of an optimization algorithm to assist this motion, the algorithm can have the objective of optimizing body posture while regulating the amount of assistance. Keeping the back as straight as possible during lifting loads is beneficial according to ergonomic guidelines, therefore an optimization algorithm could use back angle as an objective to optimize. For this application an algorithm may adapt stiffness of the actuator 120 while optimizing the back angle with respect to a straight posture. For this application the variable to be optimized is amount of stiffness in the actuator 120 and the objective would be peak torso angle while performing the task. This can be particularly useful in situations where workers are performing a task for the first time to assist as much as possible but at the same time to promote a good body posture while performing the task.

Example 8

Optimizing Controls for Back Assistance to Support Standing for a Long Time

When holding a static posture for a long time, some areas of the body can become strained. Injuries or fatigue at the back may develop from sustaining a posture for extended periods of time without adequate recovery time. In order to mitigate this issue, an assistive device can provide torque to the back so that the user back have to do less work during that time. This can allow a worker to maintain this posture without affecting his/her musculoskeletal health.

For this application, a device such as that shown in FIG. 21 can be helpful as explained above. Where the actuator 120 will provide forces that can provide back support during a standing position. This device can be useful when sustaining a standing position for a long time to avoid back injuries.

Suitable optimization can include device power consumption, EMG on muscles around the back joint, and overall posture. For example, a device that can assist the back when the wearer is in a standing position, depending on how much assistance the device gives, can improve the posture of the wearer. In this case, perfect posture can be defined as the user standing straight (back as straight as possible) while performing the task or as close as possible that the user had when not wearing the device on (reference angle for back).

An objective function can provide as much assistance as possible without affecting the overall posture of the wearer compared to the posture that the wearer typically has when performing the same task. The device can integrate sensors 230 such as IMUs on the thigh, torso to measure back angles. When the device is set to a fully transparent mode (i.e. not actuating) but turned on, the system can allow the user to perform the task in the same way as when he is not wearing the device but at the same time is able to measure and record sensor and device information. In this fully-transparent situation, the device will record back angles so as to use it as a reference when the assistance starts. In the next step, the actuator 120 will apply force an initial tension (medium tension) and an optimization algorithm may adapt the level of assistance while minimizing the error in joint angles with respect to the angles that the user had when the device was turned into a fully transparent mode.

This optimization can be useful to guarantee that the device is providing as much assistance as possible without changing the overall ergonomics of the task, given the experience of the user when performing this activity. In other situations where the ergonomics may not be ideal to start with, the device can be set-up to minimize the error between the user joint angles when performing the task and a reference such as OSHA-recommended body posture when performing that task. This same concept could also be applied to lifting or transporting loads, etc.

Example 9

Optimizing Controls for Back Assistance to Support Transporting Loads

As mentioned above in Example 3, this method can also be applied to transporting loads, in this case, also suitable optimization can include device power consumption, EMG on muscles around the back joint, and overall posture. For example, a device that can assist the back when the wearer transporting loads, depending on how much assistance the device gives, can improve the posture of the wearer. In this case, perfect posture can be defined as the user standing straight (back as straight as possible) while performing the task or as close as possible that the user had when not wearing the device on (reference angle for back).

An objective function can provide as much assistance as possible without affecting the overall posture of the wearer compared to the posture that the wearer typically has when performing the same task. The device can integrate sensors 230 such as IMUs on the thigh, torso to measure back angles. In this case, the objective may be minimizing the error between the back angle and the OSHA-recommended body posture when performing this task.

This optimization can be useful to guarantee that the device is providing as much assistance as possible by providing maximum assistance to guarantee overall ergonomics.

Example 10

Optimizing Controls for Hand Assistance to Support Grasping Tools

Gripping components for multiple hours per day presents a hazard, applying hand force increases the risk for hand and wrist injuries. Hand gripping for extended periods is a frequent cause of hand and wrist injuries for employees. Tools must be held tight enough to maintain control, but not excessively tight. A glove that reduces static gripping forces may be helpful to avoid injuries and overexertion. Static gloves that have high friction materials have been used to improve the grip of power tools, however, an active device that provides assistance to the grip as needed to relieve the amount of effort that the user has to do to sustain a control grasp of a power tool may enhance the performance of the task and mitigate risk of injury.

Multiple tasks can require additional hand or wrist support, some examples for illustration purposes are included below:

1. Holding objects, for example, for long periods of time.
2. Pressing buttons repetitively or pressing triggers to activate tools. For instance when holding a drill, the user has to press the trigger when activating it. Although pressing a trigger of a tool once doesn't require almost any effort from the user if the user has to press the trigger of the tools a large number of times, this may result in fatigue and other complications such as carpal-tunnel syndrome.
3. Manipulating objects such as manually tightening fixtures.

An example assistive device, as shown in FIG. 32, can include one actuation unit in the back of each finger, that when pressurized can provide assistance to each finger. A typical activity in the manufacturing sector that would benefit from such a device would be holding a power tool for an extended amount of time. The hand assistive device may include an anchor member 110 positioned on a distal portion of the finger (e.g., the finger tip, as shown) and another anchor member 110 positioned on the wrist (as shown) or other suitable body part (e.g., proximal portion of the finger; the base or palm of the hand) located on a proximal side of the joint(s) to be assisted (e.g., the finger joints).

Optimization algorithms can be applied to assist the hand of healthy users when performing tasks such as holding power tools for a long amount of time or when pressing the trigger of the tool multiple times per day. Multiple repetitions or sustained activities may result in overexertion and other effects.

Typically the index will be dedicated to pressing the trigger in the tool and the rest of the fingers will be dedicated to grasping the tool to hold it.

For this application, we will focus on keeping a sustained grip of the tool for a long time.

An example objective for this optimization problem can be those associated with the effort of the wearer such as muscle activity, in this case peak muscle activity of the finger flexor muscles during the grasp.

The assistive glove may include one actuator 120 per finger that are integrated in a glove that anchors on one side to the tip of each finger and on the other side to the wrist.

A suitable parameter to control for this optimization problem would be magnitude of actuation. A device will provide an increased amount of actuation to reduce peak EMG activity.

A suitable objective function for this problem would be grasp stability or the quality of the grasp. There are multiple functions that could be good proxies to improve grasp quality such as the sum of the components of the applied forces normal to the object boundary which is an indication of the internal forces that the object withstands when an external disturbance is applied. Therefore a quality measure could be defined as the sum of the modules of the normal components of the applied forces to the object. An optimization algorithm could use this metric as a variable to optimize. A device will have then integrated sensors 230 to measure normal forces applied to the device integrated below the finger surface.

However, because the worker may be holding the power tool for a long time, a secondary objective could be battery use defined as estimating the battery level that would be remaining if that grasp is sustained for a preset amount of time (i.e. 2 hours) that the worker may use that tool for. In order to measure this, the amount of power that the device is currently using and the electrical power left in the battery could be measured by reading the voltage of the battery. A battery objective could be to maximize the battery that would be left after 2 hours of use.

An objective function may give relative weights of 0.7 and 0.3 to the quality of the grasp and the predicted remaining battery after 2 hours of use respectively. However, if the predicted remaining battery after 2 hours of use falls below 10% the weight of each objective will change to 0.4 and 0.6.

An actuation space could be parametrized such that the pressure magnitude applied to each finger would be varied to optimize the objective described above.

An optimization algorithm such as Bayesian optimization or gradient descent could be applied to solve this problem.

Example 11

Optimizing Controls for Knee Assistance to Support Crouch Poses

Some activities can require the user to stay static in a crouched position for a long time. As an example, if the worker has to perform task in a tight space he/she may need to stay in a crouched position working on knees for extended periods of time. Injuries at the knee may develop from sustaining that non-ergonomic posture for extended periods of time without adequate recovery time. In order to mitigate this issue, an assistive device may provide torque to the knee so that the user knees' have to do less work during that time. This may allow the worker to maintain this posture without affecting his/her musculoskeletal health.

Referring back, FIG. 22 shows an example of a soft wearable device 100 embodiment that is achieved by placing a cable-driven actuator 120 with a similar technology as those described in the previous examples with anchor members 110 on both sides of the knee (front of the thigh and front of the calf). This actuator 120 may be attached to the calf by wearing a calf-wrap device around the shank and then to the upper-side of the knee by attaching to a thigh-wrap. When tensioned, the actuator 120 will provide forces that will provide knee support during a crouched position; this device could be very useful when sustaining a crouching position for a long time to avoid knee injuries. This activity involves a posture that may need to be sustained over time where an optimization algorithm may be useful to optimize the amount of assistance that this device is providing to the knee.

Suitable optimization can include device power consumption, EMG on muscles around the knee joint, and overall posture. For example, a device that can assist the knee when the wearer is in a crouched position, depending on how much assistance the device gives, can improve the posture of the wearer. In this case, perfect posture can be defined as the user standing straight (back as straight as possible, knees as straight as possible) while performing the task or as close as possible that the user had when not wearing the device on (reference angle for back and knees).

An objective function can provide as much assistance as possible without affecting the overall posture of the wearer compared to the posture that the wearer typically has when performing the same task. The device can integrate sensors 230 such as IMUs on the calf, thigh, and back to measure knee and back angles. When the device is set in a fully transparent mode (i.e., not actuating) but turned on, the system can allow the user to perform the task in the same way as when he is not wearing the device, but at the same time can be able to measure and record sensor and/or device information. In this fully-transparent situation, the device will record knee and back angles so as to use it as a reference when the assistance starts. In the next step, the actuator 120 will be tensioned with an initial tension (medium tension) and an optimization algorithm may adapt the level of assistance while minimizing the error in joint angles with respect to the angles that the user had when the device was turned into a fully transparent mode.

This optimization can be useful to guarantee that the device is providing as much assistance as possible without changing the overall ergonomics of the task, given the experience of the user when performing this activity. In other situations where the ergonomics may not be ideal to start with, the device can be set-up to minimize the error between the user joint angles when performing the task and a reference such as OSHA-recommended body posture when performing that task. This same concept could also be applied to lifting or transporting loads, etc.

Example 12

Optimizing Controls for Elbow Assistance to Support Lifting Loads

When lifting objects, a user can need elbow support to hold the weight of the object. A device similar to the device depicted in FIG. 27 can be worn on the elbow by attaching on one end to the forearm and on the other end to the arm. When tensioned, the device can provide assistance to the elbow joint therefore minimizing the level of effort that the user has to do.

Suitable optimization can include device power consumption and EMG on muscles around the elbow joint. For example, a device that can assist the elbow when the wearer lifts loads, can use peak EMG activity of muscles around the elbow joint as an objective function.

The device can integrate sensors 230 such as IMUs on the arm and forearm, to measure elbow angles, also may include EMGs to measure muscle activity of the targeted muscles in the elbow. A suitable parameter to optimize may be the level of assistance.

A sample parametrized assistance may be defined as a impedance function (stiffness) based on the elbow angle. The impedance coefficients may be optimized by the algorithm in order to maximize or minimize the objective function.

This optimization can be useful to guarantee that the device is providing as much assistance as possible while reducing the targeted EMG muscles.

Wearable Devices to Assist the Back and/or Hip Joints

Oftentimes, individuals perform tasks that may lead to fatigue, lost productivity and eventually increased injuries. Overexertion injuries and fatigue result in a large economic and public health issue for applications such as industry (warehouse, logistics, manufacturing, caregivers, etc.), sports, consumer and elderly. Back pain, fatigue and injuries is one of the most common disabilities that have a large impact in our lives and in our ability to be effective at work. A wearable device 100 that reduces fatigue, increases productivity and/or mitigates risk of injury by providing assistance to the wearer's joint(s) to assist with motion and/or posture during tasks such as lifting, reaching and holding a static posture may have a big impact on productivity, enhancing our ability to do more, reduced fatigue and mitigation of risk of injury.

Figure 36:
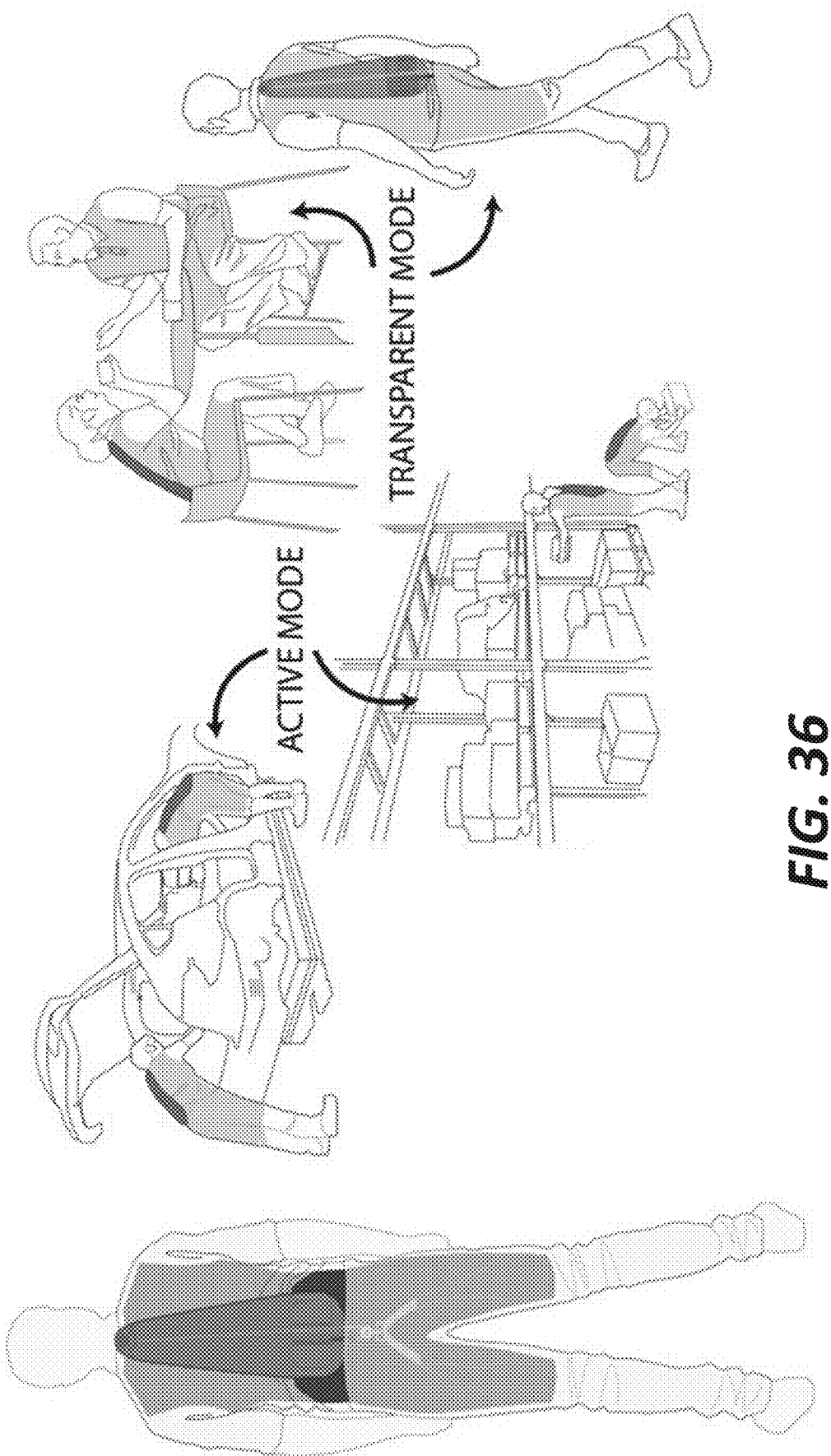
FIG. 36 illustrates a concept of a device that can be worn to assist user's motion or posture during lifting and/or reaching tasks.

FIG. 36 illustrates a concept of a device that can be worn to assist user's motion or posture during lifting and/or reaching tasks. These tasks are common in industrial settings (e.g. warehouse, logistics, automotive, construction, caregivers), the elderly, consumer, recreational and sports. Robotic apparel is able to provide assistive forces when needed (e.g., during lifting and reaching tasks), but also to become fully transparent when desired so as to be unobtrusive during tasks that don't require assistance (e.g. driving a truck, having lunch, taking a break). This means, that robotic apparel could potentially be worn for a full day of work to be able to assist when needed, but be fully unobtrusive otherwise.

Robotic apparel can be configured to assist one or multiple joints by anchoring on both sides of the targeted joint(s) to provide assistive tensile forces to the wearer that provide support during motion and/or posture. In an embodiment, an active device may assist both the back and hip joints by providing tensile forces that cross both joints, this is inspired by the way muscles and tendons generate forces during tasks such as lifting.

FIG. 37A shows a diagram that illustrates how tensile forces can generate assistive torques across the back and hip joints. Tensile forces cross the joints at a distance from the center of rotation (moment arm), this creates a torque around the joint(s) that assist the joint(s) movement and/or posture so as to reduce fatigue and stress on the musculoskeletal system. For an example embodiment, tensile forces may be routed across the hip and back joints that would translate into a torque assistance that may assist with hip and back motion and/or posture. This system architecture could be helpful to assist the wearer during multiple activities such as during lifting, holding static postures and/or reaching tasks.

FIG. 37B shows an implementation of a fully portable device that is able to assist the back and hip joints by following the architecture depicted in FIG. 37A. The device may comprise textile components that wrap around the thighs and shoulders of the user, additionally a textile component may wrap around the waist to be able to anchor system components to the body. In its current implementation, the system may comprise two anchor members 110 (one per leg), and both anchor members 110 may be connected via a load-balancing strap 112 to create an anchor member 110 on the lower back (anchor 1). The load balancing strap 212 can slide with respect to the anchor member 110 via an element such as a low-friction roller, bearing, pulley, low-friction buckle, etc. as it was presented in FIG. 13. The load balancing element 212 allows the user to move the legs freely during tasks such as walking and creates tension in the wearable device 100 during tasks that involve bending the trunk and/or both legs (lifting, reaching, etc.). Moreover, this load balancing element 212 distributes the tensile forces to both legs by splitting the load to both anchor members 110. On the upper side of the torso, shoulder straps wrap around the shoulders of the wearer to create an anchor point on the upper back (anchor 2) as shown in FIG. 37B. Additionally, in order to maximize comfort and moment arm (relative distance between the center of rotation of the joint and the tensile forces in the wearable device 100), a conformal textile element (e.g. padding, foam, etc.) may be added to the system on the back. This element may include pockets to integrate system components such as batteries or electronic components.

An actuator 120 component such as a cable-driven system may be connected between the two anchor members 110 in the system (anchor 1 and 2). As the motor rotates, see direction R, connecting element 150 wraps around a pulley in order to generate forces between those two anchor members 110 as shown in FIG. 34A, FIG. 34B, FIG. 34C and FIG. 38. It should be noted that alternative approaches and anchor members 110 may be considered where, for instance, two motors could be used to independently provide tensile forces to the back and hip joints. Given that there are synergies between the hip and back joints during lifting and holding static postures, here we focus on the description of an embodiment that simultaneously assists both joints. This has the advantage of reducing weight, complexity and cost compared to a solution that would independently provide assistance to both the hip and the back or to independently assist the hip or the back. It should also be noted that alternative actuation approaches such as fluidic (pneumatic, hydraulic), electroactive materials, electro-mechanical actuation systems, cable driven actuation systems, alternative transmission materials (e.g. strings, cables, ribbon, tape materials, etc), clutches, etc. may be used to generate tension across the different anchor members 110.

Figure 38:
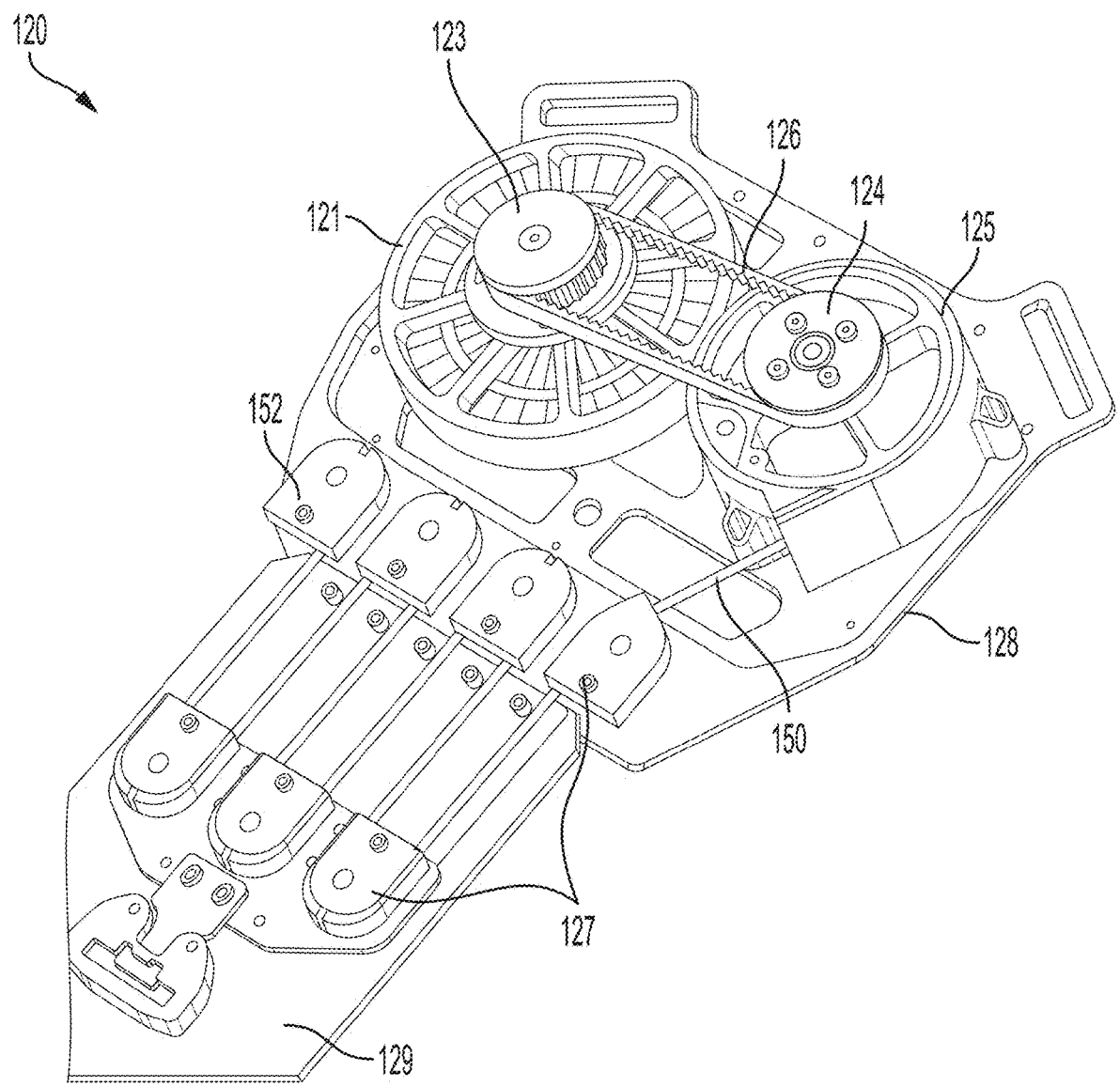
FIG. 38 shows a cable-driven actuation system that may be connected between the two anchor members.

FIG. 38 shows the detailed design and implementation of an electro-mechanical actuator 120 system comprising a motor 121 and a cable-transmission system (series of guides 127). As an example, a system may integrate a T-motor which is a motor commonly used for consumer applications (drone industry, etc.) and therefore high performance and lower cost than other available options. The axis 122 (not shown) of the motor 121 is connected to a first rotating pulley element 123 ("input belt pulley") which connects to a second rotating pulley element 124 ("output belt pulley") by using a timing belt 126, the ratio of the size of both pulleys 123, 124 conforms an initial gear reduction in the system (in this case 2:1). As the motor 121 rotates, this movement is transferred to the output pulley 124 via timing belt 126. Connecting element 150 wraps around a third rotating pulley element 125 (e.g., spindle) connected to output belt pulley 124.

Additional reduction is achieved via a series of guides 127 (e.g., pulleys, or "cable pulleys") that are distributed as shown in FIG. 38. As explained previously this concept behaves as an alternative to a gearbox which can capture the benefits of a geared reduction without some of its disadvantages such as friction, inefficiency and noise. FIG. 38 shows how by routing the actuating element 150 around rotating or low-friction elements, we can achieve reductions equivalent to having a (n+1):1 ratio gearbox where n is the number of rotating or low-friction elements. In this case, we use 5 pulleys which achieves an additional reduction of 6:1. The advantage of incorporating the 6:1 ratio in this fashion is that by adding this 6:1 reduction, the size of the pulleys can be kept smaller which has benefits in actuation packaging and size.

As shown in FIG. 38, actuator 120 may include a first planar member 128 coupled to the first anchor member 110 and a second planar member 129 coupled to the second anchor member 110. A plurality of guides 127 (e.g., rotating pulley elements; low-friction grommets or studs, and the like) may be arranged on the first planar member 128 and the second planar member 129, and connecting element 150 (e.g., cable, ribbon, and the like) passes over opposing guides 127 on the first planar member 128 and the second planar member 129 in an alternating fashion to couple the first planar member 128 and the second planar member 129. A first end 151 of the connecting element 150 may be anchored to the first anchor member 110 and a second end 152 of the flexible elongate element 150 may be coupled to a motor 121. Actuating motor 121 may pull the second end 152 of the connecting element 150, thereby pulling the first anchor member 110 and the second anchor member 110 toward one another.

In another embodiment (not shown), guides 127 may additionally or alternatively be coupled directly to first anchor member 110 and second anchor member 110 rather than to planar members. One of ordinary skill in the art will recognize that the planar member construction may provide for actuator 120 to be selectably attached and detached from wearable device 100.

Figure 39B:
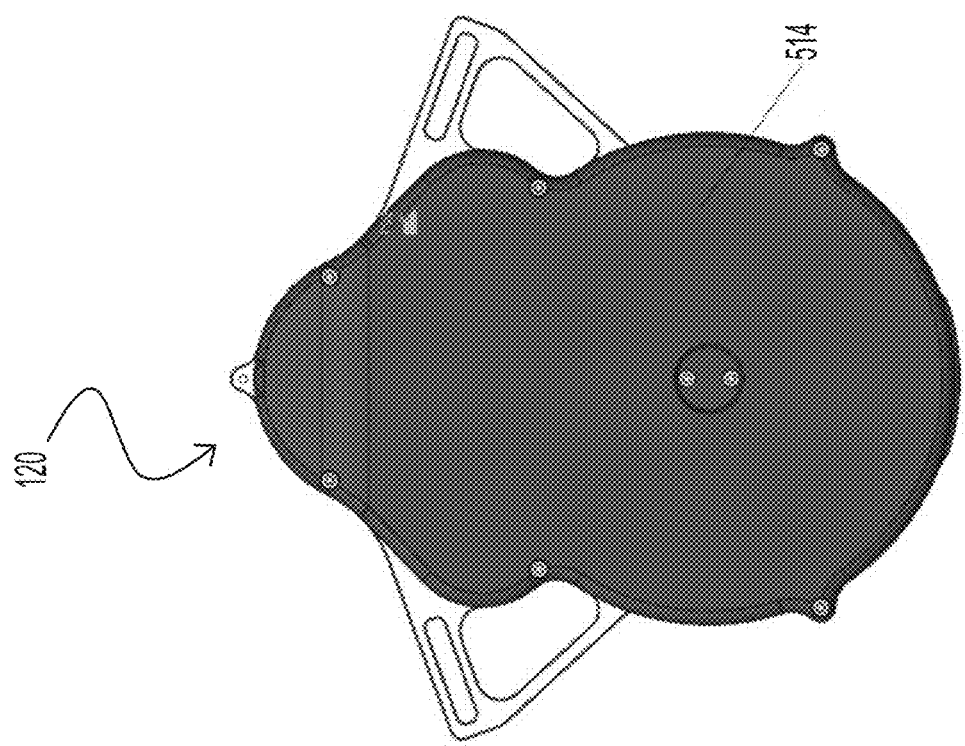
FIG. 39A, FIG. 39B, FIG. 40A, FIG. 40B, FIG. 41A, and FIG. 41B show an alternative cable-driven actuation system design. As shown, this actuation element includes wearable device quick attachment features to be able to attach textile components to a machined feature in the design.
Figure 39A:
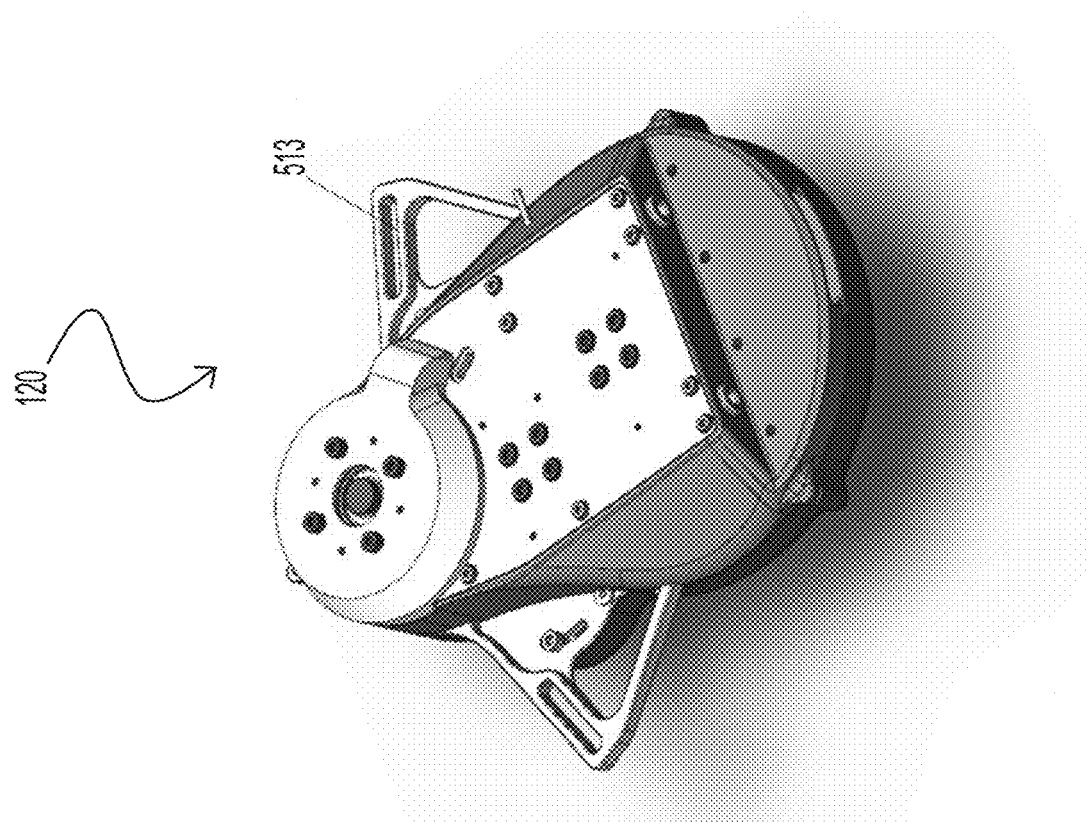
Figure 40B:
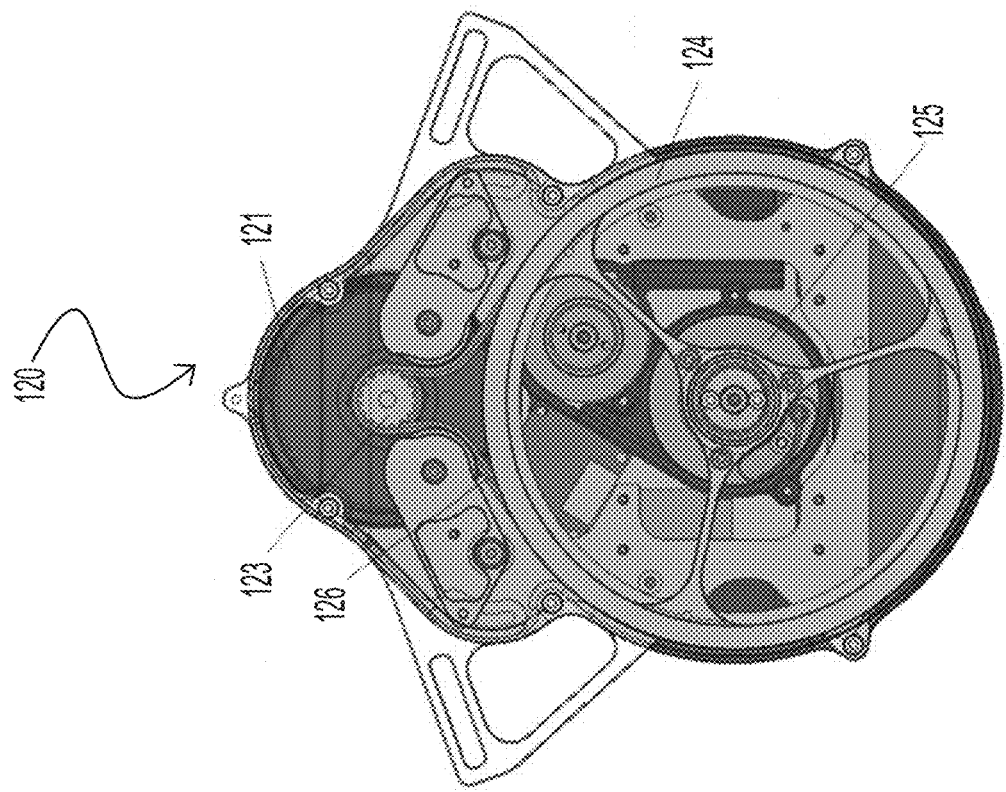
Figure 40A:
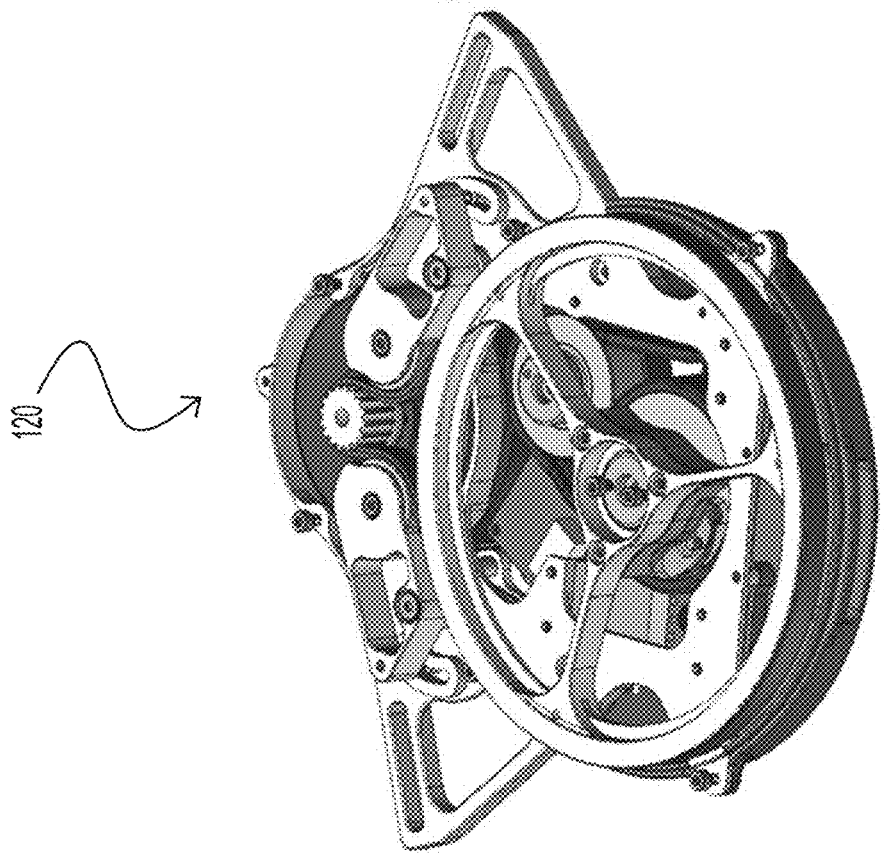
Figure 41B:
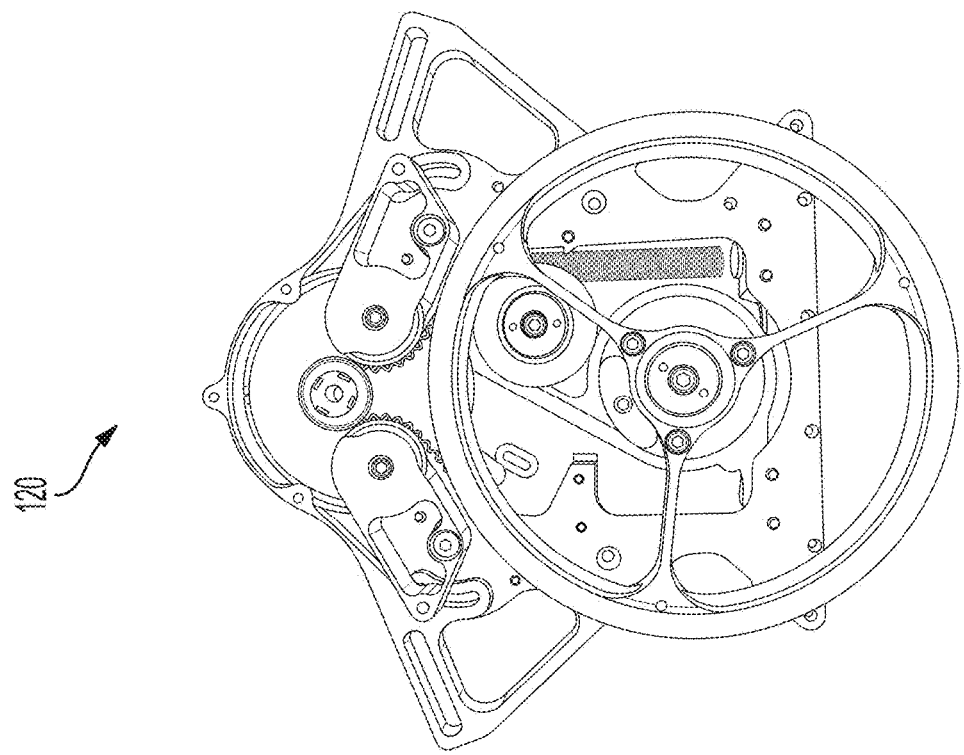
Figure 41A:
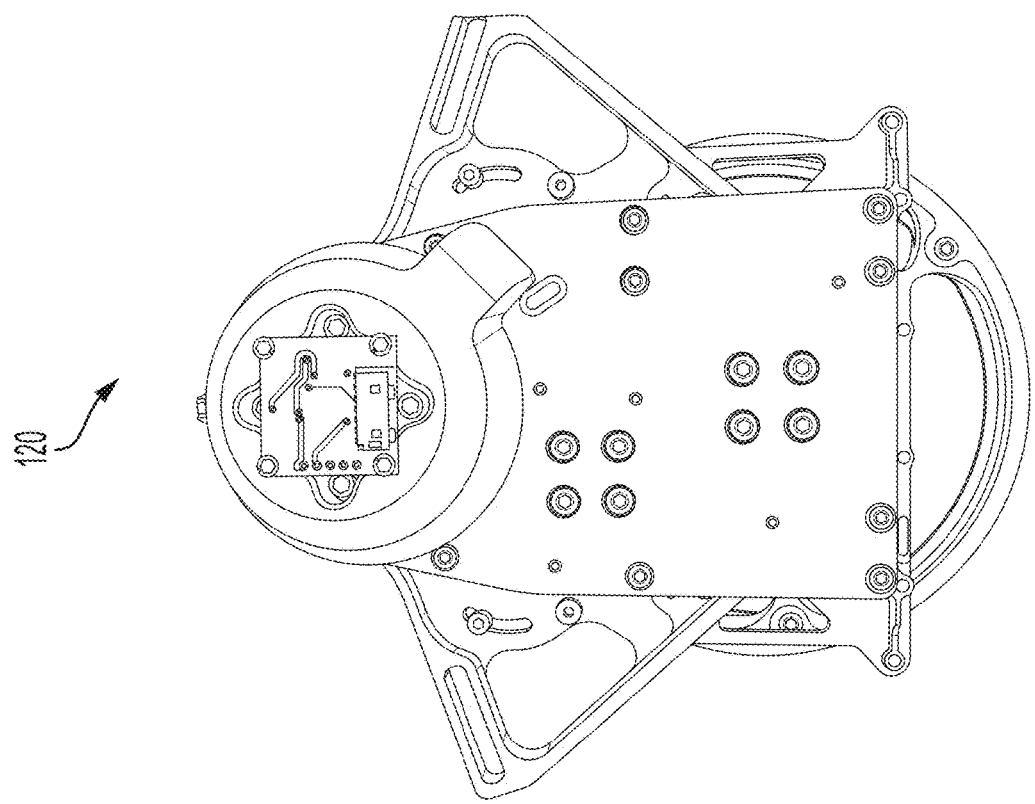

Referring ahead to FIG. 39A, FIG. 39B, FIG. 40A, FIG. 40B, FIG. 41A, and FIG. 41B show an alternative cable-driven actuation system design. As shown, this actuation element includes wearable device 100 quick attachment features 513 to be able to attach textile components to a machined feature in the design. As shown in FIG. 39A and FIG. 39B, this version may be fully enclosed by a cover 514. FIG. 40A and FIG. 40B, show the detailed mechanical design and the different components that configure the system. The electro-mechanical actuator 120 system may comprise a brushless DC motor and a cable- or ribbon-based transmission system. As an example, a system may integrate an outrunner motor such as an U7 280 kv motor manufactured by T-motor which is commonly used for consumer applications (drone industry, etc.) and therefore high performance and lower cost than other available options. The axis of the motor is connected to an "input belt pulley" which connects to the "output belt pulley" by a timing belt, the ratio of the size of both pulleys conforms an initial gear reduction in the system (in this case 7.75:1). An actuation cable wraps around the cable spindle which is connected to the "output belt pulley". Additional reduction is achieved via one pulley ("Cable pulleys). As explained previously this concept behaves as an alternative to a gearbox which can capture the benefits of a geared reduction without some of its disadvantages such as friction, inefficiency, weight, cost, and noise. FIG. 41A and FIG. 41B show the real system following the design described in FIG. 39A, FIG. 39B, FIG. 40A and FIG. 40B. Referring back to FIG. 34B, by routing the actuating element around rotating or low-friction elements, we can achieve reductions equivalent to having an: 1 ratio gearbox where n is the number of parallel cable segments. In this case, we use 2 parallel cables which achieves an additional reduction of 2:1. The advantage of incorporating the 2:1 ratio in this fashion is that by adding the reduction, the size of the internal reduction such as the timing belt transmission can be kept small which has benefits in actuation packaging, mass, cost, and size.

As shown in FIG. 40B, actuator 120 may be coupled to a first anchor member 110 may include a motor 121 and a first rotating pulley element 123 connected to an output 122 of motor 121. A second rotating pulley element 124 may be situated coplanar with and radially offset from the first rotating pulley element 123, and coupled to the first rotating pulley element 123 via a timing belt 126. A third rotating pulley element 125 may be situated coaxial with and axially offset from the first rotating pulley element 123, and fixedly coupled to the first rotating pulley element 123. Connecting element 150 may be wound about the third rotating pulley 125 and second end 152 or an intermediate portion 153 of the connecting element 150 may be coupled to the second anchor member 110. Actuating motor 121 may cause connecting element 150 to shorten, thereby pulling the first anchor member 110 and the second anchor member 110 toward one another.

Figure 42:
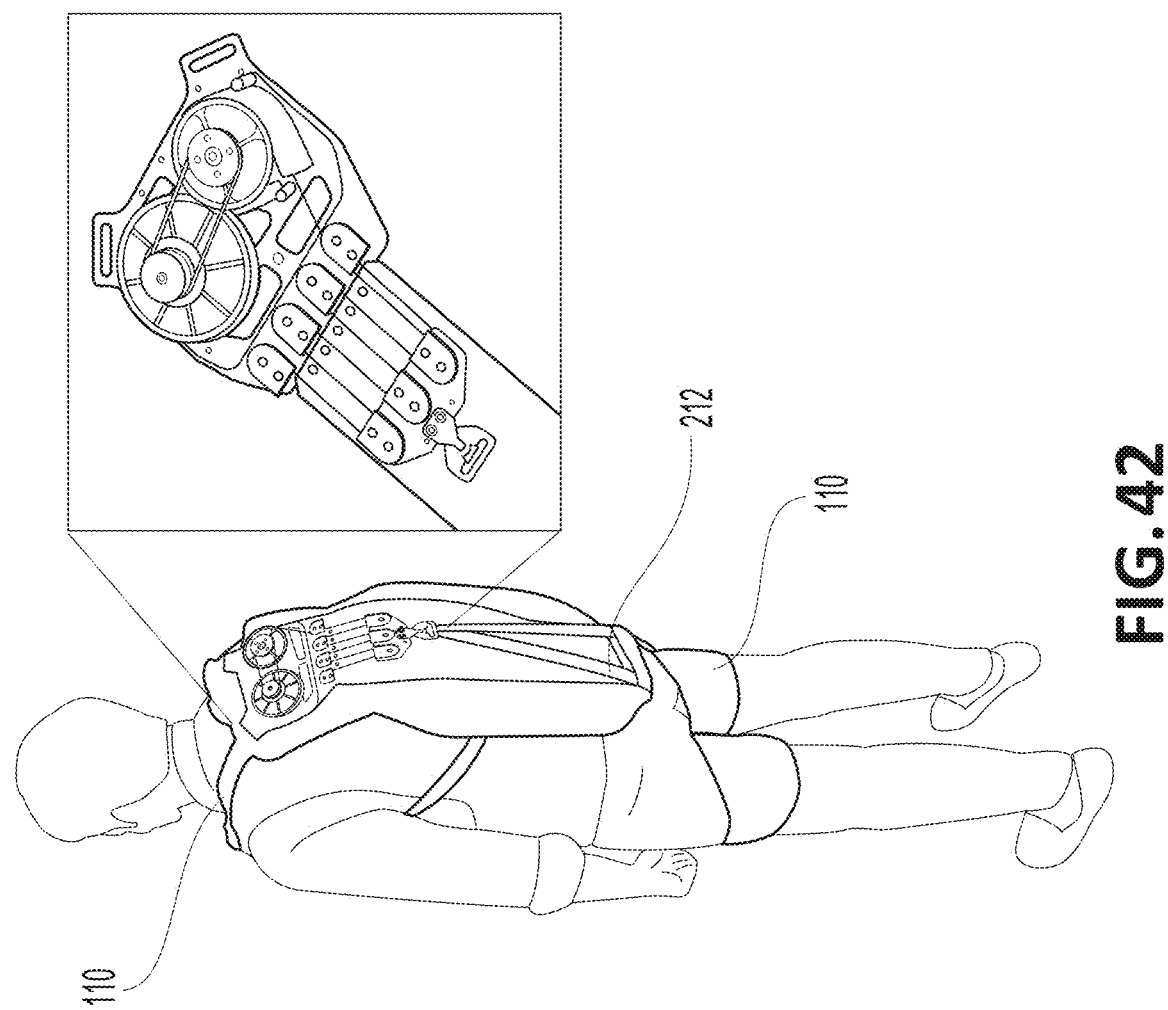
FIG. 42 shows a device including a cable-driven electromechanical actuation system being worn by a user.

FIG. 42 shows a device including a cable-driven electro-mechanical actuation system being worn by a user. This system integrates the actuation system described previously and shown in FIG. 38. In this embodiment, the actuator 120 is located on the upper torso, anchored to the upper torso at the place where both shoulder straps connect, the end of the cable 150 is connected to the load-balancing strap 112 such that as the motor rotates, tensile forces can be generated between the shoulder strap and the load balancing element 212 which as explained previously (FIG. 37A). generates torques across the hip and back joints when needed. Another advantage of this system is that if the cable were to be "slack" no forces will be transferred to the user. As shown in FIG. 42, a user may wear the above-mentioned system over clothing to provide assistance to the back and hip joints during lifting and holding static postures. FIG. 42 shows the details of an embodiment in which the actuator 120 is positioned on the upper-torso of the user. The cable-driven actuator 120 may alternatively be placed on different areas of the body such as the lower back, the waist, the legs, etc. or mounted to a backpack or rucksack depending on the application. FIG. 43A, FIG. 43B, and FIG. 43C show additional details of the actuator 120 system located on the upper-torso of the user and its integration into apparel. The actuator 120 may be covered by a textile component (as shown in FIG. 43C), soft material or by a rigid case. If covered by a textile component, this component may include flexible boning elements so as to be able to keep a shape around the motor without being in contact with components.

Robotic Apparel, Over or Under Clothing Version

Robotic apparel may be designed to be worn over standard or work clothing. FIG. 43A, FIG. 43B, and FIG. 43C show an embodiment of the device that can be worn over clothing. For this embodiment, the system is composed of:

- Thigh-wraps, one for each leg. These components wrap around the thighs of the user and can either be worn over or under clothing.
- Load balancing element 212. Connects to both anchor members 110 and creates a loop as explained previously to create an anchor point on the lower back.
- Shoulder straps. These components wrap around the shoulders of the user and can be either worn on top or under clothing.
- Actuation system: This component is designed to be integrated into the apparel components. FIG. 43A, FIG. 43B, and FIG. 43C show an example of how the actuator 120 may be positioned on the upper torso of the user. In this case, the cable-driven system is grounded on one side to the anchor point created by the shoulder strap and on the other side to the anchor point created by the load-balancing strap 112. As the actuator 120 moves, a cable is able to generate forces across the user's joints to provide assistance to the user. Additional actuation concepts or mechanisms that may be used to generate forces between anchor points may include fluidic (pneumatic, hydraulic), electromechanical actuation, electrostatic, passive systems (springs, damping, etc.), semi-active (clutch, etc.), etc. Alternatively, the actuator 120 may be positioned in other parts of the body such as the waist, the thighs, a backpack/rucksack, etc.).
- Sensing elements: in the proposed embodiment, the system may integrate motion sensors 230, e.g. one on each thigh to measure leg movement, one on the lower torso and/or one on the upper torso. A load-sensing element 230 may be used to measure or estimate forces that the device generates on the person. This may include (current sensing, torque sensors, loadcell sensors, strain gauges, sensors that change electrical properties as stretch or load is applied, etc.). Other embodiments may additionally include pressure sensors to measure ground reaction forces, force sensors on different parts of the body to estimate load or user-environment interaction forces, EMG sensors to estimate muscle activity, motion sensors such as IMUs, gyros, accelerometers, encoders, resolvers, potentiometers, sensing units that change electrical properties (resistance, capacitance, etc.) based on deformation or load applied to them, etc.
- Adjustment points: the embodiment shown in FIG. 43A, FIG. 43B and FIG. 43C, has adjustment points to be able to adjust strap length or tension of textile components to different body sizes or to user preferences. A ratcheting system (e.g. BOA) or Velcro may be used to adjust the compression of the anchor members 110 in the leg and adjust based on thigh size and user preferences/comfort. A ratcheting system 516 or Velcro component in line with the load-balancing strap 112 may be used to change the length of the load-balancing strap 112. Changing the initial length of the load-balancing strap 112 is practical to adjust the length of the device to different user heights, to adjust the length of the cable based on the initial positioning of thigh/wraps components 515. In the case of a passive system where the connecting element 150 between anchor members 110 is a passive element 190, changing the length of this strap may be used to set the initial tension of this components which will define parameters such a how much assistance the user will receive as he/she moves or initial point within the user movement that will start to generate forces.
- Quick connect/disconnect features: a device may include quick connect/disconnect features to be able to selectably attach and detach/disconnect actuation, battery or sensing elements from the textile components. These may include, Velcro straps that wrap around sensing/actuator 120 features to ground them to the textile components, click-in mechanisms, pogo pins or electrical connections to be able to connect electrically the click in actuation/power/sensing elements for power/data transmission, etc. Quick connect/disconnect of actuation, power or sensing components may be practical to allow to wash textile elements in contact with the user, to be able to wear the textile and/or sensing portion of the wearable device 100 without actuation for some applications, etc.

FIG. 44 and FIG. 45 show different users wearing the proposed system over clothing to perform different tasks that involve reaching or lifting loads.

Anchor Member and Connecting Element Integration into Apparel

Figure 46B:
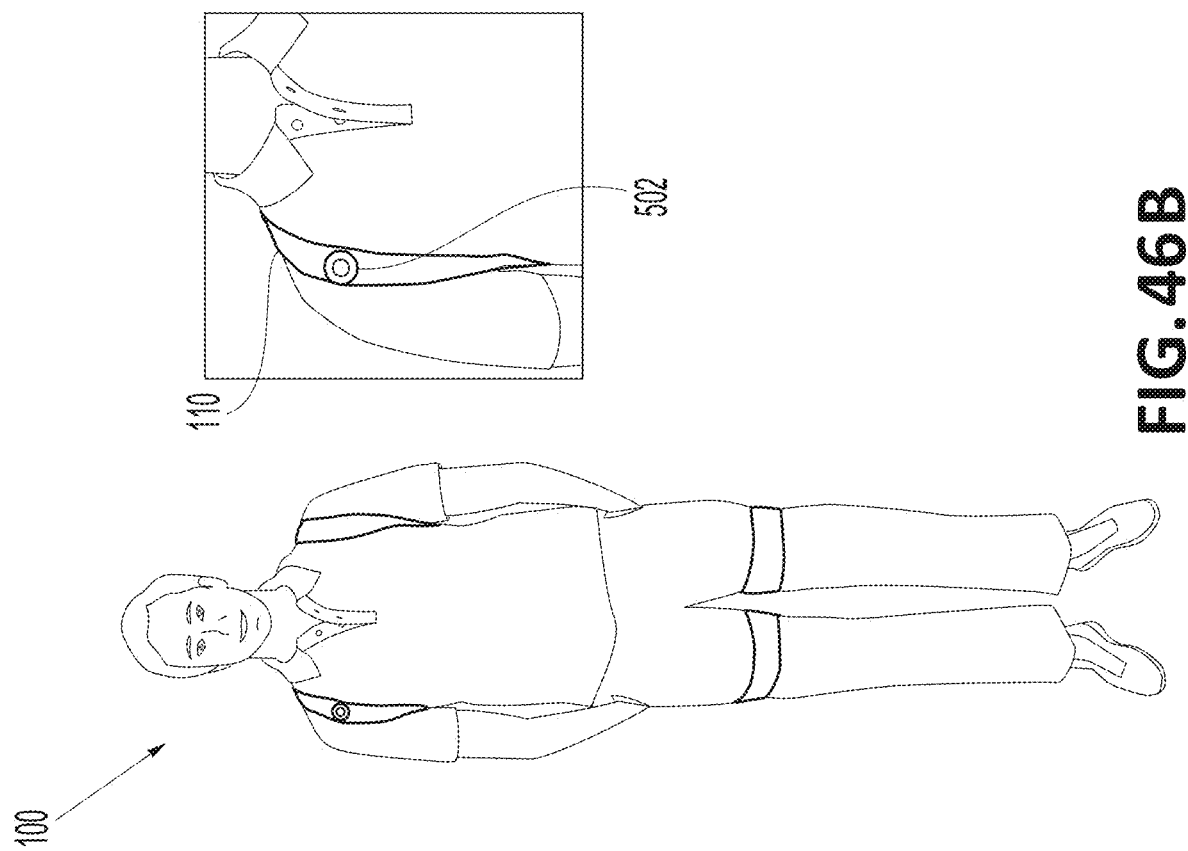
FIG. 46A and FIG. 46B, in an embodiment, the wearable device components, architecture and the actuator system may be incorporated into typical apparel for daily use.
Figure 46A:
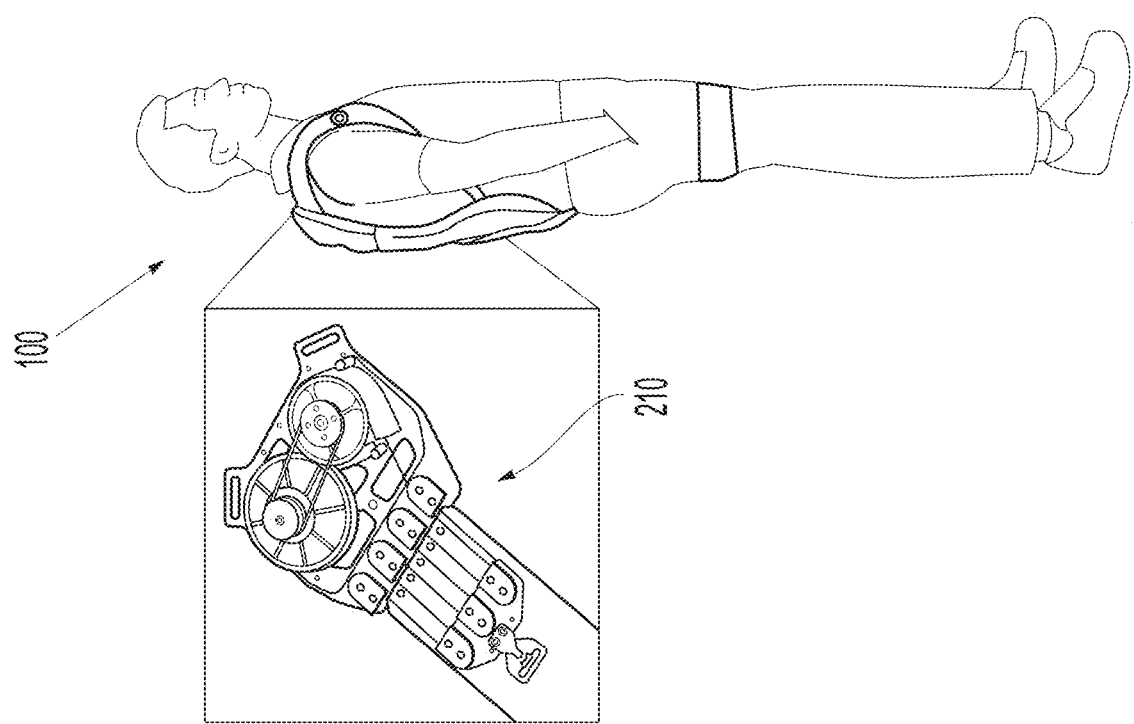

Referring now to FIG. 46A and FIG. 46B, in an embodiment, the wearable device 100 components, architecture and the actuator 120 system may be incorporated into typical apparel for daily use. Apparel may define standard clothing worn by users for different applications (e.g. workwear, workforce uniforms, military uniforms, athletic apparel such as sports uniforms and casual apparel such as jeans, pants, t-shirts or polos). FIG. 46A and FIG. 46B show a version of the device that consists of workwear with attachment points and a removable, cable-driven sensor and actuator 120 system that could click into the workwear to assist to the wearer. These components can be easily removed in just a few seconds by using components such as straps, Velcro straps, buckles, click-in mechanisms, etc. this is especially important to facilitate the process of washing the textile components. The user may then click out the actuation and/or sensing components to wash the textile components that are in contact with the user, additionally, a wearer may wear the textile components regularly and click-in the actuation and sensing components when needed. This system is composed by relatively inextensible or low-stretch fabric (e.g. woven, webbing) that is attached directly to common workwear (e.g. sewn, bonded, top-applied) to configure the wearable device 100 architecture that was described previously (shoulder straps, thigh wraps, load-balancing strap 112).

Additionally, if the pants or shirt are made of relatively inextensible or low-stretch material (e.g. woven), the structure of the pant/shirt can be part of the wearable device 100 component. For instance, if the pants are made out of a woven material, a top-applied strap that can be used to keep the pant tight fitting in a certain area (e.g. thigh) can be sufficient to transmit forces to the thigh and may not require the use of a separate thigh wrap.

Figure 48:
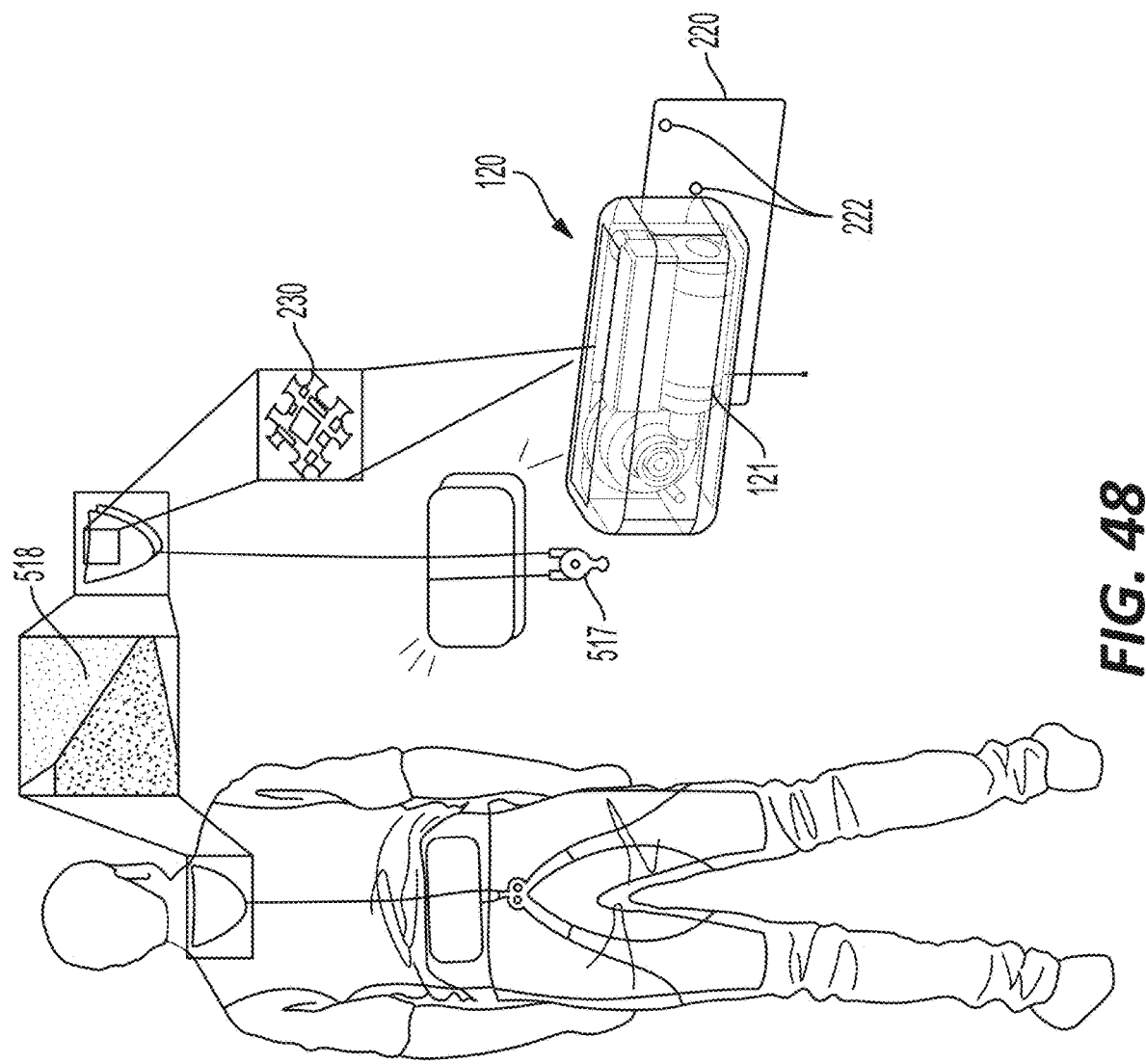
FIG. 48 shows an example where the actuator is clicked in to a mounting plate sown into the textile components on the waist, the mounting plate may have click-in mechanical and electrical features.

FIG. 47A, FIG. 47B, FIG. 47C, and FIG. 47D show additional details of an embodiment that integrates robotic components into apparel. For this embodiment, the actuator 120 is attached to the textile elements via fast strap attachments as shown in the top left of FIG. 47A. As an example, a relatively inextensible fabric strap is looped around a slot in the machined components of the actuator 120 and fixed with Velcro or a buckle to keep the actuator 120 in place. In a different embodiment, other approaches could be used such as: a click-in method in which the actuator 120 integrates click in features and the apparel integrates a mounting plate 220 to which the actuator 120 can be clicked-in guaranteeing a secure mechanical and/or electrical connection with the textile components. In this case, the electrical connections could be made by using electrical connectors 222 such as pogo-pins FIG. 48. shows an example where the actuator 120 is clicked in to a mounting plate 220 sown into the textile components on the waist, the mounting plate 220 may have click-in mechanical and electrical features. The actuation cable may click-in via a mechanical connector 517 to the load-balancing strap 112 on one end and via a connector or Velcro attachment to the upper back, some embodiments may use conductive fabrics to power sensors 230 distributed in the textiles (e.g. IMUs, strain gauges, soft sensors 230). FIG. 48 shows an example where an IMU sensor 230 on the upper back is powered by using conductive textiles 518 and Velcro components. Having fast click in features may be useful to disconnect the electromechanical components from the apparel to, for instance, allow washability of the apparel. In another situation, this approach could be helpful if a number of user are wearing a only the textile components with integrated sensing for portions of the day and may attach the electromechanical components when needed or share these across different users.

FIG. 47A and FIG. 47B also show additional details of the different apparel components to allow for adjustability and secure compression. The bottom left picture (FIG. 47A) shows an example embodiment in which inextensible textile components (webbing, sail cloth, woven textile, etc.) are sewn directly onto the fabric of a standard polo to configure shoulder straps. Additionally, a ratchetting system (e.g. BOA) is integrated into this strap to adjust the relative length of this shoulder strap to fit different users or for customized comfort.

FIG. 47C and FIG. 47D show two implementations of integrating thigh anchor member (e.g., thigh wrap) and the load-balancing strap 112 directly into work-wear. FIG. 47C. shows an example where a thigh anchor member 110 is sewn onto workpants and a ratchetting system (e.g. BOA) can be used to apply compression to integrated thigh anchor member 110 to make sure that it can transmit forces to the thigh of the user. FIG. 47D. shows an example where the thigh anchor member 110 is sewn inside the work pants and still a ratchetting system (e.g. BOA) can be used to regulate the compression of the thigh anchor member 110 component. FIG. 47C and FIG. 47D. also show how a load-balancing strap 112 can be attached to the top of the anchor member 110 and routed either over the pants, or under the pants, or going through channel built into the pants (e.g. onto the back pocket) to route from under the pant to over the pant. FIG. 47D. also shows how an additional ratchetting system (e.g. BOA) can be used to regulate the length of this load-balancing strap 112 so as to fit different individuals or for customized comfort-functionality. This load balancing element 212 can then be clicked in to the bottom end of the actuation cable so as to provide tensile forces that are distributed to both thigh anchor members 110.

Sensor Integration into Apparel

Figure 49:
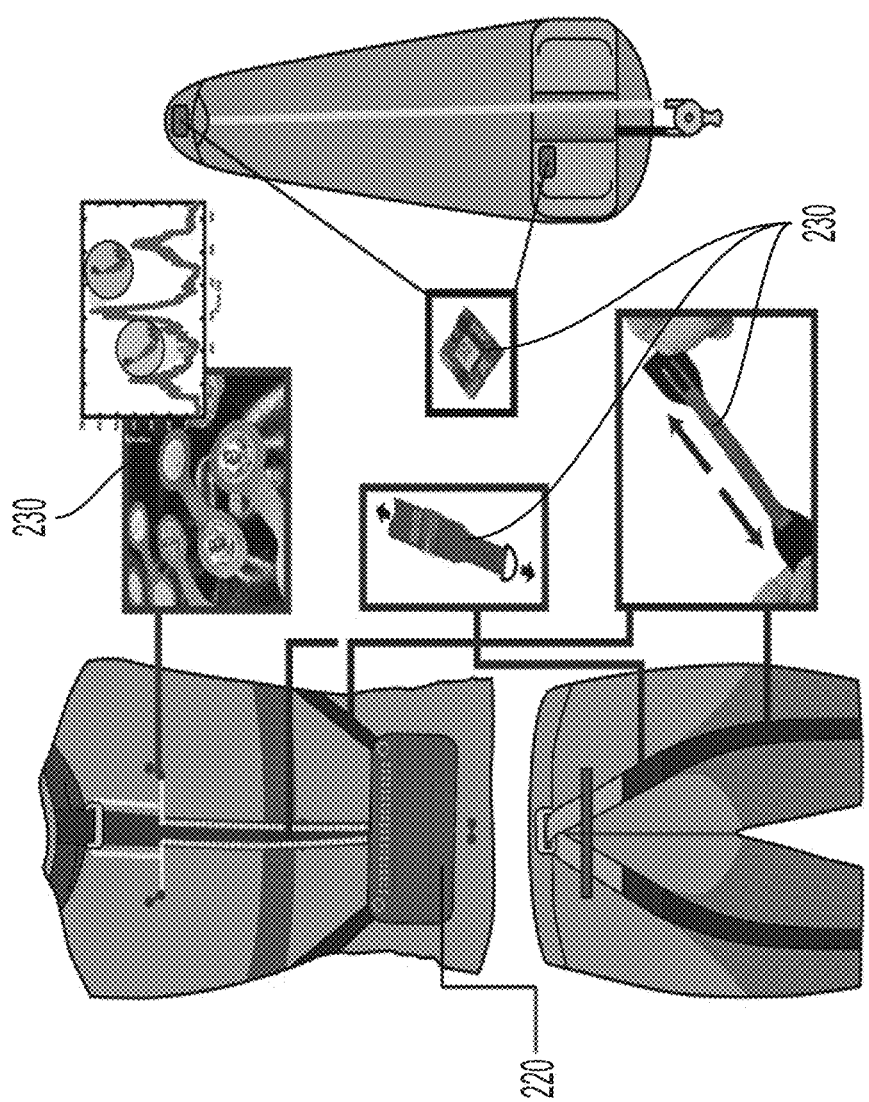
FIG. 49 illustrates sensors designed to be textile-compatible to measure human motion, strap tension, interaction forces/pressure and muscle effort.

Referring now to FIG. 49, sensors 230 may be designed to be textile-compatible to measure human motion, strap tension, interaction forces/pressure and muscle effort. Our proposed sensing wearable device 100 may combine motion sensors 230 such as IMUs, accelerometers, gyros, etc. and textile-compatible sensors 230 integrated into the system.

A) High stretch sensor for motion tracking: measuring joint kinematics and kinetics as the wearer performs activities may be used for tasks such as being able to recognize different motions and to deliver properly-timed assistance. A system may integrate customizable, lightweight, stretchable, capacitive sensors 230 with conductive knit fabrics as the electrode layer and dielectric layer from silicone elastomer that can be integrated into the high stretch regions of our proposed wearable system. As shown in FIG. 49, an embodiment may integrate soft sensors 230 to measure metrics such as body part movement e.g. torso bend (sensor along the back), torso twisting (sensor attaches to the back and crosses to the front of the garment), hip angles (sensor attached to the thigh) to measure posture and/or movement of the user.

B) Low stretch sensors for tension measurement: Monitoring the interaction forces across the actuation cables may be used to monitor the user interaction. As an alternative to commercial load cells a system may include soft tension sensors 230 that meet requirements with sufficient sensitivity. The force/tension sensors 230 may be insensitive to bending by encapsulating laser-cut conductive elements in elastomer materials and bonding them to stiff textiles. Robotic apparel may integrate tension measurement sensing along the textile force paths (as shown in FIG. 49).

C) Textile-integrated muscle activity sensors: Textile electrodes laminated to the apparel may be used to monitor EMG. These can provide information for the system to compare relative changes in peak/RMS muscle activity as a user performs repetitions of a task with different assistance patterns. We have demonstrated the feasibility of this approach by showing that an individual electrode can be used to measure muscle activity as shown in FIG. 49. Sensors 230 may be integrated as arrays of electrodes on the inside surface of the wearable undergarment (placed appropriately to enable measurement of key muscles), along with encapsulated textile-based signal traces. Electrodes may be in the areas of the are securely anchored to the wearer and through materials development such as surface modification of the textile electrodes with conductive elastomers.

D) System Integration: To integrate actuation and the textile components, a system may leverage inherent capabilities of the knit and woven materials. For example, woven materials that comprise force paths around the body are stiff enough to support semi-rigid modules such as mounting plates 220, robust attachment points for cables, and secure attachment loops for tension sensors 230. Conversely, knit materials in the garment can provide low-profile, hidden pockets used for pressure sensors 230 and low-friction, top-applied channels used for routing of strain sensors 230.

Impedance-Controlled Wearable Devices

In non-cyclical tasks such as lifting, holding static postures, crouched positions, or lifting arms up to do over-head work, defining the assistive profile as a function of time or of percentage of task completion may not be ideal. For non-cyclical tasks such as those mentioned previously, understanding activities such as how long a person is going to take to complete a lift, or how long someone is going to keep their arms up to complete a task can be challenging. In addition, the wearer may decide to accelerate the motion or change motion direction as he/she is performing the task and therefore a controller 240 that delivers assistance as a function of time or task completion percentage may not adapt fast enough and therefore would feel disruptive. In these cases, defining the assistance as a function of the wearer's motion or posture presents multiple advantages. It should be noted that providing an impedance based assistance to the user may also be useful for tasks that are cyclical under some circumstances.

Here, we present a control framework that solves these issues by calculating the tensile forces that the system applies as a function of one or more joint angles, speeds, accelerations or estimations of those variables. Joint(s) or limb(s) angles, speeds and/or accelerations may be measured by using sensing elements such as inertial measurement units, gyros, accelerometers, soft sensors 230 that change their electrical properties depending on joint movement, encoders, potentiometers, etc. Since the desired force is a function of the wearer's motion or posture, in this description, we call this approach impedance control.

As later described in more detail, embodiments of the present disclosure are directed to a wearable device 100 comprising:

at least one anchor member 110 configured for positioning on a first body part of a person wearing the wearable device 100, at least one anchor member 110 configured for positioning on a second body part of a person wearing the wearable device 100, and at least one connecting element 150 directly or indirectly coupling the at least one first body part anchor member 110 to the at least one second body part anchor member 110, at least one sensor configured to measure information relating to one or more of an angle, a velocity, and an acceleration of one or more joints of the wearer spanned by the wearable device 100, and at least one controller 240 configured to detect the start and/or type of a movement or a pose of the wearer to be assisted by the wearable device 100, determine the desired tensile force to be generated in the wearable device 100 as a function of a given angle, velocity, or acceleration of the one or more joints spanned by the wearable device 100 for assisting the wearer in performing the movement or in holding the static pose, and adjust an impedance of or a force provided by the wearable device 100 such that the desired tensile force is generated in the wearable device 100 at the given angle, velocity, or acceleration of the one or more joints.

The wearable device 100, in some embodiments, may comprise at least one mechanism configured to selectably lock a length, change a length, or change an impedance of the at least one connecting element 150, and adjusting the impedance of the wearable device 100 includes locking the length of the at least one connecting element 150 at a length configured to cause the desired tensile force to be generated in the wearable device 100 by movement or a pose of the wearer at the given angle, velocity, or acceleration of the one or more joints. The wearable device 100, in some embodiments, may comprise at least two connecting elements 150 and at least one mechanism 160 configured to selectably engage one or more of the at least two connecting elements 150. Adjusting the impedance of the wearable device 100 includes engaging one or more of the at least two connecting elements having, either alone or in combination, a spring constant or a damping constant configured to cause the desired tensile force to be generated in the wearable device 100 by movement or a pose of the wearer at the given angle, velocity, or acceleration of the one or more joints. The wearable device 100, in some embodiments, may comprise at least one actuator 120, and adjusting the impedance of the wearable device 100 includes actively actuating the at least one connecting element 150 to generate the desired tensile force in the wearable device 100 at the given angle, velocity, or acceleration of the one or more joints.

The controller 240, in various embodiments, may be configured to monitor the information relating to one or more of the angle, a velocity, and an acceleration of the one or more joints to detect when one or a combination of the angle, velocity, or acceleration exceeds a threshold indicative of the start of a motion or pose to be assisted. The controller 240, in various embodiments, may be configured to monitor the information relating to one or more of the angle, a velocity, and an acceleration of the one or more joints to detect when one or a combination of the angle, velocity, or acceleration exceeds a threshold indicative of the end of a motion or pose to be assisted.

Figure 50:
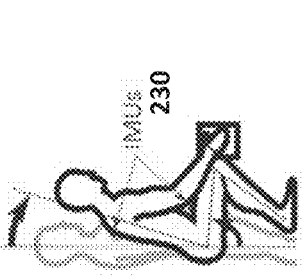
FIG. 50 shows a sample control framework.

Here, we present a new control framework to assist with an impedance based approach. It should be noted that even though lifting and holding static postures is described here, this approach may be applied to other activities such as kneeling, walking, performing over-head work, grasping, etc. FIG. 50 shows a sample control framework that consists of the following components:

1. Sensing elements are used to calculate joint angles, motion or relative limb motions, this information is used by a control algorithm to estimate the desired forces (e.g. onset, offset, assistive profile, etc.) that the device should provide to the user to assist with motion or posture for that specific task, sample embodiments of how motion and posture information measured by the wearable sensors 230 may be used to estimate the desired assistance are provided below. Additional sensing components may be added for different applications such as EMG, ground reaction forces, joint angles, body part/joint movement and position, etc.).

2. Assistive strategy: assistive profiles can be programmable as a function of the measured body movement, position, and/or a function calculated or estimated from the sensing components in the wearable device 100 (joint angle, body part movement and position, difference of joint movement, sum of joint movements or other functions, EMG, ground reaction forces, etc.) moreover, the impedance profile may be different depending on the different states of the task.

3. Transparency strategy is used so that the system doesn't apply forces when the user is performing tasks that the system is not meant to assist with, or when the user/operator decides that doesn't require assistance. As such, for transparency mode, the control algorithm may automatically detect when assistance is required, a user or operator may have a manual input mechanism to turn assistance on/off.

Sensing Elements

Figures 51A, 51B, 51C:
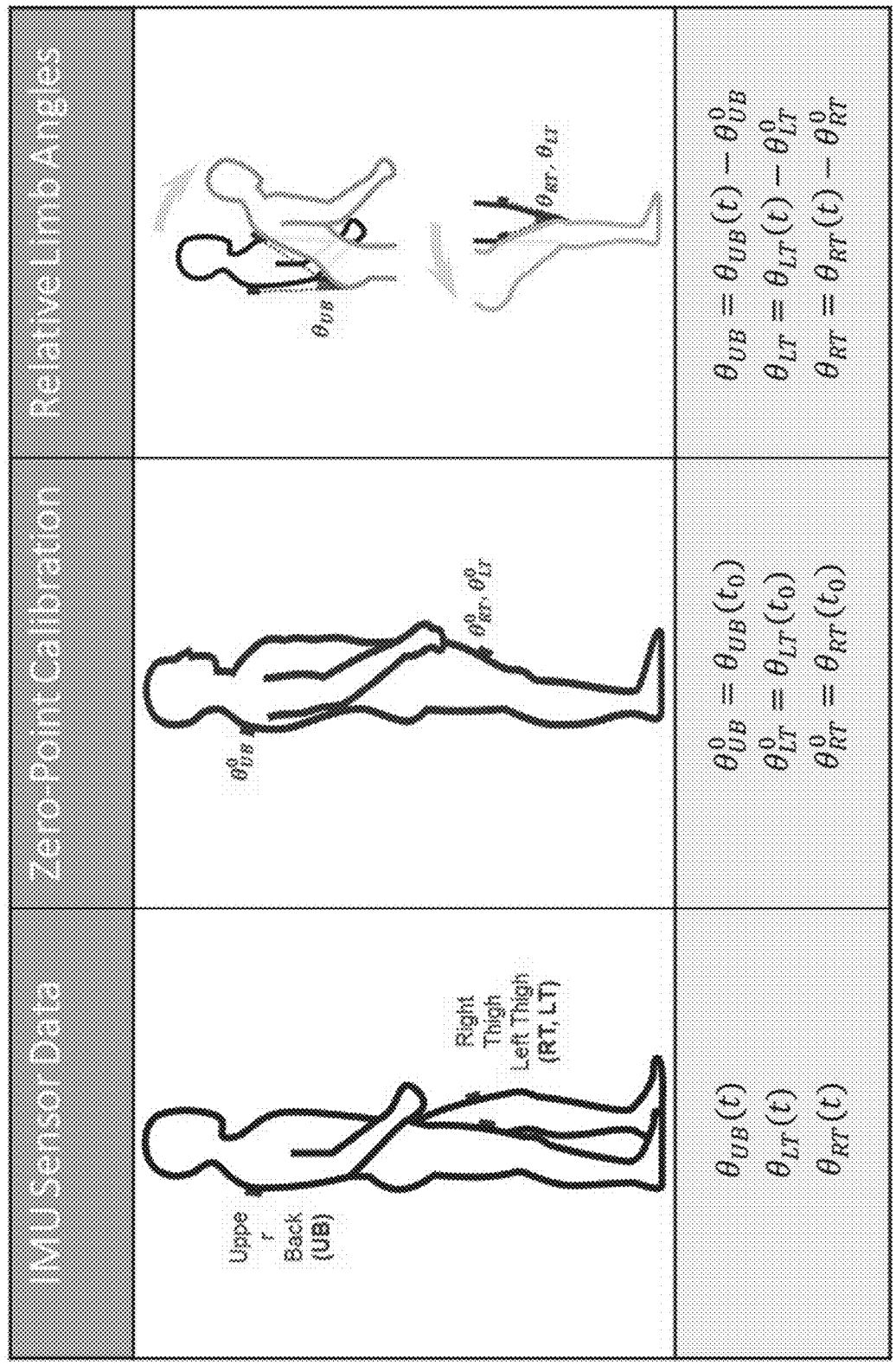
FIG. 51A, FIG. 51B and FIG. 51C, show how Inertial Measurement Units may be used to measure joint angles, speeds and accelerations.

Referring now to FIG. 51A, FIG. 51B and FIG. 51C, in an embodiment, Inertial Measurement Units may be used to measure joint angles, speeds and accelerations. In this case we use three IMUs, one on the upper back and one on each thigh as best shown in FIG. 51A.

During initialization, the user stands straight and the system measures joint angles to calculate the offset at the standing position (FIG. 51B). This step may not be needed in some applications but it has advantages such as knowing the relative limb angles with respect to the standing straight position. In a different application, the system may use sensor input as the user performs motions to estimate the neutral position. For example, a controller 240 may monitor IMU measurements as the user performs a movement (walking, running, lifting etc.) and use that information to define the neutral angle based, for example, on: average signals from movement sensors 230 to calculate a neutral position, knowledge of the task and/or position of the user at some point in time or user presses a button to initialize neutral position. The neutral position may be updated over time by the controller 240 by using this same strategy at different points during the day to compensate for small sensor positioning movement over time or small textile component movement over time with respect to the body.

The system subtracts the standing offset from the measured angles (FIG. 51C) so that we define the straight pose as $\theta=0$ for each IMU, as the user flexes the torso or thighs, this angle increases.

For this application, we use the relative angle between the thighs and the trunk as the variable that will be used to calculate the assistive profile, other relative angles may be used in other applications to define assistive profiles (e.g. relative angle between torso and upper arm for shoulder assistance, relative angle between thigh and shank for knee assistance, relative angle between shank and foot for ankle assistance, etc.).

Figures 53A, 53B:
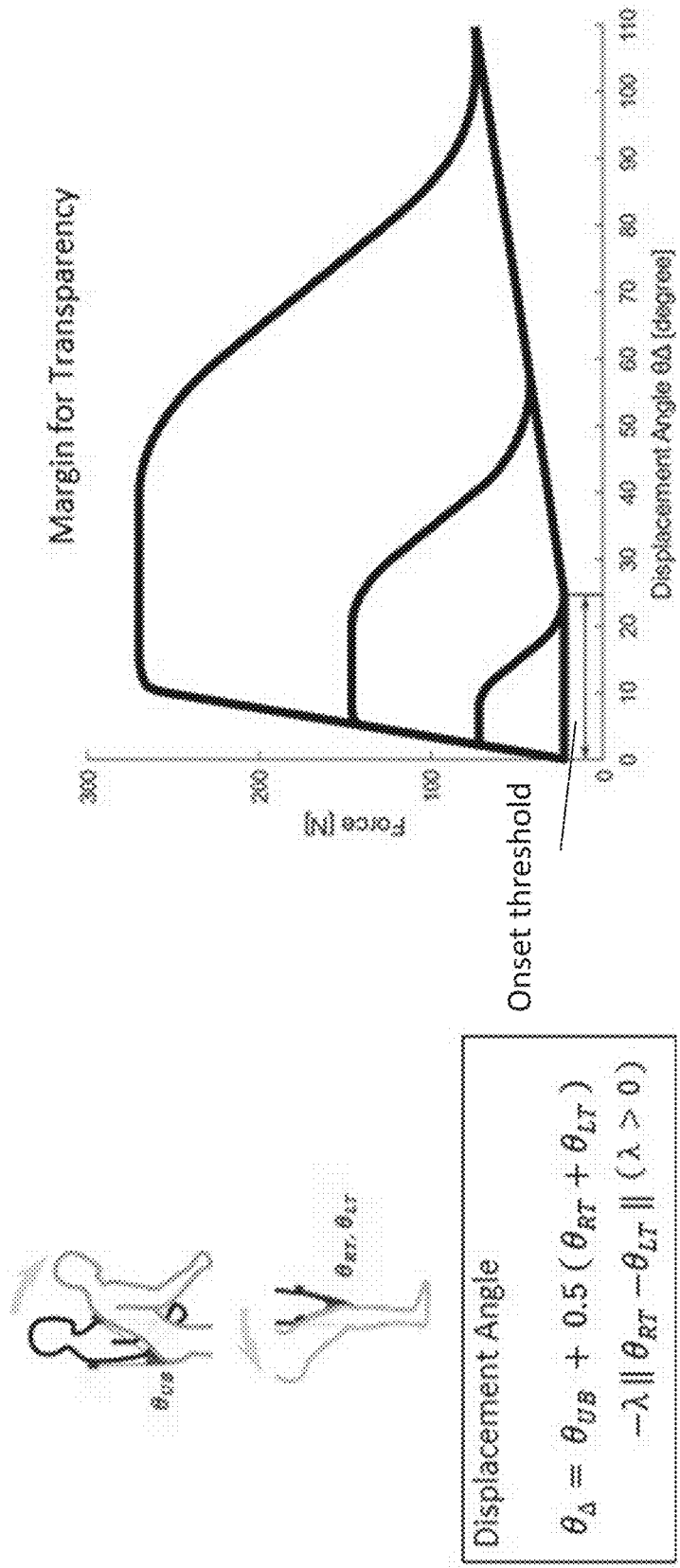
FIG. 53A illustrates an onset threshold for determining a motion state.
FIG. 53B shows an example where an initial threshold in the displacement angle can be used so that the system does not provide assistance during the initial phase as the user bends their torso or legs forward.

As shown in FIG. 53A, the trunk-thigh angle is defined as the relative angle between the trunk and the average angle of both thighs as represented in the equation below. As an example, if with respect to the standing position the user has one leg forward and one leg backward by the same angle the overall thigh angle would be neutral as shown in the equation below, while if the user has both legs with a positive angle, the overall thigh angle would be positive.

$\theta_\Delta = \theta_{UB} + 0.5(\theta_{RT} + \theta_{LT})$, where "$\Delta$" denotes the relative torso-thigh angle, "UB" denotes "upper back," "RT" denotes "right thigh," and "LT" denotes "left thigh."

Figures 52A, 52B:
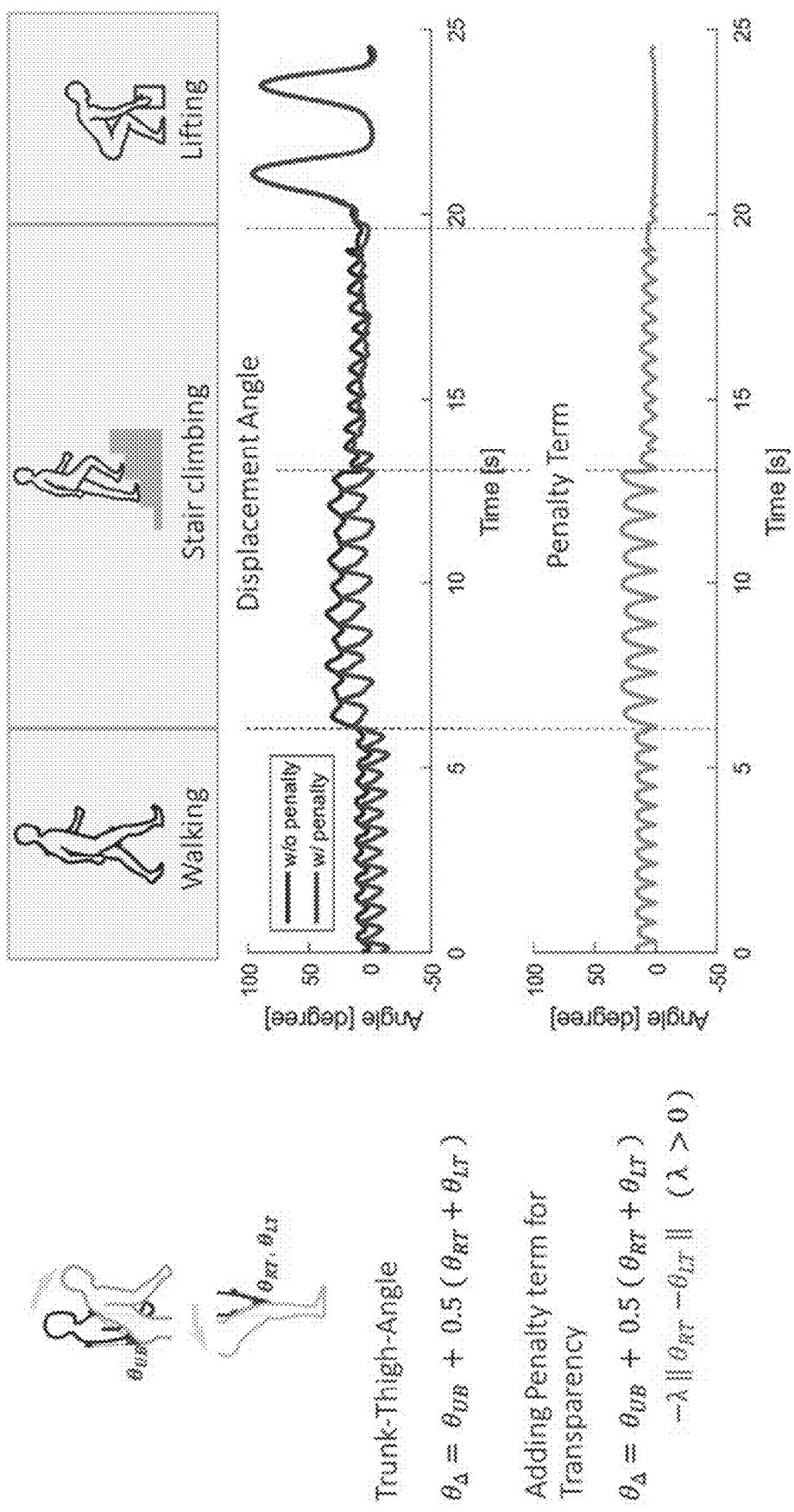
FIG. 52A and FIG. 52B show the relative angle during walking, stair climbing and lifting tasks.

FIG. 52A and FIG. 52B show this relative angle during walking, stair climbing and lifting tasks.

The system, in the present embodiment, may be configured to provide assistance during lifting tasks, but to be transparent during other tasks for which the system does not intend to assist (e.g. walking, running, stair climbing, driving a truck or car). Accordingly, it is necessary for the system to be able to differentiate between lifting or reaching tasks and walking, climbing, running tasks. In some cases, the relative torso-thigh angle measured throughout non-lifting motions can appear similar to that measured during the initial phase of a lifting motion—that is, when the user begins to bend or crouch downwards from an upright position. In particular, during walking and stair climbing tasks, the legs are typically out of phase, with one leg having a positive angle and the other leg having a negative angle. These angles mostly cancel one another out in the above equation, resulting in small relative torso-thigh angle measurements during walking and climbing stairs. During the initial phase of a lifting motion, relative torso-thigh angles is also small, and thus the two could potentially be confused. Without correction, the system could potentially generate assistance during a walking or stair climbing motion when instead it should be transparent, or to avoid such issues, the system may otherwise have to be configured to delay the onset of assistance until after the initial phase of the lifting motion as shown in FIG. 53B.

The system may be configured to overcome this issue. In an embodiment, a "penalty term" can be added to the relative torso-thigh angle equation as shown below to better differentiate between lifting or reaching and other tasks:

$\theta_\Delta = \theta_{UB} + 0.5(\theta_{RT} + \theta_{LT}) - \lambda \|\theta_{RT} - \theta_{LT}\|$ ($\lambda > 0$), where "$\lambda$" denotes a penalty term to the difference between the right and left thigh angles.

In particular, the penalty term is configured to reduce the small relative torso-angle measured during walking and stair climbing, while having no effect on the small relative torso-angle measurements taken during the initial phase of lifting tasks. As shown in FIG., this penalty term has the benefit that the relative torso to thigh angle is closer to neutral during walking and stair climbing and still identical angles are measured during lifting tasks which implies that the penalty term does not affect the relative angle measurement during lifting tasks, but is able to reduce the relative angle during tasks such as walking and climbing stairs. Having an angle closer to neutral during non-lifting tasks is advantageous when using thresholds to start assisting the wearer, if the angle is closer to zero during non-lifting tasks, a smaller threshold may be able to differentiate between non-lifting and lifting tasks. FIG. 53B shows an example where an initial threshold in the displacement angle can be used so that the system does not provide assistance during the initial phase as the user bends their torso or legs forward. This threshold may be smaller if the penalty term cancels out deviations of the relative torso to thigh angle during walking/running/climbing stairs/etc. As an alternative approach, an algorithm may use motion sensor information as the user is wearing to automatically set this initial offset value. In another embodiment, a user may be able to modify this initial offset angle to fit their specific preferences or needs.

In various embodiments, the motion or pose to be assisted may be a lifting motion or a crouching pose. The controller 240, in an embodiment, may determine a relative angle of one or more of a torso, a thigh joint, and a hip joint of the wearer, and may monitor the relative angle to detect when the relative angle exceeds a predetermined threshold indicative of the start of the lifting motion or crouching pose to be assisted. In another embodiment, the controller 240 may determine an average angle of the hip joints of the wearer, and monitor the average angle of the hip joints of the wearer to detect when the average angle of the hip joints exceeds a predetermined threshold indicative of the start of the lifting motion or crouching pose to be assisted. The controller 240 may determine the average angle of the hip joints of the wearer by calculating a relative angle between: (i) a torso of the wearer, and (ii) an average angle the thighs of the wearer. In embodiment, the controller 240 may be configured to identify whether the wearer is engaged in activities other than the lifting motion or the crouching motion to be assisted and, if so, determine that any exceedance of the predetermined threshold is not indicative of the start of the lifting motion or the crouching pose to be assisted. The controller 240 may identify whether the wearer is engaged in activities other than the lifting motion or the crouching motion to be assisted by: determining a difference between an angle of one of the hip joints and an angle of the other hip joint, applying a penalty term to the difference, subtracting the penalized difference from the average angle of the hip joints, and evaluating whether the resulting determination of the average angle of the hip joints exceeds the predetermined threshold. The controller 240, in an embodiment, may monitor the average angle of the hip joints of the wearer to detect when the average angle of the hip joints exceeds a predetermined threshold indicative of the end of the lifting motion or crouching pose to be assisted.

Assistive Strategy—Programmable Impedance Assistance Control Structure

Figure 54:
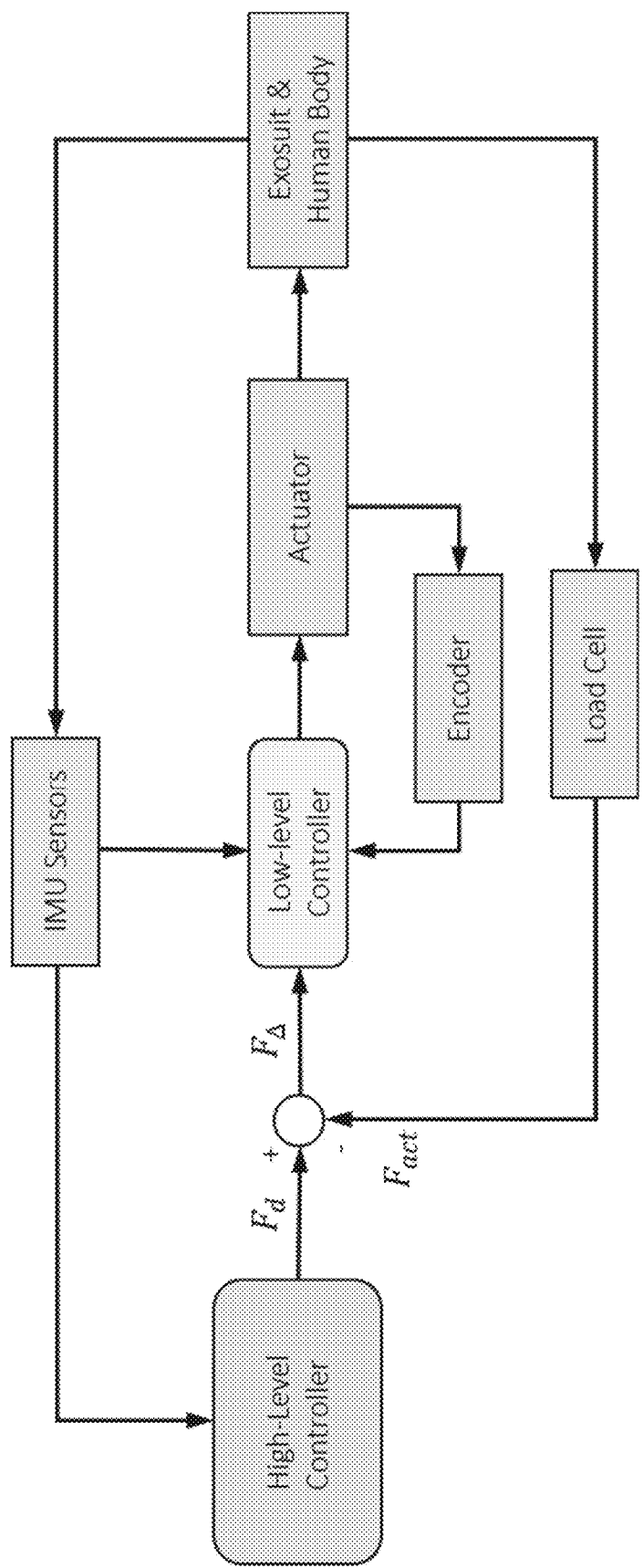
FIG. 54 illustrates a controls methodology comprising two main parts: a high-level and a low-level controller, each generating an output signal based on various sensor inputs and a control logic.

In this embodiment, the wearable device 100 may be able to control the forces delivered to the wearer. As shown in FIG. 54, the controller 240 consists of two main parts: a high-level and a low-level controller 240, each generating an output signal based on various sensor inputs and a control logic. The high-level incorporates the active/transparent and the assistance strategy. Based on the signals of the IMU sensors 230 located on the trunk and both thighs, the high-level controller 240 may classify the current movement/posture of the wearer and decide whether the suit should be assistive or transparent, alternatively, a user may be able to press a button or other user interface to turn the assistance on/off or to send the system to transparent mode. The output signal of this high-level control block is the desired force command $F_d$, that the exosuit should exert on the human.

The divergence $F_\Delta$ between the actual applied force $F_{act}$ measured or estimated with a sensor (motor current, load-cell, force sensor, torque sensor, etc.) and the desired force $F_d$ generated by the high-level controller 240 is used as an input to the low-level controller 240. The objective of this block is to ensure a stable and dynamic tracking of the desired force by sending control signals to the actuator 120. This is achieved with the use of further input signals read from sensors 230 such as IMUs and motor encoder.

Low-Level Control

Figure 55:
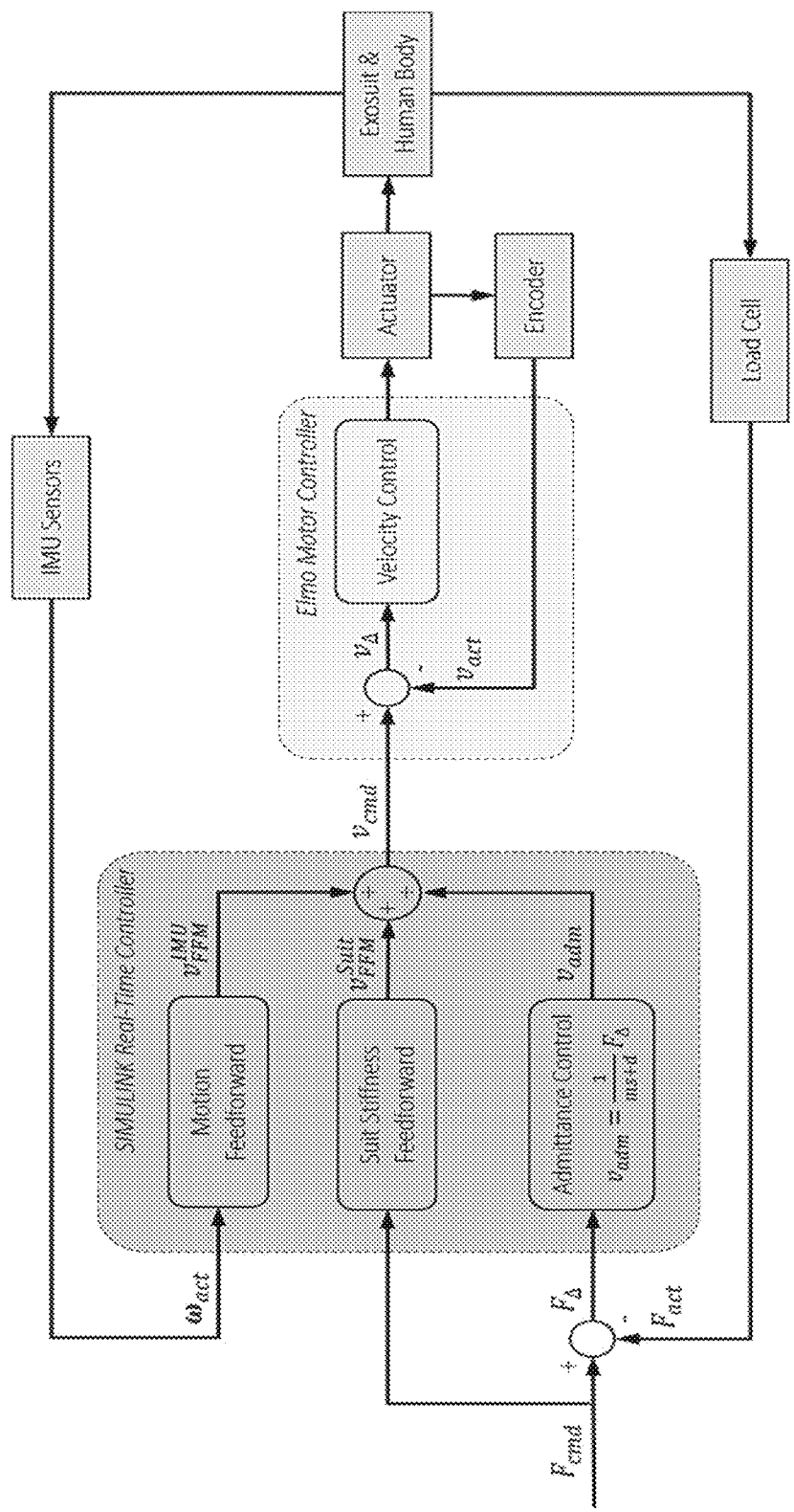
FIG. 55 shows that the low-level control scheme to control the force or tension in the system consist of two parts. An admittance controller and feedforward models described. The motor controller runs two cascaded PI-loops for velocity and current control.

In an embodiment, the low-level control scheme to control the force or tension in the system consist of two parts (FIG. 55). An admittance controller 240 and feedforward models described. The motor controller 240 runs two cascaded PI-loops for velocity and current control.

Admittance control: a possible control structure to be able to control a desired force to the wearer, is an admittance control structure. Admittance controllers 240, use sensors 230 to measure or estimate force and modify the robot trajectory according to the interaction forces. For this embodiment, an admittance controller 240 is used to control the interaction forces between the wearer and the wearable system. The generic definition of impedance can be derived from the damped simple-harmonic oscillator. The second-order differential equation describing the dynamic behavior of this mechanical system is $m\ddot{x}+d\dot{x}+kx=F(t)$ Where x denotes the position of a body with mass m, interacting with a spring with stiffness k, damper d and an external force F(t). In the Laplace domain, impedance is defined as the relationship between output force and input velocity.

$Z(s)=F(s)/\dot{X}(s)$ which can be written as $sZ(s)=F(s)/X(s)$

Conversely, admittance defines the dynamic relationship between output flow and input effort and is thus given as the inverse of impedance $Y(s)=Z(s)^{-1}=\dot{X}(s)/F(s)$ Hence, a second-order admittance, derived from the damped simple-harmonic oscillator, has the form $Y(s)=Z(s)^{-1}=(ms+d+k/s)^{-1}$ The admittance control law used to control the interaction forces exerted on the human by the proposed active exosuit can be illustrated with a similar mechanical schematic, as shown on the right of FIG. 17. Here, the spring is replaced by the actual force F_act, the human and wearable system parts impose on the actuator 120 which is measured by a load cell.

The virtual damping $d_v$ affects the steady state value of the response and the ratio of the virtual mass and damper changes the dynamics of the system. Hence, decreasing $d_v$ makes the controller 240 more responsive to force errors but may also compromise stability of the system.

A way to address this issue is variable control, where the parameters are adjusted online according to human intention or the control task. In this work, the state machine which operates in the high-level part of the controller 240 is utilized to change the virtual damping $d_v$ according to different tasks. The desired virtual damping is dependent on the level ($F_d$) and dynamics ($dF_d/dt$) of the target force as well as the dynamics ($d\theta/dt$) of the relative trunk-thigh angle $\theta$ of the wearer. Hence, appropriate virtual damping values for each state can be defined as a function.

$$d_v = f(\eta, F_d), \eta = \frac{dF_d}{dt}\frac{d\theta}{dt}$$

which is shown in FIG. 18. For variable impedance control, it is crucial to ensure stability for all possible variations of the parameters. The range of parameters is determined by many factors. Stability for static trunk bending ($\eta=0$) was found to be dependent mostly on the level of assistance $F_d$, which is shown in the left plot of FIG. 56. It shows the minimum required damping values to ensure stable tracking in static forward bending postures. For instance, in order to support static postures with an assistive force of 150 N, the virtual damping should at least be set to $0.45*10^3$ kg/s. However, keeping the virtual damping constantly at this level may reduce performance for the fast reaction to force errors for some applications which justifies the use of a damping scheduling technique.

Figure 56:
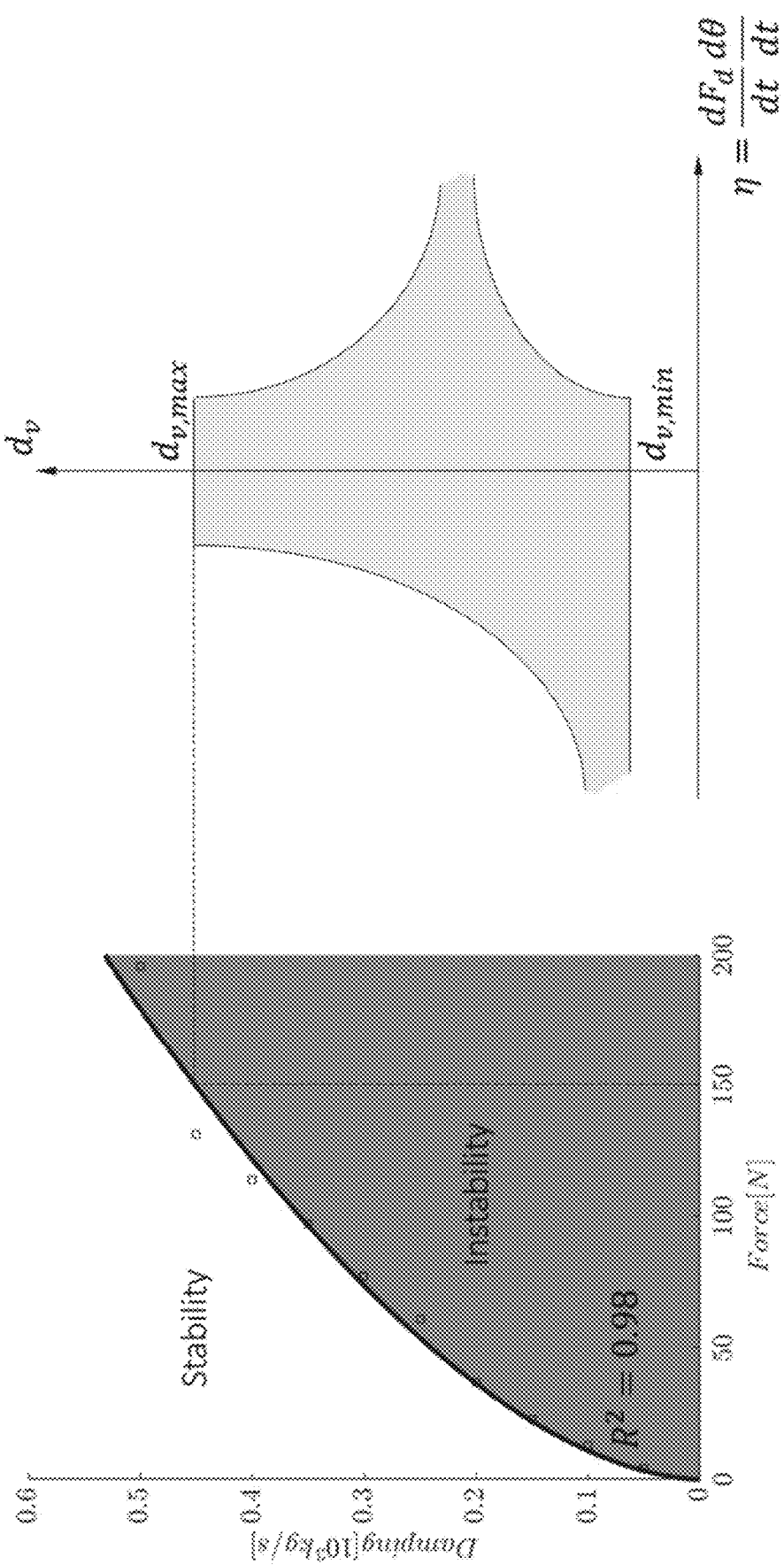
FIG. 56 illustrates that stability for static trunk bending ($\eta=0$) was found to be dependent mostly on the level of assistance $F_d$, as seen in the left plot. It shows the minimum required damping values to ensure stable tracking in static forward bending postures. The right plot illustrates the damping scheduling approach by qualitatively outlining the range of reasonable damping values to control the exosuit based on the dynamics factor $\eta$. The shaded area in the right plot represents the ideal damping value determined for each task.

The right plot of FIG. 56 illustrates the damping scheduling approach by qualitatively outlining the range of reasonable damping values to control the exosuit based on the dynamics factor $\eta$. The box where $\eta \approx 0$ covers a wide range of damping values and is shaped by two tasks: On the upper end, the box is limited by the minimum required damping for static postures $d_{v,max}$. The lower bound $d_{v,min}$ is required for walking, where the force command is constant as well $$\left(\frac{dF_d}{dt} = 0\right)$$

but the controller Lou needs to be very responsive due to high dynamics of the relative trunk angle. When the user is lifting an object $$\left(\frac{d\theta}{dt} < 0\right),$$

the desired force can be increased to provide more assistance $$\left(\frac{dF_d}{dt} > 0\right).$$

In this case, η is negative and the actuator 120 (and controller 240) must be highly dynamic in order to move the cable faster than the user to increase the force. This requires a low virtual damping $d_{v,min}$. On the contrary, if force and relative trunk-thigh angle increase/decrease simultaneously (η>0) and point in the same direction, higher virtual damping values are more beneficial. As represented by the shaded area in the right plot of FIG. 56 the ideal damping value was determined for each task.

The tracking performance of an admittance controller 240 can be improved for soft exosuits by incorporating knowledge about the suit, the movements of the wearer and the actuation system in the form of feedforward models. Similar to their approach, motion and suit feedforward models have been developed for the exosuit, as explained next.

Suit Stiffness Feedforward Model

As indicated earlier, when forces are applied to the suit, the system may deform. To model the deformation of the suit, three male subjects were asked to stand in a stooped posture (~60° trunk inclination angle in the sagittal plane). During the trial, the cable was tensioned with a constant velocity of 60 mm/s until the maximum force of 250 N was reached and released with the same speed thereafter. This cycle was repeated 10 times for each subject.

Figure 57:
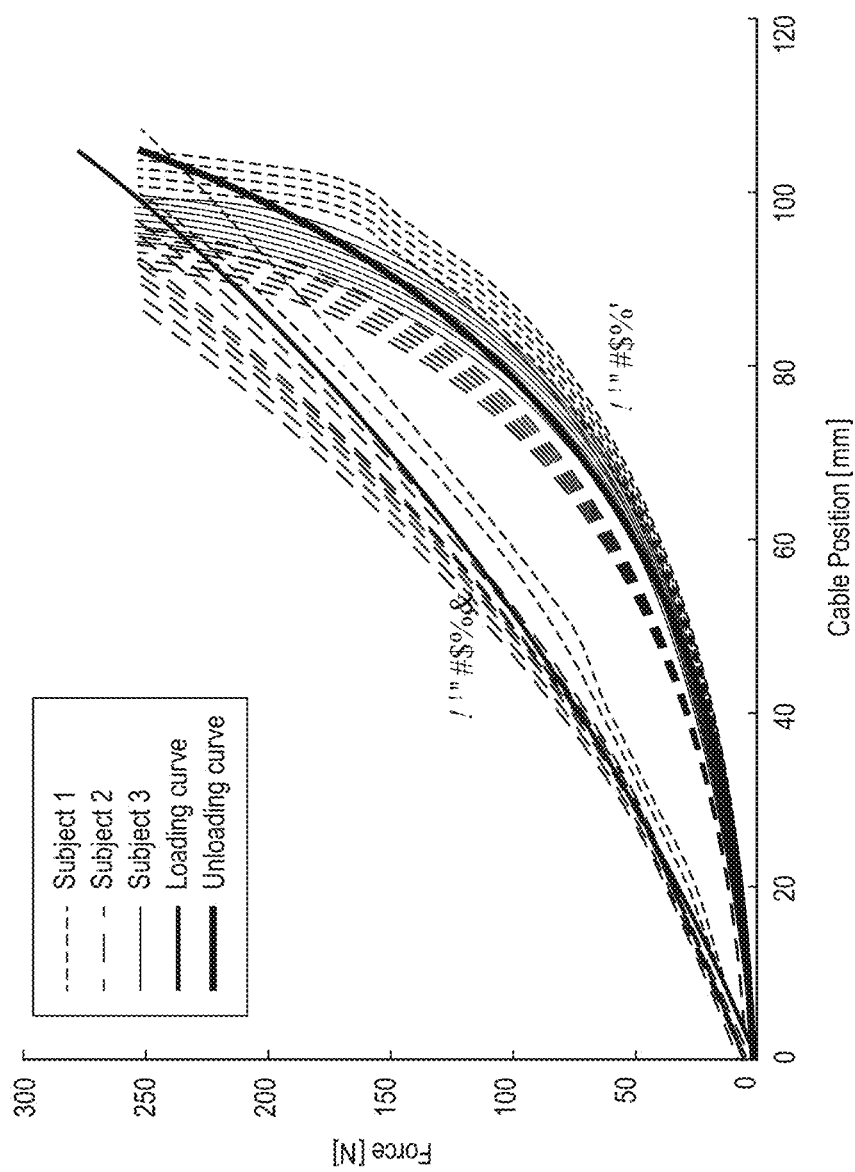
FIG. 57 shows the behavior of the suit including hysteresis for tensioning (loading) and releasing (unloading) the cable.

FIG. 57 shows the behavior of the suit including hysteresis for tensioning (loading) and releasing (unloading) the cable. As shown in the graph, increasing the force from a low level requires a more dynamic movement of the cable compared to higher force levels. This knowledge can be incorporated into the controller 240 using a feedforward model so as to improve tracking performance.

The elasticity of the suit can be modeled by the following equation $$F = f(p_c) = \alpha(e^{\beta p_c} - 1)$$

In the low-level controller 240, the velocity command is superimposed with a feedforward velocity $v_{FFM}^{Suit}(F_d)$, which is a function of the desired force command $F_d$. This function can be obtained with the time derivative of the inverse function as follows.

$$v_{FFM}^{Suit}(F_d) = \frac{d}{dt} f^{-1}(F_d) = \frac{d}{dt}(\beta^{-1} \cdot \ln(\alpha^{-1} F_d + 1)) = \frac{\dot{F}_d}{\beta(F_d + \alpha)}$$

The parameters α and β are obtained from the regression curves for loading and unloading (see FIG. 57). The algebraic sign of $\dot{F}_d$ can be used to switch between the loading ($\dot{F}_d > 0$) and unloading ($\dot{F}_d < 0$) feedforward model in the controller 240. According to equation (3.10), the feedforward term increases the cable velocity for low force levels $F_d$ and high derivatives $\dot{F}_d$.

Motion Feed-Forward Model

However, the more challenging task for the low-level controller 240 is to ensure a good force tracking performance for dynamic tasks. These tasks include movements such as squatting or walking and are characterized by independent, relative movements between the thighs and the trunk. To measure these movements, in this embodiment, inertial measurement units (IMUs) are placed on the upper sides of the thighs as well as the upper back. IMUs may comprise accelerometers, gyroscopes and magnetometers and combine the data generated by these sensors 230 to measure the Euler angles of the transformation between a global coordinate frame and the local coordinate frame of the IMU. If the IMUs are placed appropriately.

Figure 58:
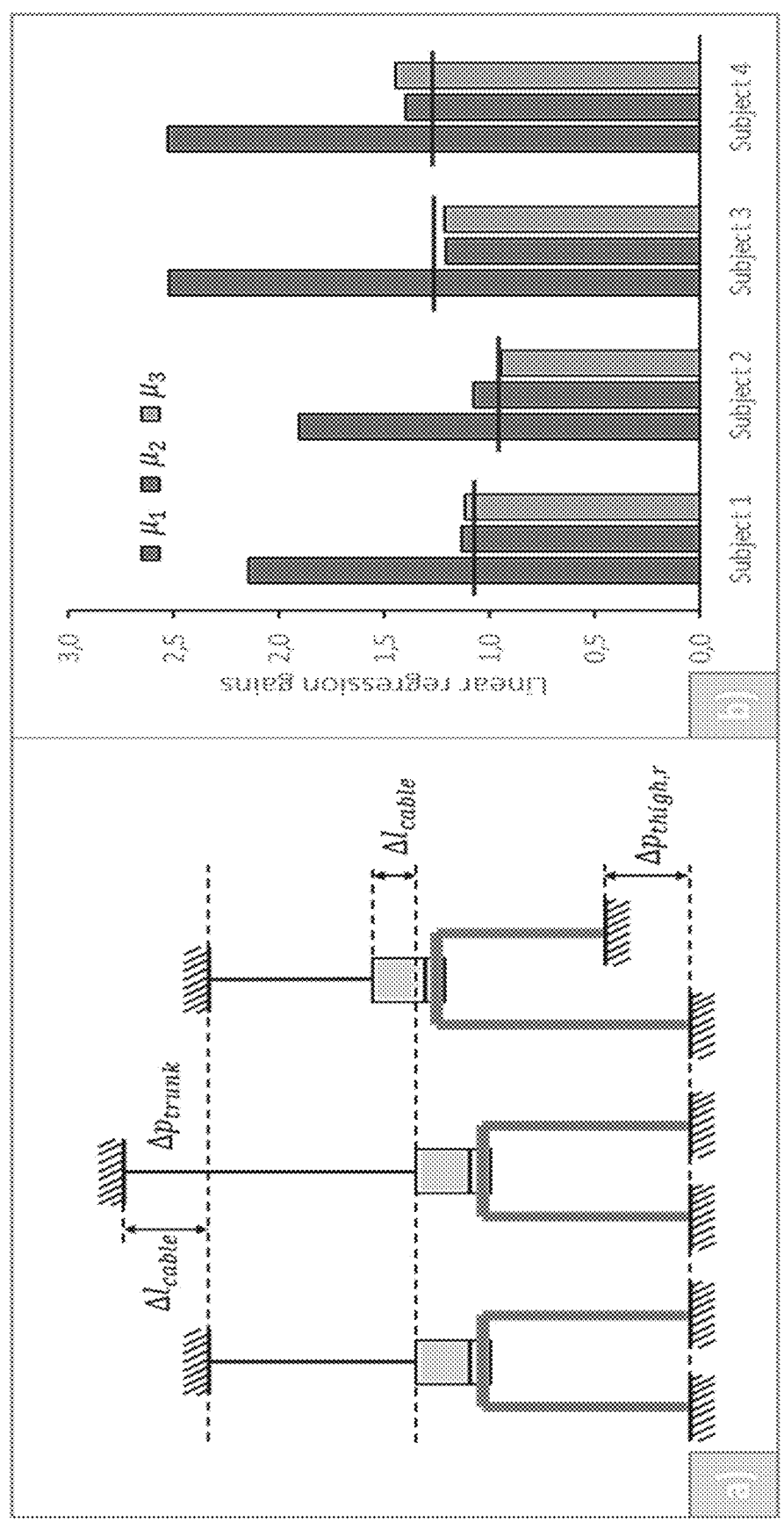
FIG. 58 illustrates the theoretical relationship between trunk and thigh movements and the corresponding cable length, neglecting deformations of the suit.

The thighs and the trunk are connected via the load-balancing strap 112 to the cable 150 on the upper end. The length of the relatively inelastic webbing is fixed whereas the cable length can be changed by the actuation system 120. FIG. 58 illustrates the theoretical relationship between trunk and thigh movements and the corresponding cable length, neglecting deformations of the suit. The drawing on the left represents the user standing in an upright position with a pretension of the cable. During a stoop, the position of the thighs and thus the connection point, which is connected to the thighs via the inelastic webbing, stays the same. Consequently, the flexion of the trunk and the corresponding stretching of the skin $\Delta p_{trunk}$ is associated with the same extension of the cable (gain: 1). However, this does not hold for movements of the thighs as can be seen in the right drawing of FIG. 58. The movement of one thigh, which corresponds to a change $\Delta p_{thigh}$ in the webbing on this side, is only related to a change of $0.5 \Delta p_{thigh}$ in cable length (gain: 0.5).

It is assumed, that the movement $\Delta p_i$ of a body i is proportional to a change of the inclination angle $\Delta \varphi_i$ measured by the IMUs:

$$\Delta p_i \sim \Delta \varphi_i$$

where the Δ operator denotes the change between the current value of the variable and its value in an upright position. The inclination angles φ are defined positive for flexion of the corresponding body.

Combining this assumption with the gains from FIG. 58 leads to the following hypothesis:

$$\Delta l_{cable} = \mu \cdot [\Delta \varphi_{trunk} + 0.5(\Delta \varphi_{thigh,l} + \Delta \varphi_{thigh,r})]$$

The following experiment was conducted to validate the made assumptions and hypotheses: Three male and one female subject were asked to do a full range of motion (ROM) stoop (1), fully flex and extend their right resp. left leg (2/3) and do a full ROM squat (4). All four tasks were performed with a speed of 20 bpm and repeated 10 times each. During the trials, the admittance controller 240 kept the cable at a pretension level of 15 N and the cable length as well as the trunk and thigh inclination angles were recorded.

Figure 59:
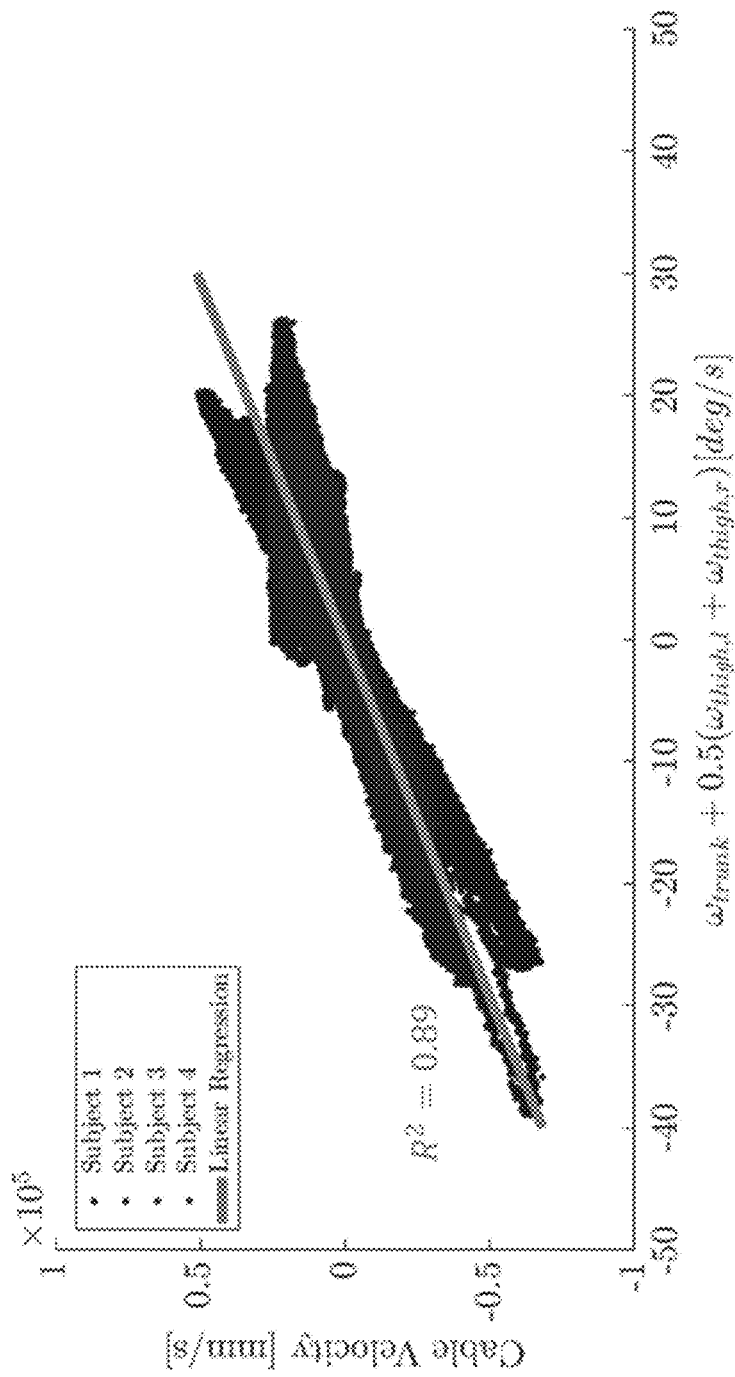
FIG. 59 shows the performance of the feedforward model to describe the effect of human motions on cable velocity.

The equation for the feedforward model is defined with the time derivative of equation (3.12), leading to the following equation:

$$v_{FFM}^{IMU} = \mu \cdot [\omega_{trunk} + 0.5(\omega_{thigh,l} + \omega_{thigh,r})]$$

with $\omega_i$ being the angular velocity of body i in the sagittal plane. The performance of the feedforward model to describe the effect of human motions on cable velocity is shown in FIG. 59.

While this embodiment describes an admittance-control approach to control the force delivered to the user, it should be noted that other approaches may be used. Possible approaches include direct force control where the desired force is compared against the force measured or estimated via sensors 230 (current, force, etc.) and a closed-loop approach minimizes this error to guarantee high-quality tracking. Alternatively, direct current control may be used, if a model between the measured current and the delivered force is known, a system may translate a desired force to a desired current and then close a current loop to guarantee proper tracking.

High-Level Control

Previously, we defined an approach to track desired force profiles $F_{cmd}$. The force command is generated by the high-level controller 240 which comprises two main strategies: the active/transparent strategy and the assistance strategy. The former distinguishes between movements of the wearer, where the system must be assistive (e.g. lifting) and tasks where the system should only track the wearer's movements without exerting forces (e.g. walking). If the active/transparent strategy identifies an 'active' task where the device is supposed to assist, the assistance strategy generates an assistance profile $F_{cmd}$ which is sent to the low-level controller 240.

Assistance Strategy

Defining a force command in the time domain, has multiple challenges, firstly, the force command must be increased and decreased on time as soon as the wearer starts or stops to move, respectively. Secondly, it has to be assured that the desired force level can be reached considering the lifting dynamics of the user. Both points are challenging to be achieved by a time-based approach where $F_{cmd}=F_{cmd}(t)$ for several reasons. If we assume that the user lifts the object with a relatively constant speed, this speed would have to be estimated at the beginning of the movement to determine appropriate time windows for the increase and decrease of the force, respectively. However, it was found that suitable indicators such as trunk velocity and acceleration, measured by the trunk IMU, show a high variance in the initial stage (~10%) of the movement and are in a similar range for slow (2.5 s) and fast (1 s) lifts. Moreover, the assumption of constant lifting speed is not valid because the user could accelerate or decelerate his movement during the lift which would entail jerks in the force command.

Figures 60A, 60B, 60C:
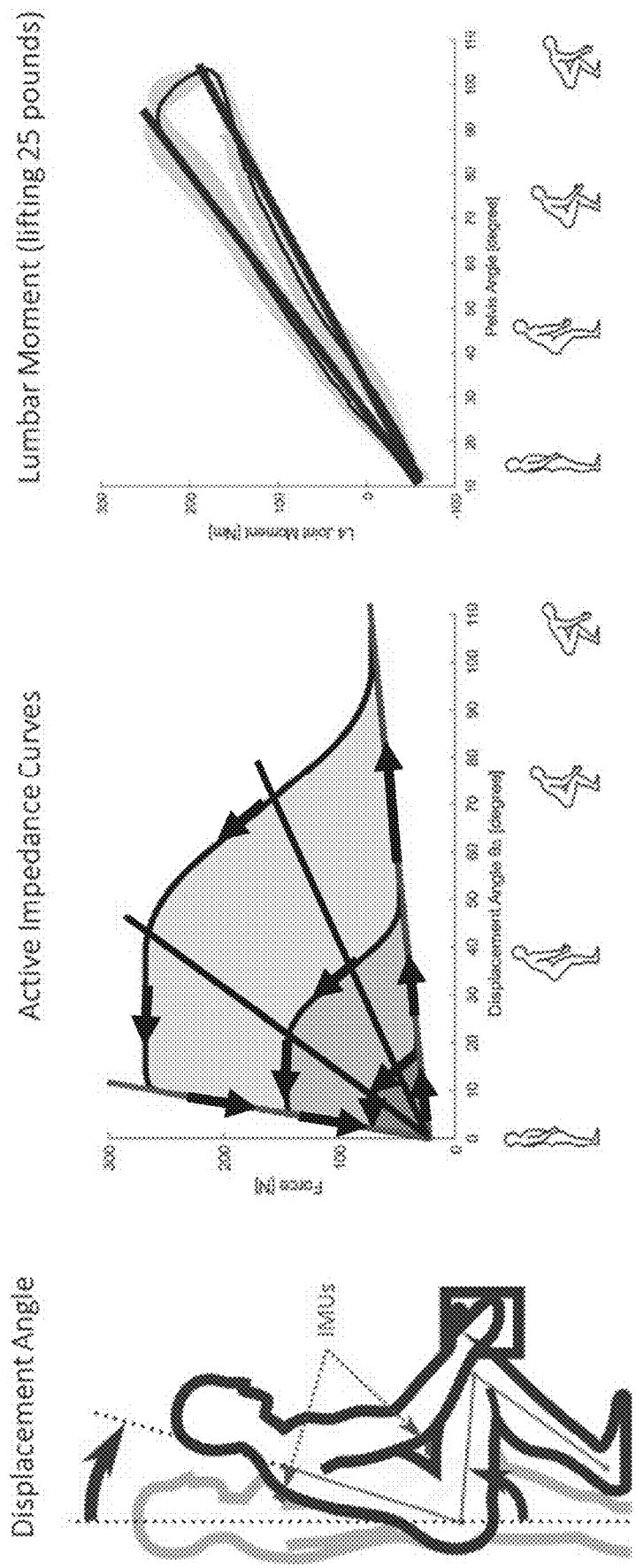
FIG. 60A, FIG. 60B, and FIG. 60C, illustrate that the assistance may be defined as a function of the torso-thigh angle.

For this reason, an embodiment may integrate an impedance-based approach defined such that $F_{cmd}=F_{cmd}(\theta_A)$, where the force command is dependent on the displacement angle $\theta_A$, which is a measure for the deviation of the trunk and thigh angles from an upright position as illustrated in FIG. 51C. Consequently, a displacement angle of zero corresponds to an upright pose. Referring now to FIG. 60A, FIG. 60B, and FIG. 60C, in an embodiment, the assistance may be defined as a function of the torso-thigh angle as illustrated in FIG. 60A and defined above.

FIG. 60B shows an example of how the impedance can be programmed as a function of joint movement. In this case, the impedance rendered as the user moves down (blue line), is different compared to when the user is going up (black line) during the lift and when the user is going up but getting close to a standing position (green line). These assistance curves may be customized for different individuals and tasks by using the optimization strategies described above, by having a user interface that allows to set parameters of the assistance profile as the user wears the system, and/or by using results and evaluation of biomechanics experiments or on reference biomechanics data (average from a number of users performing a task, etc.). The underlying principle of the assistance strategy is defining a force profile such that when the wearer descends in order to grab an object, the system applies a force that increases as the user bends down the torso to help move the torso as it moves in the same direction as gravity. As soon as the wearer starts to lift an object up and extends his back, the force may be increased to a higher level to help lift the additional load and for the fact that it has to move against gravity, finally the assistance may be decreased when the wearer approaches an upright position.

The controller 240, in various embodiments, may be configured to monitor the information relating to one or more of the angle, a velocity, and an acceleration of the one or more joints to detect one or more states of the motion to be assisted. The controller 240 detects the different states to transition between going down, going up and holding static postures by looking at changes in the joint angles, speed and acceleration, as later described in more detail. As an example, FIG. 60C shows a sample biological lumbar moment as a function of relative torso to thigh angle as a user lifts 25 lb of weight. As the user goes down to lift the load, the lumbar moment follows a lower impedance line, followed by a transition period to a higher-impedance state as the user transitions from moving down to moving up and finally, a higher-impedance curve as the user is moving upwards fighting gravity with the load. An assistive approach may use the relative torso to thigh angle measurement to command tensile forces to the user that mimic the biological torque, or use a scaled version of the biological torque (e.g. user selected maximum assistance through an input controller 240, optimization-based maximum torque for a given movement, initial settings).

Figure 61A:
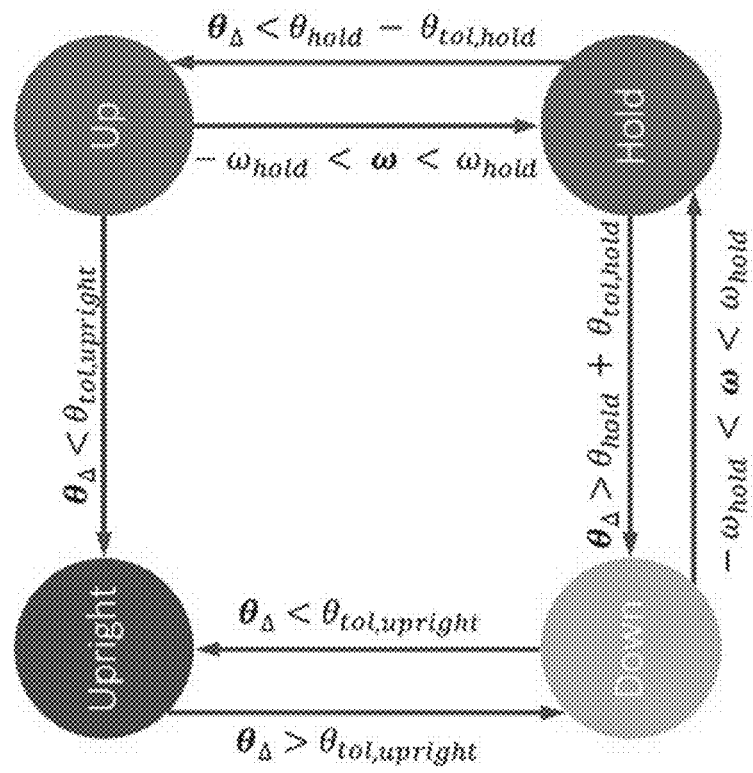
FIG. 61A and FIG. 61B illustrate the different states of lifting and how different impedances may be defined.
Figure 61B:
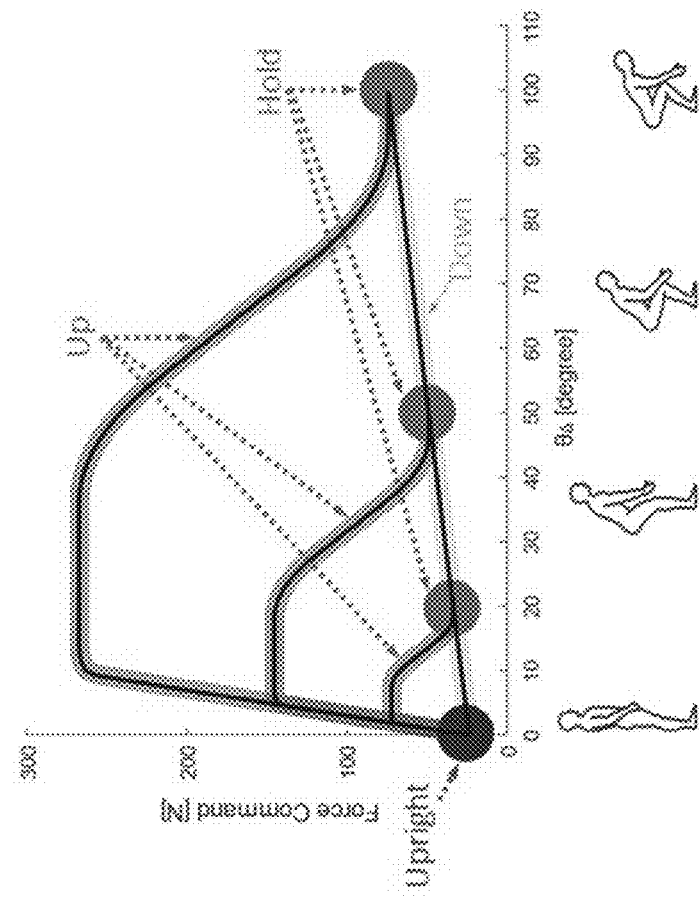

FIG. 61A and FIG. 61B, illustrate the different states of lifting and how different impedances may be defined. As depicted under the graph of FIG. 61B and denoted in the circles of FIG. 61A, the user starts in a standing position ($\theta_A=0$), as the user moves downwards to grab an object, the user bends the torso and/or thighs ($\theta_A>0$), while the user is moving down the assistive force will be determined by an impedance profile (e.g. yellow line in FIG. 61B). As the user changes from going down to going up, the system will record the angle at which the user did this transition ($\theta_A=C$), and from that point define an impedance profile as a function of the user torso-thigh angle (green line in FIG. 61B). The plot shows three different cases in which the user decided to move upwards at three different angles (~20°, ~50° and ~100°). From this point, a high-impedance transition is defined to provide additional assistance when the user is moving against gravity, when the transition crosses the red line, the force is held at a maximum level until the user approaches a position that is close to standing straight, at that point, the force will ramp down to no assistance as the user finalizes the lift.

As an alternative to this profile, as the user moves up, an approach may define the assistance to follow a linear stiffness (green line in FIG. 61B) when moving up as opposed to holding a force. Holding a force at a higher level may have the advantage that more power is delivered to the user as the user moves up and following a linear higher-impedance profile has the advantage of matching more closely the shape of the biological lumbar moment (FIG. 60C).

The assistance of a linear passive system is illustrated with a red line in FIG. 60B. For an ideal passive device, the force exerted by the exoskeleton increases as the user moves downwards and decreases in the same as the user moves upwards, which means the wearer stores the energy into the passive spring and regains the same energy when lifting the object. If the stiffness of the spring is increased, the suit is more assistive but might restrict the movements of the wearer because a higher energy must be stored into the spring to reach a certain position. On the other hand, a low stiffness enables a free range of motion but the suit might not be assistive enough because the force levels are lower for a given position. This tradeoff between assistance and restriction can be solved with active systems as explained above. The gravity compensation of the user during trunk flexion may be tuned designed in a way that the suit is assistive but not restrictive and allows for a full range of motion, approaches such as online optimization or manual selection of impedance may be used to adapt to different users or movements. With an active system, significantly higher force levels can be achieved compared to passive devices as the user moves up. In this way, the system provides a net energy to the assisted joints for one lifting cycle. Assuming a constant moment arm of the force provided by the suit, the net energy is proportional to the area enclosed by the hysteresis curve, as shown by the blue area in FIG. 60B.

FIG. 60C illustrates key advantages of the impedance control approach: adapting the assistance to different biological moments and lifting speeds. FIG. 60C shows the mean and standard deviation of the lumbo-sacral moment during lifting of 25 pounds, which is plotted in the impedance space using the pelvis angle. The moment was calculated for 5 lifts and one subject with inverse dynamics using motion capture data and force plates. It shows that the biological moment of the L5-S1 scales linearly with trunk flexion as indicated by the linear regression lines. As explained previously with an impedance control approach, the assistance of the suit is adapted to the biological torque automatically. The plot in FIG. 60C shows two active assistance curves: one in which the user bent to an angle of approximately 50 degrees and one for 100 degrees. Similar to the biological moment, the maximum force level of the 50 degree curve amounts to 50 percent of the level for 100 degree trunk flexion. The fact that the force is increased and decreased based on the movement or posture of the user also enables the automatic adaption of the assistance to different lifting speeds. If the force is changed between two force levels in a certain angular window, and the wearer moves faster within this angular window, the force increases faster as well. This approach guarantees smooth force profiles for every lift, independent of the lifting speed of the user. Both advantages can be illustrated by plotting the assistance curves in the time domain.

Detecting Different States During Lifting

As discussed previously, the assistive profile may be a function of the different states that the user follows. FIG. 61A shows a state-machine that detects whether the user is standing upright, going down, holding a position or going up against gravity. These transitions define different impedance profiles that are programmable. These transitions could be detected by measuring joint angles, speeds and/or accelerations to decide what the user is doing.

The user may go from being upright to going down and this may be detected by using a small threshold and compare it against the torso-thigh angle. As an example, an algorithm may use a threshold of 7 degrees, this number was found experimentally as successful in discriminating a lifting/reaching posture against other motions such as standing straight, walking, etc. It should be noted that threshold values may be modified depending on the application automatically or manually. From this point, the assistance will be defined by following the yellow line as the user moves downwards. At some point the user may decide to hold a position, say for instance to sort different objects on a logistics application, to perform a task such as inspecting a surface, drilling, etc., to lean over to perform a procedure such as a surgeon in the operating room. In those situations, the force will be maintained at a defined level. The hold state may be detected by using a small threshold on the motion (e.g. angular speed) of the relative torso to thigh angle. When the user transitions from a motion (e.g. going up/going down) state to a hold state. The relative thigh to torso angle as the user enters the holds state is saved as the hold angle ($\theta_{hold}$) which will be compared against the measured torso to thigh angle while at the hold state to decide whether the user intention is to start moving upwards/downwards. At this point, the user can either hold the position, continue to move down or go up. If the user moves away from the hold position by slightly moving downwards, the state will change to "moving down" and the assistance will continue to follow the yellow impedance line. If the user moves away from the hold position to a higher angle, the state will change to "moving up" and at this point, the assistance will be following the green line in the impedance space. At this point, the user may decide to hold a position again (state change to "hold") or continue moving upwards until the angle is close to the upright position at which point, the state will change to "upright".

Figure 62:
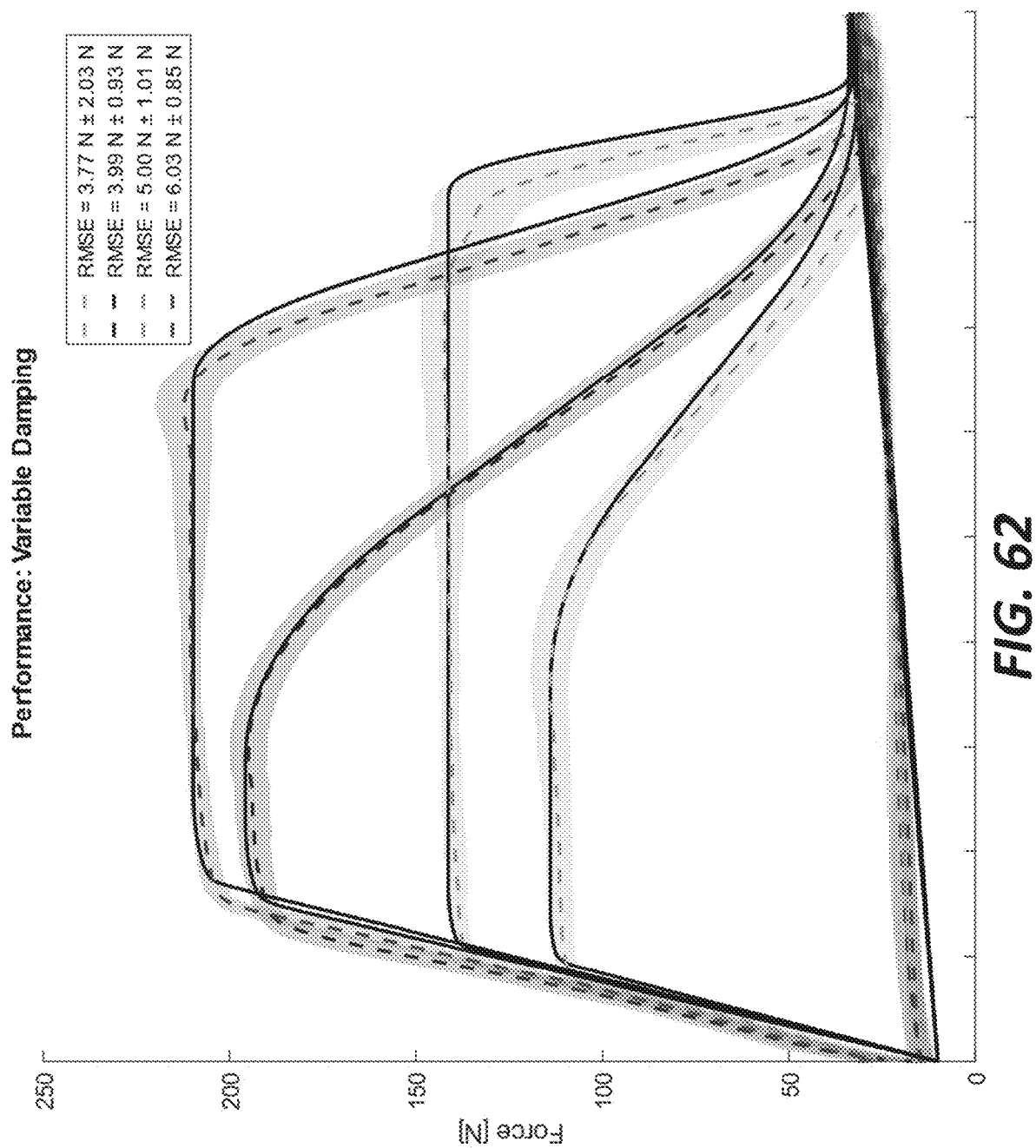
FIG. 62 is a plot that shows measurements from the device in which five different users performed a series of fifty lifting cycles and the system rendered different types of impedance profiles.

Referring to FIG. 62, this plot shows measurements from the device in which five different users performed a series of fifty lifting cycles and the system rendered different types of impedance profiles. In particular, this plot shows the mean and standard deviation of the assistance across these subjects and lifting repetitions. Four different assistive strategies were presented to the user to show that the device can render different types of forces as defined by the impedance space. These tests show that the device i) is able to render different types of impedance profiles to the user, ii) that the device achieves a high tracking performance of the impedance profiles, and iii) that the states of lifting where successfully detected and the forces accurately follow the impedance profiles without significant delay.

Figure 63B:
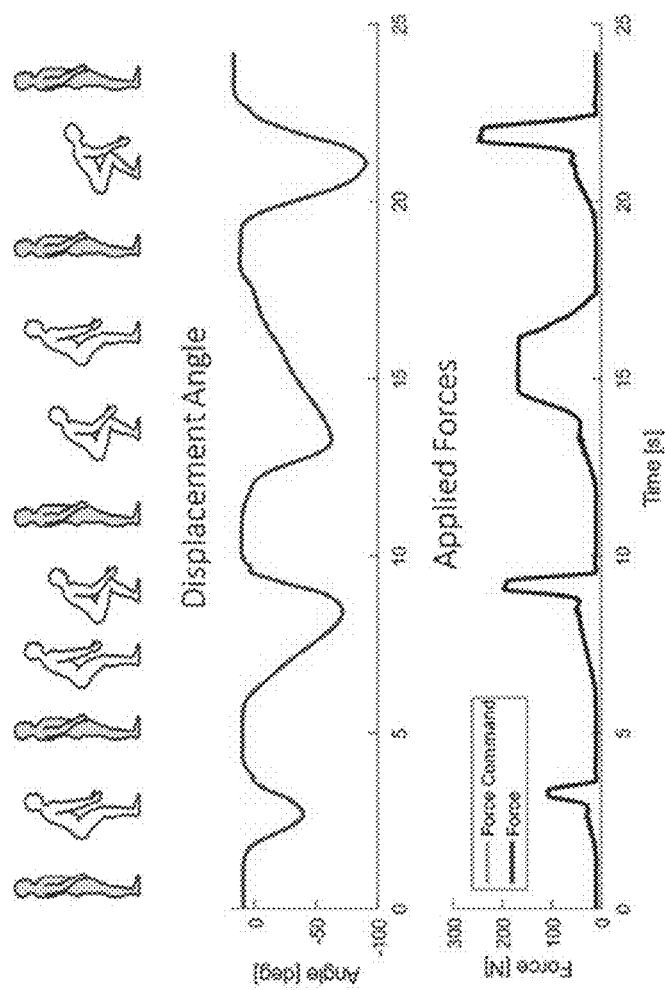
FIG. 63A and FIG. 63B show applied force and displacement angle measurements from the device following the assistive strategy that was presented in which the user started in a standing straight position and performed a series of four lifts at different speeds and ranges.
Figure 63A:
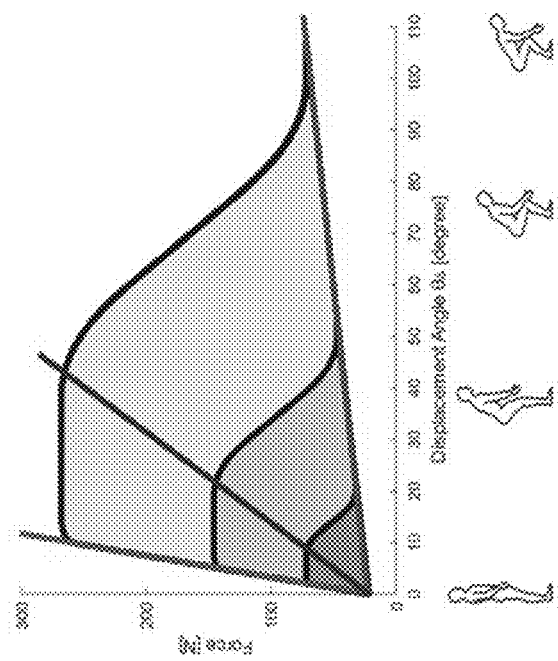

FIG. 63A and FIG. 63B show applied force and displacement angle measurements from the device following the assistive strategy that was presented in which the user started in a standing straight position and performed a series of four lifts at different speeds and ranges. The device was able to successfully track the impedance profile to deliver forces to the user, and this method showed to be adaptive to different speeds and ranges of movement.

In various embodiments, the movement to be assisted may be a lifting motion. The controller 240 may determine an average angle of the hip joints of the wearer, and may monitor the average angle of the hip joints of the wearer to detect when the average angle of the hip joints exceeds a threshold indicative of the start or end of a stage of the lifting motion. The threshold, in an embodiment, may be indicative of an initial moving down state of the lifting motion, and may be an average angle of the hip joints increasing to about seven degrees from a neutral angle of the hip joints. The threshold, in an embodiment, may be indicative of a hold state of the lifting motion, and may be an average angular velocity of the hips decreasing to about zero degrees per second. During the hold state, the controller 240 may monitor the average angle of the hip joints to detect a transition to a moving up state or a moving down state. A change in the average angle of the hip joints to a lower angle may be indicative of a transition to a moving up state, and change in the average angle of the hip joints to a higher angle may be indicative of a transition to a moving down state.

The controller 240 may be configured to adjust the impedance of the wearable device 100 as a function of the state the movement or pose being assisted.

Detecting and Classifying User Movements

In an embodiment, a controller 240 may use sensors 230 integrated into the robotic apparel device to classify user movements. Classifying user movements may be useful for certain applications. For example, multiple repetitions of the same movement for extended periods of time may increase the risk of injury, and as such, if the system detects that a user is performing multiple twisting motions during lifting or other physical activity it may use this information to alert the user or to aggregate this data with a group of users to inform of best practices to avoid future injuries. As another example, the system may modify assistive profile based on the type of movement detected. For example, an assistive profile that may be optimal for a stoop lift, may be different than that for a squat lift.

Machine learning algorithms such as decision network trees, Markov models, etc. may be used to classify different movements based on sensor data.

An algorithm may use some portion of data to classify movement. For instance, as explained previously, there are different phases during lifting (going down, changing direction, going up to lift an object). If the user goes down by following a squat strategy (flexing knees), when going upwards, the user will also need to go up by extending the knees, if the user goes down with a side lift, he/she will likely go up by following a side lift as well.

Figure 64:
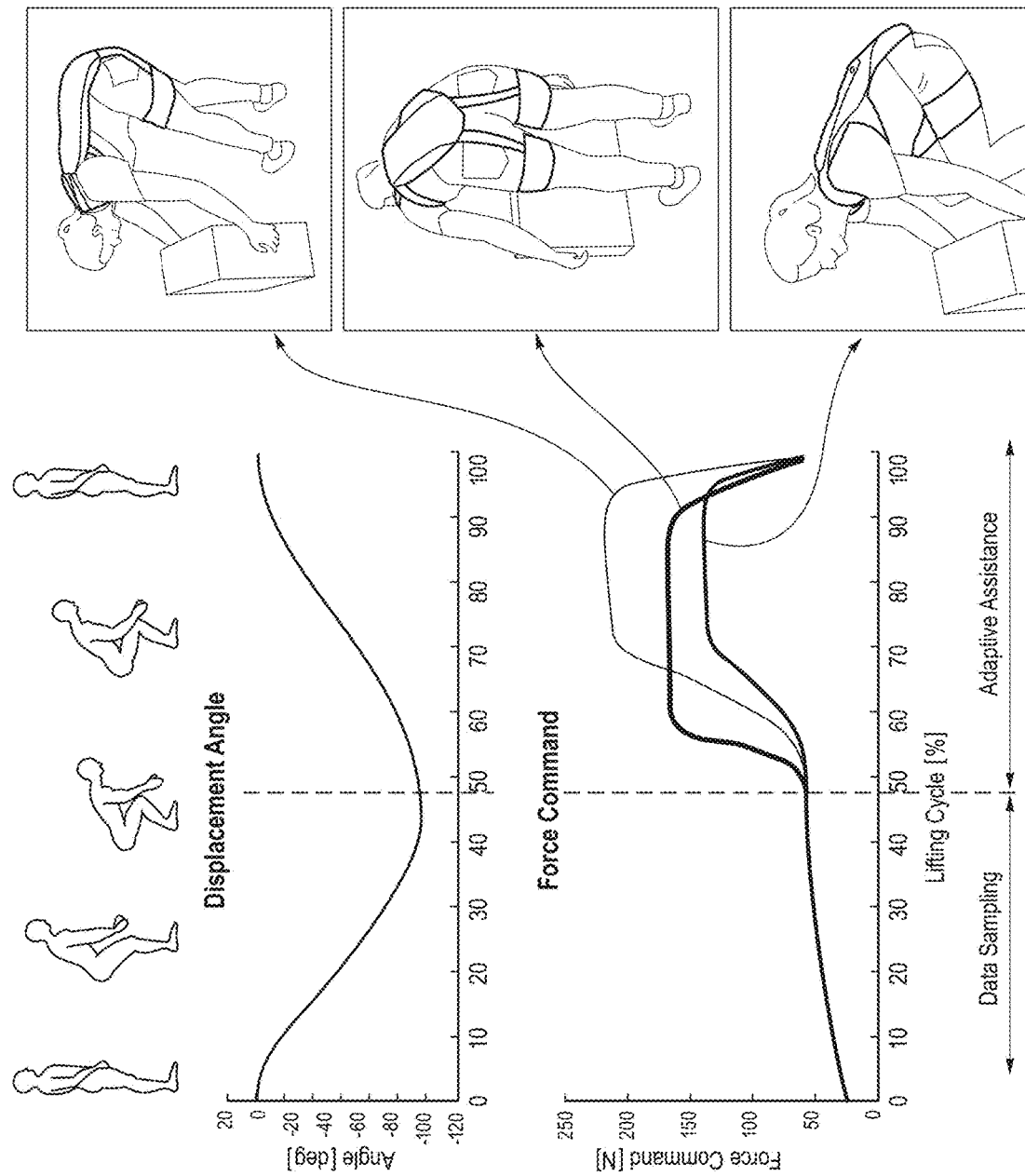
FIG. 64 shows a device that detects different movements by using sensing data as the user moves down, to detect the user movement and adapt the assistive forces to a profile that is more adequate for that specific movement.

In this step, segments of the data stream are identified which are likely to contain information about activities. In different embodiments, windowing techniques may be applied such as sliding windows, event-defined windows and activity defined windows to define the portion of data that will be used to define an activity. A popular approach is a sliding window approach where a fixed time window is moved over the data stream to segment it. The size of the sliding window heavily depends on the application and the relationship between the length of an activity and the sampling rate of the sensors 230. In the context of this work, a fixed-size sliding window approach may not be ideal for some applications because the length of an activity varies significantly due to different lifting speeds. Selecting a small window size could result in several labels for one movement whereas a large window size could include several lifts. For this reason, an event-based approach is used in this work, which utilizes the state machine of the high-level controller 240 described previously to segment the data stream. The state machine itself recognizes different states of a lifting cycle using information about the motion or posture of the user. For this embodiment, the lifting style of the wearer is analyzed when the user is descending to reach the object. The start of the data segment used for classification is triggered by a state transition from state 'Upright' to 'Down' (1-2) and data acquisition stops when the state machine switches to state 'Hold' (3) or 'Upwards'. Consequently, the size of the data segment varies for different lifting speeds. In contrast to fixed-length sliding windows, this approach ensures that each movement is only classified with one label and that the data segment captures the whole movement. Another advantage of this approach is that the data segments can be labeled automatically during training by using the state flags of the state machine. A controller 240 may use a strategy in which data collected as the user is going down is used to decide the assistive strategy as the user goes up. FIG. 64 shows a device that detects different movements by using sensing data as the user moves down, to detect the user movement and adapt the assistive forces to a profile that is more adequate for that specific movement. In an embodiment, the system may include motion sensors 230 (e.g. IMU sensors 230 of the suit located on the torso and both thighs as shown previously) to classify the wearer's movement or posture. The 3-axis accelerations (accX, accY, accZ) measured by the accelerometer and angular velocities (gyroX, gyroY, gyroZ) measured by the gyroscope may be used for each sensor, resulting in 18 raw data signals in total.

Figures 65A, 65B:
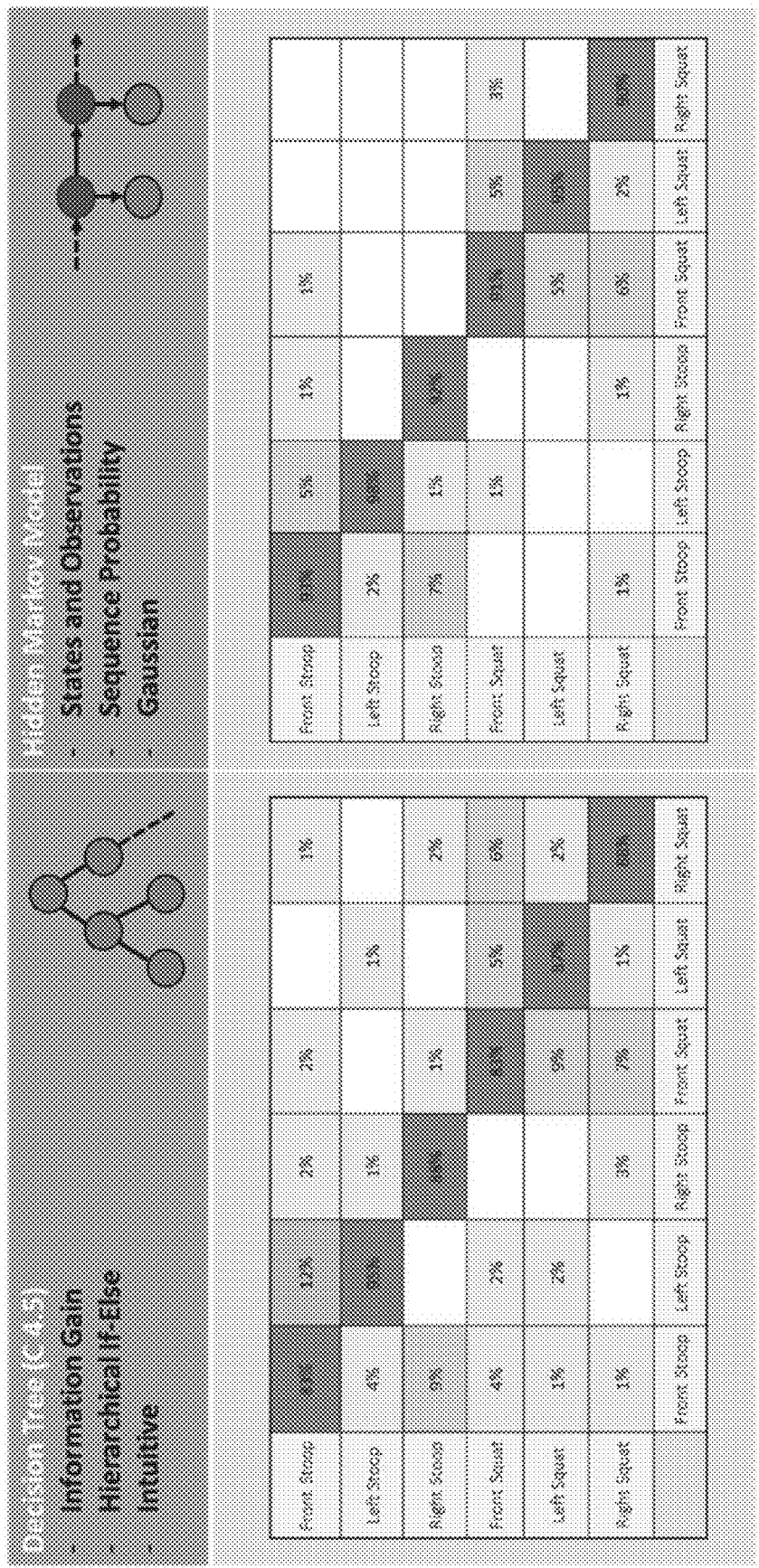
FIG. 65 shows machine learning algorithms such as decision trees (FIG. 65A) Hidden Markov Networks (FIG. 65B), etc. may be used to classify user motions.

Referring to FIG. 65, in various embodiments, machine learning algorithms such as decision trees (FIG. 65A), Hidden Markov Networks (FIG. 65B), etc. may be used to classify user motions. FIG. 65A and FIG. 65B also show experimental data confusion matrix for an implementation of these two algorithms, this data shows that relatively high accuracy rates can be achieved to properly detect the type of lift that a user is performing (stoop, squat, side lifts, etc.).

Additionally, these algorithms may also be used to detect other type of motions such as walking, running, jumping, squatting, reaching tasks, etc.

In an embodiment, the movement to be assisted may be a lifting movement. The controller 240 may be configured to classify the lifting motion as a stoop lifting motion, a squat lifting motion, or a bend and twist lifting motion based on the information relating to one or more of the angle, a velocity, and an acceleration of the one or more joints. The controller 240 may be configured to adjust the impedance of the wearable device 100 as a function of the type of the movement or pose being assisted.

3-D Impedance Profile

Figure 66B:
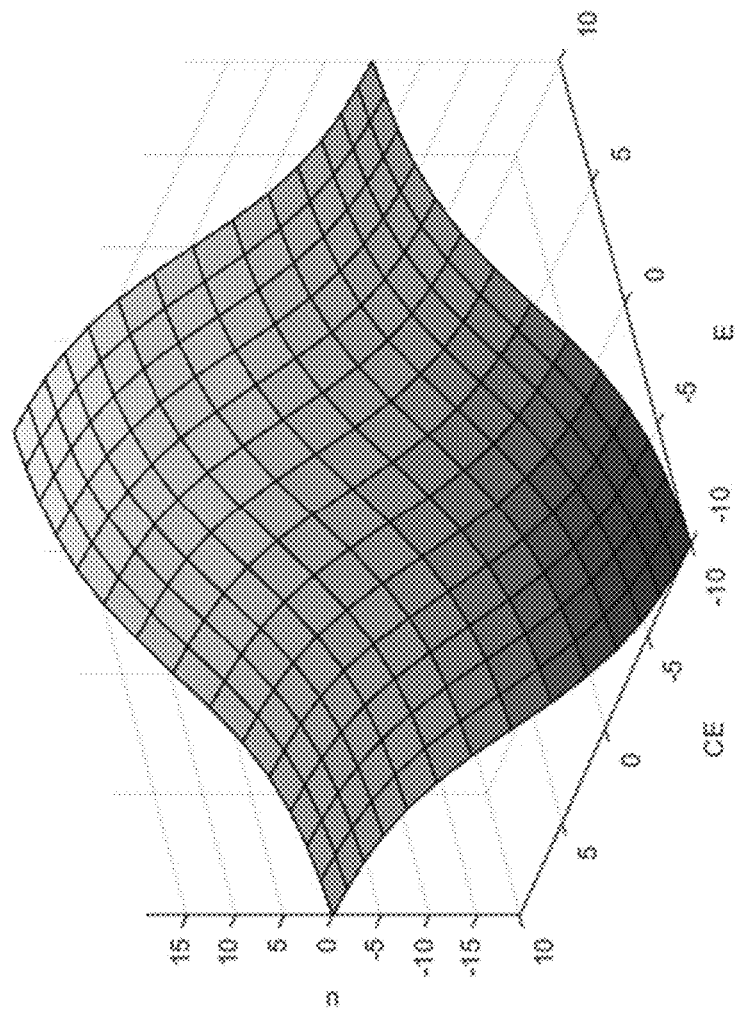
FIG. 66A and FIG. 66B. show the concept of a 3-d impedance space.
Figure 66A:
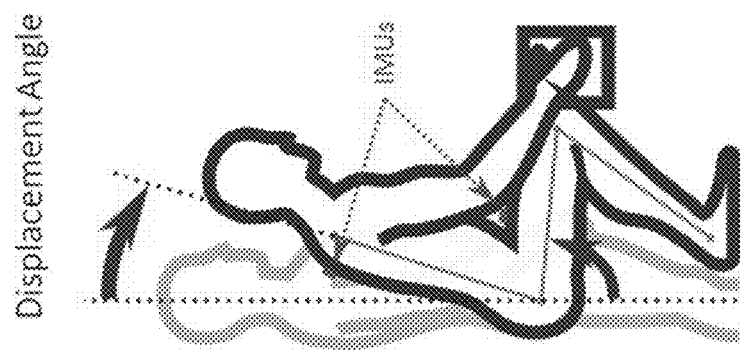

In previous implementations, we have described a 2-d impedance space as a function of the torso-thigh angle in the sagittal plane. In some cases, it may be useful to define a 3-d impedance based on the trunk-thigh angle as a function of the three coordinates of this angle. The advantage of this approach, is that it presents an assistive strategy that would automatically adapt to different motions of the user and program assistive profiles that may be more suitable for lifting in different planes. This concept will allow the assistive profiles to adapt to different types of lift depending on the user movement. For instance, a user may perform lifts in the sagittal plane, or perform lateral lifts or lifts that require twisting motions due to constrains in the environment or in the object. A profile defined in a 3d space based on the user movement/position will automatically and continuously adapt to these motions. The 3d-impedance profile may be defined in different ways, some examples include using knowledge of biomechanics characteristics of the different type of lifts considered, by using an optimization method as defined above to maximize user performance and/or by having a user interface that allows to select different parameters of the assistive profile based on subjective feedback. FIG. 66A and FIG. 66B. show the concept of a 3-d impedance space.

Strategies for Holding a Static Posture

Holding a fixed position for a long time can place a significant strain on the body. There are multiple occupations where this is a common ergonomic issue, for instance, surgeons have to stay long hours with a fixed position during the course of a surgery, additionally workers in the manufacturing, maintenance sector have to hold poses for extended periods of timing when installing fixtures or when performing tasks in tight spaces.

Referring back to the states of a task, a control strategy may increase the amount of assistance depending on the time that the wearer stays in a "hold" position. A sample embodiment of this approach is shown in FIG. 67.

1) Normal impedance profile: Assistance force is generated according to the impedance curve and user states as described above (4 sample system states: Upright, Down, Hold, Up)
2) At the hold state, if a user holds his/her position for more than a predefined designated time, assistance force is increased at a certain rate over time.
3) A maximum assistance force for holding is set, thus assistance force is not increased more the set value.
4) If a user enters the up state from the hold state, assistance force profile is generated from the static holding force following the normal upstate impedance profile.

5) If a user enters the down state from the hold state, assistance force is reduced at a certain rate to the level that was specified for the down state.

Additionally, as explained previously, thresholds may be used to detect whether a user is staying in a hold position or whether the user is transitioning to an upright or going down state. Depending on the industrial setting, these thresholds may be modified to favor a more dynamic behavior versus a static posture. For instance, a surgeon may rarely perform very fast dynamic motions with his/her trunk or legs during his work such as those found in repetitive lifting while a worker in the logistics sector may perform dynamic lifts more often than holding a static posture. In the first case, the thresholds to detect transitions between the hold state and the going up or down states may be larger, while these thresholds may be set-up lower for use-cases where the task is more dynamic. These sensitivity or threshold parameters may be tuned manually during the first set-up of an algorithm may detect which of those situations is more common for a particular wearer and automatically modified the sensitivity/thresholds of the device.

The impedance controlled wearable device 100 to assist both the hip and back joints during lifting and holding static postures for a prolonged time was evaluated in human subject studies to show efficacy.

During this study subjects performed two series of tests. The first one involved performing 15 repetitions lifting a box with a weight equivalent to 17% body mass. The second test involved holding a static posture with the torso at 40 degrees and maintain this posture for 45 seconds. Subjects performed both activities both with and without the device. During these trials muscle activity, joint torque and power were evaluated to compare the level of effort of the subject when wearing the device versus when not wearing the device.

Figure 67A:
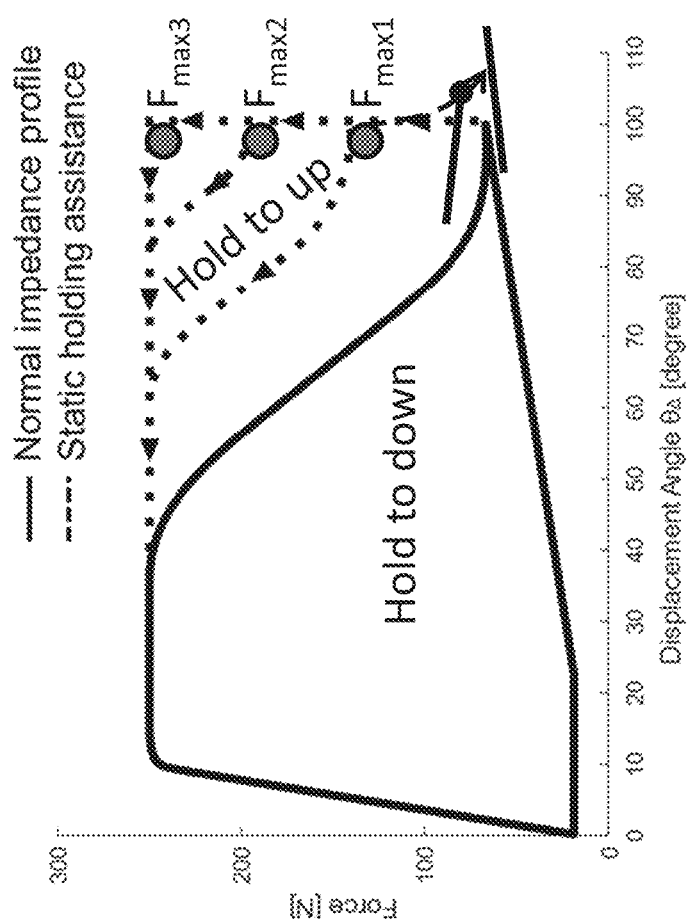
FIG. 67A, FIG. 67B, FIG. 67C, FIG. 67D, and FIG. 67E depict a representative approach for assisting a static hold, wherein a control strategy may increase the amount of assistance depending on the time that the wearer stays in a "hold" position.
Figures 67B, 67C:
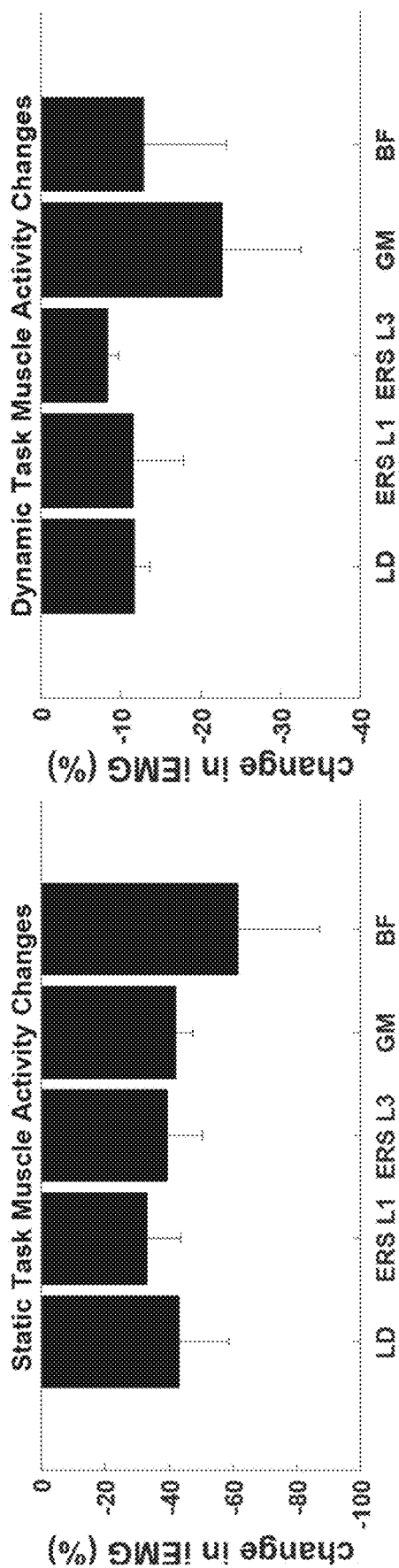

Preliminary results on 3 subjects suggest that the proposed device and control method is effective in reducing the muscle activity of the key back and hip muscles involved during lifting (FIG. 67B) and holding static postures (FIG. 67C). For the task involving static postures, the integrated muscle activity of the latissimus dorsi, erector spinae at two different levels (L1 and L3), gluteus maximus and biceps femoris muscles was reduced by 35-60%. During lifting, the same muscles were reduced by 10-25%. Cumulative loading of muscles is a key variable that increases the risk of injury and so the fact that these devices reduced the integrated muscle activity of key muscles during the targeted activities suggest that the developed methods/systems may be effective In mitigating risk of injury, reducing fatigue and enhancing productivity.

Figure 67E:
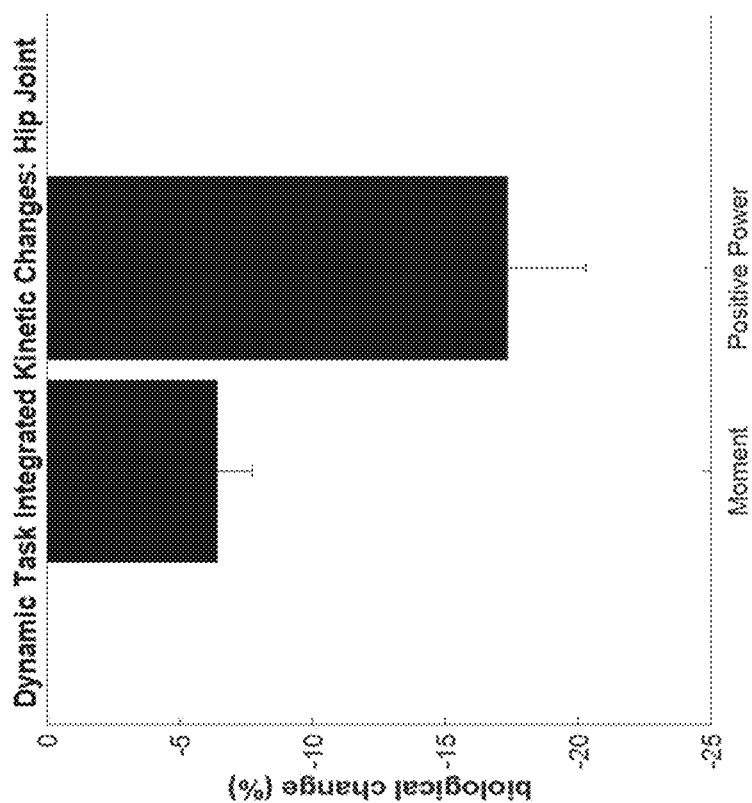
Figure 67D:
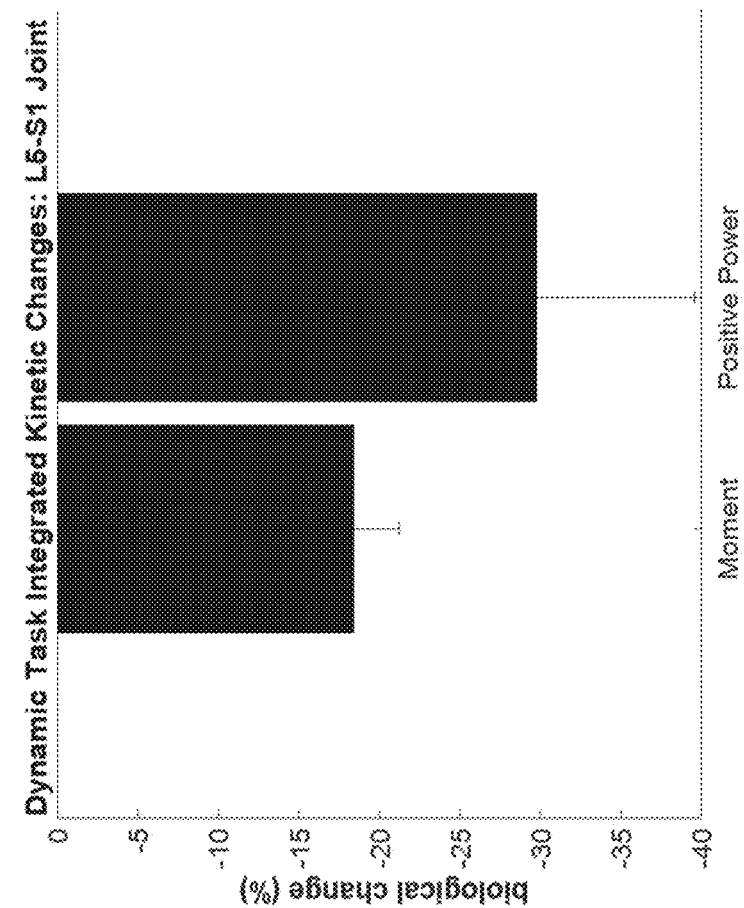

Moreover, kinetic changes during the lifting task suggest that the integrated L5-S1 joint moment is reduced by ~18% and the integrated positive power that the joint has to produce is reduced by ~28%, comparing wearing the device vs not wearing it at all (FIG. 67D). This effect is also seen in the hip joint where the integrated moment is reduced by ~8% and the integrated positive power is reduced by ~18% (FIG. 67E). These significant reductions suggest that the device is successful in unloading both the hip and back joints during lifting and thus such a device may be effective in augmenting productivity, mitigating risk of injury and reducing fatigue.

Alternative Embodiments of Wearable Device Architecture

Decoupling the Load Balancing Strap

As mentioned previously, the load-balancing strap 112 requires a pulley, rolling or low friction element to, as an example, be able to slide and distribute load equally among both legs. The distances from the upper back to the left leg and the right leg may be independent and driven by the position of the legs, and thus a coupling mechanism may be needed to connect the device to the left leg and the right leg while applying similar forces to both. To accommodate this functionality, the load balancing assembly 210 may comprise a floating external decoupling mechanism, i.e., further include a load balancing mechanism 215 that may slide up and down the torso to decouple the load-balancing strap 112 movement from the connecting element 150 (e.g., cable component), as shown in FIG. 68A. As shown, wearable device 100 may comprise a first anchor member 110 configured for positioning on an upper body of the wearer, a second anchor member 110 configured for positioning on a first leg of the wearer, and a third anchor member 110 configured for positioning on a second leg of the wearer. Actuation of the at least one actuator 120 generates a tensile force in the wearable device 100 for generating a moment about at least one of: (i) a hip joint of the first leg and a hip joint of the second leg of the wearer, and (ii) one or more back joints of the wearer. The wearable device 100 may further comprise a load balancing assembly 210 coupling the actuator 120 to the second anchor member 110 and the third anchor member 110. The load balancing assembly 210 may comprise: a flexible elongate member 212 (e.g., strap) having a first end coupled to the second anchor member 110 and a second end connected to the third anchor member 110, and a load balancing mechanism 215 coupling the actuator 120 to an intermediate portion 214 of the flexible elongate member 212 between the first end and the second end, and configured to allow the flexible elongate member 212 to translate within the load balancing mechanism 215 and thereby balance the tensile force distributed to the first leg and the second leg of the wearer.

Figure 68C:
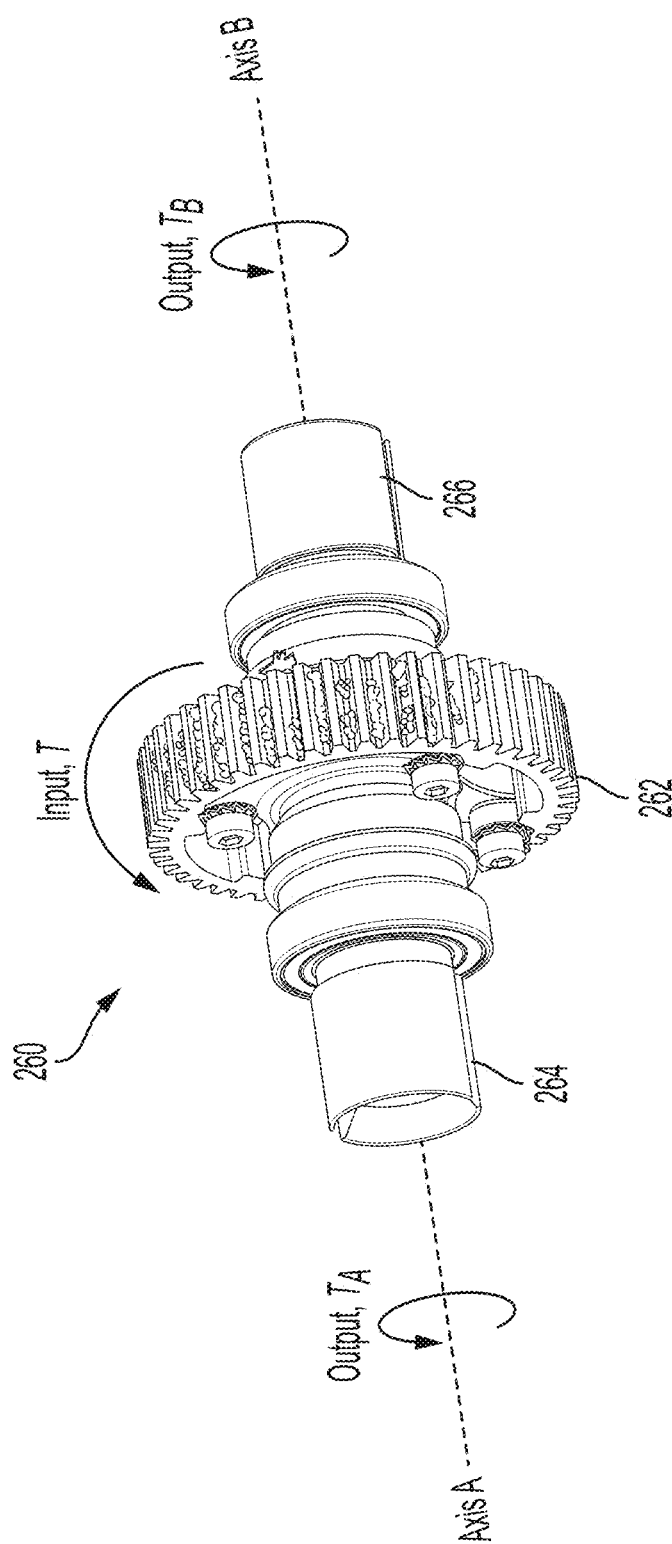
FIG. 68C shows a representative decoupling mechanism built into the actuator.

In another embodiment, one or more decoupling components may be integrated into the actuation system itself For example, FIG. 68B illustrates a representative configuration in which a decoupling mechanism 260, i.e., a stationary internal decoupling mechanism, (later shown in FIG. 68C) may be integrated in the actuator module to split forces equally between two load paths while allowing for different relative positioning of each load path. In this section, we describe different embodiments of each of these options.

FIG. 68C shows a concept in which the assistance is decoupled by an internal decoupling mechanism 260 built into the actuator. As mentioned previously, the goal of the decoupling mechanisms 210, 260 is to apply equal forces to both thighs using only one motor. Since the legs of the wearer can move independently and the goal is to use only one motor, the system needs other degree of freedom to allow for the different lengths from the actuator to each leg. Decoupling mechanisms 210, 260 may be used to guarantee that the force transmitted to each leg is even but allowing their positions to be independent so that both legs can move independently. A differential achieves a similar task in cars, where the torque from the engine is evenly distributed between the two back wheels while allowing them to rotate independently so that the car can go around turns. A similar concept may be integrated in the actuation system 120. A motor would rotate the middle section 262 applying a torque, T. Rotating members 264 (axis A) and 266 (axis B) are able to rotate independently of the middle section 262 and each other, but the internal differential mechanism ensures the input torque is split evenly to the outputs $T_A$ and $T_B$. Rotating members 264, 266 would be connected to spindles with their own connecting elements 150 spooled upon each. Distal ends of connecting elements 150 may be connected to an anchor member 110 on the left leg of the wearer and to an anchor member 110 on the right leg of the wearer. This is where our second degree of freedom comes from and allows the legs of the person to move independently.

Figure 68D:
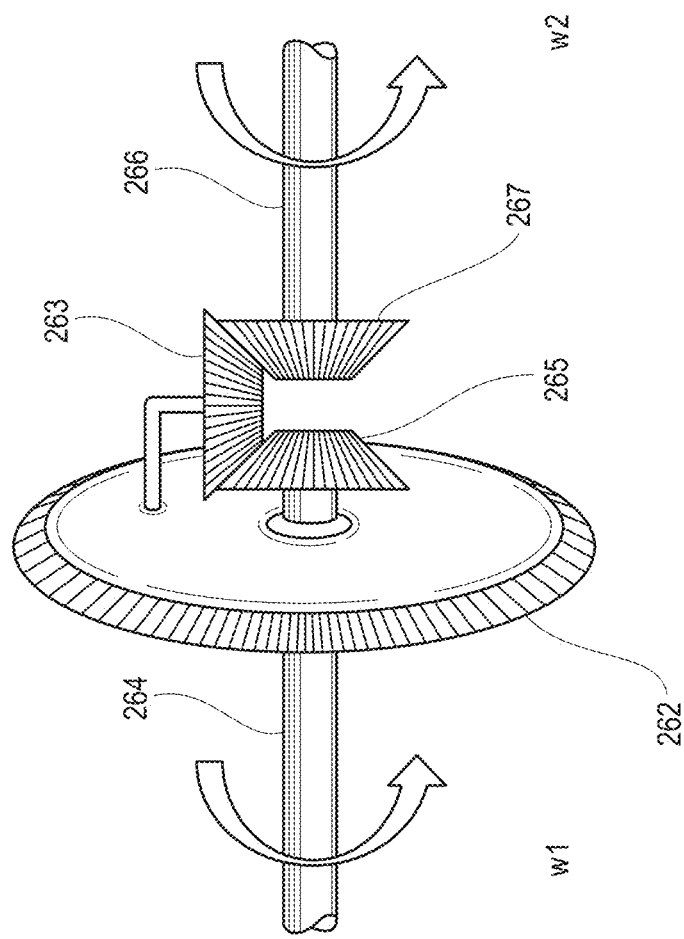
FIG. 68D shows the different components in a sample differential system.

FIG. 68D shows the different components in a sample differential system. In this example, motor 121 drives a crown wheel 262, which as it rotates drives a sun gear 263 around a gear 265 associated with rotating member 264 and a gear 267 associated with rotating member 266. In the case that both legs move at the same speed (w1=w2), the pinions of gear 265, gear 267, and sun gear 263 do not rotate, thus, all of these components move as a solid piece without spinning with respect to each other around the crown wheel 262. Note that the crown wheel 262 is not directly connected to rotating member 264 but transfers torque from to rotating member 264 and rotating member 266 through sun gear 263.

In the event that the left leg does not move at all but the right leg moves, the pinion of sun gear 263 will rotate as it travels around the shaft such that gear 265 stays static and gear 267 can rotate at a speed (w1=0; w2). In the event that both legs move at different speeds, the decoupling mechanism 260 acts the same—as sun gear 263 travels around the shaft, the pinion of sun gear 263 will rotate at a speed equal to the difference between the angular speed of rotating member 264 and rotating member 266 so that gear 265 and gear 267 can rotate at different relative speeds.

FIG. 69A shows a concept in which the load-balancing 212 is decoupled from the cable component 150, i.e., a floating external decoupling mechanism, by using a load balancing mechanism 215 such as a low-friction, roller, bearing, pulley, etc. in this case two implementations may be considered:
1) Cable-based: as shown in FIG. 69B, the force-generating cable 150 attaches to a load balancing mechanism 215 that includes the low-friction element, bearing or pulley. The load-balancing elongate element 212 (e.g., strap, ribbon) is routed through the low-friction or rolling component 215 to be able to slide with respect to the force-generating cable 150.
2) Ribbon or strap based: as shown in FIG. 69C, the force-generating element 150 may be a ribbon or a strap that attaches to the flexible elongate element 212, the load-balancing elongate element 212 is able to slide with respect to the force generating element 150.
D) Example: FIG. 70 describes a different way, a stationary internal decoupling mechanism, of achieving the load balancing assembly 210. In this case, two independent motors 519a, 519b are used to actuate each load-balancing elongate element 212 individually. This concept allows to apply independent forces to each strap and thus be able to control whether the forces on each leg are different or identical depending on the type of movement that the user is performing, additionally, it allows to be able to control the forces on each side of the back differently which allows to control off-axis torques which may be practical to assist twisting and bending motions of the back. For instance, when performing a side lift, the tension in each strap/cable may be different to provide additional off-axis support to the back and thighs. Additionally, this may allow applying assistance to the hip extensors during tasks such as walking by independently actuating each strap.

As shown, wearable device 100 may comprise a first anchor member 110 configured for positioning on an upper body of the wearer, a second anchor member 110 configured for positioning on a first leg of the wearer, and a third anchor member 110 configured for positioning on a second leg of the wearer. A first actuator 120 may directly or indirectly couple the first anchor member 110 and the second anchor member 110, and actuation thereof generates a tensile force in the wearable device 100 for generating a moment about at least one of: (i) a hip joint of the first leg of the wearer, and (ii) a back joint of the wearer. A second actuator 120 may directly or indirectly couple the first anchor member 110 to the third anchor member 110, and actuation thereof generates a tensile force in the wearable device 100 for generating a moment about at least one of: (i) a hip joint of the second leg of the wearer, and (ii) a back joint of the wearer.

Wearable Device Architecture for Coupled Hip Assistance

Most exoskeleton/exosuits systems with the goal to assist the hips of a user, have been designed to independently assist each hip of the user and therefore typically require two active elements to be able to control each hip independently. This is due in part to the fact that most of these systems were originally envisioned to assist impaired individuals to walk again or healthy individuals to walk more efficiently. However, there are multiple tasks where simultaneous assistance to both thighs is needed, examples include lifting, sit-to-stand, jumping, kneeling, crouching, etc. these tasks are common for the elderly, consumer and industrial applications.

A system may thus be designed to provide assistance simultaneously to both legs, this has the advantage that it may be possible to design an exoskeleton or exosuit to only use 1 degree of freedom which has important implications regarding cost, simplicity and weight.

Figure 71:
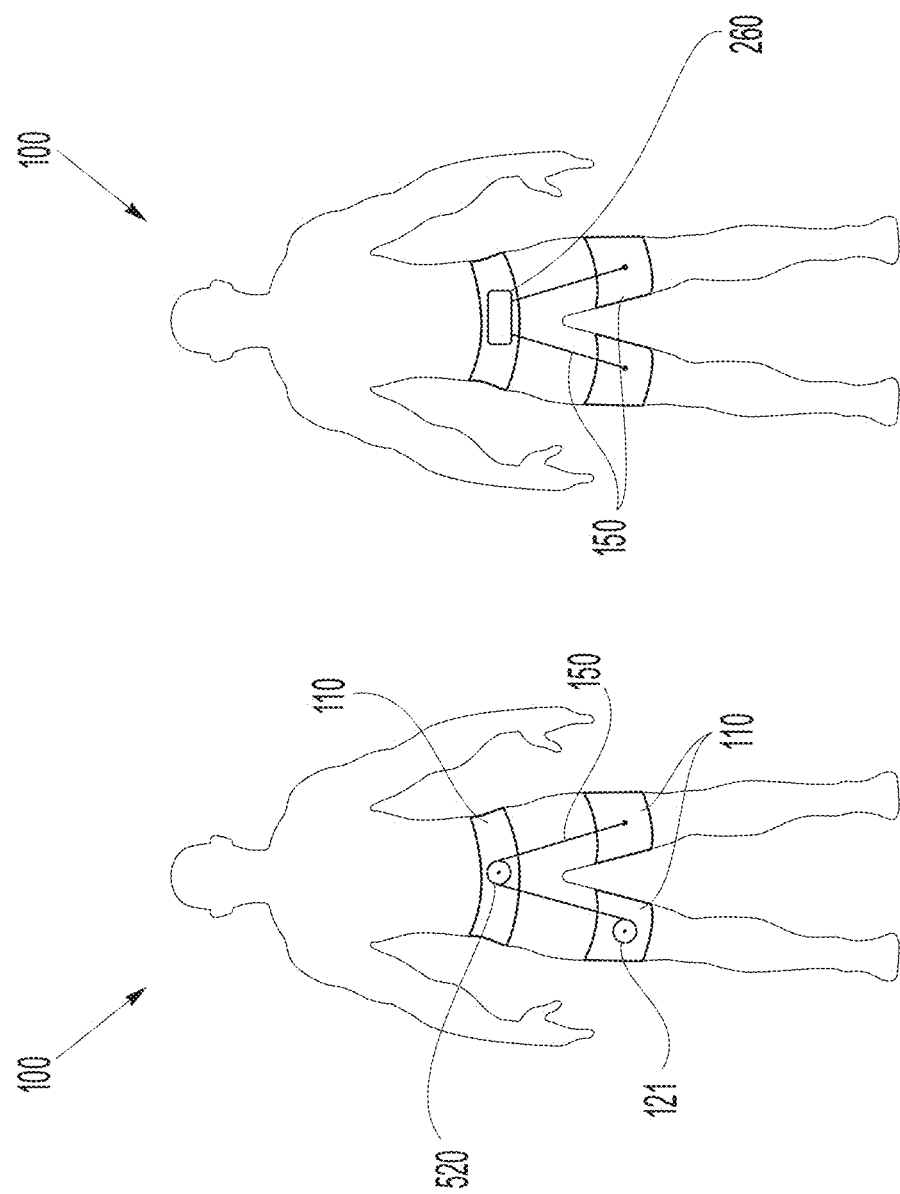
FIG. 71 shows an embodiment in which the wearable device.

FIG. 71 shows an embodiment in which the wearable device 100 is composed of the following components:
  A load balancing element 212 is connected to both thighs (as explained before),
  A waistbelt: the waistbelt wraps around the user's waist and guides the load balancing element 212 to route from the thigh to a point in the waistbelt, and from this point to the user's anchor member 110. In one embodiment, a waistbelt may include a pulley 520 and connecting element 150. In another embodiment, the waistbelt may comprise a decoupler 260.
  Anchor members 110 that wrap around the user's thighs and provide anchor points for the load balancing element 212.
  Sensors 230: sensing elements such as those described previously may be integrated in the system including but not limited to sensors 230 to sense user's movement, position and forces delivered from the wearable device 100 to the user.
  Actuation or force generating elements: a cable driven actuation element to be able to pull on the load balancing element 212 in order to generate forces on the load balancing element 212 that will then create a joint torque on the user's hips. The cable-driven actuation may be located on one of the user's thighs connected to the load balancing element 212, on the user's waist, on a different part of the body using a Bowden cable to route the forces from the actuator 120 to the point in which the actuation cable connects to the load-balancing strap. Additionally, other types of actuators 120 such as fluidic, electrostatic or passive components (springs, dampers, etc.) may be used to generate forces with such an architecture.

As shown, wearable device 100 may comprise a first anchor member 110 configured for positioning on a waist of the wearer, a second anchor member 110 configured for positioning on a first leg of the wearer, and a third anchor member 110 configured for positioning on a second leg of the wearer. At least one actuator 120 directly or indirectly couples the first anchor member 110, the second anchor member 110, and the third anchor member 110, and actuation of the at least one actuator 120 generates a tensile force in the wearable device 100 for generating a moment about a hip joint of the first leg of the wearer and about a hip joint of the second leg of the wearer.

Wearable Device Architecture to Independently Assist the Back and Hip Joints

While simultaneously assisting the hip and back joints presents several advantages, for some applications, independently assisting the hips and the back may have additional benefits. Possible advantages include, higher degree of adaptation of assistance since assistance at the back doesn't need to be coupled to assistance to the thighs.

Figure 72:
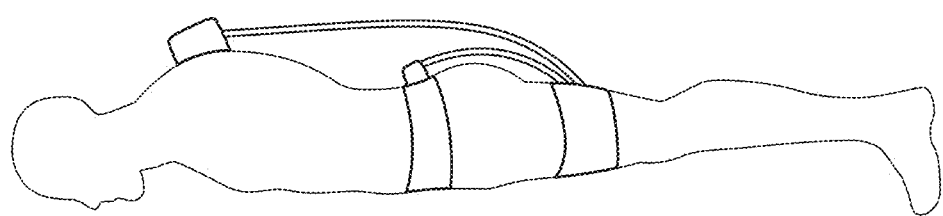
FIG. 72 illustrates that a control strategy may leverage the fact that the sum of the forces applied to both legs (which would apply a downward force to the waistbelt) is higher than the force at the back (which applies an upward force to the waistbelt) keeping the waistbelt in place is easier since the shape of the body helps to keep the waistbelt in place to independently control back and hip assistance but limiting the amount of back assistance to a force that is close to or lower than the sum of the forces applied to both legs.

Sample embodiments, may be comprise:

Single DOF assistance to simultaneously assist both thighs and an additional DOF to assist the back (FIG. 72).

Independent assistance to each hip and independent assistance to the back of the user.

The back assistance will be achieved by anchoring the assistive element on an upper side of the torso or shoulders of the user and on the other side to a position close to the waist of the user.

If assisting the back alone, without assisting the thighs may be challenging since the body is shaped in a way that if a waistbelt is pulled upwards, it tends to move upwards with respect to the body and may present anchoring challenges. However, if the sum of the forces applied to both legs (which would apply a downward force to the waistbelt) is higher than the force at the back (which applies an upward force to the waistbelt) keeping the waistbelt in place is easier since the shape of the body helps to keep the waistbelt in place. A control strategy may leverage this fact to independently control back and hip assistance but limiting the amount of back assistance to a force that is close to or lower than the sum of the forces applied to both legs (FIG. 72).

A system like this, will be able to assist the legs of the user during walking by applying forces to the user's thighs, when walking over stairs, running, jogging, etc. and optionally simultaneously assist the back to support a user who may be carrying a load or who requires back assistance. In addition, a control algorithm may apply higher forces to the user's legs when performing certain types of lifts e.g. during a squat motion, the user bends the legs and may require higher assistance to the legs than during a stoop lift (lifting with legs straight).

Figure 73:
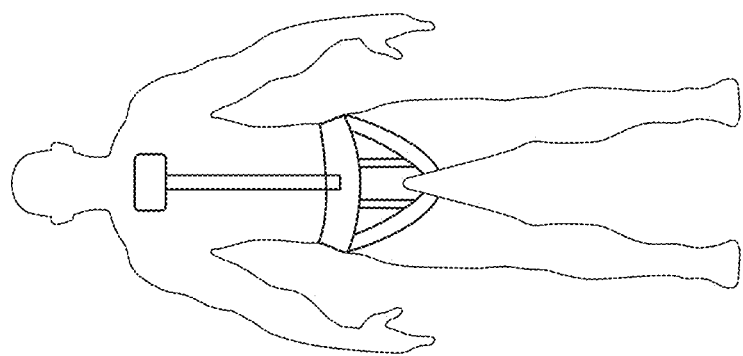
FIG. 73 shows how straps routed through the legs (e.g. harness) or a semi-rigid component that anchors on one side to the waistbelt and on the other side to a position on the upper torso anchored to the shoulders of the user may provide additional support to the waistbelt to avoid upwards motion.

It is worth noting, that an embodiment may also assist the back independently of the thighs, for instance, if the applied forces are low, comfort and waistbelt anchoring may not be an issue. Additionally, straps routed through the legs (e.g. harness) or a semi-rigid component 200 that anchors on one side to the waistbelt and on the other side to a position on the upper torso anchored to the shoulders of the user may provide additional support to the waistbelt to avoid upwards motion (FIG. 73).

While the presently disclosed embodiments have been described with reference to certain embodiments thereof, it should be understood by those skilled in the art that various changes may be made and equivalents may be substituted without departing from the true spirit and scope of the presently disclosed embodiments. In addition, many modifications may be made to adapt to a particular situation, indication, material and composition of matter, process step or steps, without departing from the spirit and scope of the present presently disclosed embodiments. All such modifications are intended to be within the scope of the claims appended hereto.

A wearable device 100 comprising of at least one anchor member 110 configured for positioning on an upper body of a person wearing the wearable device 100, at least one anchor member 110 configured for positioning on a lower body of a person wearing the wearable device 100, and at least one actuator 120 directly or indirectly coupling the at least one upper body anchor member 110 to the at least one lower body anchor member 110, wherein actuation of the at least one actuator 120 generates a tensile force in the wearable device 100 for generating a moment about at least one of: (i) one or more hip joints of the wearer, and (ii) one or more back joints of the wearer.

A wearable device 100 comprising of at least one anchor member 110 configured for positioning on an upper body of a person wearing the wearable device 100, at least one anchor member 110 configured for positioning on a lower body of a person wearing the wearable device 100, at least one connecting element 150 directly or indirectly coupling the at least one upper body anchor member 110 to the at least one lower body anchor member 110, and at least one mechanism configured to selectably lock a length, change a length, or change an impedance of the at least one connecting element 150 to control a level of tension generated in the wearable device 100 by movement or a pose of the wearer, such that the wearable device 100 generates a moment about at least one of: (i) one or more hip joints of the wearer, and (ii) one or more back joints of the wearer.

A wearable device 100 comprising of at least one anchor member 110 configured for positioning on an upper body of a person wearing the wearable device 100, at least one anchor member 110 configured for positioning on a lower body of a person wearing the wearable device 100, and at least one connecting element 150 directly or indirectly coupling the at least one upper body anchor member 110 to the at least one lower body anchor member 110; configured to absorb energy generated by movement or a pose of the wearer. Additionally, at least one mechanism is configured to selectably lock the at least one connecting element 150 to store the absorbed energy, and unlock the at least one connecting element 150 to release the absorbed energy such that the wearable device 100 generates a moment about at least one of: (i) one or more hip joints of the wearer, and (ii) one or more back joints of the wearer.

A wearable device 100 comprising of at least one anchor member 110 configured for positioning on an upper body of a person wearing the wearable device 100, at least one anchor member 110 configured for positioning on a lower body of a person wearing the wearable device 100, and at least one passive element 190 directly or indirectly coupling the at least one upper body anchor member 110 to the at least one lower body anchor member 110 such that movement or a pose of the wearer generates tension in the wearable device 100 and the wearable device 100 provides a moment about at least one of: (i) one or more hip joints of the wearer, and (ii) one or more back joints of the wearer.

A wearable device 100 comprising of at least one anchor member 110 configured for positioning on a torso of a person wearing the wearable device 100, at least one anchor member 110 configured for positioning on an upper arm of a person wearing the wearable device 100, and at least one actuator 120 directly or indirectly coupling the at least one torso anchor member 110 to the at least one upper arm anchor member 110, wherein actuation of the at least one actuator 120 generates a tensile force in the wearable device 100 for generating a moment about at least a shoulder joint of the wearer.

A wearable device 100 comprising of at least one anchor member 110 configured for positioning on a torso of a person wearing the wearable device 100, at least one anchor member 110 configured for positioning on an upper arm of a person wearing the wearable device 100, and at least one connecting element 150 directly or indirectly coupling the at least one torso anchor member 110 to the at least one upper arm anchor member 110. Additionally, at least one mechanism configured to selectably lock a length, change a length, or change an impedance of the at least one connecting element 150 to increase a level of tension generated in the wearable device 100 by movement or a pose of the wearer, such that the wearable device 100 generates a moment about at least a shoulder joint of the wearer.

A wearable device 100 comprising of at least one anchor member 110 configured for positioning on a torso of a person wearing the wearable device 100, at least one anchor member 110 configured for positioning on an upper arm of a person wearing the wearable device 100, and at least one connecting element 150 directly or indirectly coupling the at least one torso anchor member 110 to the at least one upper arm anchor member 110, and configured to absorb energy generated by movement or a pose of the wearer. Additionally, at least one mechanism configured to selectably lock the at least one connecting element 150 to store the absorbed energy, and unlock the at least one connecting element 150 to release the absorbed energy such that the wearable device 100 generates a moment about at least a shoulder joint of the wearer.

A wearable device 100 comprising of at least one anchor member 110 configured for positioning on a torso of a person wearing the wearable device 100, at least one anchor member 110 configured for positioning on an upper arm of a person wearing the wearable device 100, and at least one passive element 190 directly or indirectly coupling the at least one torso anchor member 110 to the at least one upper arm anchor member 110 such that movement or a pose of the wearer generates tension in the wearable device 100 and the wearable device 100 provides a moment about at least a shoulder joint of the wearer.

A wearable device 100 comprising of at least one anchor member 110 configured for positioning on an upper leg of a person wearing the wearable device 100, at least one anchor member 110 configured for positioning on a lower leg of a person wearing the wearable device 100, and at least one actuator 120 directly or indirectly coupling the at least one upper leg anchor member 110 to the at least one lower leg anchor member 110, wherein actuation of the at least one actuator 120 generates a tensile force in the wearable device 100 for generating a moment about at least a knee joint of the wearer.

A wearable device 100 comprising of at least one anchor member 110 configured for positioning on an upper leg of a person wearing the wearable device 100, at least one anchor member 110 configured for positioning on a lower leg of a person wearing the wearable device 100, and at least one connecting element 150 directly or indirectly coupling the at least one upper leg anchor member 110 to the at least one lower leg anchor member 110. Additionally, at least one mechanism configured to selectably lock a length, change a length, or change an impedance of the at least one connecting element 150 to increase a level of tension generated in the wearable device 100 by movement or a pose of the wearer, such that the wearable device 100 generates a moment about at least a knee joint of the wearer.

A wearable device 100 comprising of at least one anchor member 110 configured for positioning on an upper leg of a person wearing the wearable device 100, at least one anchor member 110 configured for positioning on a lower leg of a person wearing the wearable device 100, and at least one connecting element 150 directly or indirectly coupling the at least one upper leg anchor member 110 to the at least one lower leg anchor member 110, and configured to absorb energy generated by movement or a pose of the wearer. Additionally, at least one mechanism configured to selectably lock the at least one connecting element 150 to store the absorbed energy, and unlock the at least one connecting element 150 to release the absorbed energy such that the wearable device 100 generates a moment about at least a knee joint of the wearer.

A wearable device 100 comprising of at least one anchor member 110 configured for positioning on an upper leg of a person wearing the wearable device 100, at least one anchor member 110 configured for positioning on a lower leg of a person wearing the wearable device 100, and at least one passive element 190 directly or indirectly coupling the at least one upper leg anchor member 110 to the at least one lower leg anchor member 110 such that movement or a pose of the wearer generates tension in the wearable device 100 and the wearable device 100 provides a moment about at least a knee joint of the wearer.

A wearable device 100 comprising of at least one actuator 120 configured to generate a force in the wearable device 100 or to cause a force to be generated in the wearable device 100, such that the wearable device 100 generates a moment about one or more joints of the wearer to assist the wearer in performing a non-cyclic movement or to hold a static pose; at least one sensor configured to measure information for evaluating an objective function associated with at least one of providing physical assistance to the wearer, an interaction between the wearer and the wearable device 100, and an operation of the wearable device 100; and at least one controller 240 configured to actuate the at least one actuator 120 according to at least one actuation profile, evaluate the objective function based on the information measured by the at least one sensor to determine a resulting change in the objective function, adjust at least one parameter of the at least one actuation profile based on the resulting change in the objective function, and continue to actuate, evaluate, and adjust to optimize the at least one actuation parameter for maximizing or minimizing the objective function. The at least one controller 240 is configured to identify two or more actuation parameters to be optimized for maximizing or minimizing the objective function; actuate the at least one actuator 120 according to two or more actuation profiles having different sets of baseline values of the two or more actuation parameters to be optimized; evaluate the objective function for each of the two or more actuation profiles based on the information measured by the at least one sensor; define, based on corresponding evaluations of the objective function, a mathematical correlation between the two or more actuation parameters and the corresponding evaluations of the objective function; evaluate the baseline mathematical correlation to determine a candidate set of values of the two or more actuation parameters for maximizing or minimizing the objective function; update the mathematical correlation based on a corresponding evaluation of the objective function for an actuation of the at least one actuator 120 according to an actuation profile associated with the candidate set of values of the two or more actuation parameters; and continue to update the mathematical correlation until an evaluation of the objective function reaches a global maximum or a global minimum value, or when a predetermined termination criteria is met.

A wearable device 100 comprising of at least one anchor member 110 configured for positioning on a first body part of a person wearing the wearable device 100, at least one anchor member 110 configured for positioning on a second body part of a person wearing the wearable device 100, and at least one connecting element 150 directly or indirectly coupling the at least one first body part anchor member 110 to the at least one second body part anchor member 110, at least one sensor configured to measure information relating to one or more of an angle, a velocity, and an acceleration of one or more joints of the wearer spanned by the wearable device 100, and at least one controller 240 configured to detect the start and/or type of a movement or a pose of the wearer to be assisted by the wearable device 100; determine the desired tensile force to be generated in the wearable device 100 as a function of a given angle, velocity, or acceleration of the one or more joints spanned by the wearable device 100 for assisting the wearer in performing the movement or in holding the static pose; and adjust an impedance of or a force provided by the wearable device 100 such that the desired tensile force is generated in the wearable device 100 at the given angle, velocity, or acceleration of the one or more joints. In an embodiment the wearable device 100 comprises at least one mechanism configured to selectably lock a length, change a length, or change an impedance of the at least one connecting element 150, and wherein adjusting the impedance of the wearable device 100 includes locking the length of the at least one connecting element 150 at a length configured to cause the desired tensile force to be generated in the wearable device 100 by movement or a pose of the wearer at the given angle, velocity, or acceleration of the one or more joints. In an embodiment, the wearable device 100 comprises at least two connecting element 150s, wherein the wearable device 100 comprises at least one mechanism configured to selectably engage one or more of the at least two connecting element 150s; wherein adjusting an impedance of the wearable device 100 includes engaging one or more of the at least two connecting element 150s having, either alone or in combination, a spring constant or a damping constant configured to cause the desired tensile force to be generated in the wearable device 100 by movement or a pose of the wearer at the given angle, velocity, or acceleration of the one or more joints. In an embodiment, the wearable device 100 comprises at least one actuator 120, and wherein adjusting an impedance of the wearable device 100 includes actively actuating the at least one connecting element 150 to generate the desired tensile force in the wearable device 100 at the given angle, velocity, or acceleration of the one or more joints. In an embodiment, wherein the controller 240 is configured to monitor the information relating to one or more of the angle, a velocity, and an acceleration of the one or more joints to detect when one or a combination of the angle, velocity, or acceleration exceeds a threshold indicative of the start of a motion or pose to be assisted. In an embodiment, wherein the controller 240 is configured to monitor the information relating to one or more of the angle, a velocity, and an acceleration of the one or more joints to detect when one or a combination of the angle, velocity, or acceleration exceeds a threshold indicative of the end of a motion or pose to be assisted. The motion or pose to be assisted is a lifting motion or a crouching pose, wherein the controller 240 determines a relative angle of one or more of a torso, a thigh joint, and a hip joint of the wearer, and wherein the controller 240 monitors the relative angle to detect when the relative angle exceeds a predetermined threshold indicative of the start of the lifting motion or crouching pose to be assisted. The motion or pose to be assisted is a lifting motion or a crouching pose, wherein the controller 240 determines an average angle of the hip joints of the wearer, and wherein the controller 240 monitors the average angle of the hip joints of the wearer to detect when the average angle of the hip joints exceeds a predetermined threshold indicative of the start of the lifting motion or crouching pose to be assisted. The controller 240 determines the average angle of the hip joints of the wearer by calculating a relative angle between: (i) a torso of the wearer, and (ii) an average angle the thighs of the wearer. The controller 240 is configured to identify whether the wearer is engaged in activities other than the lifting motion or the crouching motion to be assisted and, if so, determine that any exceedance of the predetermined threshold is not indicative of the start of the lifting motion or the crouching pose to be assisted. The controller 240 identifies whether the wearer is engaged in activities other than the lifting motion or the crouching motion to be assisted by determining a difference between an angle of one of the hip joints and an angle of the other hip joint; applying a penalty term to the difference; subtracting the penalized difference from the average angle of the hip joints; and evaluating whether the resulting determination of the average angle of the hip joints exceeds the predetermined threshold. The motion or pose to be assisted is a lifting motion or a crouching pose, wherein the controller 240 determines an average angle of the hip joints of the wearer, and wherein the controller 240 monitors the average angle of the hip joints of the wearer to detect when the average angle of the hip joints exceeds a predetermined threshold indicative of the end of the lifting motion or crouching pose to be assisted. In an embodiment, the controller 240 is configured to monitor the information relating to one or more of the angle, a velocity, and an acceleration of the one or more joints to detect one or more states of the motion to be assisted. Wherein the motion to be assisted is a lifting motion, wherein the controller 240 determines an average angle of the hip joints of the wearer, and wherein the controller 240 monitors the average angle of the hip joints of the wearer to detect when the average angle of the hip joints exceeds a threshold indicative of the start or end of a stage of the lifting motion. In the embodiment, the threshold is indicative of an initial moving down state of the lifting motion, and wherein the threshold is an average angle of the hip joints increasing to about seven degrees from a neutral angle of the hip joints. The threshold is indicative of a hold state of the lifting motion, and wherein the threshold is an average angular velocity of the hips decreasing to about zero degrees per second. In the embodiment, during the hold state, the controller 240 monitors the average angle of the hip joints to detect a transition to a moving up state or a moving down state, wherein a change in the average angle of the hip joints to a lower angle is indicative of a transition to a moving up state, and wherein a change in the average angle of the hip joints to a higher angle is indicative of a transition to a moving down state. In the embodiment, wherein the motion to be assisted is a lifting motion, wherein the controller 240 is configured to classify the lifting motion as a stoop lifting motion, a squat lifting motion, or a bend and twist lifting motion based on the information relating to one or more of the angle, a velocity, and an acceleration of the one or more joints. The controller 240 is configured to adjust the impedance of the wearable device 100 as a function of the state or type of the movement or pose being assisted.

What is claimed is:

1. A flexible exosuit, comprising:
a first anchor configured for positioning on an upper body of a person wearing the flexible exosuit;
a second anchor configured for positioning on a first leg of the person wearing the flexible exosuit;
a third anchor configured for positioning on a second leg of the person wearing the flexible exosuit;
a connecting element;
an actuator secured with respect to the first anchor and configured to control a length of the connecting element;
a load balancing assembly coupling the actuator to the second anchor and the third anchor, wherein actuation of the actuator generates a tensile force in the flexible exosuit for generating a moment about one or more joints of the person, the load balancing assembly is configured to balance a tensile force distributed from the actuator to the first leg and the second leg of the person wearing the flexible exosuit, wherein the load balancing assembly comprises:
a flexible elongate member having a first end portion coupled to the second anchor and a second end portion connected to the third anchor; and
a mechanism coupling the connecting element to an intermediate portion of the flexible elongate member between the first end portion and the second end portion, wherein the mechanism is configured to allow the flexible elongate member to translate within the mechanism to balance the tensile force distributed to the first leg and the second leg of the person, and
wherein the actuator comprises an electromechanical motor configured to generate the tensile force by controlling the length of the connecting element by rotating a pulley the connecting element is wound on;
at least one controller; and
an inertial measurement unit (IMU) configured for positioning on the body of the person wearing the flexible exosuit and to output signals related to motions of one or more portions of the person's body during a user activity, wherein the at least one controller is configured to determine the user activity based at least in part on the signals and to control the actuator to generate the tensile force based on the determined user activity.

2. The flexible exosuit of claim 1, wherein: the inertial measurement unit (IMU) is one of a plurality of inertial sensors configured for positioning on the upper body, first leg, and second leg of the person, and the at least one controller is further configured to: determine a torso angle of the person wearing the flexible exosuit based at least in part on signals received from the plurality of inertial sensors;
determine a user activity is lifting based at least in part on the signals received from the plurality of inertial sensors; and at least in part in response to determining the user activity is lifting, control the actuator to vary the tensile force in the connecting element based at least in part upon the torso angle.

3. The flexible exosuit of claim 2, wherein the at least one controller is further configured to:
determine the user activity is not lifting based at least in part on the signals received from the plurality of inertial sensors, and
in response to determining the user activity is not lifting, control the actuator to maintain the tensile force in the connecting element at a pretension level.

4. The flexible exosuit of claim 3, wherein the at least one controller is configured to determine the user activity is not lifting by: interpreting the signals to determine an angle of a first hip joint and an angle of a second hip joint of the person wearing the flexible exosuit, and determine the user activity is not lifting based at least in part on the angle of the first hip joint and the angle of the second hip joint.

5. The flexible exosuit according to claim 2, wherein the at least one controller is configured to: determine the user activity is one of a set of possible activities based at least in part on the signals, the set of possible activities including at least a stoop lifting motion and a squat lifting motion, and control the actuator based at least in part on the determined user activity.

6. The flexible exosuit according to claim 5, wherein the at least one controller is configured to control the actuator to generate the tensile force based on an assistive profile correlating an angle of one or more body portions of the person during the user activity to appropriate assistive forces during the user activity.

7. The flexible exosuit of claim 1, wherein the actuator is releasably coupled to the first anchor and the second anchor such that the actuator can be selectably attached to and detached from the flexible exosuit.

8. The flexible exosuit of claim 7, further comprising a mounting plate coupled to at least one selected from the group of the first anchor and the second anchor, to which the actuator releasably couples.

9. The flexible exosuit of claim 8, wherein the mounting plate includes one or more electrical connectors for placing one or more electrical components of the actuator in electrical communication with one or more electrical components associated with at least one selected from the group of the first anchor and the second anchor.

10. The flexible exosuit of claim 1, further comprising at least one tension sensor configured to measure the tensile force in the flexible exosuit, and wherein the at least one controller is further configured to control the actuator to control the length of connecting element to the generate the tensile force based at least in part on signals received from the at least one tension sensor.

11. The flexible exosuit of claim 10, wherein the at least one tension sensor is configured to measure tension in the flexible elongate member.

12. The flexible exosuit of claim 1, wherein the one or more joints of the person comprise at least one selected from the group of: (i) one or more hip joints, and (ii) one or more back joints.

13. The flexible exosuit of claim 1, further comprising at least one semi-rigid component extending between the first anchor and the second anchor, wherein the semi-rigid component is flexible to bending but resistant to deformation under compression forces.

14. The flexible exosuit of claim 1, wherein actuation of the actuator generates a tensile force in the flexible exosuit for generating a moment about at least one selected from the group of: (i) a hip joint of the first leg and a hip joint of the second leg of the person, and (ii) one or more back joints of the person.

15. The flexible exosuit of claim 1, wherein the load balancing assembly allows the person to move the first and second legs freely during tasks such as walking and creates tension in the flexible exosuit during tasks that involve bending the torso and/or both the first and second legs.

16. The flexible exosuit of claim 1, wherein actuation of the actuator generates a tensile force in the flexible exosuit for generating a moment about at least one selected from the group of:
   (i) a hip joint of the first leg and a hip joint of the second leg of the person, and
   (ii) one or more back joints of the person; and
   wherein the flexible exosuit further comprises a decoupling mechanism integrated into the actuator, the decoupling mechanism comprising: a gear engaging an output of the motor of the actuator and configured to rotate when the motor is activated; a first rotating member situated coaxial with and extending from a first side of the gear; and a second rotating member situated coaxial with and extending from a second side of the gear, wherein the first rotating member and the second rotating member are configured to rotate independently of one another to distribute torque generated by the motor evenly between the second anchor and the third anchor and thereby balance the tensile force distributed to the first leg and the second leg of the person.

17. The flexible exosuit of claim 1, wherein actuation of the actuator generates a tensile force in the flexible exosuit for generating a moment about at least one selected from the group of: (i) a hip joint of the second leg of the person, and (ii) a back joint of the person.

18. The flexible exosuit of claim 1, wherein the actuator indirectly couples the first anchor to the second anchor.

19. The flexible exosuit of claim 1, further comprising a clutch configured to selectably lock a length of the connecting element between two or more selected from the group of the first anchor, the second anchor, and the third anchor to control a level of tension generated in the flexible exosuit.

20. The flexible exosuit of claim 1, wherein the connecting element includes an energy storage device configured to store and release energy between two or more of the first anchor, the second anchor, and the third anchor.

21. The flexible exosuit of claim 1, wherein the upper body includes a waist of the person.

22. The flexible exosuit of claim 1, wherein the second anchor is configured to be on at least a portion of the back of a thigh of the first leg and the third anchor is configured to be on at least a portion of the back of a thigh of the second leg.

23. The flexible exosuit of claim 1, wherein the actuator is an electric actuator.

24. The flexible exosuit of claim 1, wherein the connecting element connects the actuator and the mechanism.

25. The flexible exosuit of claim 1, wherein the flexible elongate member is rotatably or slidably coupled with the mechanism to allow the flexible elongate member to translate within the mechanism during wearer movement.

26. The flexible exosuit of claim 1, wherein the actuator is configured to extend the length of the connecting element such that the tensile force in the flexible exosuit is reduced in at least one mode of operation.

27. The flexible exosuit according to claim 1, wherein the controller is further configured to:
   control the actuator to adjust the length of the connecting element in response to relative movement of components of the flexible exosuit to pretension the flexible exosuit.

28. The flexible exosuit according to claim 1, wherein the pulley is configured to wind the connecting element along a sagittal plane of an upper body of a person wearing the flexible exosuit.

* * * * *